(12) United States Patent
Li

(10) Patent No.: US 11,517,567 B2
(45) Date of Patent: Dec. 6, 2022

(54) PHARMACEUTICAL COMPOSITIONS

(71) Applicant: Birdie Biopharmaceuticals, Inc., Grand Cayman (KY)

(72) Inventor: Lixin Li, Beijing (CN)

(73) Assignee: Birdie Biopharmaceuticals, Inc., Grand Cayman (KY)

( * ) Notice: Subject to any disclaimer, the term of this patent is extended or adjusted under 35 U.S.C. 154(b) by 395 days.

(21) Appl. No.: 16/624,860

(22) PCT Filed: Jun. 23, 2017

(86) PCT No.: PCT/CN2017/089718
§ 371 (c)(1),
(2) Date: Dec. 19, 2019

(87) PCT Pub. No.: WO2018/232725
PCT Pub. Date: Dec. 27, 2018

(65) Prior Publication Data
US 2021/0330664 A1 Oct. 28, 2021

(51) Int. Cl.
*A61K 31/4745* (2006.01)
*C07D 471/04* (2006.01)

(52) U.S. Cl.
CPC ........ *A61K 31/4745* (2013.01); *C07D 471/04* (2013.01)

(58) Field of Classification Search
CPC .......................... A61K 31/4745; C07D 47/104
See application file for complete search history.

(56) References Cited

U.S. PATENT DOCUMENTS

| | | |
|---|---|---|
| 4,689,338 A | 8/1987 | Gerster |
| 5,352,784 A | 10/1994 | Nikolaides |
| 5,389,640 A | 2/1995 | Gerster et al. |
| 5,482,936 A | 1/1996 | Lindstrom |
| 6,110,929 A | 8/2000 | Gerster et al. |
| 6,194,425 B1 | 2/2001 | Gerster et al. |
| 6,331,539 B1 | 12/2001 | Crooks et al. |
| 6,451,810 B1 | 9/2002 | Coleman et al. |
| 6,924,271 B2 | 8/2005 | Averett |
| 7,488,802 B2 | 2/2009 | Collins et al. |
| 7,576,068 B2 | 8/2009 | Averett |
| 7,943,743 B2 | 5/2011 | Korman et al. |
| 7,994,135 B2 | 8/2011 | Doronina et al. |
| 8,008,449 B2 | 8/2011 | Korman et al. |
| 8,067,546 B2 | 11/2011 | McDonagh et al. |
| 8,138,172 B2 | 3/2012 | Crook et al. |
| 8,246,968 B2 | 8/2012 | Zale et al. |
| 8,337,856 B2 | 12/2012 | Blattler et al. |
| 8,383,768 B2 | 2/2013 | Singh et al. |
| 8,552,154 B2 | 10/2013 | Freeman et al. |
| 8,575,180 B2 | 11/2013 | Kurimoto et al. |
| 8,663,643 B2 | 3/2014 | Berry et al. |
| 8,779,108 B2 | 7/2014 | Queva et al. |
| 8,951,528 B2 | 2/2015 | Stoermer et al. |
| 9,259,459 B2 | 2/2016 | Keler et al. |
| 9,308,253 B2 | 4/2016 | Kim et al. |
| 9,522,958 B2 | 12/2016 | Epstein et al. |
| 9,827,329 B2 | 11/2017 | Li |
| 9,878,052 B2 | 1/2018 | Li |
| 10,328,158 B2 | 6/2019 | Li |
| 10,548,985 B2 | 2/2020 | Li |
| 10,548,988 B2 | 2/2020 | Li |
| 10,660,971 B2 | 5/2020 | Li |
| 10,744,206 B2 | 8/2020 | Li |
| 10,780,180 B2 | 9/2020 | Li |
| 11,046,781 B2 | 6/2021 | Li |
| 11,053,240 B2 | 7/2021 | Li et al. |
| 11,130,812 B2 | 9/2021 | Li et al. |
| 11,136,397 B2 | 10/2021 | Li |
| 11,220,552 B2 | 1/2022 | Li |
| 11,279,761 B2 | 3/2022 | Li |
| 2003/0119861 A1 | 6/2003 | Gerster |
| 2003/0139364 A1 | 7/2003 | Krieg et al. |
| 2004/0014779 A1 | 1/2004 | Gorden et al. |
| 2004/0162309 A1 | 8/2004 | Gorden et al. |
| 2005/0180983 A1 | 8/2005 | Keler et al. |
| 2005/0239735 A1 | 10/2005 | Miller et al. |
| 2006/0110383 A1 | 5/2006 | Honjo et al. |
| 2006/0135459 A1 | 6/2006 | Epstein et al. |
| 2006/0142202 A1 | 6/2006 | Alkan et al. |
| 2006/0188913 A1 | 8/2006 | Krieg et al. |
| 2008/0025980 A1 | 1/2008 | Hardy et al. |
| 2008/0031887 A1 | 2/2008 | Lustgarten |
| 2009/0004194 A1 | 1/2009 | Kedl |
| 2009/0111756 A1 | 4/2009 | Doronina et al. |

(Continued)

FOREIGN PATENT DOCUMENTS

| | | |
|---|---|---|
| AR | 086196 A1 | 11/2013 |
| EA | 200800781 | 8/2008 |

(Continued)

OTHER PUBLICATIONS

Byrn et al., Pharmaceutical Research; vol. 12, No. 7, pp. 945-954 (1996).*
Berge et al. J. Pharm. Sci., 1977, 66 (1), 1-19.*
Balmana et al., BRCA in breast cancer: ESMO clinical recommendations. Annals of Oncology, 20 (Supplement 4): iv19-iv20 (2009).
Barnes, Sheri. A20: Modeling B cell lymphoma in mice. Covance by labcorp. Scientific Development (Oct. 2017).
Butte et al., Interaction of human PD-L1 and B7-1. Molecular Immunology, 45:3567-3572 (2008).
Campione et al., Lack of efficacy of imiquimod in patients with basal cell carcinoma previously treated with rituximab for B cell lymphoma. J. Medical Case Reports, 10(1):57-59 (2016).
Cang et al., Novel CD20 monoclonal antibodies for lymphoma therapy Journal of Hematology & Oncology, 5:64, 9 pp (2012).
Coiffier et al., Rituximab (anti-CD20 monoclonal antibody) for the treatment of patients with relapsing or refractory aggressive lymphoma: a multicenter phase II study. Blood, vol. 92(6), pp. 1927-1932 (1998).

(Continued)

*Primary Examiner* — Alicia L Otton
(74) *Attorney, Agent, or Firm* — K&L Gates LLP; Louis C. Cullman; Benjamin D. Heuberger

(57) ABSTRACT

The present disclosure relates to new crystal forms of chemical compounds, formulations including, methods of forming, and methods of using same.

21 Claims, 52 Drawing Sheets

(56) References Cited

U.S. PATENT DOCUMENTS

| | | |
|---|---|---|
| 2009/0123467 A1 | 5/2009 | Atul et al. |
| 2009/0182005 A1 | 7/2009 | Maus et al. |
| 2009/0202626 A1 | 8/2009 | Carson et al. |
| 2010/0143301 A1 | 6/2010 | Desai et al. |
| 2010/0256169 A1 | 10/2010 | Averett |
| 2011/0077263 A1 | 3/2011 | Kast et al. |
| 2011/0123629 A1 | 5/2011 | Pitcovski et al. |
| 2011/0195923 A1 | 8/2011 | Cherfils et al. |
| 2011/0274685 A1 | 11/2011 | Keler et al. |
| 2012/0027806 A1 | 2/2012 | Ilyinskii et al. |
| 2012/0039916 A1 | 2/2012 | Zurawski et al. |
| 2012/0219615 A1 | 8/2012 | Hersherg et al. |
| 2012/0231023 A1 | 9/2012 | Zurawski et al. |
| 2013/0022595 A1 | 1/2013 | Rotem-Yehudar et al. |
| 2013/0309250 A1 | 11/2013 | Cogswell et al. |
| 2014/0044738 A1 | 2/2014 | Langemann et al. |
| 2014/0088085 A1 | 3/2014 | Burgess et al. |
| 2015/0141625 A1 | 5/2015 | Stoermer et al. |
| 2015/0174268 A1 | 6/2015 | Li |
| 2015/0374815 A1 | 12/2015 | Kishimoto et al. |
| 2016/0324983 A1 | 11/2016 | Li |
| 2016/0339090 A1 | 11/2016 | Hacohen et al. |
| 2016/0375148 A1 | 12/2016 | Li |
| 2017/0028079 A1 | 2/2017 | Li |
| 2017/0056391 A1 | 3/2017 | Li |
| 2017/0114137 A1 | 4/2017 | Li |
| 2017/0128477 A1 | 5/2017 | Seong et al. |
| 2017/0290923 A1 | 12/2017 | Li |
| 2018/0110874 A1 | 4/2018 | Li |
| 2018/0134701 A1 | 5/2018 | David et al. |
| 2018/0148452 A1 | 5/2018 | Ding et al. |
| 2018/0177887 A1 | 6/2018 | Li |
| 2018/0177888 A1 | 6/2018 | Li |
| 2018/0346572 A1 | 12/2018 | Li |
| 2019/0002583 A1 | 1/2019 | Li |
| 2019/0016808 A1 | 1/2019 | Li |
| 2019/0016819 A1 | 1/2019 | Li |
| 2019/0048084 A1 | 2/2019 | Li |
| 2019/0099415 A1 | 4/2019 | Li |
| 2019/0269789 A1 | 9/2019 | Li |
| 2019/0269790 A1 | 9/2019 | Li |
| 2020/0055851 A1 | 2/2020 | Li |
| 2020/0155700 A1 | 5/2020 | Li |
| 2020/0179527 A1 | 6/2020 | Li |
| 2020/0345860 A1 | 7/2020 | Li |
| 2020/0246478 A1 | 8/2020 | Li |
| 2020/0276327 A1 | 9/2020 | Li |
| 2020/0353093 A1 | 11/2020 | Li |
| 2021/0214354 A1 | 7/2021 | Yang |
| 2021/0261548 A1 | 8/2021 | Li et al. |
| 2021/0261549 A1 | 8/2021 | Li et al. |
| 2021/0347911 A1 | 11/2021 | Li |
| 2021/0363271 A1 | 11/2021 | Li |
| 2022/0016152 A1 | 1/2022 | Li et al. |
| 2022/0033503 A1 | 2/2022 | Li et al. |
| 2022/0089749 A1 | 3/2022 | Li |
| 2022/0175762 A1 | 6/2022 | Li |

FOREIGN PATENT DOCUMENTS

| | | |
|---|---|---|
| EP | 0145340 A2 | 6/1985 |
| JP | 2010-270129 | 12/2010 |
| RU | 2412942 C2 | 2/2011 |
| RU | 2426734 C2 | 8/2011 |
| RU | 2475487 C2 | 2/2013 |
| WO | 2001/000244 A2 | 1/2001 |
| WO | 2001/034709 | 5/2001 |
| WO | 2002/046191 A2 | 6/2002 |
| WO | 2002/046192 | 6/2002 |
| WO | 2002/046194 | 6/2002 |
| WO | 2003/043572 A2 | 5/2003 |
| WO | 2013/067597 A1 | 5/2003 |
| WO | 2003/050121 A1 | 6/2003 |
| WO | 2003/070234 A1 | 8/2003 |
| WO | 2004/029206 A2 | 4/2004 |
| WO | 2004/056875 | 7/2004 |
| WO | 2004/058759 A1 | 7/2004 |
| WO | 2004/062603 A2 | 7/2004 |
| WO | 2005/025583 A2 | 3/2005 |
| WO | 2005/032484 A2 | 4/2005 |
| WO | 2005/034979 A2 | 4/2005 |
| WO | 2005/079195 A2 | 9/2005 |
| WO | 2006/020266 A2 | 2/2006 |
| WO | 2006/071997 A2 | 7/2006 |
| WO | 2006/091720 A2 | 8/2006 |
| WO | 2006/091769 A1 | 8/2006 |
| WO | 2006/108627 A1 | 10/2006 |
| WO | 2006/116423 A2 | 11/2006 |
| WO | 2006/134423 | 12/2006 |
| WO | 2007/024612 | 3/2007 |
| WO | 2007/030642 A2 | 3/2007 |
| WO | 2007/040840 | 4/2007 |
| WO | 2007/103048 A2 | 9/2007 |
| WO | 2008/052187 A2 | 5/2008 |
| WO | 2008/079924 A1 | 7/2008 |
| WO | 2008/082601 A2 | 7/2008 |
| WO | 2008/097870 A2 | 8/2008 |
| WO | 2008/115319 A2 | 9/2008 |
| WO | 2009/018500 A1 | 2/2009 |
| WO | 2009/089900 A1 | 7/2009 |
| WO | 2009/093250 A2 | 7/2009 |
| WO | 2009/099650 A2 | 8/2009 |
| WO | 2011/066389 A1 | 6/2011 |
| WO | 2011/084725 | 7/2011 |
| WO | 2011/084726 | 7/2011 |
| WO | 2012/078771 A1 | 6/2012 |
| WO | 2012/104344 A1 | 8/2012 |
| WO | 2012/143143 A1 | 10/2012 |
| WO | 2013/019906 A1 | 2/2013 |
| WO | 2013/022595 A1 | 2/2013 |
| WO | 2013/043647 A1 | 3/2013 |
| WO | 2013/063275 A1 | 5/2013 |
| WO | 2013/0166110 A1 | 11/2013 |
| WO | 2014/012479 A1 | 1/2014 |
| WO | 2014/022758 A1 | 2/2014 |
| WO | 2014/032021 A1 | 2/2014 |
| WO | 2014/060112 A1 | 4/2014 |
| WO | 2014/060113 A1 | 4/2014 |
| WO | 2014/161887 | 10/2014 |
| WO | 2015/103987 A1 | 7/2015 |
| WO | 2015/103989 A1 | 7/2015 |
| WO | 2015/103990 A1 | 7/2015 |
| WO | 2016/004875 A1 | 1/2016 |
| WO | 2016/004876 A1 | 1/2016 |
| WO | 2016/034085 A1 | 3/2016 |
| WO | 2017/118405 A1 | 7/2017 |
| WO | 2017/118406 A1 | 7/2017 |
| WO | 2018/196823 A1 | 11/2018 |
| WO | 2018/232725 A1 | 12/2018 |
| WO | 2020/051356 A1 | 3/2020 |
| WO | 2020/139618 A1 | 7/2020 |
| WO | 2022/047083 A9 | 3/2022 |

OTHER PUBLICATIONS

European Examination Report for Application No. 17735845.4 dated Nov. 9, 2020.
Extended European Search Report for European Patent Application No. 17914627.9 dated Nov. 18, 2020.
Gorden et al., Synthetic TLR agonists reveal functional differences between human TLR7 and TLR8. J Immunol, 174:1259-1268 (2005).
International Search Report and Written Opinion, dated Dec. 27, 2019, for International Application Serial No. PCT/US2019/049784 filed Sep. 5, 2019.
Johnston et al., The immunoreceptor TIGIT regulates antitumor and antiviral CD8+ T cell effector function. Cancer Cell 26, 923-937 (2014).
Kataja et al., Primary breast cancer: ESMO clinical recommendations for diagnosis, treatment and follow-up. Annals of Oncology, 20 (Supplement 4): iv10-iv14 (2009).

(56) References Cited

OTHER PUBLICATIONS

Kim et al., Establishment and characterization of BALB/c lymphoma lines with B cell properties. The Journal of Immunology, 122:549-554 (1979).

Lau et al., Tumour and host cell PD-L1 is required to mediate suppression of anti-tumor immunity in mice. Nat. Commun. 8, 14572, 11 pp. (2017).

Lee et al., Molecular basis for the immunostimulatory activity of guanine nucleoside analogs: Activation of Toll-like receptor 7. PNAS, vol. 100, No. 11, pp. 6646-6651 (2003).

Malm et al., Abstract 3976: PD-1 blockade combined with TEGVAX (TLR agonists-enhanced GVAX) can induce regression of established palpable tumors. Cancer Research, 73 (8 Supplment) abstract 3976 (2013).

Matin et al., Therapeutic targeting of Toll-like receptors in cutaneous disorders. Expert Opinion on Therapeutic Targets, vol. 19(12), pp. 1651-1663 (2015).

Mbow et al., Small molecule and biologic modulators of the immune response to hepatitis C virus. Mini-Reviews in Medicinal Chemistry, 6:527-531 (2006).

Nelson et al., Screening for breast cancer: an update for the U.S. preventive services task force. Ann. Intern Med., 151:727-737 (2009).

Parvinen et al., Primary non-hodgkin's lymphoma ('Reticulum Cell Sarcoma') of bone in adults. Acta Radiologica Oncology, 22:6, 449-454 (1983).

Rituxan Prscribing Information. Revised Aug. 2020.

Schaer et al., The CDK4/6 inhibitor Abemaciclib induces a T cell inflamed tumor microenvironment and enhances the efficacy of PD-L1 checkpoint blockade. Cell Reports 22, 2978-2994 (2018).

Search results list for resiquimod | Cancer. ClinicalTrials.gov, accessed Apr. 16, 2021.

Shukla et al., Regioisomerism-dependent TLR7 agonism and antagonism in an imidazoquinoline. Bioorg. Med. Chem. Lett., 19:2211-2214 (2009).

Shukla et al., Structure-activity relationships in human toll-like receptor 7-active imidazoquinoline analogues. J. Med. Chem., vol. 53, No. 11, pp. 4450-4465 (2010).

Singaporean Written Opinion for Singaporean Patent Application No. 11201909325R dated Feb. 5, 2021.

Smits et al., The use of TLR7 and TLR8 ligands for the enhancement of cancer immunotherapy. The Oncologist, 13:859-875 (2008).

Third Party Observation submitted Aug. 27, 2019 for PCT International Patent Application Serial No. PCT/CN2018/084674 filed on Apr. 26, 2018.

U.S. Appl. No. 17/315,156, filed May 7, 2021.
U.S. Appl. No. 17/315,162, filed May 7, 2021.
U.S. Appl. No. 17/328,103, filed May 24, 2021.
U.S. Appl. No. 17/328,116, filed May 24, 2021.
U.S. Appl. No. 17/417,357, filed Jun. 22, 2021.

<https://en.wikipedia.org/wiki/Epidermal_growth_factor_receptor>, downloaded May 7, 2021 (cited by Examiner in U.S. Appl. No. 16/068,338 in Non-Final Office Action dated May 11, 2021).

<https://en.wikipedia.org/wiki/Resiquimod>, downloaded May 7, 2021 (cited by Examiner in U.S. Appl. No. 16/068,338 in Non-Final Office Action dated May 11, 2021).

Bastin et al., Salt selection and optimisation procedures for pharmaceutical new chemical entities. Organic Process Research & Development, 4(5):427-435 (2000).

Miakkouk et al., The potential use of toll-like receptor (TLR) agonists and antagonists as prophylactic and/or therapeutc agents. Immunopharmacology and Immunotoxicology, vol. 31, No. 3, pp. 331-338 (2009).

Morissette et al., High-throughput crystallization: polymorphs, salts, co-crystals and solvates of pharmaceutical solids. Advanced Drug Delivery Reviews, 56:275-300 (2004).

Office Action, dated Aug. 19, 2020 for Russian Patent Application No. 2020102453 (Original and Translation enclosed).

Search Report for Russian Patent Application No. 2020102453 (Original and Translation enclosed).

Shi et al., Discovery of imidazoquinolines with Toll-like receptor 7/8 independent cytokine induction. ACS Medicinal Chemistry Letters, vol. 3, No. 6, pp. 501-504 (2012).

Supplementary European Search Report, dated Jul. 14, 2020, for European Patent Application Serial No. 18792253.

Tanji et al., Structural reorganization of the toll-like receptor 8 dimer induced by agonistic ligands. Science, vol. 339, pp. 1426-1429 (2013) (also includes supplementary materials).

Damiano et al., A Novel Toll-Like Receptor 9 Agonist Cooperates with Trastuzumab in Trastuzumab-Resistant Breast Tumors through Multiple Mechanisms of Action. Clinical Cancer Research, 15(22):6921-6930 (2009).

Shah et al., Toll-like receptor 2 Ligands Regulate Monocyte Fc gamma Receptor Expression and Function J. Biol. Chem., 288(17):12345-12352 (2013).

Van Egmond et al., Cross-talk between pathogen recognizing Toll-like receptors and immunoglobulin Fc receptors in immunity. Immunological Reviews, 268(1):311-327 (2015).

U.S. Appl. No. 16/940,697, filed Jul. 28, 2020.

McMahon et al., VEGF receptor signaling in tumor angiogenesis. The Oncologist, 5(suppl 1):3-10 (2000).

Pinedo et al., Translational Research: The role of VEGF in tumor angiogenesis. The Oncologist, 5(supp1):1-2 (2000).

U.S. Appl. No. 16/878,010, filed May 19, 2020.

Butchar et al., Reciprocal regulation of activating and inhibitory Fcgamma receptors by TLR7/8 activation: Implications for tumor immunotherapy. Clin. Cancer Res., 16(7): 2065-2075 (2010).

Hengge et al., Letter to the editor: Topical imiquimod to treat recurrent breast cancer. Breast Cancer Research and Treatment, 94:93-94 (2005).

International Patent Application Serial No. PCT/US2019/049784 filed on Sep. 5, 2019.

International Search Report and Written Opinion, dated Dec. 27, 2019, for International Patent Application Serial No. PCT/US2019/049784 filed on Sep. 5, 2019.

Lu et al., VTX-2337 is a novel TLR8 agonist that activates NK cells and augments ADCC. Clin. Cancer Res., 18(2):499-509(2011).

U.S. Appl. No. 16/794,056, filed Feb. 18, 2020.
U.S. Appl. No. 16/794,069, filed Feb. 18, 2020.

Schneble et al., Breast cancer immunotherapy. Medica—A Journal of Clinical Medicine, 10(2):185-191 (2015).

Smorlesi et al., Imiquimod and S-27609 as adjuvants of DNA vaccination in a transgenic murine model of HER2/neu-positive mammary carcinoma. Gene Therapy, 12:1324-1332 (2005).

Tomai et al., Resiquimod and other immune response modifiers as vaccine adjuvants. Expert Rev. Vaccines 6(5):835-847 (2007).

Vippagunta et al., Crystalline solids. Advanced Drug Delivery Reviews, 48:3-26 (2001).

West, Anthony. Solid State Chemistry and its Applications. Wiley, New York, 358 (1988).

Grosso et al., Association of tumor PD-L1 expression and immune biomarkers with clinical activity in patients (pts) with advanced solid tumors treated with nivolumab (anti-PD-1; BMS-936558; ONO-4538). J. Clin. Oncol., Jun. 1, 2013, vol. 31, No. 15.

Hamid et al., Safety and tumor responses with lambrolizumab (anti-PD-1) in melanoma. New Engl. J. Med., Jun. 2, 2013, vol. 369, No. 2, pp. 134-144.

Search results by the Chinese Patent Office for Chinese Patent Application No. CN201410325480 dated Dec. 21, 2018 (English translation included).

Singaporean Further Written Opinion for Singaporean Patent Application No. 11201700079V filed on Jul. 8, 2015, dated Mar. 20, 2019.

Roses et al., Differential production of IL-23 and IL-12 by myeloid-derived dendritic cells in response to TLR agonists. J. Immunol., 181:5120-5127 (2008).

Yrlid et al., Regulation of intestinal dendritic cell migration and activation by plasmacytoid dendritic cells, TNF-alpha and Type 1 IFNs after feeding a TLR7/8 ligand. J. Immunol., 176:5205-5212 (2006).

(56) References Cited

OTHER PUBLICATIONS

Pockros et al., Oral resiquimod in chronic HCV infection: Safety and efficacy in 2 placebo-controlled, double-blind phase IIa studies Journal of Hepatology, 47:174-182 (2007).
Johnson et al., Impact of NRAS Mutations for Patients with Advanced Melanoma Treated with Immune Therapies. Dancer Immunol Res, 3(3):288-295 (2015).
Lee et al., Resiquimod, a TLR7/8 agonist, promotes differentiation of myeloid-derived suppressor cells into macrophages and dendritic cells Arch. Pharm. Res., 37:1234-1240 (2014).
Lu et al., TLR agonists for cancer immunotherapy: tipping the balance between the immune stimulatory and inhibitory effects Front. Immunol., vol. 5, pp. 1-4 (2014).
Melani, et al., Targeting of Interleukin 2 to human ovarian carcinoma by fusion with a single-chain Fv of antifolate receptor antibody. Cancer Research, vol. 58, No. 18, pp. 4146-4154 (1998).
Miller et al., Imiquimod applied topically: a novel immune response modifier and new class of drug. Int. J. Immunopharmacol. 21:1-14 (1999).
Mosser et al., Exploring the full spectrum of macrophage activation. Nat Rev Immunol., 8(12):958-969 (2008).
Pribble et al., EC145: A novel targeted agent for adenocarcinoma of the lung. Expert Opin. Investig. Drugs 21:755-761 (2012).
Rudnick et al., IT-020: A dramatic clinical and cytologic response to ipilimumab in a multi-drug regiment with bevacizumab. Neuro-Oncology, vol. 15, Suppl. 3, pp. iii68-iii74 (2013).
Scott et al., Antibody therapy of cancer. Nat. Rev. Cancer 12:278-87 (2012).
Singaporean Search Report and Written Opinion for Singaporean Patent Application No. 112015003995 filed on Jul. 16, 2013 (Search completed on Mar. 16, 2016 and dated Apr. 12, 2016).
Singaporean Search Report and Written Opinion for Singaporean Patent Application No. 11201700079V filed on Jul. 8, 2015 (search completed on Mar. 6, 2018 and dated Mar. 9, 2018).
Smyth et al., Activation of NK cell cytotoxicity. Molecular Immunology, 42:501-510 (2005).
Sznol et al., Antagonist antibodies to PD-1 and B7-H1 (PD-L1) in the treatment of advanced human cancer. Clin. Vancer Res., 19(5): 1021-1034 (2013).
Sousa, Activation of dendritic cells: translating innate into adaptive immunity. Current Opinion in Immunology, 16:21-25 (2004).
Stephenson et al., TLR8 Stimulation enchances cetuximab-mediated natural killer cell lysis of head and neck cancer cells and dendritic cell cross priming of EGFR-specific CD8+ T cells. Cancer Immunol. Immunother., vol. 62, No. 8, pp. 1347-1357 (2013).
Stier et al., Combinations of TLR Ligands: A Promising Approach in Cancer Immunotherapy. Clin. & Dev. Immunol. 2013:1-14 (2013).
Supplementary European Search Report for European Patent Application No. 13820359.1 filed on Jul. 16, 2013 (Search completed on Jan. 27, 2016 and dated Apr. 1, 2016).
Supplementary Partial European Search Report for European Patent Application No. 13820359.1 filed on Jul. 16, 2013 (Search completed on Jan. 27, 2016 and dated Feb. 3, 2016).
Supplementary European Search Report for European Patent Application No. 15735122 dated Aug. 23, 2017.
Supplementary European Search Report for European Patent Application No. 15735519 dated Aug. 23, 2017.
Supplementary European Search Report and Opinion for European Patent Application No. 15818970 (search completed on Jan. 29, 2018 and dated May 14, 2018).
Supplementary Partial European Search Report for European Patent Application No. 15818970 (search completed on Jan. 29, 2018 and dated Feb. 8, 2018).
Supplementary European Search Report and Opinion for European Patent Application No. 15819519 (search completed on Jan. 29, 2018 and dated Feb. 2, 2018).
Supplementary European Search Report and Opinion for European Patent Application No. 15839010 (search completed on Feb. 20, 2018 and dated Mar. 1, 2018).
Supplementary European Search Report and Opinion for European Patent Application No. 15734849 (search completed on Aug. 11, 2017 and dated Apr. 13, 2018).
Suzanne et al., Targeting the PD-1/B7-H1(PD-L1) pathway to activate anti-tumor immunity. Current Opinion in Immunology, vol. 24, No. 2, pp. 207-212 (2012).
Timmerman, et al., In vivo activity of rituximab-CpG oligodeoxynucleotide conjugate against rituximab-resistant human CD20+ B-cell lymphoma. Journal of Clinical Oncology (ASCO Annual Meeting Proceedings—Post-Meeting Edition), vol. 27, No. 158: 8529 (2009).
Topalian et al., Targeting the PD-1/B7-H1(PD-L1) pathway to activate anti-tumor immunity. Curr. Opin. Immunol., 24(2):207-212 (2012).
International Search Report and Written Opinion for International Application No. PCT/CN2015/083585 filed on Jul. 8, 2015.
International Search Report and Written Opinion for International Application No. PCT/CN2015/070377 filed on Jan. 8, 2015.
International Search Report and Written Opinion for International Application No. PCT/CN2015/070380 filed on Jan. 8, 2015.
International Search Report and Written Opinion for International Application No. PCT/CN2015/070379 filed on Jan. 8, 2015.
International Search Report of PCT/CN2015/070379 dated Apr. 8, 2015.
International Search Report and Written Opinion for International Application No. PCT/CN2015/088456 filed on Aug. 29, 2015.
Gerster, John F. Synthesis and structure-activity-relationships of 1H-imidazo[4, 5-c]quinolines that induce interferon production. Journal of Medicinal Chemistry, No. 10, vol. 48, pp. 3481-3491 (2005).
International Search Report and Written Opinion, dated Aug. 6, 2018, for International Application No. PCT/CN2018/084674 filed on Apr. 26, 2018.
International Search Report and Written Opinion, dated Mar. 28, 2018, for International Application No. PCT/CN2017/089718 filed on Jun. 23, 2017.
U.S. Appl. No. 16/608,581, filed Oct. 25, 2019.
U.S. Appl. No. 16/711,652, filed Dec. 12, 2019.
Berenbaum, M.C. Synergy, additivism and antagonism in immunosuppression. Clin. Exp. Immunol., 28, 1-18 (1977).
Wiesenthal, http://weisenthal.org/feedback, 2002.
Agata et al., Expression of the PD-1 antigen on the surface of stimulated mouse T and B lymphocytes. Int. Immunol. 8(5)765-772 (1996).
Betting, et al., In vivo eradication of a rituximab-resistant human CD20+ B cell lymphoma by rituximab-CpG oligodeoxynucleotide conjugate is mediated by natural killer cells and complement. Blood (ASH Annual Meeting Abstracts), 114: Abstract 723 (2009).
Blencowe et al., Self-immolative linkers in polymeric delivery systems. Polym. Chem., 2:773-790 (2011).
Bonifaz, et al., Efficient targeting of protein antigen to the dendritic cell receptor DEC-205 in the steady state leads to antigen presentation on major histocompatibility complex class I products and peripheral CD8+ T cell tolerance. The Journal of Experimental Medicine, vol. 196, No. 12, pp. 1627-1638 (2002).
Braga et al., Crystal polymorphism and multiple crystal forms. Struct Bond, 132:25-50 (2009).
Butchar et al., TLR7/8 Agnosits overcome the suprresion of Fc gamma R activity in monocytes from chronic lymphocytic leukemia patients. Blood, vol. 120, No. 21, p. 4595 (2012).
Carter, et al., Preferential induction of CD4+ T cell responses through in vivo targeting of antigen to dendritic cell-associated C-type lectin-1. The Journal of Immunology, vol. 177, No. 4, pp. 2276-2284 (2006).
Cherfils-Vicini et al., Triggering of TLR7 and TLR8 expressed by human lung cancer cells induces cell survival and chemoresistance. J Clin. Investigation 120(4):1285-1297 (2010).
Dummer et al., Imiquimod in basal cell carcinoma: How does it work? Br. J. Dermatol., 149(Suppl. 66):57-58 (2003).
Engel et al., The pharmacokinetics of Toll-like receptor agonists and the impact on the immune system. Expert Rev. Clin. Pharmacol., 4(2):275-289 (2011).

(56) References Cited

OTHER PUBLICATIONS

Extended European Search Report for European Patent Application No. 15818970.4 dated May 14, 2018.
Hofman et al., Phase I evaluation of intralesionally injected TLR9-agonist PF-3512676 in patients with basal cell carcinoma or metastatic melanoma. J. Immunother. 31:520-527 (2008).
Hurvitz et al., The potential for trastuzumab emtansine in human epidermal growth factor receptor 2 positive metastatic breast cancer: latest evidence and ongoing studies. Therapeutic Advances in Medical Oncology, 4(5):235-245 (2012).
International Search Report and Written Opinion for International Application No. PCT/CN2015/083583 filed on Jul. 8, 2015.
Eriksson et al., Gemcitabine reduces MDSCs tregs and TGFB.1 while restoring the teff/treg ratio in patients with pancreatic cancer. J. Transl. Med., 14:282, 12 pp (2016).
International Patent Application Serial No. PCT/US2019/066796 filed on Dec. 17, 2019.
International Search Report and Written Opinion, dated Mar. 9, 2020, for International Patent Application Serial No. PCT/US2019/066796 filed on Dec. 17, 2019.
Dotan et al., Impact of Rituximab (Rituxan) on the treatment of B-cell non-hodgkin's lymphoma. P&T, 35(3):148-157 (2010).
Dovedi et al., Systemic delivery of a TLR7 agonist in combination with radiation primes durable antitumor immune responses in mouse models of lymphoma. Blood, 121(2):251-259 (2013).
Extended European Search Report for European Patent Application No. 22151690.9 dated Apr. 28, 2022.
Pirker et al., Cetuximab in non-small-cell lung cancer. Transl Lung Cancer Res 1(1): 54-60 (2012).
Schon et al., Review: TLR7 and TLR8 as targets in cancer therapy. Oncogene 27, 190-199 (2008).
U.S. Appl. No. 17/669,177, filed Feb. 10, 2022.
Berge et al., Review Article: Pharmaceutical Salts. J. Pharm. Sci., 66(1):1-19 (1977).
U.S. Appl. No. 17/546,779, filed Dec. 9, 2021.
Caira, Crystalline polymorphism of organic compounds. Topics in Current Chemistry, Springer Verlag, Berlin/Heidelberg, 1998, vol. 198, pp. 163-208 (1998).
Caisova et al., Effective cancer immunotherapy based on combination of TLR agonists with stimulation of phagocytosis. International Immunopharmacology., 59:86-96 (2018).
International Search Report and Written Opinion, dated Feb. 3, 2022, for International Application Serial No. PCT/US2021/047826 filed Aug. 26, 2021.
Kukes, Clinical Pharmacokinetics: Theoretical, Applied, and Analytical Aspects, A Guide, Ed. (Chapter 11.2: Relationship between the Crystal Structure of the Substance, on the One Hand, and the Pharmacokinetics and Efficiency of the Medicine, on the Other, by I.G. Smirnova and V.V. Chistyakov) (2009). (Original and Translation enclosed).
Mathijssen et a., Flat-fixed dosing versus body surface area-based dosing of anticancer drugs in adults: Does it make a difference? The Oncologist, 12(8):913-923 (2007).
Meyer et al., Resiquimod, a topical drug for viral skin lesions and skin cancer. Expert Opinion on Investigational Drugs, vol. 22, Issue 1, pp. 149-159 (2013).
Gandini et al., PD-L1 expression in cancer patients receiving anti PD-1/PD-L1 antibodies: A systematic review and meta-analysis. Critical Reviews in Oncology/Hematology 100, pp. 88-98 (2016).
International Search Report and Written Opinion, dated Aug. 12, 2020, for International Application Serial No. PCT/US2020/022575 filed Mar. 13, 2020.
Krishnan et al., PD-1 expression in T-cell lymphomas and reactive lymphoid entities: Potential overlap in staining patterns between lymphoma and viral lymphadenitis. Am. J. Surg. Pathol., vol. 34, No. 2, pp. 178-179 (2010).
Ma et al., The TLR7 agonists imiquimod and gardiquimod improve DC-based immunotherapy for melanoma in mice. Cellular and Molecular Immunology, 7, pp. 381-388 (2010).
Patnaik et al., Phase I study of MK-3475 (anti-PD-1 monoclonal antibody) in patients with advanced solid tumors. Journal of Clinical Oncology, vol. 30, No. 15, pp. 2512 (2012).
Sharpe et al., The diverse functions of the PD1 inhibitory pathway. Nature Reviews: Immunology, vol. 18, pp. 153-167 (2018).
Topalian et al., Safety, activity, and immune correlates of anti-PD-1 antibody in cancer. The New England Journal of Medicine, vol. 366, No. 26 (2012).

\* cited by examiner

PHARMACEUTICAL COMPOSITIONS

TECHNICAL FIELD

The present disclosure relates to crystal forms of pharmaceutical compounds, formulations including, methods of forming, and methods of using these crystal forms.

SUMMARY

Described herein are new crystal forms of pharmaceutical compounds. In one embodiment, the pharmaceutical compounds are included in a pharmaceutical composition useful for treating a disease or condition. In one embodiment, the disease or condition is cancer.

In some embodiments, pharmaceutical compositions are described including resiquimod in the form of a sulfate salt in crystal form A. The sulfate salt can be a monosulfate salt and/or an anhydrate. This crystal form can be prepared in an appropriate dosage from.

In one embodiment, the sulfate salt in crystal form A is characterized by x-ray powder diffraction spectrum that comprises peaks at about 7 to about 8 degrees 2θ, about 13.5 to about 14.5 degrees 2θ, about 18 to about 19 degrees 2θ, and/or about 15 to about 16 degrees 2θ.

The sulfate salt in crystal form A can be stable at room temperature for at least about 2 days or at least about 1 week.

Other embodiments describe pharmaceutical compositions comprising a crystal form of a compound of Formula I:

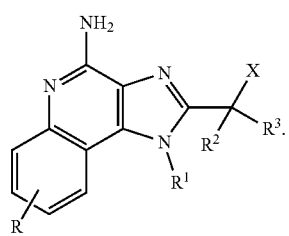

(I)

Formula I can be a compound having a formula 4-amino-α-butyl-1-(2-methylpropyl)-1H-imidazo-[4,5-c]-quinoline-2-methanol hemihydrate, 4-amino-α,α-dimethyl-2-ethoxymethyl-1H-imidazo-[4,5-c]-quinoline-1-ethanol, 2-ethoxymethyl-1-(2-methylpropyl)-1H-imidazo-[4,5-c]-quinolin-4-amine, or 4-amino-1-phenylmethyl-1H-imidazo-[4,5-c]-quinoline-2-methanol. In one embodiment, Formula I is resiquimod.

In some embodiments, the crystal form of a compound of Formula I can be in form A and/or be a sulfate salt. In one embodiment, a sulfate salt is a monosulfate salt and/or an anhydrate.

Other embodiments provide methods of treating diseases or conditions. In one embodiment, methods of treating cancer are described. The methods can comprise: administering a pharmaceutical composition including a crystal form of a compound having a Formula I:

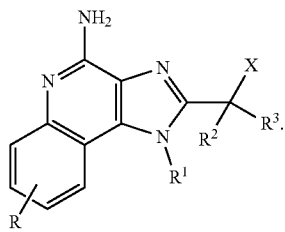

(I)

BRIEF DESCRIPTION OF THE DRAWINGS

FIG. 120 illustrates XRPD patterns of nitrate crystal form Type B (807919-07-B20).

FIG. 121 illustrates TGA/DSC curves of nitrate crystal form Type A (807919-07-D20).

FIG. 122 illustrates TGA/DSC curves of nitrate crystal form Type B (807919-07-B20).

FIG. 123 illustrates an inter-conversion of freebase crystal forms.

FIG. 124 illustrates a XRPD pattern of crystal form Type A (807920-05-A).

FIG. 125 illustrates TGA/DSC curves of crystal form Type A (807920-05-A).

FIG. 126 illustrates a XRPD pattern of crystal form Type C (807920-11-A11).

FIG. 127 illustrates a XRPD pattern of crystal form Type F (807920-09-A4).

FIG. 128 illustrates XRPD patterns of isomorphic Type B.

FIG. 129 illustrates TGA/DSC curves of a first batch of crystal form Type B (807920-07-A13).

FIG. 130 illustrates TGA/DSC curves of a second batch of crystal form Type B (807920-07-A13).

FIG. 131 illustrates TGA/DSC curves of a third batch of crystal form Type B (807920-07-A13).

Figure 132:
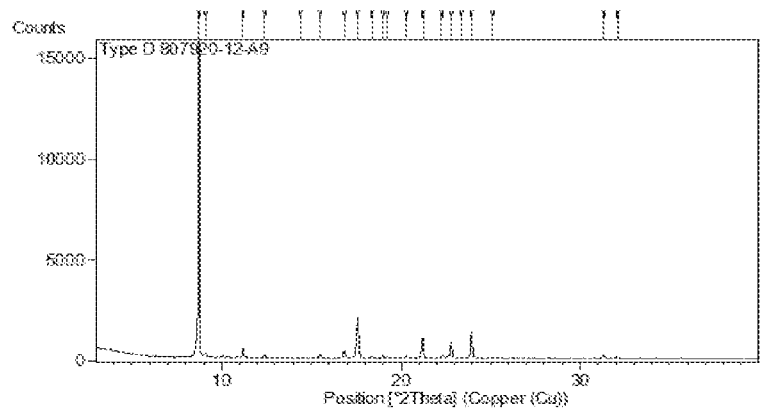

FIG. 132 illustrates a XRPD pattern of crystal form Type D (807920-12-A9).

Figure 133:
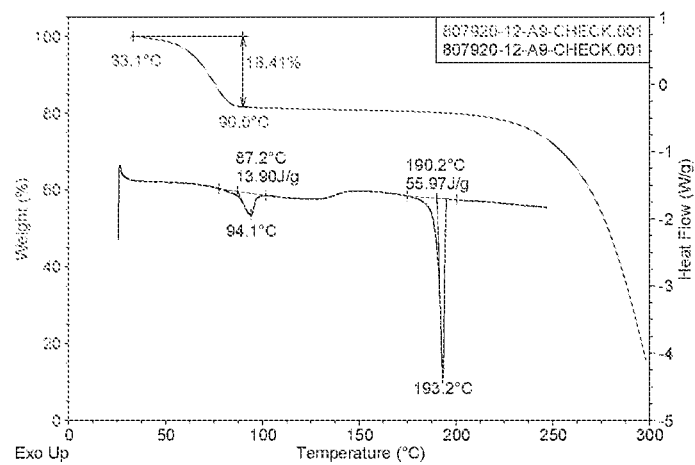

FIG. 133 illustrates TGA/DSC curves of crystal form Type D (807920-12-A9).

Figure 134:
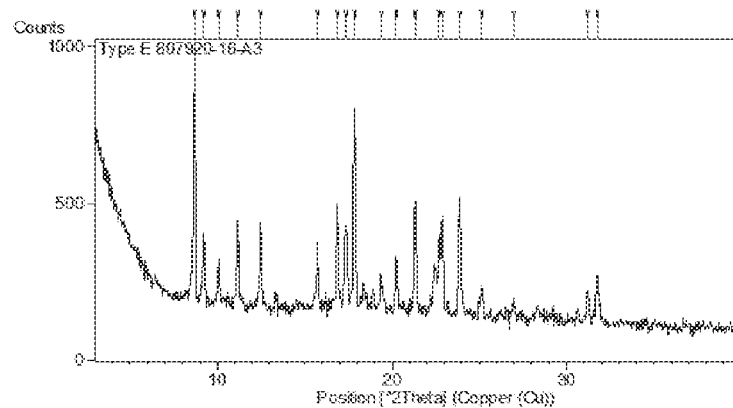

FIG. 134 illustrates a XRPD pattern of crystal form Type E (807920-16-A3).

Figure 135:
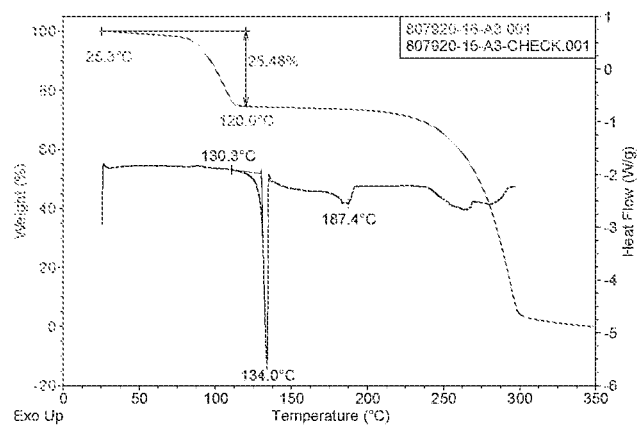

FIG. 135 illustrates TGA/DSC curves of crystal form Type E (807920-16-A3).

Figure 136:
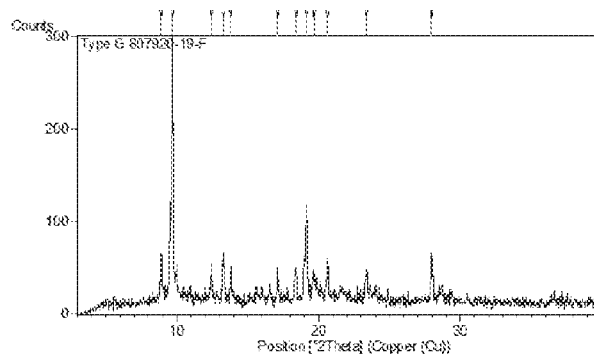

FIG. 136 illustrates a XRPD pattern of crystal form Type G (807920-19-F).

Figure 137:
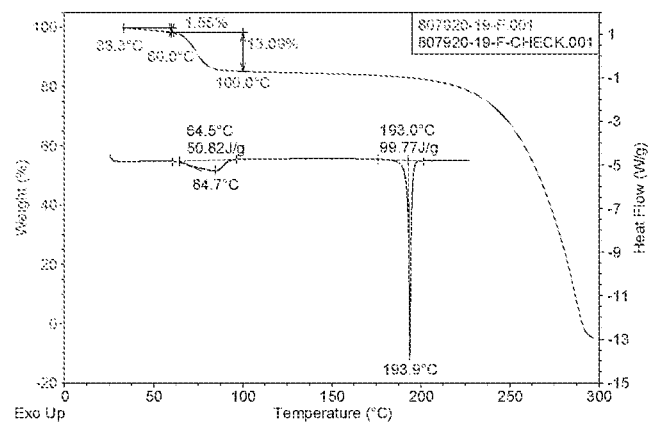

FIG. 137 illustrates TGA/DSC curves of crystal form Type G (807920-19-F).

Figure 138:
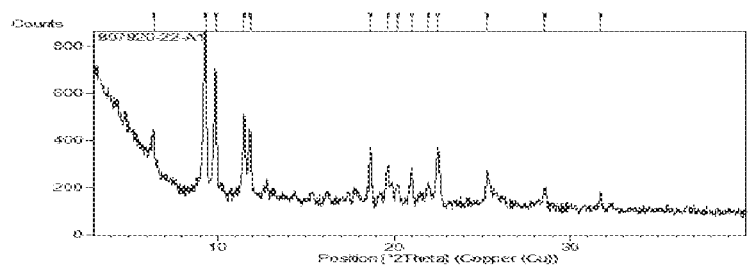

FIG. 138 illustrates a XRPD pattern of sample H (807920-22-A1).

Figure 139:
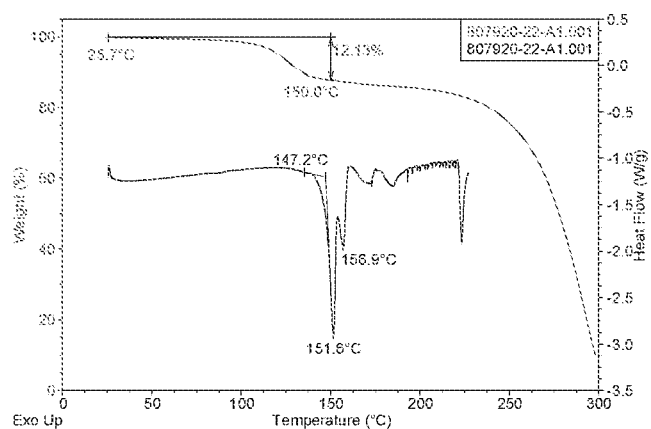

FIG. 139 illustrates TGA/DSC curves of sample H (807920-22-A1).

Figure 140:
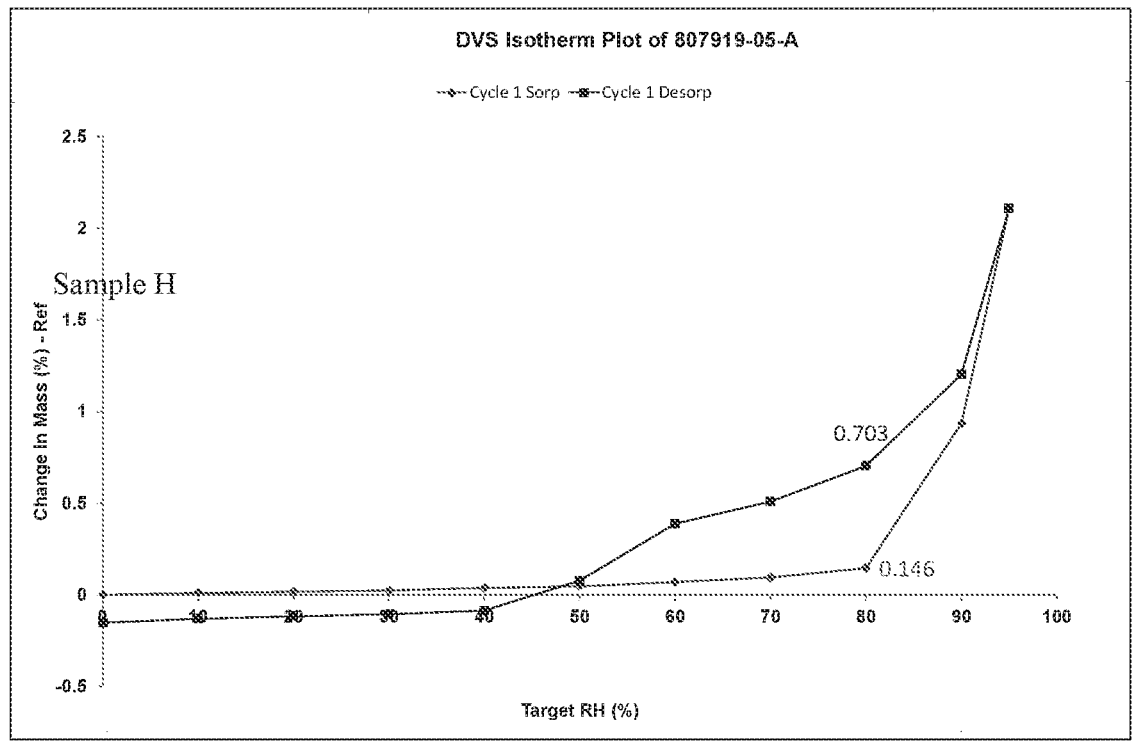

FIG. 140 illustrates a DVS plot of crystal form Type A (807919-05-A).

Figure 141:
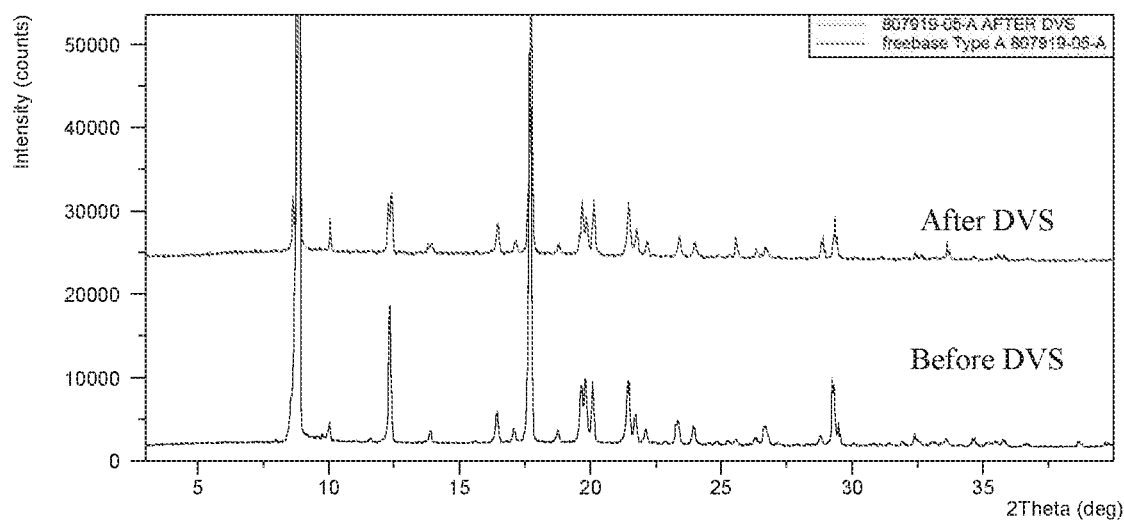

FIG. 141 illustrates a XRPD overlay of crystal form Type A (807919-05-A) before and after DVS test.

Figure 142:
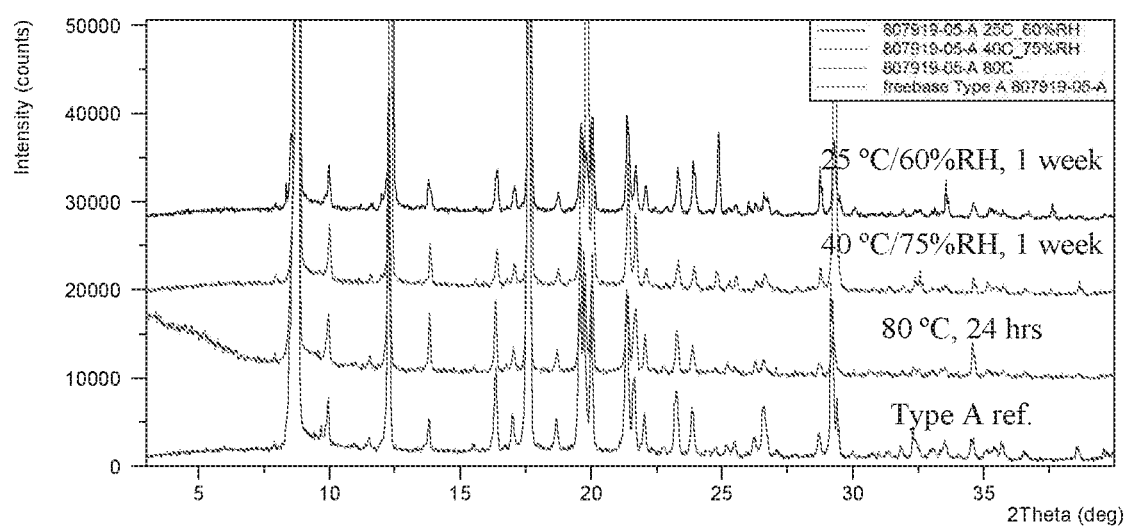

FIG. 142 illustrates a XRPD overlay of crystal form Type A (807919-05-A) before and after stability test.

DETAILED DESCRIPTION

Described herein are new crystal forms of chemical compounds, formulations including these crystal forms, methods of forming these crystal forms, and methods of using these crystal forms. In some embodiments, these new crystal forms can be referred to as polymorphs or isomorphs. Pharmaceutical polymorphism can have a direct effect on delivery of a given pharmaceutical active agent, ingredient, or drug. Polymorphic purity of samples can be checked using techniques such as powder X-ray diffraction, IR/Raman spectroscopy, and utilizing the differences in their optical properties.

In general, active pharmaceutical ingredients (APIs) in pharmaceutical compositions can be prepared in a variety of different forms including prodrugs, amorphous forms, solvates, hydrates, co-crystals, salts, and the like. The discovery of novel API forms may provide an opportunity to improve the performance characteristics of a pharmaceutical composition. Additionally, discovery of drug forms expands the array of resources available for designing pharmaceutical dosage forms with targeted release profiles or other desired characteristics.

A specific characteristic that can be targeted includes the crystal form of an API. The alteration of the crystal form of a given API can result in modification of target molecule physical properties. For example, various polymorphs of a given API can exhibit different aqueous solubility, while the thermodynamically stable polymorph would exhibit a lower solubility than the meta-stable polymorph. In addition, pharmaceutical polymorphs can also differ in properties such as rate of dissolution, shelf life, bioavailability, morphology, vapor pressure, density, color, and compressibility. Accordingly, it may be desirable to enhance the properties of an API by forming molecular complexes such as a crystal, a co-crystal, a salt, a solvate or a hydrate with respect to aqueous solubility, rate of dissolution, bioavailability, $C_{max}$, $T_{max}$, physicochemical stability, down-stream processibility (e.g., flowability, compressibility, degree of brittleness, particle size manipulation), decrease in polymorphic form diversity, toxicity, taste, production costs, manufacturing methods, or a combination thereof.

New crystal forms of compounds and pharmaceutical compositions including the new crystal forms of these compounds are disclosed. The crystal forms can be of compounds having a structure of Formula I:

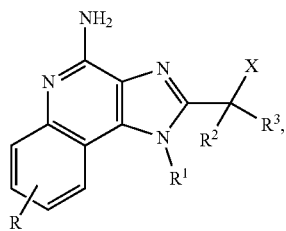

(I)

or a pharmaceutically acceptable salt thereof,
wherein $R^1$ is hydrogen; $C_1$-$C_{10}$ straight chain or branched chain substituted or unsubstituted alkyl, wherein the substituent is $C_3$-$C_6$ cycloalkyl or $C_3$-$C_6$ cycloalkyl substituted by straight chain or branched chain $C_1$-$C_4$ alkyl; straight chain or branched chain $C_2$-$C_{10}$ alkenyl; or substituted straight chain or branched chain $C_2$-$C_{10}$ alkenyl, wherein the substituent is $C_3$-$C_6$ cycloalkyl or $C_3$-$C_6$ cycloalkyl substituted by straight chain or branched chain $C_1$-$C_4$ alkyl; $C_1$-$C_6$ hydroxyalkyl; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl) ethyl; or phenyl; the benzyl, (phenyl)ethyl, or phenyl substituent being optionally substituted on the benzene ring by one or two moieties independently selected from $C_1$-$C_4$ alkyl, $C_1$-$C_4$ alkoxy, or halogen, with the proviso that if the benzene ring is substituted by two moieties, then the moieties together contain no more than six carbon atoms;
$R^2$ and $R^3$ are independently selected from hydrogen, $C_1$-$C_4$ alkyl, phenyl, or substituted phenyl, wherein the substituent is $C_1$-$C_4$ alkyl, $C_1$-$C_4$ alkoxy, or halogen;
X is $C_1$-$C_4$ alkoxy, alkoxyalkyl wherein the alkoxy moiety contains one to about four carbon atoms and the alkyl moiety contains one to about four carbon atoms, $C_1$-$C_4$ hydroxyalkyl, $C_1$-$C_4$ haloalkyl, alkylamido wherein the alkyl group contains one to about four carbon atoms, amino, substituted amino wherein the substituent is $C_1$-$C_4$ alkyl or $C_1$-$C_4$ hydroxyalkyl, azide, chloro, hydroxy, 1-morpholino, 1-pyrrolidino, or $C_1$-$C_4$ alkylthio; and
R is hydrogen, straight chain or branched chain $C_1$-$C_4$ alkoxy, halogen, or straight chain or branched chain $C_1$-$C_4$ alkyl.

In some embodiments, the crystal form of compounds having a structure of Formula I is a hydrochloric acid salt, a sulfate salt, a phosphate salt, a maleate salt, a malate salt, an adipate salt, a glycolate salt, a hippurate salt, a tartrate salt, a fumarate salt, a citrate salt, a lactate salt, a succinate salt, a tosylate salt, mesylate salt, an oxalate salt, a gentisate salt, a benzoate salt, or a nitrate salt in crystalline form A, B, C, D, E, F or G.

In some embodiments, $R^1$ may contain two to about ten carbon atoms. In other embodiments, $R^1$ may contain two to about eight carbon atoms. In still other embodiments, $R^1$ is 2-methylpropyl or benzyl.

In some embodiments, X can be azido, hydroxy, ethoxy, methoxy, 1-morpholino, or methylthio. In some embodiments, X can be azido, hydroxy, ethoxy, methoxy, 1-morpholino, or methylthio when $R^1$ is 2-methylpropyl, 2-hydroxy-2-methylpropyl, or benzyl.

Other substituents in compounds of Formula I that contain an alkyl radical (e.g., R when R is alkoxy or alkyl, or X when X is alkylamido) can contain two carbon atoms or, in some embodiments, one carbon atom in each alkyl radical.

In some embodiments, R is hydrogen.

Compounds of Formula I can include 4-amino-α-butyl-1-(2-methylpropyl)-1H-imidazo-[4,5-c]-quinoline-2-methanol hemihydrate, 4-amino-α,α-dimethyl-2-ethoxymethyl-1H-imidazo-[4,5-c]-quinoline-1-ethanol, 2-ethoxymethyl-1-(2-methylpropyl)-1H-imidazo-[4,5-c]-quinolin-4-amine, and 4-amino-1-phenylmethyl-1H-imidazo-[4,5-c]-quinoline-2-methanol.

In one embodiment, a compound of Formula I can be resiquimod (1-[4-amino-2-(ethoxymethyl)imidazo-[4,5-c]-quinolin-1-yl]-2-methylpropan-2-ol). Resiquimod can have a structure

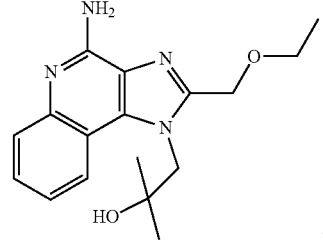

Halogen or halo groups in any of the compounds described herein can be F, Cl, Br, I, or At. In some embodiments, halogen or halo groups in any of the compounds described herein can be F, Cl, Br, or I.

These new crystal forms of Formula I compounds can be a HCl salt, a sulfate salt, a phosphate salt, a maleate salt, a malate salt, an adipate salt, a glycolate salt, a hippurate salt, a tartrate salt, a fumarate salt, a citrate salt, a lactate salt, a succinate salt, a tosylate salt, mesylate salt, an oxalate salt, a gentisate salt, a benzoate salt, or a nitrate salt in crystalline form A, B, C, D, E, F or G.

One embodiment includes resiquimod in the form of a monosulfate salt in crystal form A. The crystal form A can be characterized by an x-ray powder diffraction spectrum that comprises peaks at about 7 to about 8 degrees 2θ, about 13.5 to about 14.5 degrees 2θ, about 19 to about 20 degrees 2θ, and/or about 19.5 to about 20.5 degrees 2θ.

Another embodiment includes resiquimod in the form of a sulfate salt in crystal form A. The crystal form A can be characterized by x-ray powder diffraction spectrum that comprises peaks at about 7 to about 8 degrees 2θ, about 9 to about 10 degrees 2θ, about 11 to about 12 degrees 2θ, about 14 to about 14.5 degrees 2θ, about 15 to about 16 degrees 2θ, about 17 to about 20 degrees 2θ, and/or about 24 to about 26 degrees 2θ. Resiquimod can also be formed as a sulfate salt in crystal form A characterized by x-ray powder diffraction spectrum that comprises peaks at about 7 to about 8 degrees 2θ, about 11.5 to about 12 degrees 2θ, about 14 to about 14.5 degrees 2θ, about 16 to about 16 degrees 2θ, about 17 to about 18.5 degrees 2θ, about 19.5 to about 20.5 degrees 2θ, and/or about 24 to about 25 degrees 2θ.

Resiquimod can be formed as a sulfate salt in crystal form B. Such a crystal form B can be characterized by x-ray powder diffraction spectrum that comprises peaks at about 7 to about 8 degrees 2θ, about 9 to about 10 degrees 2θ, and/or about 19 to about 20.5 degrees 2θ.

Resiquimod can also be formed as a hemi-sulfate salt in crystal form A. Such a crystal form can be characterized by x-ray powder diffraction spectrum that comprises peaks at about 6 to about 6.5 degrees 2θ, about 7 to about 8 degrees 2θ, about 8 to about 9 degrees 2θ, about 11 to about 12 degrees 2θ, about 12.5 to about 13 degrees 2θ, about 15 to about 15.5 degrees 2θ, about 16 to about 17 degrees 2θ, about 19 to about 19.5 degrees 2θ, about 21 to about 21.5 degrees 2θ, and/or about 23 to about 24 degrees 2θ.

Other compounds of resiquimod can be formed in an acetate/acetic acid co-crystal of the resiquimod freebase form. Such a crystal form can be characterized by x-ray powder diffraction spectrum that comprises peaks at about 6 to about 7 degrees 2θ, about 9 to about 10.5 degrees 2θ, about 11 to about 12 degrees 2θ, about 18 to about 19 degrees 2θ, about 19 to about 20 degrees 2θ, about 20.5 to about 21 degrees 2θ, about 22 to about 23 degrees 2θ, and/or about 25 to about 26 degrees 2θ.

Sulfate salts can also be provided in crystal form C, D, E, F, G, and H. Conversion of sulfate salt form C can be interconverted to form A by storage at ambient temperature, for example, overnight. Conversion of sulfate salt form D can be interconverted to form A by heating, for example, to 100° C. Conversion of sulfate salt form E can be interconverted to form A by heating, for example, to 120° C. Conversion of sulfate salt form F can be interconverted to form A by storage at ambient temperature, for example, for two days. Conversion of sulfate salt form G can be interconverted to form A by heating, for example, to 80° C. Because interconversion of each metastable forms and solvates converted to form A, in some embodiments, form A is the thermodynamically stable form at room temperature.

Resiquimod can be formed as an anhydrate (Type A) sulfate salt. Such a crystal form can be characterized by x-ray powder diffraction spectrum that comprises peaks at about 8.5 to about 9 degrees 2θ, about 12 to about 13 degrees 2θ, about 16 to about 17 degrees 2θ, about 17.5 to about 18 degrees 2θ, about 19 to about 20.5 degrees 2θ, about 21 to about 22 degrees 2θ, about 23 to about 24 degrees 2θ, and/or about 29 to about 30 degrees 2θ.

Resiquimod can be formed as a solvate (Type B) sulfate salt. Such a crystal form can be characterized by x-ray powder diffraction spectrum that comprises peaks at about 6 to about 6.5 degrees 2θ, about 12 to about 12.5 degrees 2θ, about 16 to about 16.5 degrees 2θ, about 21 to about 22.5 degrees 2θ, and/or about 24.5 to about 25 degrees 2θ.

Resiquimod can be formed as a sulfate salt Type C. Such a crystal form can be characterized by x-ray powder diffraction spectrum that comprises peaks at about 9 to about 10 degrees 2θ, about 12 to about 12.5 degrees 2θ, about 14 to about 15 degrees 2θ, about 18 to about 19 degrees 2θ, about 19 to about 21.5 degrees 2θ, and/or about 28 to about 29 degrees 2θ.

Resiquimod can be formed as a DMAc solvate (Type D) sulfate salt. Such a crystal form can be characterized by x-ray powder diffraction spectrum that comprises peaks at about 8 to about 9 degrees 2θ, about 11 to about 11.5 degrees 2θ, about 16.5 to about 17 degrees 2θ, about 17.5 to about 18 degrees 2θ, about 21 to about 21.5 degrees 2θ, about 22.5 to about 23 degrees 2θ, and/or about 23.5 to about 24.5 degrees 2θ.

Resiquimod can be formed as a NMP solvate (Type E) sulfate salt. Such a crystal form can be characterized by x-ray powder diffraction spectrum that comprises peaks at about 8 to about 9 degrees 2θ, about 9 to about 9.5 degrees 2θ, about 11 to about 11.5 degrees 2θ, about 12 to about 13 degrees 2θ, about 16.5 to about 18 degrees 2θ, about 21 to about 21.5 degrees 2θ, about 22.5 to about 23 degrees 2θ, and/or about 23.5 to about 24 degrees 2θ.

Resiquimod can be formed as a sulfate salt Type F. Such a crystal form can be characterized by x-ray powder diffraction spectrum that comprises peaks at about 8 to about 8.5 degrees 2θ, about 10 to about 11 degrees 2θ, about 12 to about 13 degrees 2θ, about 16 to about 17 degrees 2θ, about 17 to about 18 degrees 2θ, about 20.5 to about 21.5 degrees 2θ, about 24.5 to about 25 degrees 2θ, and/or about 28.5 to about 29 degrees 2θ.

Resiquimod can be formed as a anisole solvate (Type G) sulfate salt. Such a crystal form can be characterized by x-ray powder diffraction spectrum that comprises peaks at about 8.5 to about 9 degrees 2θ, about 9.5 to about 10 degrees 2θ, about 13 to about 14 degrees 2θ, about 19 to about 19.5 degrees 2θ, and/or about 27.5 to about 28.5 degrees 2θ.

Other Formula I compounds described herein can be formed in similar salt configurations.

Crystal forms of Formula I compounds can be in Type A, Type B, Type C, Type D, Type E, Type F, Type G, and/or Type H. In some embodiments, the forms can be described as Type A: anhydrate, Type B: solvate, Type C: mestable, Type D: dimethylacetamide (DMAc) solvate, Type E: N-methyl-2-pyrolidone (NMP) solvate, Type F: mestable, Type G: anisole solvate, and Type H: acetate/acetic acid co-crystal.

Still other compounds of Formula I described herein can be formed as a sulfate salt in crystal form B. Sulfate salt in crystal form B can be a dimethyl sulfoxide (DMSO) solvate. Still other compounds of Formula I described herein can be formed as a hemi-sulfate salt in crystal form A.

In some embodiments, form A can be stable at room temperature for at least about 1 day, at least about 2 days, at least about 3 days, at least about 1 week, at least about 2 weeks, at least about 1 month, at least about 6 months, or at least about 1 year.

Still other compounds of Formula I described herein can be formed as a HCl salts, sulfate salts, phosphate salts, maleate salts, malate salts, adipate salts or combinations thereof. In some embodiments, the salts can be formed in form or type A.

In one embodiment, compounds of Formula I described herein can be formed as a mono-HCl salt in crystal form A. In one embodiment, compounds of Formula I described herein can be formed as a di-HCl salt in crystal form A. Either form of HCl salt can be formed as an anhydrate.

One embodiment includes resiquimod in the form of a HCl salt in crystal form A. The crystal form A can be characterized by x-ray powder diffraction spectrum that comprises peaks at about 6 to about 7 degrees 2θ, about 9 to about 10 degrees 2θ, about 12 to about 13 degrees 2θ, about 14 to about 16 degrees 2θ, about 18 to about 23 degrees 2θ, about 23 to about 25 degrees 2θ, about 26 to about 27.5 degrees 2θ, and/or about 26 to about 27.5 degrees 2θ.

Another embodiment includes resiquimod in the form of a HCl salt in crystal form B. The crystal form B can be characterized by x-ray powder diffraction spectrum that comprises peaks at about 6 to about 8 degrees 2θ, about 19 to about 21 degrees 2θ, about 23 to about 24.5 degrees 2θ, about 26 to about 27 degrees 2θ, and/or about 28 to about 29 degrees 2θ.

Another embodiment includes resiquimod in the form of a mono-HCl salt in crystal form A. The crystal form A can be characterized by x-ray powder diffraction spectrum that comprises peaks at about 6 to about 7 degrees 2θ, about 9 to about 10 degrees 2θ, about 13 to about 14 degrees 2θ, about 17 to about 18 degrees 2θ, about 20 to about 21 degrees 2θ, about 27 to about 28 degrees 2θ, and/or about 34 to about 35 degrees 2θ.

Another embodiment includes resiquimod in the form of a di-HCl salt in crystal form A. The crystal form A can be characterized by x-ray powder diffraction spectrum that comprises peaks at about 7 to about 8 degrees 2θ, about 8 to about 9 degrees 2θ, about 14 to about 15 degrees 2θ, about 15 to about 16 degrees 2θ, about 19 to about 20 degrees 2θ, about 25 to about 26 degrees 2θ, and/or about 26.5 to about 27.5 degrees 2θ.

In one embodiment, compounds of Formula I described herein can be formed as an anhydrate phosphate salt in crystal form A.

Another embodiment includes resiquimod in the form of a phosphate salt in crystal form A. The crystal form A can be characterized by x-ray powder diffraction spectrum that comprises peaks at about 7 to about 8 degrees 2θ, about 10 to about 14.5 degrees 2θ, about 15 to about 16 degrees 2θ, about 20 to about 21 degrees 2θ, and/or about 25 to about 26 degrees 2θ. Other embodiments include resiquimod in the form of a phosphate salt in crystal form A characterized by x-ray powder diffraction spectrum that comprises peaks at about 7 to about 8.5 degrees 2θ, about 10 to about 15.5 degrees 2θ, about 16 to about 18.5 degrees 2θ, about 19 to about 21 degrees 2θ, about 22 to about 23 degrees 2θ, about 23 to about 27 degrees 2θ, and/or about 28 to about 29 degrees 2θ.

In one embodiment, compounds of Formula I described herein can be formed as an anhydrate maleate salt in crystal form A. In another embodiment, compounds of Formula I described herein can be formed as an anhydrate mono-maleate salt in crystal form A.

Another embodiment includes resiquimod in the form of a maleate salt in crystal form A. The crystal form A can be characterized by x-ray powder diffraction spectrum that comprises peaks at about 7 to about 8 degrees 2θ, about 9 to about 10 degrees 2θ, about 10 to about 11 degrees 2θ, about 15 to about 17 degrees 2θ, about 20 to about 21 degrees 2θ, about 21 to about 22 degrees 2θ, about 27 to about 28 degrees 2θ, and/or about 30 to about 31 degrees 2θ. Other embodiments include resiquimod in the form of a maleate salt in crystal form A characterized by x-ray powder diffraction spectrum that comprises peaks at about 7 to about 8 degrees 2θ, about 9 to about 10 degrees 2θ, about 10 to about 11 degrees 2θ, about 11 to about 12 degrees 2θ, about 15 to about 16.5 degrees 2θ, about 17 to about 19 degrees 2θ, about 20 to about 21 degrees 2θ, about 21 to about 22 degrees 2θ, about 24 to about 25 degrees 2θ, about 27 to about 28 degrees 2θ, and/or about 30 to about 31 degrees 2θ.

In one embodiment, compounds of Formula I described herein can be formed as a anhydrate malate salt in crystal form A.

Another embodiment includes resiquimod in the form of a malate salt in crystal form A. The crystal form A can be characterized by x-ray powder diffraction spectrum that comprises peaks at about 6 to about 7 degrees 2θ, about 8 to about 9 degrees 2θ, about 13 to about 14 degrees 2θ, about 17 to about 18 degrees 2θ, and/or about 24 to about 25.5 degrees 2θ. Other embodiments include resiquimod in the form of a malate salt in crystal form A characterized by x-ray powder diffraction spectrum that comprises peaks at about 6 to about 7 degrees 2θ, about 8 to about 9 degrees 2θ, about 17 to about 18 degrees 2θ, about 21.5 to about 23.5 degrees 2θ, and/or about 25 to about 26 degrees 2θ.

In one embodiment, compounds of Formula I described herein can be formed as an anhydrate adipate salt in crystal form A.

Another embodiment includes resiquimod in the form of an adipate salt in crystal form A. The crystal form A can be characterized by x-ray powder diffraction spectrum that comprises peaks at about 5.5 to about 6 degrees 2θ, about 11 to about 12 degrees 2θ, about 12 to about 13 degrees 2θ, about 13 to about 14 degrees 2θ, about 14 to about 15 degrees 2θ, about 18 to about 19 degrees 2θ, about 19 to about 20 degrees 2θ, about 21 to about 22 degrees 2θ, about 22 to about 23 degrees 2θ, and/or about 25 to about 28 degrees 2θ. Other embodiments include resiquimod in the form of an adipate salt in crystal form A characterized by x-ray powder diffraction spectrum that comprises peaks at about 5 to about 6.5 degrees 2θ, about 9 to about 11 degrees 2θ, about 12 to about 13.5 degrees 2θ, about 14 to about 15.5 degrees 2θ, about 17 to about 18 degrees 2θ, about 18 to about 19 degrees 2θ, about 19.5 to about 22 degrees 2θ, about 22 to about 25 degrees 2θ, and/or about 26 to about 27.5 degrees 2θ.

Formula I compounds can also be formed as glycolate salts. In one embodiment, compounds of Formula I described herein can be formed as a glycolate salt in crystal form A.

One embodiment includes resiquimod in the form of a glycolate salt in crystal form A. The crystal form A can be characterized by x-ray powder diffraction spectrum that comprises peaks at about 9 to about 10 degrees 2θ, about 11.5 to about 12.5 degrees 2θ, about 18 to about 19 degrees 2θ, about 19.5 to about 23 degrees 2θ, about 25 to about 26.5 degrees 2θ, and/or about 32 to about 33 degrees 2θ.

Formula I compounds can also be formed as hippurate salts. In one embodiment, compounds of Formula I described herein can be formed as a hippurate salt in crystal form A.

One embodiment includes resiquimod in the form of a hippurate salt in crystal form A. The crystal form A can be characterized by x-ray powder diffraction spectrum that comprises peaks at about 5.5 to about 6.5 degrees 2θ, about 9 to about 10 degrees 2θ, about 11.5 to about 12.5 degrees 2θ, about 18.5 to about 19.5 degrees 2θ, about 21 to about 22 degrees 2θ, and/or about 25 to about 26 degrees 2θ.

Formula I compounds can also be formed as tartrate salts. In another embodiment, compounds of Formula I described herein can be formed as a tartrate salt in crystal forms A, B, and/or C.

One embodiment includes resiquimod in the form of a tartrate salt in crystal form A. The crystal form A can be characterized by x-ray powder diffraction spectrum that comprises peaks at about 6 to about 7 degrees 2θ, about 9 to about 10 degrees 2θ, about 18 to about 19 degrees 2θ, about 20 to about 22 degrees 2θ, and/or about 25 to about 26 degrees 2θ.

One embodiment includes resiquimod in the form of a tartrate salt in crystal form B. The crystal form B can be characterized by x-ray powder diffraction spectrum that comprises peaks at about 8.5 to about 9 degrees 2θ, about 11 to about 12 degrees 2θ, about 13 to about 14 degrees 2θ, about 14 to about 15 degrees 2θ, about 16 to about 17 degrees 2θ, and/or about 23 to about 24.5 degrees 2θ.

One embodiment includes resiquimod in the form of a tartrate salt in crystal form C. The crystal form C can be characterized by x-ray powder diffraction spectrum that comprises peaks at about 7 to about 8 degrees 2θ, about 10 to about 11.5 degrees 2θ, and/or about 20 to about 21 degrees 2θ.

Formula I compounds can also be formed as fumarate salts. In another embodiment, compounds of Formula I described herein can be formed as a fumarate salt in crystal forms A, B, and/or C.

One embodiment includes resiquimod in the form of a fumarate salt in crystal form A. The crystal form A can be characterized by x-ray powder diffraction spectrum that comprises peaks at about 6 to about 7 degrees 2θ, about 7 to about 8 degrees 2θ, about 9 to about 10.5 degrees 2θ, about 12 to about 14 degrees 2θ, about 18 to about 19 degrees 2θ, about 19 to about 20 degrees 2θ, about 23 to about 24.5 degrees 2θ, and/or about 25 to about 26 degrees 2θ.

One embodiment includes resiquimod in the form of a fumarate salt in crystal form B. The crystal form B can be characterized by x-ray powder diffraction spectrum that comprises peaks at about 9.5 to about 10.5 degrees 2θ, about 12 to about 13 degrees 2θ, about 15 to about 16 degrees 2θ, about 17 to about 18 degrees 2θ, about 19 to about 21 degrees 2θ, and/or about 25 to about 26 degrees 2θ.

One embodiment includes resiquimod in the form of a fumarate salt in crystal form C. The crystal form C can be characterized by x-ray powder diffraction spectrum that comprises peaks at about 6 to about 7 degrees 2θ, about 9 to about 10 degrees 2θ, about 11 to about 12 degrees 2θ, about 15 to about 16 degrees 2θ, about 21 to about 22 degrees 2θ, about 26 to about 27 degrees 2θ, and/or about 27.5 to about 28.5 degrees 2θ.

Formula I compounds can also be formed as citrate salts. In another embodiment, compounds of Formula I described herein can be formed as a citrate salt in crystal forms A and/or B.

One embodiment includes resiquimod in the form of a citrate salt in crystal form A. The crystal form A can be characterized by x-ray powder diffraction spectrum that comprises peaks at about 5 to about 6.5 degrees 2θ, about 11 to about 12 degrees 2θ, about 14.5 to about 15.5 degrees 2θ, about 17 to about 18.5 degrees 2θ, about 19 to about 20.5 degrees 2θ, about 21 to about 22 degrees 2θ, about 26 to about 27 degrees 2θ, and/or about 27.5 to about 28.5 degrees 2θ.

One embodiment includes resiquimod in the form of a citrate salt in crystal form B. The crystal form B can be characterized by x-ray powder diffraction spectrum that comprises peaks at about 5.5 to about 6.5 degrees 2θ, about 8 to about 9 degrees 2θ, about 9.5 to about 10.5 degrees 2θ, about 11 to about 12.5 degrees 2θ, about 18 to about 19.5 degrees 2θ, and/or about 21 to about 24.5 degrees 2θ.

Formula I compounds can also be formed as lactate salts. In another embodiment, compounds of Formula I described herein can be formed as a lactate salt in crystal forms A and/or B.

One embodiment includes resiquimod in the form of a lactate salt in crystal form A. The crystal form A can be characterized by x-ray powder diffraction spectrum that comprises peaks at about 5 to about 8 degrees 2θ, about 8 to about 9 degrees 2θ, about 10 to about 11 degrees 2θ, about 12.5 to about 13.5 degrees 2θ, about 18.5 to about 19.5 degrees 2θ, and/or about 22 to about 23 degrees 2θ.

One embodiment includes resiquimod in the form of a lactate salt in crystal form B. The crystal form B can be characterized by x-ray powder diffraction spectrum that comprises peaks at about 5 to about 6 degrees 2θ, about 6.5 to about 8 degrees 2θ, about 9 to about 10.5 degrees 2θ, and/or about 13.5 to about 14.5 degrees 2θ.

Formula I compounds can also be formed as succinate salts. In another embodiment, compounds of Formula I described herein can be formed as a succinate salt in crystal forms A and/or B.

One embodiment includes resiquimod in the form of a succinate salt in crystal form A. The crystal form A can be characterized by x-ray powder diffraction spectrum that comprises peaks at about 5 to about 8 degrees 2θ, about 9 to about 11.5 degrees 2θ, about 18 to about 19 degrees 2θ, about 23 to about 24 degrees 2θ, and/or about 24.5 to about 25.5 degrees 2θ.

One embodiment includes resiquimod in the form of a succinate salt in crystal form B. The crystal form B can be characterized by x-ray powder diffraction spectrum that comprises peaks at about 8 to about 9 degrees 2θ, about 10 to about 11 degrees 2θ, about 12 to about 13 degrees 2θ, about 14 to about 15 degrees 2θ, about 16 to about 17 degrees 2θ, about 17 to about 18 degrees 2θ, and/or about 23.5 to about 24.5 degrees 2θ.

Formula I compounds can also be formed as tosylate salts. In another embodiment, compounds of Formula I described herein can be formed as a tosylate salt in crystal forms A and/or B.

One embodiment includes resiquimod in the form of a tosylate salt in crystal form A. The crystal form A can be characterized by x-ray powder diffraction spectrum that comprises peaks at about 4 to about 5 degrees 2θ, about 9 to about 10 degrees 2θ, about 16 to about 17 degrees 2θ, about 19 to about 21 degrees 2θ, and/or about 24 to about 28 degrees 2θ.

One embodiment includes resiquimod in the form of a tosylate salt in crystal form B. The crystal form B can be characterized by x-ray powder diffraction spectrum that comprises peaks at about 5 to about 6 degrees 2θ, about 7 to about 9 degrees 2θ, about 9.5 to about 11.5 degrees 2θ, about 12 to about 14 degrees 2θ, about 15 to about 19 degrees 2θ, about 19 to about 20.5 degrees 2θ, and/or about 23 to about 24 degrees 2θ.

Formula I compounds can also be formed as mesylate salts. In one embodiment, compounds of Formula I described herein can be formed as a mesylate salt in crystal form A.

One embodiment includes resiquimod in the form of a mesylate salt in crystal form A. The crystal form A can be characterized by x-ray powder diffraction spectrum that comprises peaks at about 8 to about 9 degrees 2θ, about 12 to about 13 degrees 2θ, about 14 to about 15 degrees 2θ, about 16 to about 17 degrees 2θ, about 18 to about 19.5 degrees 2θ, about 21 to about 22 degrees 2θ, and/or about 25.5 to about 26.5 degrees 2θ.

Formula I compounds can also be formed as oxalate salts. In another embodiment, compounds of Formula I described herein can be formed as an oxalate salt in crystal forms A and/or B.

One embodiment includes resiquimod in the form of an oxalate salt in crystal form A. The crystal form A can be characterized by x-ray powder diffraction spectrum that comprises peaks at about 9 to about 10 degrees 2θ, about 14 to about 15 degrees 2θ, about 17 to about 18 degrees 2θ, about 18.5 to about 20 degrees 2θ, about 21 to about 22 degrees 2θ, about 23 to about 25.5 degrees 2θ, and/or about 30 to about 31 degrees 2θ.

One embodiment includes resiquimod in the form of an oxalate salt in crystal form B. The crystal form B can be characterized by x-ray powder diffraction spectrum that comprises peaks at about 5 to about 6 degrees 2θ, about 9.5 to about 10 degrees 2θ, about 10.5 to about 11.5 degrees 2θ, about 13 to about 13.5 degrees 2θ, about 14.5 to about 15.5 degrees 2θ, about 16.5 to about 18 degrees 2θ, about 22 to about 24.5 degrees 2θ, and/or about 27 to about 28 degrees 2θ.

Formula I compounds can also be formed as gentisate salts. In another embodiment, compounds of Formula I described herein can be formed as a gentisate salt in crystal forms A and/or B.

One embodiment includes resiquimod in the form of a gentisate salt in crystal form A. The crystal form A can be characterized by x-ray powder diffraction spectrum that comprises peaks at about 6 to about 7.5 degrees 2θ, about 8 to about 9 degrees 2θ, about 10 to about 11 degrees 2θ, about 14 to about 15 degrees 2θ, about 16 to about 17 degrees 2θ, about 18 to about 19 degrees 2θ, about 20 to about 21.5 degrees 2θ, and/or about 22.5 to about 23.5 degrees 2θ.

One embodiment includes resiquimod in the form of a gentisate salt in crystal form B. The crystal form B can be characterized by x-ray powder diffraction spectrum that comprises peaks at about 6 to about 7 degrees 2θ, about 10 to about 10.5 degrees 2θ, about 12 to about 13 degrees 2θ, about 20 to about 21 degrees 2θ, about 24 to about 24.5 degrees 2θ, and/or about 26 to about 26.5 degrees 2θ.

Formula I compounds can also be formed as benzoate salts. In another embodiment, compounds of Formula I described herein can be formed as a benzoate salt in crystal forms A and/or B.

One embodiment includes resiquimod in the form of a benzoate salt in crystal form A. The crystal form A can be characterized by x-ray powder diffraction spectrum that comprises peaks at about 7 to about 9 degrees 2θ, about 10 to about 11.5 degrees 2θ, about 12 to about 12.5 degrees 2θ, about 14 to about 16.5 degrees 2θ, about 19 to about 22 degrees 2θ, about 23.5 to about 24.5 degrees 2θ, about 28.5 to about 29 degrees 2θ, and/or about 29 to about 30 degrees 2θ.

One embodiment includes resiquimod in the form of a benzoate salt in crystal form B. The crystal form B can be characterized by x-ray powder diffraction spectrum that comprises peaks at about 7 to about 8.5 degrees 2θ, about 12 to about 14 degrees 2θ, about 18 to about 19 degrees 2θ, about 19.5 to about 20.5 degrees 2θ, about 21 to about 23 degrees 2θ, about 24 to about 25 degrees 2θ, and/or about 26 to about 27 degrees 2θ.

Formula I compounds can also be formed as nitrate salts. In another embodiment, compounds of Formula I described herein can be formed as a nitrate salt in crystal forms A and/or B.

One embodiment includes resiquimod in the form of a nitrate salt in crystal form A. The crystal form A can be characterized by x-ray powder diffraction spectrum that comprises peaks at about 9 to about 9.5 degrees 2θ, about 10 to about 10.5 degrees 2θ, about 11.5 to about 12.5 degrees 2θ, about 14 to about 15 degrees 2θ, about 16 to about 17.5 degrees 2θ, about 20 to about 22.5 degrees 2θ, about 25 to about 26 degrees 2θ, and/or about 28.5 to about 29.5 degrees 2θ.

One embodiment includes resiquimod in the form of a nitrate salt in crystal form B. The crystal form B can be characterized by x-ray powder diffraction spectrum that comprises peaks at about 9 to about 10 degrees 2θ, about 12.5 to about 13 degrees 2θ, about 14 to about 16 degrees 2θ, about 19.5 to about 21 degrees 2θ, about 25 to about 26 degrees 2θ, and/or about 26 to about 27 degrees 2θ.

In some embodiments, a monosulfate salt in crystal form A can convert to a hemi-sulfate at water activity of 0.8. Further, a monosulfate salt in crystal form A can demonstrate good physicochemical stability at 80° C. for 24 hours or more.

In some embodiments, crystal forms of compounds described herein have an XRPD pattern of FIG. 1, FIG. 4, FIG. 7, FIG. 10, FIG. 13, FIG. 16, FIG. 19, FIG. 48, FIG. 50, FIG. 54, FIG. 59, FIG. 61, FIG. 63, FIG. 65, FIG. 67, FIG. 69, FIG. 71, FIG. 73, FIG. 75, FIG. 77, FIG. 78, FIG. 79, FIG. 83, FIG. 84, FIG. 85, FIG. 89, FIG. 90, FIG. 93, FIG. 94, FIG. 97, FIG. 98, FIG. 101, FIG. 102, FIG. 105, FIG. 107, FIG. 108, FIG. 111, FIG. 112, FIG. 115, FIG. 116, FIG. 119, FIG. 120, FIG. 124, FIG. 126, FIG. 127, FIG. 128, FIG. 132, FIG. 134, FIG. 136, or FIG. 138.

In some embodiments, crystal forms of Formula I compounds may be slightly hygroscopic. In other embodiments, crystal forms of Formula I compounds may be non-hygroscopic. These crystal forms may also exhibit no form change after a Dynamic Vapor Sorption (DVS) test.

In other embodiments, when compared to a freebase form of a Formula I compound, crystal forms show improved or comparable solubility in water and bio-relevant media at room temperature.

Further, the crystal forms can have physical and chemical stability when compared to a Formula I compound freebase. In some embodiments, no form change and/or purity decrease may be exhibited when compared to freebase form, at 25° C./60% RH and 40° C./75% RH. In some embodiments, this absence of form change and/or purity decrease may remain for at least about 1 week, at least about 2 weeks, at least about 1 month, at least about 6 months, or at least about 1 year.

Another aspect provides improved aqueous solubility of Formula I compound crystal forms compared with the parent compound or a freebase form thereof. Another aspect provides improved aqueous solubility of resiquimod crystal forms compared with the parent compound or a freebase form thereof.

Another aspect provides modified oral bioavailability values of Formula I compound crystal forms compared with the orally delivered parent compound or a freebase form thereof. Another aspect provides modified oral bioavailability values of resiquimod crystal forms compared with the orally delivered parent compound or a freebase form thereof.

The techniques and approaches set forth in the present disclosure can further be used by the person of ordinary skill in the art to prepare variants thereof; the variants are considered to be part of the present disclosure.

The presently described crystal forms of Formula I compounds can be used to treat a disease or condition. In some embodiments, the disease or condition is a cancer. Cancers can include breast cancer, head and neck cancer, ovarian cancer, uterine cancer, skin cancer, brain cancer, bladder cancer, thyroid cancer, liver cancer, pancreatic cancer, lung cancer, ocular cancer, throat cancer, esophageal cancer, stomach cancer, intestinal cancer, rectal cancer, testicular cancer, ovarian cancer, vaginal cancer, bone cancer, blood cancer, prostate cancer, and the like.

The presently described crystal forms of Formula I compounds can be used to treat a tumor in a subject in need thereof. In some embodiments, the tumor is a carcinoma, a sarcoma, a blastomas, or a combination thereof.

A carcinoma can include, without limitation, an adrenal gland tumor, a bone tumor, a brain tumor, a breast tumor, a bronchi tumor, a colon tumor, a gallbladder tumor, a kidney tumor, a larynx tumor, a liver tumor, a lung tumor, a neural tumor, a pancreatic tumor, a prostate tumor, a parathyroid tumor, a skin tumor, a stomach tumor, and a thyroid tumor. In other aspects of this embodiment, a carcinoma includes, without limitation, an adenocarcinoma, an adenosquamous carcinoma, an anaplastic carcinoma, a large cell carcinoma, a small cell carcinoma, and a squamous cell carcinoma. In other aspects of this embodiment, a carcinoma includes, without limitation, a small cell carcinoma, a combined small cell carcinoma, a verrucous carcinoma, a squamous cell carcinoma, a basal cell carcinoma, a transitional cell carcinoma, an inverted papilloma, a linitis plastica, a familial adenomatous polyposis, an insulinoma, a glucagonoma, a gastrinoma, a VIPoma, a somatostatinoma, a cholangiocarcinoma, a Klatskin tumor, a hepatocellular adenoma, a hepatocellular carcinoma, a renal cell carcinoma, a endometrioid tumor, a renal oncocytoma, a prolactinoma, a multiple endocrine neoplasia, an adrenocortical adenoma, an adrenocortical carcinoma, a Hurthle cell, a neuroendocrine tumor, an adenoid cystic carcinoma, an oncocytoma, a clear cell adenocarcinoma, an apudoma, a cylindroma, a papillary hidradenoma, a hidrocystoma, a syringoma, a syringocystadenoma papilliferum, a cystadenoma, a cystadenocarcinoma, signet ring cell carcinoma, a mucinous cystadenoma, a mucinous cystadenocarcinoma, a mucoepidermoid carcinoma, an ovarian serous cystadenoma, a pancreatic serous cystadenoma, a serous cystadenocarcinoma, a papillary serous cystadenocarcinoma, a mammary ductal carcinoma, a pancreatic ductal carcinoma, a comedocarcinoma, a Paget's disease of the breast, an extramammary Paget's disease, a lobular carcinoma in situ, an invasive lobular carcinoma, a medullary carcinoma of the breast, a medullary thyroid cancer, an acinic cell carcinoma, a Warthin's tumor, or a thymoma.

Sarcomas can include, without limitation, a soft tissue sarcoma, a connective tissue sarcoma, a lipomatous sarcoma, a myomatous sarcoma, a complex mixed and stromal sarcoma, and a mesothelial. In aspects of this embodiment, a non-hematologic sarcoma includes, without limitation, an adenomatoid tumor, an adenomyoma, an aggressive infantile fibromatosis, an alveolar rhabdomyosarcoma, an angiolipoleiomyoma, an angiomyolipoma, an angioleiomyoma, an angiomyxoma, an angiosarcoma, an aponeurotic fibroma, an Askin's tumor, an atypical fibroxanthoma, a benign lipoblastomatosis, a Brenner tumor, a carcinosarcoma, a chondroid lipoma, a chondrosarcoma, a clear-cell sarcoma, a clear-cell sarcoma of the kidney, a collagenous fibroma, a cystosarcoma phyllodes, a dermatofibrosarcoma, a dermatofibrosarcoma protuberans (DFSP), a desmoplastic fibroma, a desmoplastic small round cell tumor, a diffuse infantile fibromatosis, an Ewing's/PNET sarcoma, a familial myxovascular fibroma, a fibroadenoma, a fibroma of tendon sheath, a fibromatosis colli, a fibrous histiocytoma, a fibrosarcoma, a gastrointestinal stromal tumor (GIST), a genital leiomyoma, a hemangioendothelioma, a hepatoblastoma, a hibernoma, a histiocytoma, an infantile digital fibromatosis, an intradermal spindle cell lipoma, a juvenile hyaline fibromatosis, a Kaposi's sarcoma, a leiomyosarcoma, a liposarcoma, a mesoblastic nephroma, a mesothelioma, a mixed Müllerian tumor, a multiple cutaneous leiomyoma, a multiple cutaneous and uterine leiomyomatosis syndrome, a myelolipoma, a myosarcoma, a myxoid liposarcoma, a myxosarcoma, a neural fibrolipoma, a neurofibrosarcoma, an oral submucous fibrosis, an ossifying fibromyxoid tumor, an osteosarcoma, a pancreatoblastoma, a phyllodes tumor, a plantar fibromatosis, a pleomorphic adenoma, a pleomorphic fibroma, a pleomorphic lipoma, a rhabdomyosarcoma, a sarcoma botryoides, a schwannoma sarcoma, a solitary cutaneous leiomyoma, a solitary fibrous tumor, a spindle cell lipoma, a stromal tumor of undetermined malignant potential (STUMP), a synovial sarcoma, a vascular sarcoma, or a Wilms' tumor.

Blastomas can include, without limitation, a chondroblastoma, a hepatoblastoma, a medulloblastoma, a nephroblastoma, a neuroblastoma, a pancreatoblastoma, a pleuropulmonary blastoma, a retinoblastoma, or a lioblastoma multiforme.

Resiquimod and related Formula I compounds described herein can be agonists of TLR7/TLR8. Studies have found that many solid tumors, such as breast cancer, head and neck cancer, or ovarian cancer, have pDC's invasion and factors secreted by tumor cells that inhibit DC maturation. These immature DC cells did not play a role in promoting anti-tumor immunity. By contrast, DCs within the tumor microenvironment promote tumor growth by inhibiting anti-tumor immunity and by promoting angiogenesis. There is evidence that Toll-like receptor 7 agonist imiquimod, and Toll-like receptor 9 agonist CpG drugs can stimulate pDC within the tumor microenvironment to inhibit tumor development.

Natural killer (NK) cells are a type of cytotoxic lymphocyte that constitutes a major component of the immune system. NK cells are a subset of peripheral blood lymphocytes defined by the expression of CD56 or CD 16 and the absence of the T cell receptor (CD3). They recognize and kill transformed cell lines without priming in an MHC-unrestricted fashion. NK cells play a major role in the rejection of tumors and cells infected by viruses. The process by which an NK cell recognizes a target cell and delivers a sufficient signal to trigger target lysis is determined by an array of inhibitory and activating receptors on the cell surface. NK discrimination of self from altered self involves inhibitory receptor recognition of MHC-I molecules and non-MHC ligands like CD48 and Clr-1b. NK recognition of infected or damaged cells (altered self) is coordinated through stress induced ligands (e.g., MICA, MICB, Rae1, H60, Mult1) or virally encoded ligands (e.g., m157, hemagluttinin) recognized by various activating receptors, including NKG2D, Ly49H and NKp46/Ncr1.

NK cells represent the predominant lymphoid cell in the peripheral blood for many months after allogeneic or autologous stem cell transplant and they have a primary role in immunity to pathogens during this period.

Human NK cells mediate the lysis of tumor cells and virus-infected cells via natural cytotoxicity and antibody-dependent cellular cytotoxicity (ADCC).

Human NK cells are controlled by positive and negative cytolytic signals. Negative (inhibitory) signals are transduced by C-lectin domain containing receptors CD94/NKG2A and by some Killer Immunoglobulin-like Receptors (KIRs). The regulation of NK lysis by inhibitory signals is known as the "missing self" hypothesis in which specific HLA-class I alleles expressed on the target cell surface ligate inhibitory receptors on NK cells. The down-regulation of HLA molecules on tumor cells and some virally infected cells (e.g. CMV) lowers this inhibition below a target threshold and the target cells may become susceptible to NK cell-mediated lysis if the target cells also carry NK-priming and activating molecules. TLR7, TLR8 or TLR9 agonists can activate both mDC and pDCs to produce type I IFNs and express costimulatory molecules such as GITR-ligand, which subsequently activate NK cells to produce IFN-g and potently promote NK cell killing function.

Inhibitory receptors fall into two groups, those of the Ig-superfamily called Killer Immunoglobulin-like Receptors (KIRs) and those of the lectin family, the NKG2, which form dimers with CD94 at the cell surface. KIRs have a 2- or 3-domain extracellular structure and bind to HLA-A, -B or -C. The NKG2/CD94 complexes ligate HLA-E.

Inhibitory KIRs have up to 4 intracellular domains which contain ITIMs and the best characterized are KIR2DL1, KIR2DL2 and KIR2DL3 which are known to bind HLA-C molecules. KIR2DL2 and KIR2DL3 bind the group 1 HLA-C alleles while KIR2DL1 binds to group 2 alleles. Certain leukemia/lymphoma cells express both group 1 and 2 HLA-C alleles and are known to be resistant to NK-mediated cell lysis.

With regards to positive activating signals, ADCC is thought to be mediated via CD 16, and a number of triggering receptors responsible for natural cytotoxicity have been identified, including CD2, CD38, CD69, NKRP-I, CD40, B7-2, NK-TR, NKp46, NKp30 and NKp44. In addition, several KIR molecules with short intracytoplasmic tails are also stimulatory. These KIRs (KIR2DS1, KIR2DS2 and KIR2DS4) are known to bind to HLA-C; their extracellular domains being identical to their related inhibitory KIRs. The activatory KIRs lack the ITIMs and instead associate with DAP 12 leading to NK cell activation. The mechanism of control of expression of inhibitory versus activatory KIRs remains unknown.

Several reports have described the expression of TLRs in mouse or human cancer or cancer cell lines. For example, TLR1 to TLR6 are expressed by colon, lung, prostate, and melanoma mouse tumor cell lines, TLR3 is expressed in human breast cancer cells, hepatocarcinoma and gastric carcinoma cells express TLR2 and TLR4, and TLR9 and TLR4 are expressed by human lung cancer cells. TLR7 and TLR8 are found in tumor cells of human lung cancer.

TLR are a family of proteins that sense a microbial product and/or initiates an adaptive immune response. TLRs activate a dendritic cell (DC). TLRs are conserved membrane spanning molecules containing an ectodomain of leucine-rich repeats, a transmembrane domain and an intracellular TIR (Toll/interleukin receptor) domain. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity.

TLR7 and TLR8 are phylogenetically and structurally related. TLR7 is selectively expressed by human pDCs and B cells. TLR8 is predominantly expressed mDCs, monocytes, macrophages and myeloid suppressor cells. TLR7-specific agonists activate plasmacytoid DCs (pDCs) to produce large amounts of type 1 IFNs and expressing high levels of costimulatory molecules that promote activation of T cells, NK cells, B cells and mDCs. TLR8-specific agonists activate myeloid DCs, monocytes, macrophages or myeloid-derived suppressor cells to produce large amounts of type 1 IFN, IL-12 and IL-23, and express high levels of MHC class I, MHC class II and costimulatory molecules that promote the activation of antigen specific CD4 and CD8+ T cells.

Pharmaceutical compositions including the crystal forms of the herein described compounds can be administered to an animal, such as a mammal. In some embodiments, the mammal can be a human, a cat, a dog, a horse, a pig, a cow, a whale, or the like.

Pharmaceutical compositions may be prepared by combining a therapeutically effective amount of at least one crystal form of a herein described compound with conventional acceptable pharmaceutical excipients, and by preparation of unit dosage forms suitable for therapeutic use. As used herein, the term "pharmaceutical composition" and refers to a therapeutically effective concentration of an active compound, such as, e.g., any of the crystal forms of herein described compounds. Preferably, the pharmaceutical composition does not produce an adverse, allergic, or other untoward or unwanted reaction when administered. A pharmaceutical composition disclosed herein can be useful for medical and veterinary applications. A pharmaceutical composition may be administered alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

A pharmaceutical composition can be a liquid formulation, semi-solid formulation, or a solid formulation. A formulation disclosed herein can be produced in a manner to form one phase, such as, e.g., an oil or a solid. Alternatively, a formulation disclosed herein can be produced in a manner to form two phase, such as, e.g., an emulsion. A pharmaceutical composition disclosed herein intended for such administration may be prepared according to any method known to the art for the manufacture of pharmaceutical compositions.

Liquid formulations suitable for injection or topical (e.g., ocular) delivery may comprise physiologically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethyleneglycol (PEG), glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

Semi-solid formulations suitable for topical administration include, without limitation, ointments, creams, salves, and gels. In such solid formulations, the active compound may be admixed with at least one inert customary excipient (or carrier) such as, a lipid and/or polyethylene glycol.

Solid formulations suitable for oral administration include capsules, tablets, pills, powders and granules. In such solid formulations, the active compound may be admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

In liquid and semi-solid formulations, a concentration of crystal forms of the herein described compounds may be between about 50 mg/mL to about 1,000 mg/mL. In aspects of this embodiment, a therapeutically effective amount of a crystal form of the herein described compounds may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

In semi-solid and solid formulations, an amount of a crystal form of the herein described compounds may be between about 0.01% to about 45% by weight. In aspects of this embodiment, an amount of a crystal form of the herein described compounds may be from, e.g., about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, or about 25% to about 30% by weight.

A pharmaceutical composition disclosed herein can optionally include a pharmaceutically acceptable carrier that facilitates processing of an active compound into pharmaceutically acceptable compositions. Such a carrier generally is mixed with an active compound or permitted to dilute or enclose the active compound and can be a solid, semi-solid, or liquid agent. Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole, and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., sodium chlorite and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor.

Method of treating a disease or condition, such as a cancer, include administering a Formula I new crystal form such as in a pharmaceutical form. Administration can be once daily, twice daily, three times daily four times daily or more. In other embodiments, administration can be one every other day, once every three days, every four day, every five days, every six days, one a week, once every other week, once every three weeks, once a month, once every other month, every six months, once a year, or the like.

EXAMPLES

Example 1

1. Summary

Salt screening for resiquimod freebase was conducted to identify salt candidates with suitable physicochemical properties. Additionally, polymorph screening was carried out to identify leading crystal forms of the salt candidate.

Initial salt screening was performed under 100 conditions using 19 acids (two molar ratios of HCl) and five solvent systems. A total of 32 crystalline hits were isolated and characterized by X-ray powder diffraction (XRPD), thermogravimetric analysis (TGA), differential scanning calorimetry (DSC), with the stoichiometry determined using proton nuclear magnetic resonance ($^1$H NMR) or HPLC/IC. Considering the safety class of acids used, number of polymorphs observed, and physicochemical properties, seven crystalline salts namely mono-HCl salt, di-HCl salt, sulfate, phosphate, maleate, malate, and adipate were selected as leading salts for further evaluation.

All the seven salt leads were re-prepared to hundreds of milligrams (except di-HCl salt was provided) and further evaluated on hygroscopicity, kinetic solubility, and solid-state stability. As results show, 1) all salt leads were slightly hygroscopic with no form change after DVS test except HCl salts, 2) compared with freebase Type A, all salt leads show improved or comparable solubility in water and bio-relevant media (SGF, FaSSIF, and FeSSIF) at room temperature (RT, 20±3° C.) except maleate, 3) no form change and decrease of HPLC purity were detected for salt leads and freebase Type A under 25° C./60% RH and 40° C./75% RH for one week except di-HCl salt, suggesting good physical and chemical stability.

Based on the characterization and evaluation results, sulfate was selected as a salt candidate and re-prepared on 6-g scale for polymorphism investigation. Using sulfate Type A as starting material, a polymorph screening was performed under 100 conditions. A total of three crystal forms were obtained, including one anhydrate (Type A), one DMSO solvate (Type B), and one hemi-sulfate. Thus, sulfate Type A was selected as the leading form of mono-sulfate. Disproportionation risk and thermo-stability were investigated on sulfate Type A, and the result shows, 1) sulfate Type A converted to hemi-sulfate at water activity of 0.8, indicating the disproportionation risk at high relative humidity, 2) sulfate Type A shows good physicochemical stability at 80° C. for 24 hours.

2. Salt Screening 2.1 Experiment Summary

According to the pKa value of 7.2 determined on Sirius T3 and approximate solubility of freebase (807919-05-A) at RT, nineteen salt formers and five solvent systems were used for the screening. Freebase was dispersed in selected solvent with a glass vial and corresponding salt former was added with a molar charge ratio of 1:1 (for HCl/freebase, two ratios of both 1:1 and 2:1 were used). The mixtures of freebase and acid were stirred at RT for 2.5 days. Clear solutions obtained were slurried at 5° C. overnight to induce precipitation. If the samples were still clear, they would be subjected to evaporation to dryness at RT, in order to maximize the chance of identifying as many crystalline hits as possible. Resulted solids were isolated and analyzed by XRPD.

As summarized in Table 2-1, a total of 32 crystalline hits were obtained and characterized by TGA and DSC, with the stoichiometry determined by $^1$H NMR or HPLC/IC. The characterization data were summarized in Table 2-2, and detailed information was provided in Section 5.4.

TABLE 2-1

Summary of salt screening experiments

| | | Solvent | | | | |
|---|---|---|---|---|---|---|
| | Former | Acetone A | EtOH B | EtOAc C | THF D | MeOH/H$_2$O (v/v, 9:1) E |
| 0 | blank | freebase Type A | freebase Type A* | freebase Type A | freebase Type A* | freebase Type A* |
| 1 | HCl (1:1) | HCl salt Type A | HCl salt Type A + FB Type A* | HCl salt Type A | HCl salt Type A | HCl salt Type A + FB Type A* |
| 2 | HCl (2:1) | HCl salt Type A | HCl salt Type A | HCl salt Type B | HCl salt Type A | HCl salt Type A* |
| 3 | H$_2$SO$_4$ | sulfate Type A | gel* | sulfate Type A | sulfate Type A | sulfate Type A* |
| 4 | maleic acid | maleate Type A | maleate Type A | maleate Type A | maleate Type A | maleate Type A |
| 5 | H$_3$PO$_4$ | phosphate Type A | phosphate Type A | phosphate Type A | phosphate Type A | phosphate Type A |
| 6 | L-tartaric acid | tartrate Type A | tartrate Type A | tartrate Type C | tartrate Type A | tartrate Type B |
| 7 | fumaric acid | fumarate Type A | fumarate Type A | fumarate Type C | fumarate Type A | fumarate Type B |
| 8 | citric acid | citrate Type A | citrate Type B | citrate Type A | citrate Type A | gel* |
| 9 | glycolic acid | glycolate Type A | glycolate Type A | glycolate Type A | glycolate Type A | glycolate Type A |
| 10 | L-malic acid | malate Type A | malate Type A | malate Type A | malate Type A | malate Type A |
| 11 | hippuric acid | hippurate Type A | hippurate Type A | hippurate Type A | hippurate Type A | hippurate Type A |
| 12 | L-lactic acid | lactate Type B | lactate Type A* | lactate Type A | lactate Type A** | lactate Type A* |
| 13 | succinic acid | succinate Type A | succinate Type A | succinate Type A | succinate Type A | succinate Type B |
| 14 | adipic acid | adipate Type A | adipate Type A | adipate Type A | adipate Type A | adipate Type A |
| 15 | p-toluenesulfonic acid | tosylate Type A | tosylate Type A | tosylate Type A | tosylate Type B | tosylate Type A* |
| 16 | methanesulfonic acid | mesylate Type A | mesylate Type A* | mesylate Type A | mesylate Type A | mesylate Type A + FB Type A* |
| 17 | oxalic acid | oxalate Type A | oxalate Type A | oxalate Type A | oxalate Type B | oxalate Type A* |
| 18 | gentisic acid | gentisate Type A | gentisate Type A | gentisate Type B | gentisate Type A | gentisate Type B |
| 19 | benzoic acid | benzoate Type A | benzoate Type A | benzoate Type A | benzoate Type A | benzoate Type B |
| 20 | HNO$_3$ | nitrate Type A | nitrate Type B | nitrate Type A | nitrate Type A | nitrate Type B + FB Type A* |

**Solids were generated via slurry at 5° C. overnight. FB: freebase.
*Samples were obtained via evaporation to dryness at RT.
Blank experiments were set up to detect any possible change of freebase.

TABLE 2-2

Characterization summary of crystalline hits

| Hit | | Acid | | | Weight Loss (TGA, %) | Endotherm (DSC, ° C., peak) | Molar ratio (acid/base) |
|---|---|---|---|---|---|---|---|
| | | Safety Class | Mw | Sample ID | | | |
| HCl Salt | Type A | I | 36.46 | 807919-07-D1 | 3.5 | 250.0, 266.6 | 1.00 |
| | Type B | | | 807919-07-C2 | 10.8 | 103.5, 110.2, 181.1, 249.8, 266.0 | 1.73 |
| Sulfate | Type A | I | 98.08 | 807919-07-A3 | 0.4 | 213.1 | 0.98 |
| Phosphate | Type A | I | 98.00 | 807919-07-E5 | 0.5 | 260.3 | 0.92 |
| Glycolate | Type A | I | 76.05 | 807919-07-B9 | 0.9 | 206.8 | 1.04 |
| Maleate | Type A | I | 116.08 | 807919-07-D4 | 1.4 | 226.7 | 0.98 |
| Malate | Type A | I | 134.09 | 807919-07-B10 | 0.8 | 195.0 | 1.04 |
| Adipate | Type A | I | 146.14 | 807919-07-B14 | 1.0 | 218.9 | 0.52 |
| Hippurate | Type A | I | 179.17 | 807919-07-B11 | 2.8 | 214.8 | 1.00 |
| Tartrate | Type A | I | 150.09 | 807919-07-A6 | 2.1 | 168.1 | 1.02 |
| | Type B | | | 807919-07-E6 | 3.2 | 144.9, 245.8 | 0.52 |
| | Type C | | | 807919-07-B6 | 2.1 | 72.2, 245.0 | 0.52 |
| Fumarate | Type A | I | 116.08 | 807919-07-A7 | 0.8 | 229.9, 238.0, 252.9 | 0.81 |
| | Type B | | | 807919-07-E7 | 4.2 | 109.6, 226.8, 237.9, 255.9 | 0.61 |
| | Type C | | | 807919-07-C7 | 0.4 | 156.3, 237.8, 248.8 | 1.03 |
| Citrate | Type A | I | 192.13 | 807919-07-A8 | 0.3 | 165.4 | 1.02 |
| | Type B | | | 807919-07-B8 | 2.3 | 197.7 | 0.53 |
| Lactate | Type A | I | 90.08 | 807919-07-C12 | 4.9 | 85.4, 159.5, 169.4 | 1.07 |
| | Type B | | | 807919-07-A12 | 0.6 | 142.9, 160.2 | 0.96 |
| Succinate | Type A | I | 118.09 | 807919-07-C13 | 2.0 | 175.8 | 1.00 |
| | Type B | | | 807919-07-E13 | 4.6 | 103.5, 188.4, 209.6 | 0.52 |
| Tosylate | Type A | II | 172.21 | 807919-07-B15 | 1.3 | 202.5 | 0.89 |
| | Type B | | | 807919-07-D15 | 5.3 | 61.1, 185.4, 189.9, 201.9 | 0.92 |
| Mesylate | Type A | II | 96.10 | 807919-07-A16 | 1.5 | 207.6 | 0.93 |
| Oxalate | Type A | II | 90.04 | 807919-07-B17 | 0.7 | 228.7 | 0.92 |
| | Type B | | | 807919-07-D17 | 1.8 | 190.5, 218.2 | 1.02 |
| Gentisate | Type A | II | 154.12 | 807919-07-A18 | 4.9 | 211.5 | 0.99 |
| | Type B | | | 807919-07-E18 | 1.7 | 210.7 | 1.00 |
| Benzoate | Type A | II | 122.12 | 807919-07-A19 | 0.6 | 200.1 | 0.98 |
| | Type B | | | 807919-07-E19 | 4.0 | 102.5, 200.4 | 0.99 |
| Nitrate | Type A | III | 63.02 | 807919-07-D20 | 1.6 | 214.5 | 1.04 |
| | Type B | | | 807919-07-B20 | 0.6 | 219.9 | 1.04 |

Samples were dried at 50° C. overnight before characterization.

2.2 Re-Preparation and Characterization of Salt Leads

Based on the characterization results, seven salt leads were selected and re-prepared to hundreds of milligrams (except di-HCl salt Type A). The selection criteria include but not limited to: 1) low safety concern of acid (safety class I), 2) sharp x-ray powder diffraction (XRPD) peaks without apparent amorphous halo, 3) negligible weight loss in thermogravimetric analysis (TGA), and 4) neat thermal event with a sharp melting in differential scanning calorimetry (DSC). Preparation procedures for salt leads as well as other salts described herein are described in Table 2-3.

TABLE 2-3

Preparation procedures of salts

| Crystal Form | Preparation Procedures |
|---|---|
| Mono-HCl salt Type A (807919-16-A) Method 1 | 1. Weigh 200 mg of freebase (807919-05-A) into 5 mL tetrahydrofuran (THF) and stir at 50° C. to dissolve the sample.<br>2. Add 59 µL HCl (charge ratio of 1:1) to the freebase solution, and then stir magnetically with a speed of 750 rpm at room temperature (RT).<br>3. Add ~2 mg seed (807919-07-D1) into the system. Subsequently, stir the suspension at RT for 5.5 hrs.<br>4. Characterize the wet sample by XRPD and the crystal form conforms to mono-HCl salt Type A.<br>5. Centrifuge and dry the wet cake at 50° C. for 2 hrs followed by drying under vacuum at RT for 1 hr.<br>6. Collect the solids, 205.4 mg with a yield of 92.0%. |

TABLE 2-3-continued

Preparation procedures of salts

| Crystal Form | Preparation Procedures |
|---|---|
| Mono-HCl salt Type A (807919-16-A) Method 2 | 1. Weigh 328.5 mg freebase Type A to 10.5 mL THF to get a clear solution.<br>2. Pipette 0.5 mL freebase solution to a 1.5-mL glass vial.<br>3. Pipette 4.0 µL HCl to the freebase solution and stir at RT for 2.5 days.<br>4. Isolate the solids by centrifuging and then dry at 50° C. overnight. |
| HCl Salt Type B (807919-07-C2) | 1. Weigh 14.8 mg freebase Type A to 0.5 mL EtOAc.<br>2. Add 8.0 µL HCl to the freebase suspension and stir at RT for 2.5 days.<br>3. Isolate the solids by centrifuging and then dry at 50° C. overnight. |
| Sulfate Type A (807919-11-A) Method 1 | 1. Weigh 65 mg of sulfuric acid into a 20-mL glass vial with 5 mL of THF.<br>2. Weigh 200 mg of freebase (807919-05-A, charge ratio of 1:1) to the acid solution, and stir magnetically with a speed of 750 rpm at RT.<br>3. Add ~2 mg seed (807919-07-A3) into the system and still stir at RT overnight.<br>4. Characterize the wet sample by XRPD and the crystal form conforms to sulfate Type A.<br>5. Cool the suspension to 5° C. at a rate of 0.1° C./min, and age at 5° C. overnight.<br>6. Centrifuge and dry the wet cake at 50° C. for 2 hrs followed by drying under vacuum at RT overnight.<br>7. Collect the solids, 247.1 mg with a yield of 94.2%. |
| Sulfate Type A (807919-11-A) Method 2 | 1. Weigh 330.3 mg freebase Type A to 21 mL acetone to get a clear solution.<br>2. Pipette 1.0 mL freebase solution to a 1.5 mL glass vial.<br>3. Pipette 2.7 µL sulfuric acid to the freebase solution and stir at RT for 2.5 days.<br>4. Isolate the solids by centrifuging and then dry at 50° C. overnight. |
| Sulfate Type B (807919-25-A13) | 1. Weigh 9.9 mg sulfate Type A to a 3-mL glass vial.<br>2. Add 2 mL DMSO to a 20-mL glass vial.<br>3. Seal the 3-mL vial into the 20-mL vial and keep the system at RT for 7 days.<br>4. Isolate the solids for analysis. |
| Hemi-sulfate Type A (807919-34-A) Method 1 | 1. Weigh 14.9 mg sulfate Type A to a 1,5-mL glass vial.<br>2. Add 0.5 mL acetone/H$_2$O (604:396, v/v) and stir at RT for 5 days.<br>3. Isolate the solids by centrifuging. |
| Hemi-sulfate Type A (807919-34-A) Method 2 | 1. Weigh 60.7 mg freebase Type A to 0.3 mL acetone/H$_2$O (604:396, v/v).<br>2. Pipette 5.5 µL sulfuric acid to freebase suspension.<br>3. Add ~1 mg seed and stir at RT overnight.<br>4. Isolate the solids by vacuum filter. |
| Phosphate Type A (807919-11-C) Method 1 | 1. Weigh 200 mg of freebase (807919-05-A) into 5 mL THF and stir at 50° C. to dissolve the sample.<br>2. Add 45 µL phosphoric acid (charge ratio of 1:1) to the freebase solution, and then stir magnetically with a speed of 750 rpm at RT.<br>3. Add ~2 mg seed (807919-07-E5) into the system and still stir at RT overnight.<br>4. Characterize the wet sample by XRPD and the crystal form conforms to phosphate Type A.<br>5. Cool the suspension to 5° C. at a rate of 0.1° C./min, and age at 5° C. overnight.<br>6. Centrifuge and dry the wet cake at 50° C. for 2 hrs followed by drying under vacuum at RT overnight.<br>7. Collect the solids, 234.0 mg with a yield of 89.2%. |
| Phosphate Type A (807919-11-C) Method 2 | 1. Weigh 330.7 mg freebase Type A to 10.5 mL MeOH/H$_2$O (9:1, v/v) to get a clear solution.<br>2. Pipette 0.5 mL freebase solution to a 1.5 mL glass vial.<br>3. Pipette 3.2 µL phosphoric acid to the freebase solution and stir at RT for 2.5 days.<br>4. Isolate the solids by centrifuging and then dry at 50° C. overnight. |
| Maleate Type A (807919-11-B) Method 1 | 1. Weigh 200 mg of freebase (807919-05-A) into 5 mL THF and stir at 50° C. to dissolve the sample.<br>2. Add 82 mg maleic acid (charge ratio of 1:1) to the freebase solution, and then stir magnetically with a speed of 750 rpm at RT.<br>3. Add ~2 mg seed (807919-07-D4) into the system and still stir at RT overnight.<br>4. Characterize the wet sample by XRPD and the crystal form conforms to maleate Type A.<br>5. Cool the suspension to 5° C. at a rate of 0.1° C./min, and age at 5° C. overnight.<br>6. Centrifuge and dry the wet cake at 50° C. for 2 hrs followed by drying under vacuum at RT overnight.<br>7. Collect the solids, 266.5 mg with a yield of 97.3%. |
| Maleate Type A (807919-11-B) Method 2 | 1. Weigh 328.5 mg freebase Type A to 10.5 mL THF to get a clear solution.<br>2. Add 5.9 mg maleic acid to a 1.5-mL glass vial.<br>3. Pipette 0.5 mL freebase solution to the vial and stir at RT for 2.5 days.<br>4. Isolate the solids by centrifuging and then dry at 50° C. overnight. |
| Malate Type A (807919-11-E) Method 1 | 1. Weigh 200 mg of freebase (807919-05-A) into 5 mL ethanol (EtOH) and stir at 50° C. to dissolve the sample.<br>2. Add 91 mg L-malic acid (charge ratio of 1:1) to the freebase solution, and then stir magnetically with a speed of 750 rpm at RT.<br>3. Add additional 5.0 mL EtOH and ~2 mg seed (807919-07-B10) into the system. Subsequently, stir the suspension at RT overnight.<br>4. Characterize the wet sample by XRPD and the crystal form conforms to malate Type A. |

TABLE 2-3-continued

Preparation procedures of salts

| Crystal Form | Preparation Procedures |
|---|---|
| | 5. Cool the suspension to 5° C. at a rate of 0.1° C./min, and age at 5° C. overnight.<br>6. Centrifuge and dry the wet cake at 50° C. for 4 hrs followed by drying under vacuum at RT overnight.<br>7. Collect the solids, 238.4 mg with a yield of 83.6%. |
| Malate Type A (807919-11-E) Method 2 | 1. Weigh 329.5 mg freebase Type A to 16.5 mL EtOH to get a clear solution.<br>2. Add 6.8 mg L-malic acid to a 1.5-mL glass vial.<br>3. Pipette 0.8 mL freebase solution to the vial and stir at RT for 2.5 days.<br>4. Isolate the solids by centrifuging and then dry at 50° C. overnight. |
| Adipate Type A (807919-12-A) Method 1 | 1. Weigh 150 mg of freebase (807919-05-A) into 5 mL EtOH and stir at 50° C. to dissolve the sample.<br>2. Add 45 mg adipic acid (charge ratio of 1:2, acid/base) to the freebase solution, and then stir magnetically with a speed of 750 rpm at RT.<br>3. Add ~2 mg seed (807919-07-B14) into the system. Subsequently, stir the suspension at RT overnight.<br>4. Characterize the wet sample by XRPD and the crystal form conforms to adipate Type A.<br>5. Centrifuge and dry the wet cake under vacuum at RT overnight.<br>6. Collect the solids, 159.7 mg with a yield of 86.8%. |
| Adipate Type A (807919-12-A) Method 2 | 1. Weigh 329.5 mg freebase Type A to 16.5 mL EtOH to get a clear solution.<br>2. Add 7.1 mg adipic acid to a 1.5-mL glass vial.<br>3. Pipette 0.8 mL freebase solution to the vial and stir at RT for 2.5 days.<br>4. Isolate the solids by centrifuging and then dry at 50° C. overnight. |
| Tartrate Type A (807919-07-A6) | 1. Weigh 330.3 mg freebase Type A to 21 mL acetone to get a clear solution.<br>2. Add 7.5 mg L-tartaric acid to a 1.5-mL glass vial.<br>3. Pipette 1.0 mL freebase solution to the vial and stir at RT for 2.5 days.<br>4. Isolate the solids by centrifuging and then dry at 50° C. overnight. |
| Tartrate Type B (807919-07-E6) | 1. Weigh 330.7 mg freebase Type A to 10.5 mL MeOH/$H_2O$ (9:1, v/v) to get a clear solution.<br>2. Add 7.5 mg L-tartaric acid to a 1.5-mL glass vial.<br>3. Pipette 0.5 mL freebase solution to the vial and stir at RT for 2.5 days.<br>4. Isolate the solids by centrifuging and then dry at 50° C. overnight. |
| Tartrate Type C (807919-07-B6) | 1. Weigh 329.5 mg freebase Type A to 16.5 mL EtOH to get a clear solution.<br>2. Add 7.6 mg L-tartaric acid to a 1.5-mL glass vial.<br>3. Pipette 0.8 mL freebase solution to the vial and stir at RT for 2.5 days.<br>4. Isolate the solids by centrifuging and then dry at 50° C. overnight. |
| Fumarate Type A (807919-07-A7) | 1. Weigh 330.3 mg freebase Type A to 21 mL acetone to get a clear solution.<br>2. Add 5.5 mg fumaric acid to a 1.5-mL glass vial.<br>3. Pipette 1.0 mL freebase solution to the vial and stir at RT for 2.5 days.<br>4. Isolate the solids by centrifuging and then dry at 50° C. overnight. |
| Fumarate Type B (807919-07-E7) | 1. Weigh 330.7 mg freebase Type A to 10.5 mL MeOH/$H_2O$ (9:1, v/v) to get a clear solution.<br>2. Add 5.8 mg fumaric acid to a 1.5-mL glass vial.<br>3. Pipette 0.5 mL freebase solution to the vial and stir at RT for 2.5 days.<br>4. Isolate the solids by centrifuging and then dry at 50° C. overnight. |
| Fumarate Type C (807919-07-C7) | 1. Weigh 15.2 mg freebase Type A to 0.5 mL EtOAc.<br>2. Weigh 5.9 mg fumaric acid to the freebase suspension and stir at RT for 2.5 days.<br>3. Isolate the solids by centrifuging and then dry at 50° C. overnight. |
| Citrate Type A (807919-07-A8) | 1. Weigh 330.3 mg freebase Type A to 21 mL acetone to get a clear solution.<br>2. Add 9.3 mg citric acid to a 1.5-mL glass vial.<br>3. Pipette 1.0 mL freebase solution to the vial and stir at RT for 2.5 days.<br>4. Isolate the solids by centrifuging and then dry at 50° C. overnight. |
| Citrate Type B (807919-07-B8) | 1. Weigh 329.5 mg freebase Type A to 16.5 mL EtOH to get a clear solution.<br>2. Add 9.6 mg citric acid to a 1.5-mL glass vial.<br>3. Pipette 0.8 mL freebase solution to the vial and stir at RT for 2.5 days.<br>4. Isolate the solids by centrifuging and then dry at 50° C. overnight. |
| Glycolate Type A (807919-07-B9) | 1. Weigh 329.5 mg freebase Type A to 16.5 mL EtOH to get a clear solution.<br>2. Add 4.0 mg glycolic acid to a 1.5-mL glass vial.<br>3. Pipette 0.8 mL freebase solution to the vial and stir at RT for 2.5 days.<br>4. Isolate the solids by centrifuging and then dry at 50° C. overnight. |
| Hippurate Type A (807919-07-B11) | 1. Weigh 329.5 mg freebase Type A to 16.5 mL EtOH to get a clear solution.<br>2. Add 8.4 mg hippuric acid to a 1.5-mL glass vial.<br>3. Pipette 0.8 mL freebase solution to the vial and stir at RT for 2.5 days.<br>4. Isolate the solids by centrifuging and then dry at 50° C. overnight. |
| Lactate Type A (807919-07-C12) | 1. Weigh 14.8 mg freebase Type A to 0.5 mL EtOAc.<br>2. Weigh 5.1 mg L-lactic acid to the freebase suspension and stir at RT for 2.5 days.<br>3. Isolate the solids by centrifuging and then dry at 50° C. overnight. |
| Lactate Type B (807919-07-A12) | 1. Weigh 330.3 mg freebase Type A to 21 mL acetone to get a clear solution.<br>2. Add 5.2 mg L-lactic acid to a 1.5-mL glass vial.<br>3. Pipette 1.0 mL freebase solution to the vial and stir at RT for 2.5 days.<br>4. Isolate the solids by centrifuging and then dry at 50° C. overnight. |
| Succinate Type A (807919-07-C13) | 1. Weigh 15.5 mg freebase Type A to 0.5 mL EtOAc.<br>2. Weigh 5.6 mg succinic acid to the freebase suspension and stir at RT for 2.5 days.<br>3. Isolate the solids by centrifuging and then dry at 50° C. overnight. |

TABLE 2-3-continued

Preparation procedures of salts

| Crystal Form | Preparation Procedures |
| --- | --- |
| Succinate Type B (807919-07-E13) | 1. Weigh 330.7 mg freebase Type A to 10.5 mL MeOH/H$_2$O (9:1, v/v) to get a clear solution.<br>2. Add 5.6 mg succinic acid to a 1.5-mL glass vial.<br>3. Pipette 0.5 mL freebase solution to the vial and stir at RT for 2.5 days.<br>4. Isolate the solids by centrifuging and then dry at 50° C. overnight. |
| Tosylate Type A (807919-07-B15) | 1. Weigh 329.5 mg freebase Type A to 16.5 mL EtOH to get a clear solution.<br>2. Add 9.6 mg p-toluenesulfonic acid to a 1.5-mL glass vial.<br>3. Pipette 0.8 mL freebase solution to the vial and stir at RT for 2.5 days.<br>4. Isolate the solids by centrifuging and then dry at 50° C. overnight. |
| Tosylate Type B (807919-07-D15) | 1. Weigh 328.5 mg freebase Type A to 10.5 mL THF to get a clear solution.<br>2. Add 9.4 mg p-toluenesulfonic acid to a 1.5-mL glass vial.<br>3. Pipette 0.5 mL freebase solution to the vial and stir at RT for 2.5 days.<br>4. Isolate the solids by centrifuging and then dry at 50° C. overnight. |
| Mesylate Type A (807919-07-A16) | 1. Weigh 330.3 mg freebase Type A to 21 mL acetone to get a clear solution.<br>2. Add 4.6 mg methanesulfonic acid to a 1.5-mL glass vial.<br>3. Pipette 1.0 mL freebase solution to the vial and stir at RT for 2.5 days.<br>4. Isolate the solids by centrifuging and then dry at 50° C. overnight. |
| Oxalate Type A (807919-07-B17) | 1. Weigh 329.5 mg freebase Type A to 16.5 mL EtOH to get a clear solution.<br>2. Add 6.1 mg oxalic acid to a 1.5-mL glass vial.<br>3. Pipette 0.8 mL freebase solution to the vial and stir at RT for 2.5 days.<br>4. Isolate the solids by centrifuging and then dry at 50° C. overnight. |
| Oxalate Type B (807919-07-D17) | 1. Weigh 328.5 mg freebase Type A to 10.5 mL THF to get a clear solution.<br>2. Add 6.2 mg oxalic acid to a 1.5-mL glass vial.<br>3. Pipette 0.5 mL freebase solution to the vial and stir at RT for 2.5 days.<br>4. Isolate the solids by centrifuging and then dry at 50° C. overnight. |
| Gentisate Type A (807919-07-A18) | 1. Weigh 330.3 mg freebase Type A to 21 mL acetone to get a clear solution.<br>2. Add 7.3 mg gentisic acid to a 1.5-mL glass vial.<br>3. Pipette 1.0 mL freebase solution to the vial and stir at RT for 2.5 days.<br>4. Isolate the solids by centrifuging and then dry at 50° C. overnight. |
| Gentisate Type B (807919-07-E18) | 1. Weigh 330.7 mg freebase Type A to 10.5 mL MeOH/H$_2$O (9:1, v/v) to get a clear solution.<br>2. Add 7.6 mg gensitic acid to a 1.5-mL glass vial.<br>3. Pipette 0.5 mL freebase solution to the vial and stir at RT for 2.5 days.<br>4. Isolate the solids by centrifuging and then dry at 50° C. overnight. |
| Benzoate Type A (807919-07-A19) | 1. Weigh 330.3 mg freebase Type A to 21 mL acetone to get a clear solution.<br>2. Add 6.1 mg benzoic acid to a 1.5-mL glass vial.<br>3. Pipette 1.0 mL freebase solution to the vial and stir at RT for 2.5 days.<br>4. Isolate the solids by centrifuging and then dry at 50° C. overnight. |
| Benzoate Type B (807919-07-E19) | 1. Weigh 330.7 mg freebase Type A to 10.5 mL MeOH/H$_2$O (9:1, v/v) to get a clear solution.<br>2. Add 6.0 mg benzoic acid to a 1.5-mL glass vial.<br>3. Pipette 0.5 mL freebase solution to the vial and stir at RT for 2.5 days.<br>4. Isolate the solids by centrifuging and then dry at 50° C. overnight. |
| Nitrate Type A (807919-07-D20) | 1. Weigh 328.5 mg freebase Type A to 10.5 mL THF to get a clear solution.<br>2. Pipette 0.5 mL freebase solution to a 1.5-mL vial.<br>3. Pipette 3.0 µL nitric acid to the vial and stir at RT for 2.5 days.<br>4. Isolate the solids by centrifuging and then dry at 50° C. overnight. |
| Nitrate Type B (807919-07-B20) | 1. Weigh 329.5 mg freebase Type A to 16.5 mL EtOH to get a clear solution.<br>2. Pipette 0.8 mL freebase solution to a 1.5-mL vial.<br>3. Pipette 3.0 µL nitric acid to the vial and stir at RT for 2.5 days.<br>4. Isolate the solids by centrifuging and then dry at 50° C. overnight. |
| Acetate/acetic acid co-crystal (807920-22-A1) | 1. Weigh 15.0 mg freebase Type A to 0.3 mL ethyl lactate.<br>2. Weigh 1.1 mg acetic acid to 1.5 mL n-heptane.<br>3. Pipette the acid solution to the freebase suspension and stir at RT overnight.<br>4. Isolate the solids and then dry at ambient conditions overnight. |

2.2.1 Mono-HCl Salt Type A

Figure 1:
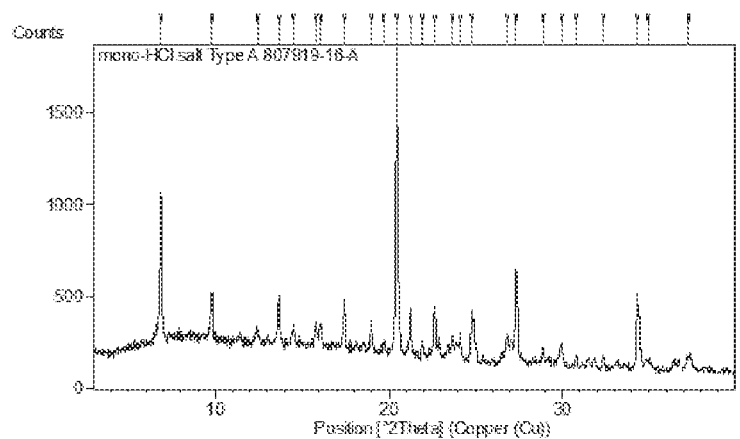
FIG. 1 illustrates XRPD patterns of mono-HCl salt crystal form Type A batches.

Mono-HCl salt Type A was successfully re-prepared as evidenced by XRPD results in FIG. 1. XRPD data for mono-HCl salt Type A provide (peak shift within ±0.2°) primary peaks at 20.5, 6.9, and 27.3; secondary peaks at 9.8, 13.7, and 34.3; and tertiary peaks at 17.4, 21.3, and 24.8.

Figure 2:
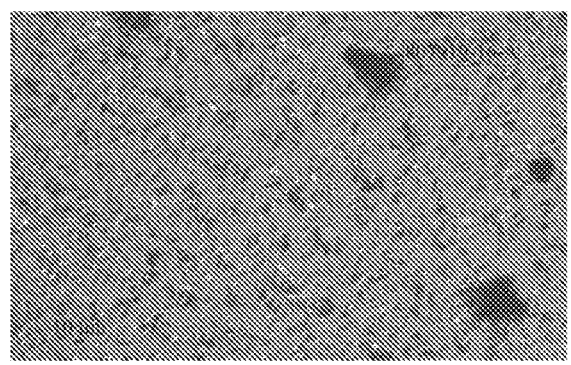
FIG. 2 illustrates a PLM image of mono-HCl salt crystal form Type A (807919-16-A).
Figure 3:
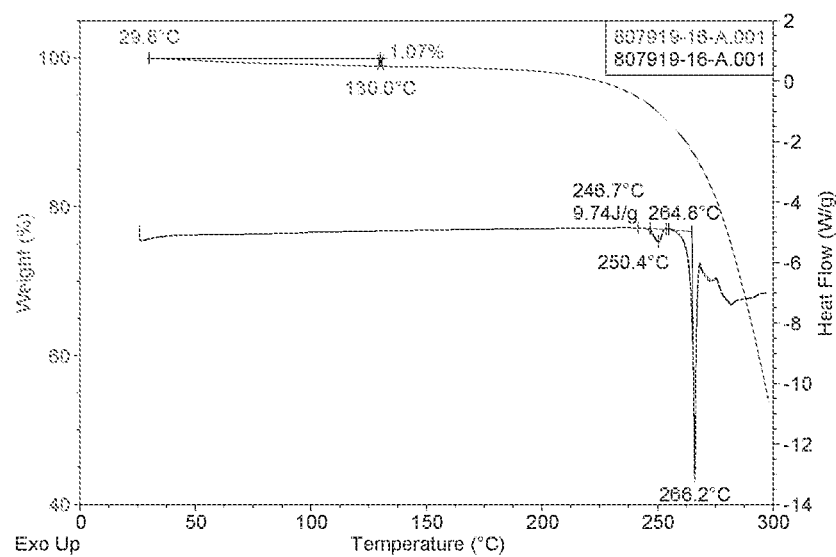
FIG. 3 illustrates TGA/DSC curves of mono-HCl salt crystal form Type A (807919-16-A).
Figure 4:
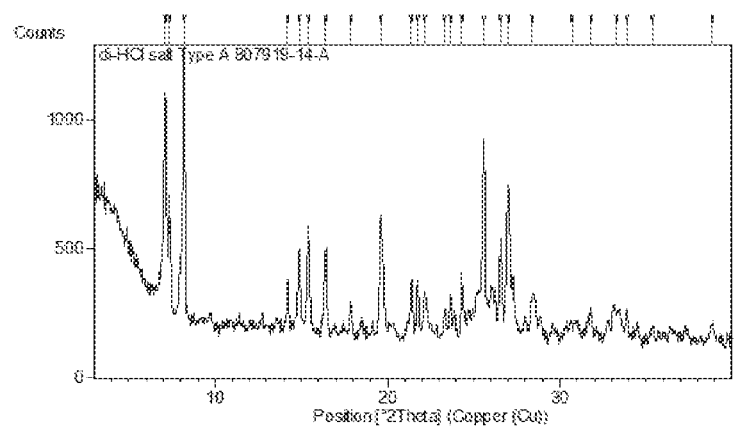
FIG. 4 illustrates an XRPD pattern of di-HCl salt crystal form Type A (807919-14-A).

PLM image displayed in FIG. 2 illustrated aggregation of small particles (<10 µm). As per TGA and DSC data in FIG. 3, sample (807919-16-A) shows a weight loss of 1.1% up to 130° C. and two endothermic peaks at 250.4° C. and 266.2° C. (peak temperature) before decomposition, indicating an anhydrate for mono-HCl salt Type A. A purity of 99.5 area % was detected by high performance liquid chromatography (HPLC) in Table 2-4. Also, the stoichiometric ratio was determined as 1.01 (acid/base) by HPLC/IC for the re-prepared sample.

TABLE 2-4

HPLC purity profile of mono-HCl salt Type A (807919-16-A)

| # | RRT | Area % |
| --- | --- | --- |
| 1 | 0.75 | 0.04 |
| 2 | 0.83 | 0.38 |
| 3 | 1.00 | 99.54 |
| 4 | 1.43 | 0.04 |

2.2.2 Di-HCl Salt Type A

Figure 5:
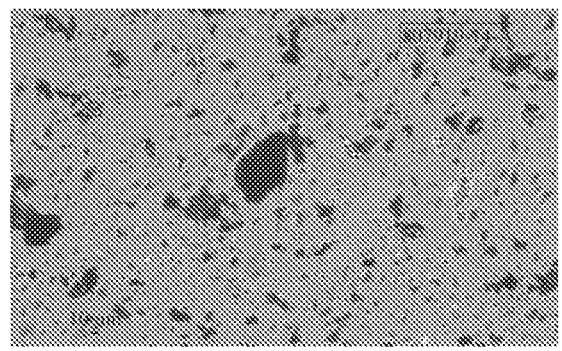
FIG. 5 illustrates a PLM image of di-HCl salt crystal form Type A (807919-14-A).

Di-HCl salt Type A was characterized by XRPD, TGA, DSC, polarized light microscope (PLM) and HPLC/IC. The XRPD pattern was shown in FIG. 4 and PLM image was displayed in FIG. 5. XRPD data for di-HCl salt Type A provide (peak shift within ±0.2°) primary peaks at 7.1, 8.2, and 19.6; secondary peaks at 15.4, 16.4, and 25.6; and tertiary peaks at 7.3, 14.9, and 27.0.

Figure 6:
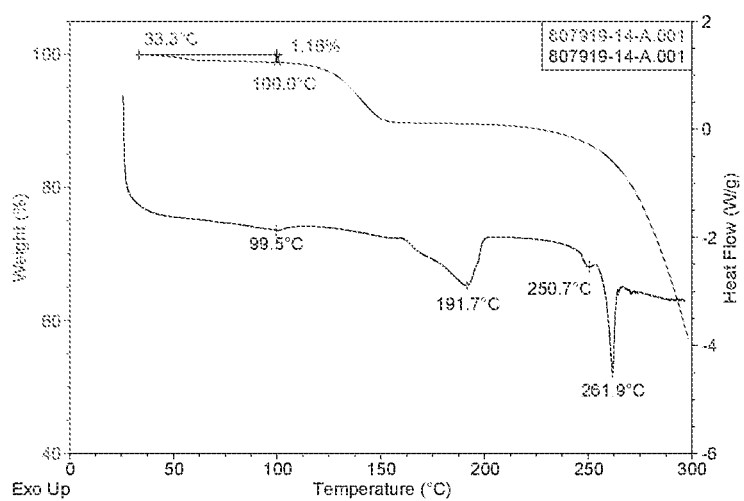
FIG. 6 illustrates TGA/DSC curves of di-HCl salt crystal form Type A (807919-14-A).

TGA and DSC results shown in FIG. 6, a weight loss of 1.2% up to 100° C. and four endothermic peaks at 99.5° C., 191.7° C., 250.7° C. and 261.9° C. (peak temperature) before decomposition. Also, a purity of 99.5 area % was detected by HPLC in Table 2-5 and the stoichiometry was calculated as 2.15 (acid/base) by HPLC/IC.

TABLE 2-5

HPLC purity profile of di-HCl salt Type A (807919-14-A)

| # | RRT | Area % |
|---|-----|--------|
| 1 | 0.75 | 0.04 |
| 2 | 0.83 | 0.39 |
| 3 | 1.00 | 99.53 |
| 4 | 1.43 | 0.04 |

2.2.3 Sulfate Type A

Figure 7:
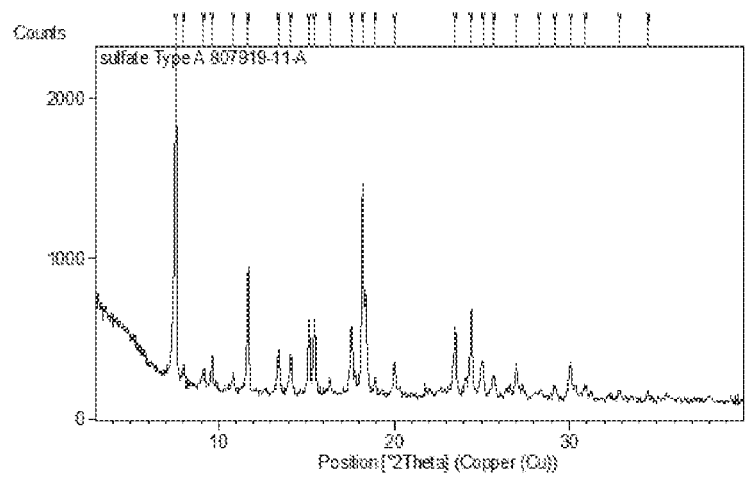
FIG. 7 illustrates XRPD patterns of sulfate crystal form Type A batches.

XRPD patterns comparison in FIG. 7 shows that the re-produced sample (807919-11-A) conformed to sulfate Type A. XRPD data for sulfate Type A provide (peak shift within ±0.2°) primary peaks at 7.6, 11.7, and 18.2; secondary peaks at 15.5, 17.6, and 24.4; and tertiary peaks at 9.6, 13.4, and 23.5.

Figure 8:
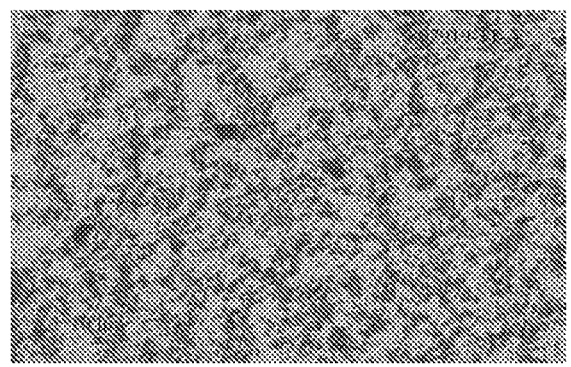
FIG. 8 illustrates a PLM image of sulfate crystal form Type A (807919-11-A).
Figure 9:
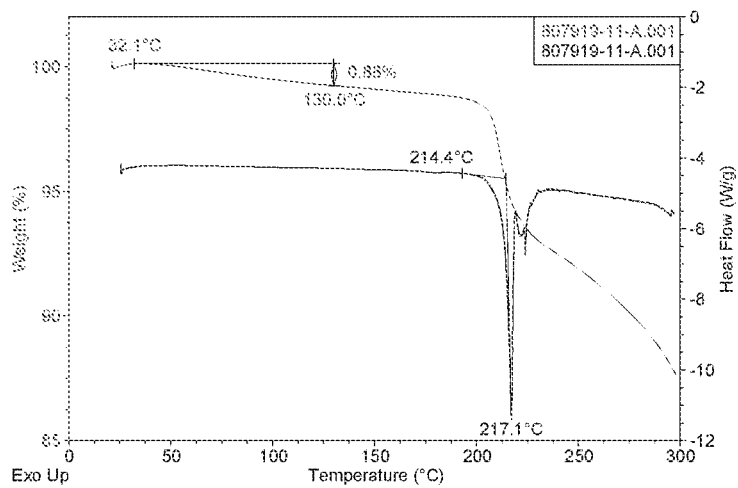
FIG. 9 illustrates TGA/DSC curves of sulfate crystal form Type A (807919-11-A).

Small particles (<10 μm) and aggregates were illustrated in FIG. 8. TGA and DSC results were displayed in FIG. 9. A weight loss of 0.9% was observed up to 130° C. in TGA and the DSC curve shows a sharp melting peak at 214.4° C. (onset temperature) before decomposition. A purity of 99.2 area % was detected by HPLC in Table 2-6. Also, the stoichiometric ratio was determined as 1.03 (acid/base) for the re-prepared batch. Combined with $^1$H NMR and TGA/DSC results, sulfate Type A was identified as an anhydrate of mono-sulfate.

TABLE 2-6

HPLC purity profile of sulfate Type A (807919-11-A)

| # | RRT | Area % |
|---|-----|--------|
| 1 | 0.75 | 0.05 |
| 2 | 0.83 | 0.68 |
| 3 | 1.00 | 99.19 |
| 4 | 1.43 | 0.09 |

2.2.4 Phosphate Type A

Figure 10:
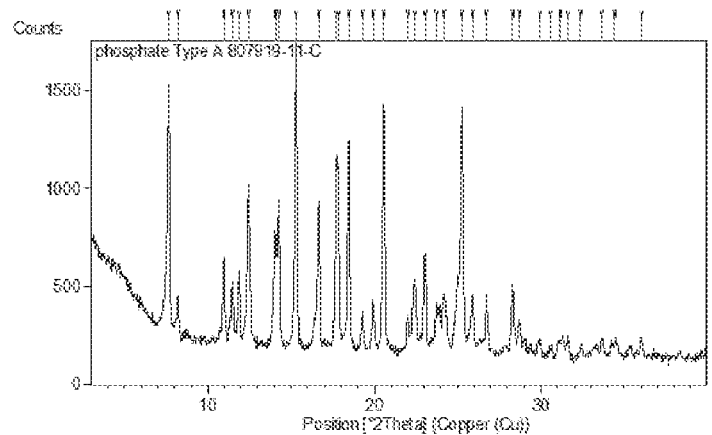
FIG. 10 illustrates XRPD patterns of phosphate crystal form Type A batches.

Phosphate Type A was successfully re-prepared as evidenced by XRPD results in FIG. 10. XRPD data for phosphate Type A provide (peak shift within ±0.2°) primary peaks at 7.7, 15.3, and 20.6; secondary peaks at 12.4, 18.5, and 25.2; and tertiary peaks at 14.3, 16.7, and 17.7.

Figure 11:
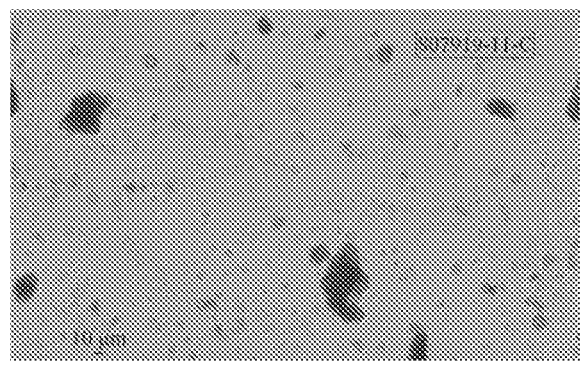
FIG. 11 illustrates a PLM image of phosphate crystal form Type A (807919-11-C).
Figure 12:
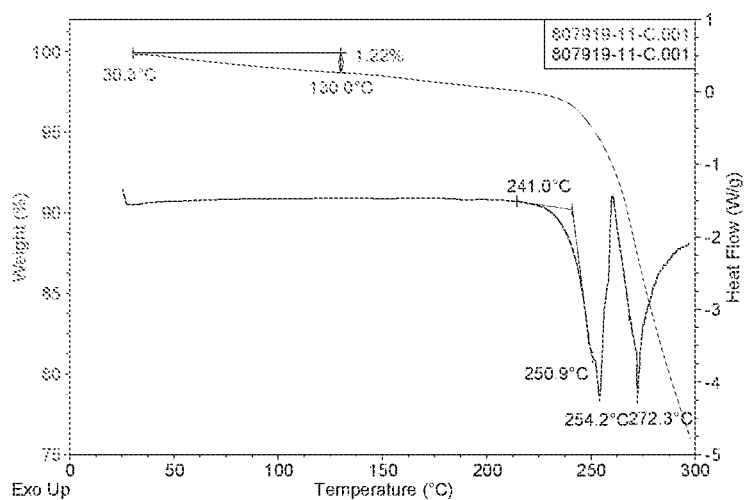
FIG. 12 illustrates TGA/DSC curves of phosphate crystal form Type A (807919-11-C).

PLM image displayed in FIG. 11 illustrated aggregation of small particles (<10 μm). As per TGA and DSC data in FIG. 12, phosphate Type A (807919-11-C) shows a weight loss of 1.2% up to 130° C. and an endothermic peak at 241.0° C. (onset temperature) before decomposition. A purity of 99.4 area % was detected by HPLC in Table 2-7. Also, the stoichiometry of re-prepared sample was determined as 1.07 (acid/base) by HPLC/IC.

TABLE 2-7

HPLC purity profile of phosphate Type A (807919-11-C)

| # | RRT | Area % |
|---|-----|--------|
| 1 | 0.83 | 0.55 |
| 2 | 1.00 | 99.36 |
| 3 | 1.43 | 0.09 |

2.2.5 Maleate Type A

Figure 13:
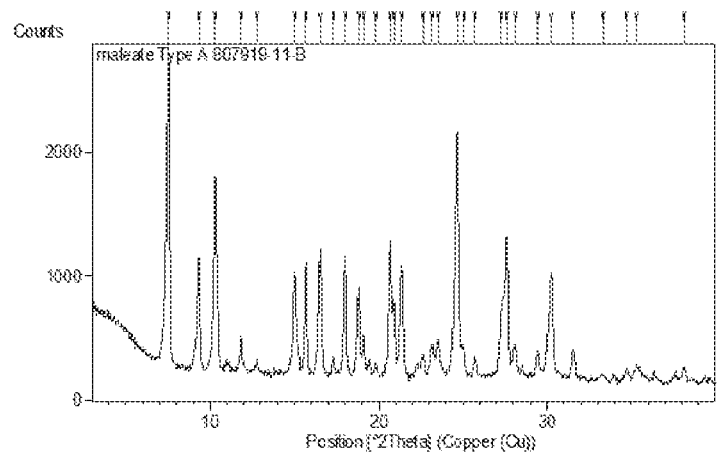
FIG. 13 illustrates XRPD patterns of maleate crystal form Type A batches.

Maleate Type A (807919-07-D4) was generated via reactive crystallization (molar ratio of 1:1) in THF at RT. XRPD results in FIG. 13 shows maleate Type A was successfully re-prepared. XRPD data for maleate Type A provide (peak shift within ±0.2°) primary peaks at 7.5, 10.3, and 24.7; secondary peaks at 9.3, 16.5, and 18.0; and tertiary peaks at 15.7, 20.7, and 21.4.

Figure 14:
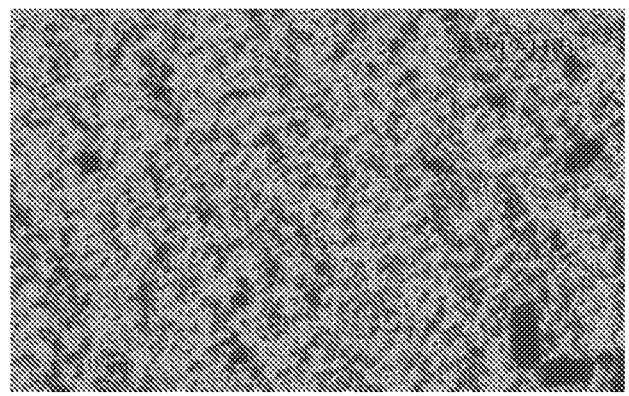
FIG. 14 illustrates a PLM image of maleate crystal form Type A (807919-11-B).
Figure 15:
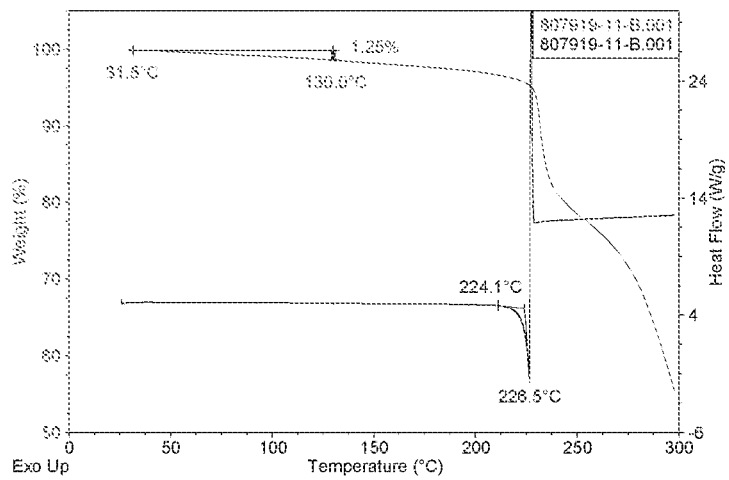
FIG. 15 illustrates TGA/DSC curves of maleate crystal form Type A (807919-11-B).

Small particles (<10 μm) and aggregates were illustrated in FIG. 14. TGA and DSC data shows a weight loss of 1.3% up to 130° C., and a possible melting endotherm at 224.1° C. (onset temperature) before decomposition was observed in DSC (FIG. 15). A purity of 99.2 area % was detected by HPLC in Table 2-8. $^1$H NMR results indicate a stoichiometry of 0.96 (acid/base) for the re-prepared maleate Type A (807919-11-B). Combined with $^1$H NMR and TGA/DSC results, maleate Type A was identified to be an anhydrate of mono-maleate

TABLE 2-8

HPLC purity profile of maleate Type A (807919-11-B)

| # | RRT | Area % |
|---|-----|--------|
| 1 | 0.75 | 0.10 |
| 2 | 0.83 | 0.63 |
| 3 | 1.00 | 99.19 |
| 4 | 1.43 | 0.09 |

2.2.6 Malate Type A

Figure 16:
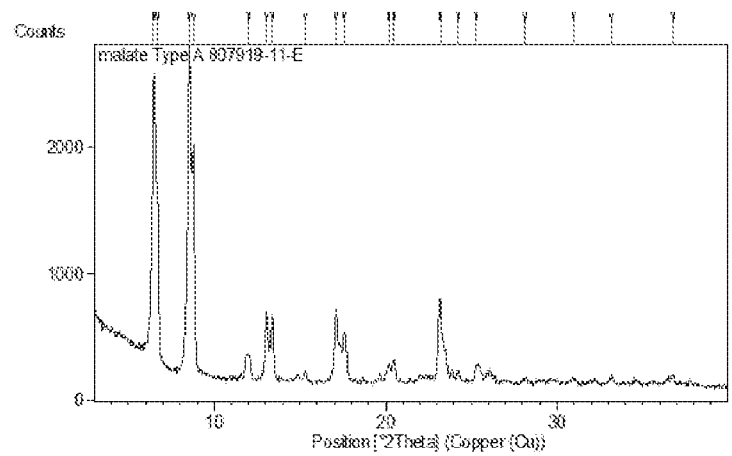
FIG. 16 illustrates XRPD patterns of malate crystal form Type A batches.

Malate Type A was successfully re-prepared as evidenced by XRPD results in FIG. 16. XRPD data for malate Type A provide (peak shift within ±0.2°) primary peaks at 6.5, 8.5, and 23.2; secondary peaks at 12.0, 13.0, and 17.1; and tertiary peaks at 8.8, 20.5, and 25.3.

Figure 17:
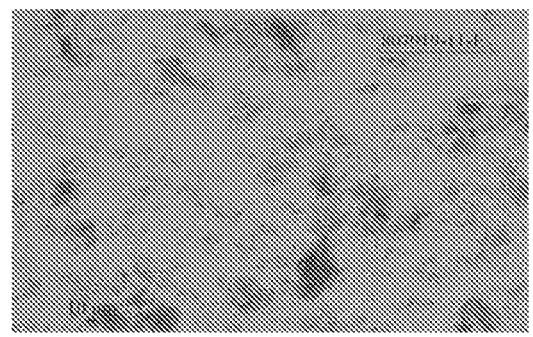
FIG. 17 illustrates a PLM image of malate crystal form Type A (807919-11-E).
Figure 18:
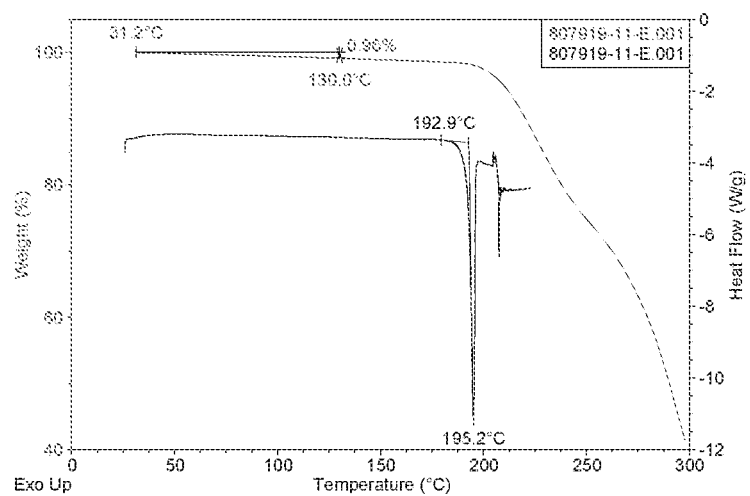
FIG. 18 illustrates TGA/DSC curves of malate crystal form Type A (807919-11-E).

PLM image displayed in FIG. 17 illustrated aggregation of irregular particles. As per TGA and DSC data in FIG. 18, malate Type A (807919-11-E) shows a weight loss of 1.0% up to 130° C. and a sharp endothermic peak at 192.9° C. (onset temperature) before decomposition. A purity of 99.9 area % was detected by HPLC in Table 2-9. Further, the stoichiometry of re-prepared sample was determined as 1.02 (acid/base) by $^1$H NMR.

TABLE 2-9

HPLC purity profile of malate Type A (807919-11-E)

| # | RRT | Area % |
|---|-----|--------|
| 1 | 0.75 | 0.55 |
| 2 | 1.00 | 99.88 |
| 3 | 1.43 | 0.07 |

2.2.7 Adipate Type A

Figure 19:
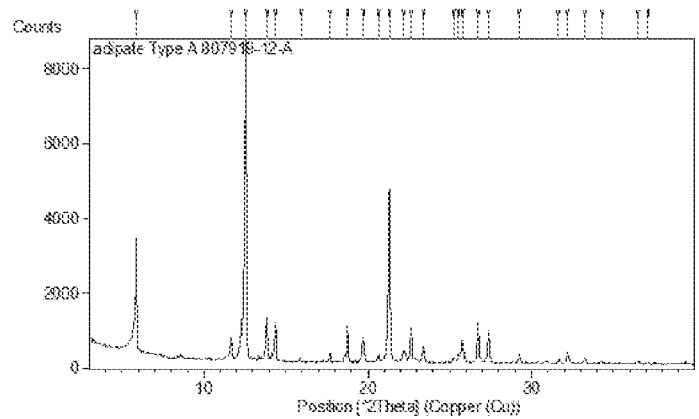
FIG. 19 illustrates XRPD patterns of adipate crystal form Type A batches.

XRPD patterns comparison in FIG. 19 shows that the re-produced sample (807919-12-A) conformed to adipate Type A. XRPD data for adipate Type A provide (peak shift within ±0.2°) primary peaks at 5.9, 12.5, and 21.3; secondary peaks at 13.9, 18.8, and 26.7; and tertiary peaks at 14.4, 19.7, and 22.6.

Figure 20:
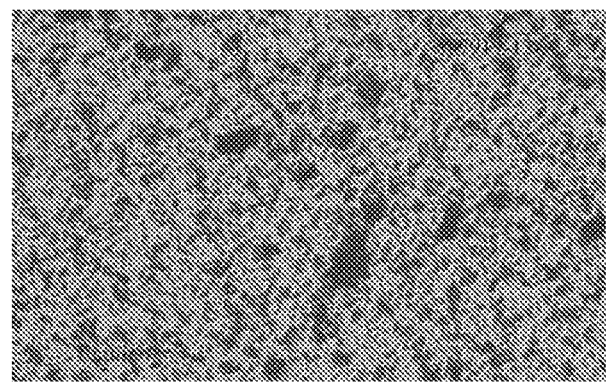
FIG. 20 illustrates a PLM image of adipate crystal form Type A (807919-12-A).
Figure 21:
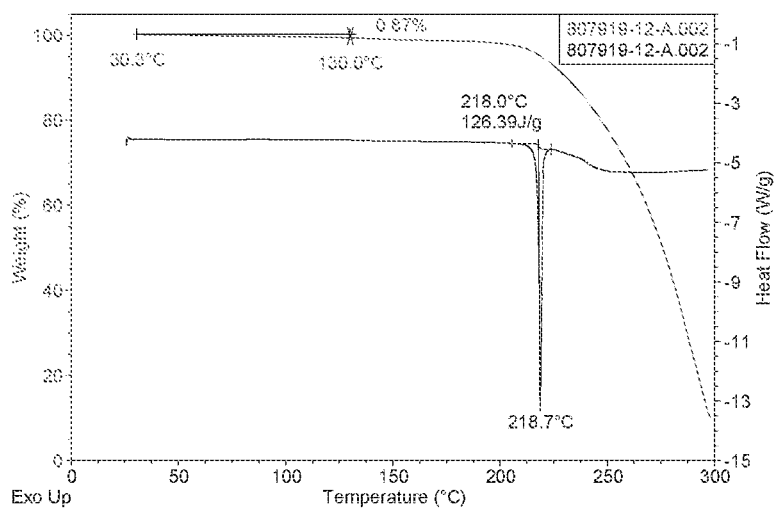
FIG. 21 illustrates TGA/DSC curves of adipate crystal form Type A (807919-12-A).
Figure 22:
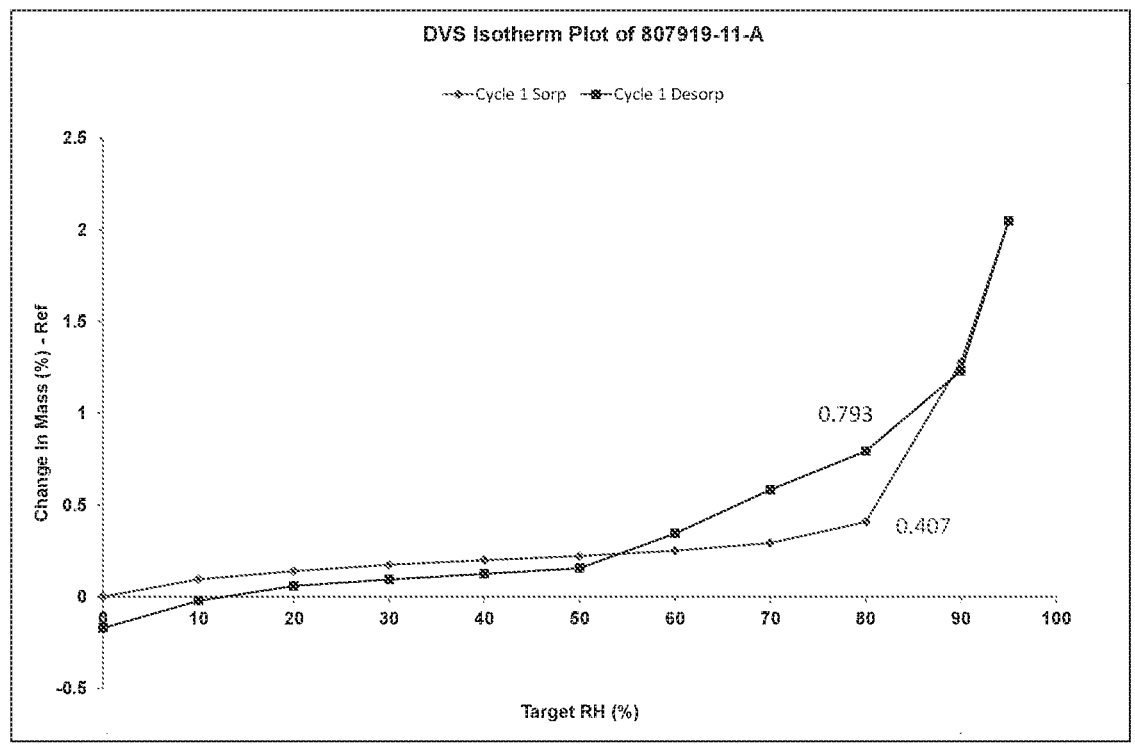
FIG. 22 illustrates a DVS plot of sulfate crystal form Type A (807919-11-A).
Figure 23:
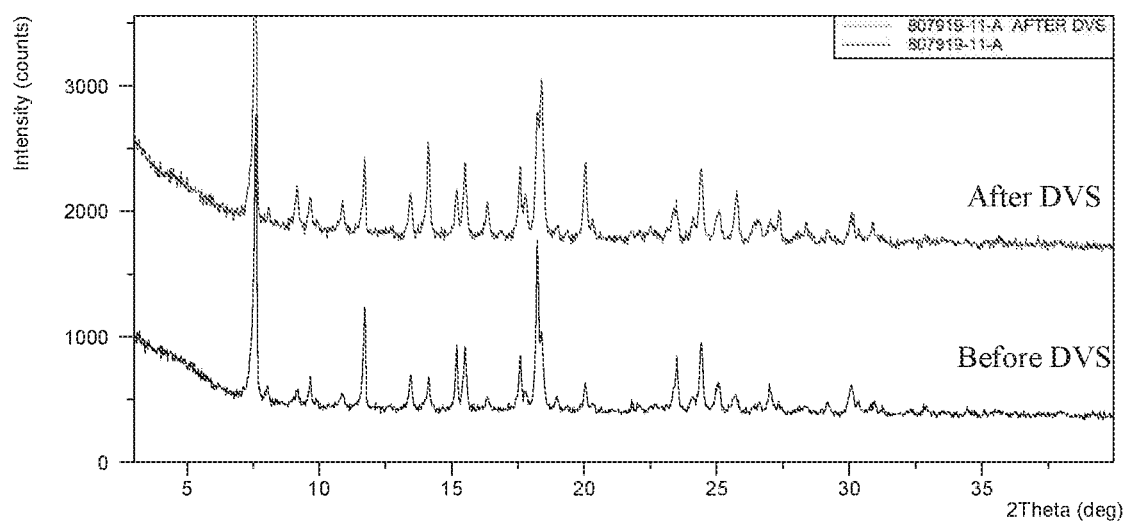
FIG. 23 illustrates a XRPD overlay of sulfate crystal form Type A (807919-11-A) pre and post DVS test.
Figure 24:
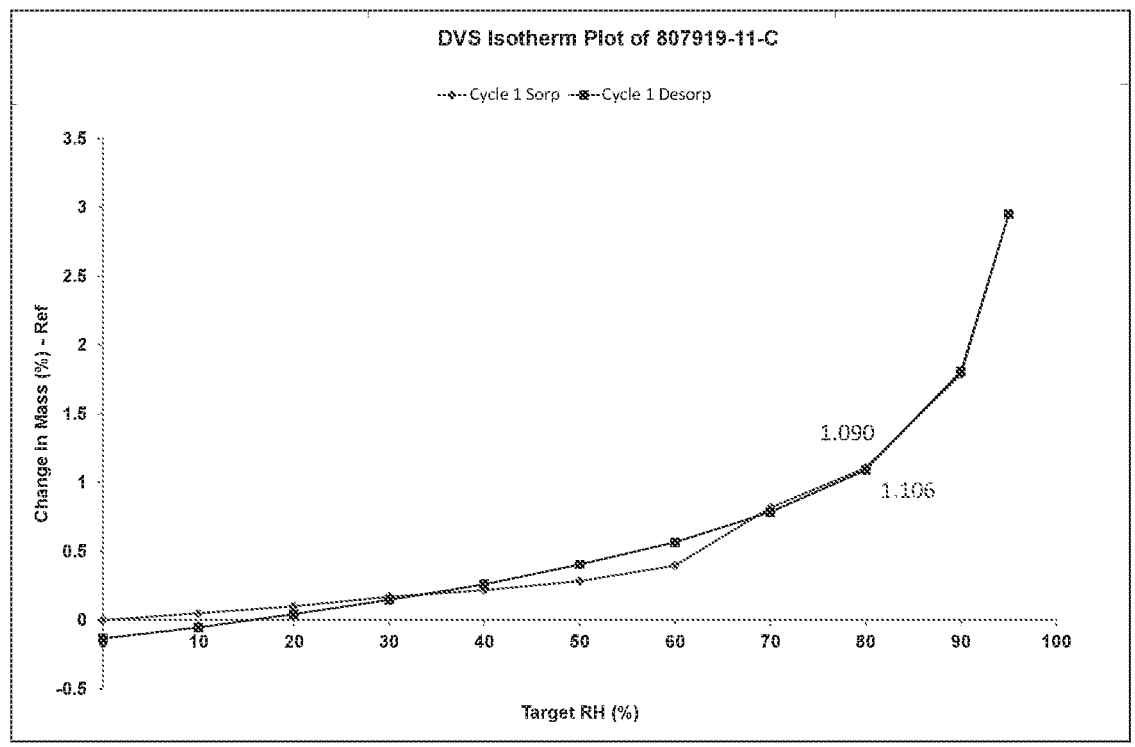
FIG. 24 illustrates a DVS plot of phosphate crystal form Type A (807919-11-C).
Figure 25:
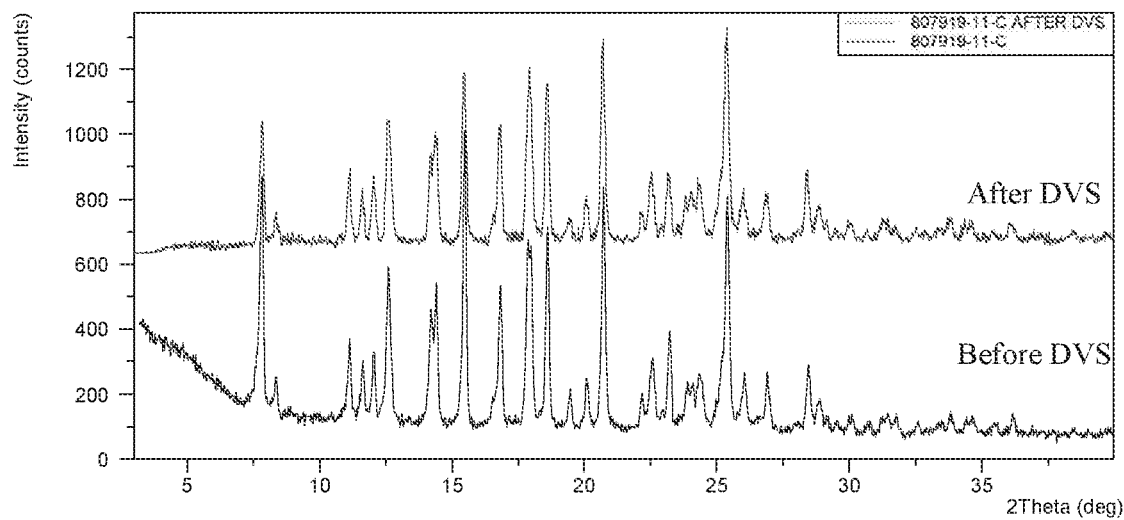
FIG. 25 illustrates a XRPD overlay of phosphate crystal form Type A (807919-11-C) pre and post DVS test.
Figure 26:
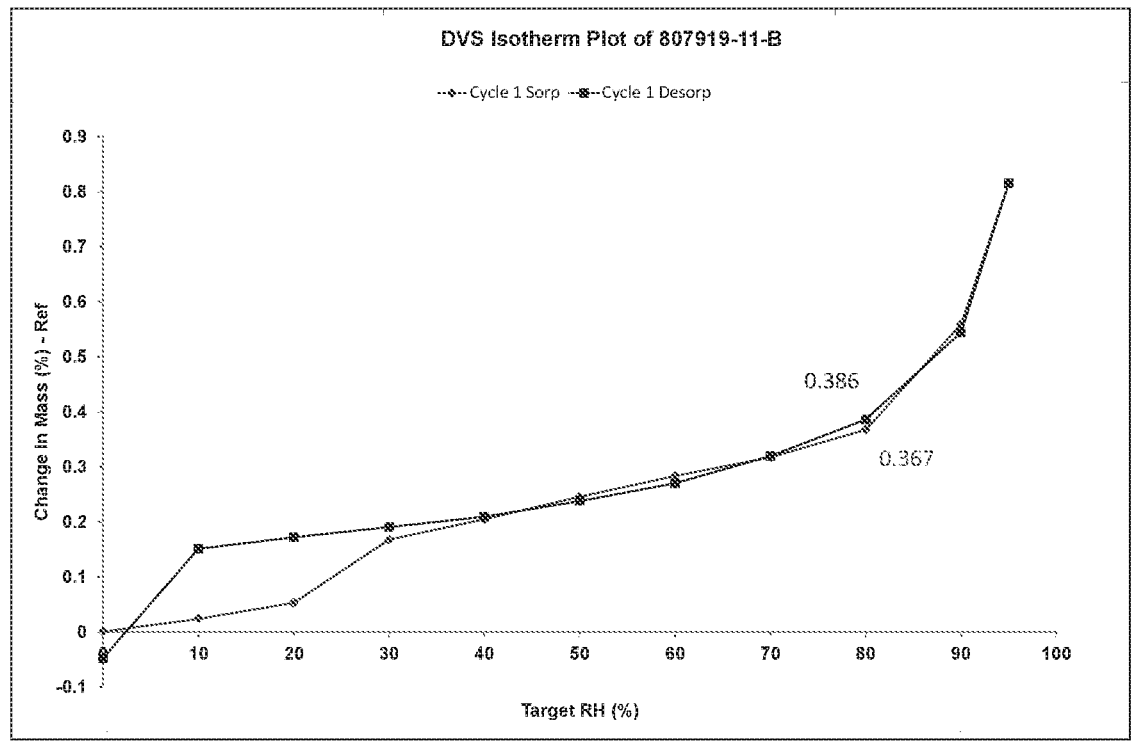
FIG. 26 illustrates a DVS plot of maleate crystal form Type A (807919-11-B).
Figure 27:
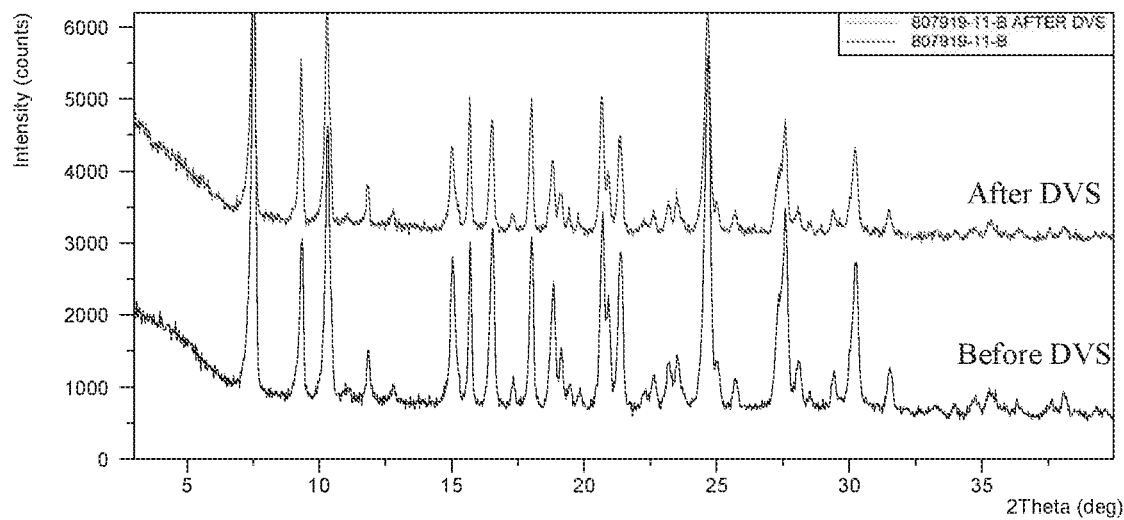
FIG. 27 illustrates a XRPD overlay of maleate crystal form Type A (807919-11-B) pre and post DVS test.
Figure 28:
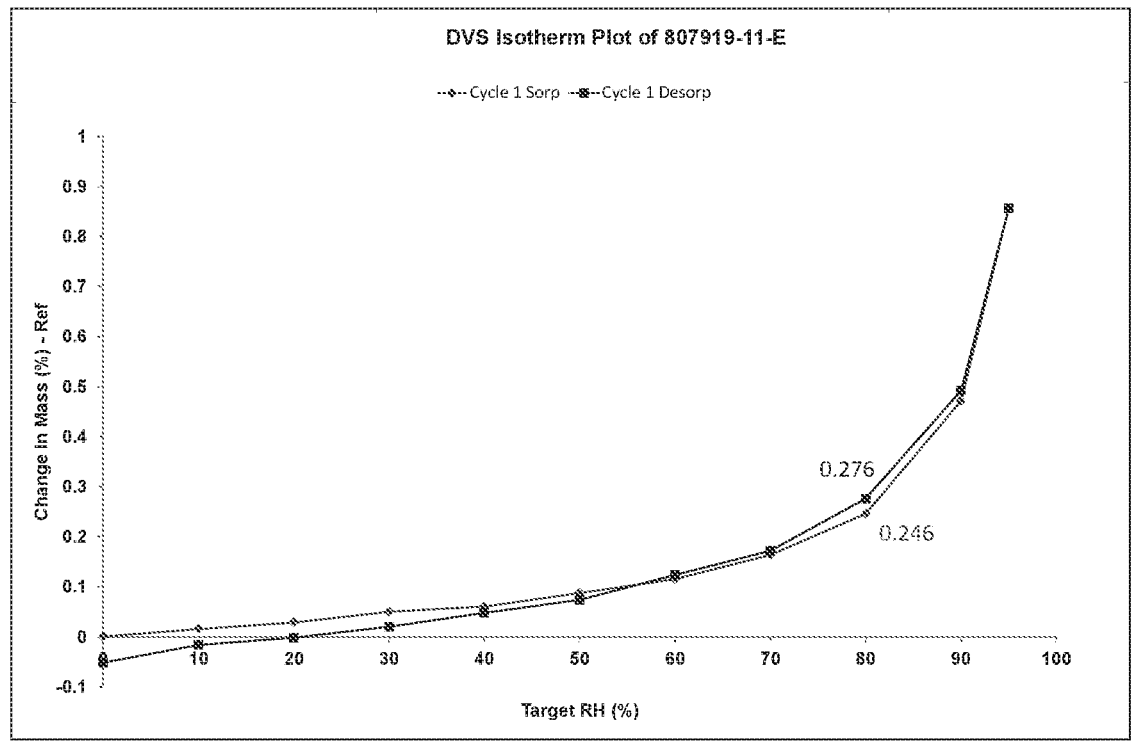
FIG. 28 illustrates a DVS plot of malate crystal form Type A (807919-11-E).
Figure 29:
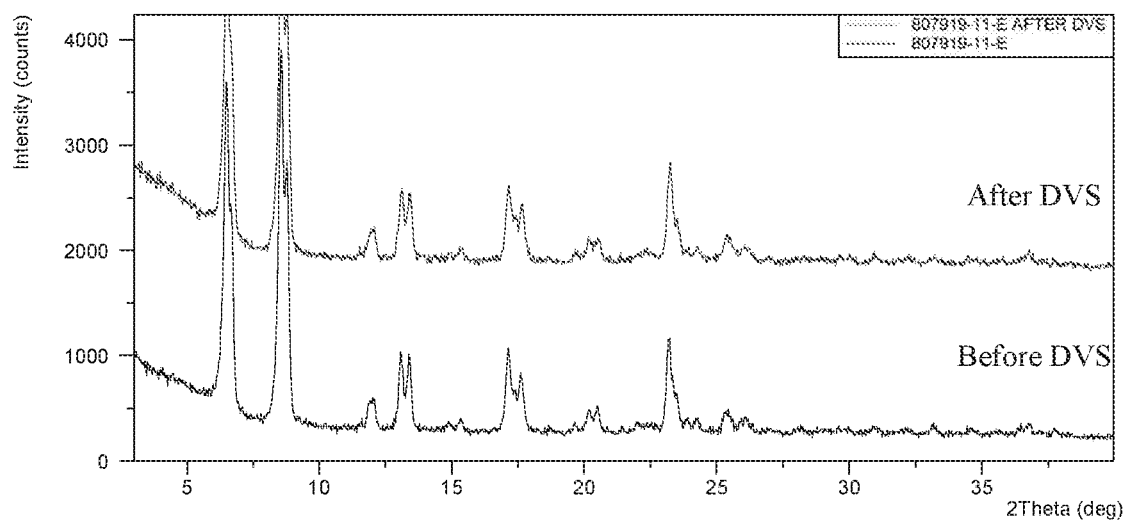
FIG. 29 illustrates a XRPD overlay of malate crystal form Type A (807919-11-E) pre and post DVS test.
Figure 30:
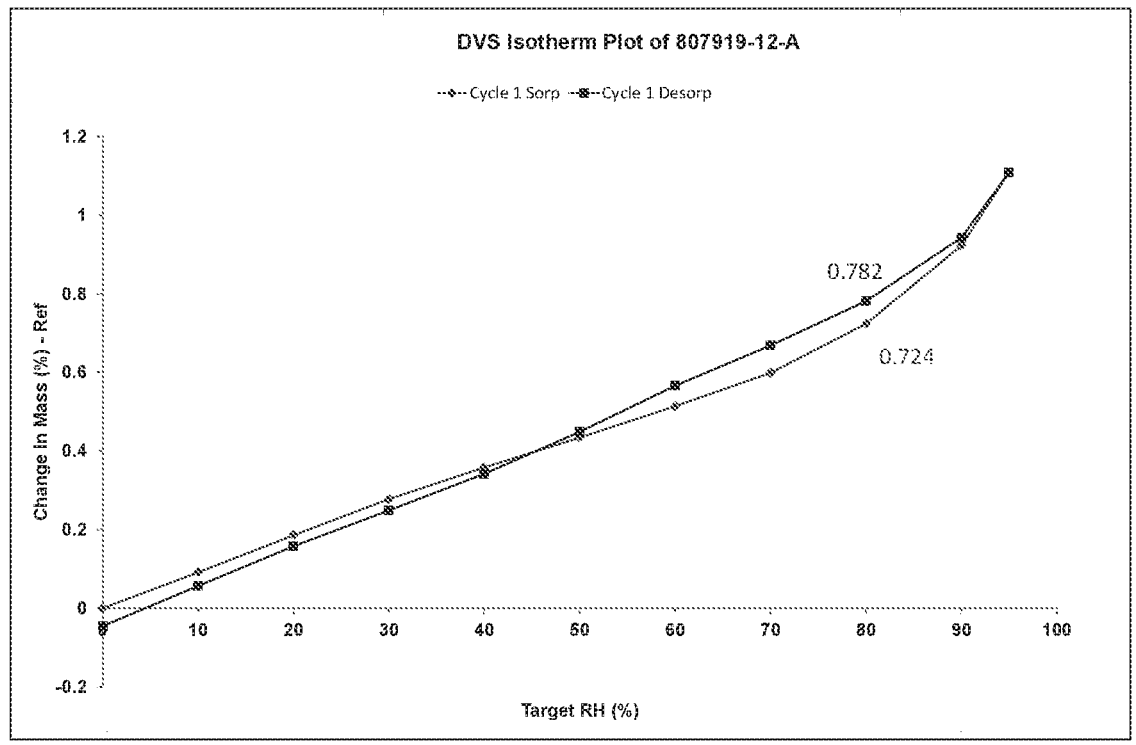
FIG. 30 illustrates a DVS plot of adipate crystal form Type A (807919-12-A).
Figure 31:
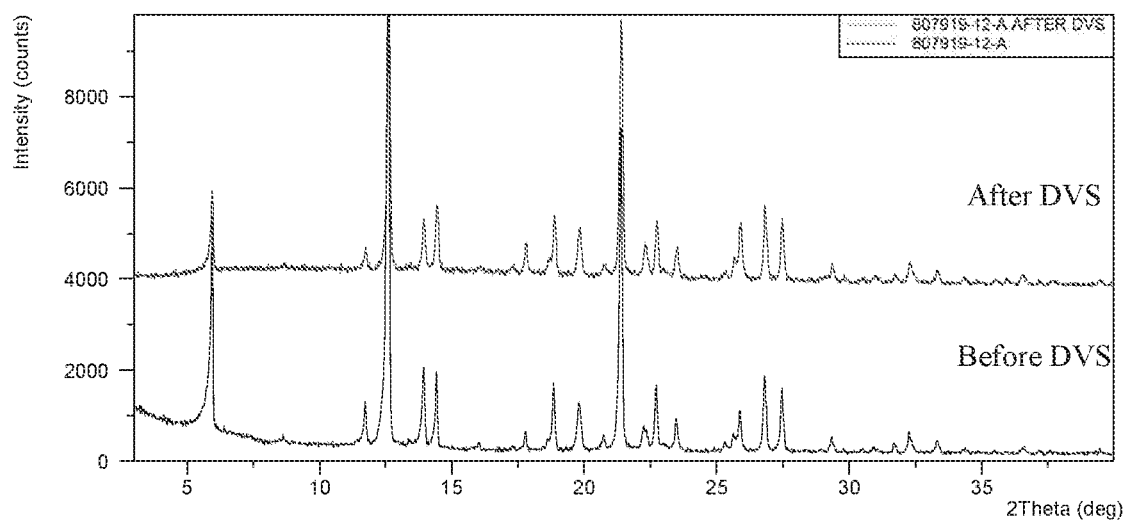
FIG. 31 illustrates a XRPD overlay of adipate crystal form Type A (807919-12-A) pre and post DVS test.

Small particles (<10 μm) and severe aggregates were illustrated in FIG. 20. TGA and DSC results were displayed in FIG. 21. A weight loss of 0.9% was observed up to 130° C. in TGA and the DSC curve shows a sharp melting peak at 218.0° C. (onset temperature) before decomposition. A purity of 99.9 area % was detected by HPLC in Table 2-10. Further, the stoichiometric ratio was determined as 0.52 (acid/base) for the re-prepared batch, suggesting the formation of hemi-adipate.

TABLE 2-10

HPLC purity profile of adipate Type A (807919-12-A)

| # | RRT | Area % |
|---|-----|--------|
| 1 | 0.83 | 0.06 |
| 2 | 1.00 | 99.94 |

2.3 Evaluation of Salt Leads

Further evaluation study of hygroscopicity, kinetic solubility, and solid-state stability was conducted to better understand the physicochemical properties of seven leads. As results shows: 1) All salt leads are slightly hygroscopic with no form change after DVS evaluation except mono-HCl salt Type A and di-HCl salt Type A, 2) Compared with freebase Type A, all salt leads displayed improved or comparable solubility in water and bio-relevant media except maleate Type A, 3) As evidenced by no substantial change in crystal form or HPLC purity, all salt leads shows good physical and chemical stability except di-HCl salt Type A.

2.3.1 Hygroscopicity

DVS isotherm plot was collected at 25° C. to investigate the solid form stability as a function of humidity. For the six anhydrous salts (mono-HCl salt Type A, sulfate Type A, phosphate Type A, maleate Type A, malate Type A, and adipate Type A), solids were pre-dried at 0% RH to remove the unbounded solvent or water before started. For the possible hydrate/solvate di-HCl salt Type A, solids were equilibrated at ambient humidity (~30% RH) before testing.

As evidenced by the water uptake of 0.2-1.1% up to 80% RH, five salt forms (sulfate Type A, phosphate Type A, maleate Type A, malate Type A, and adipate Type A) were slightly hygroscopic. No solid form change was observed for all the five leads after DVS evaluation (FIG. 22-31).

Figure 32:
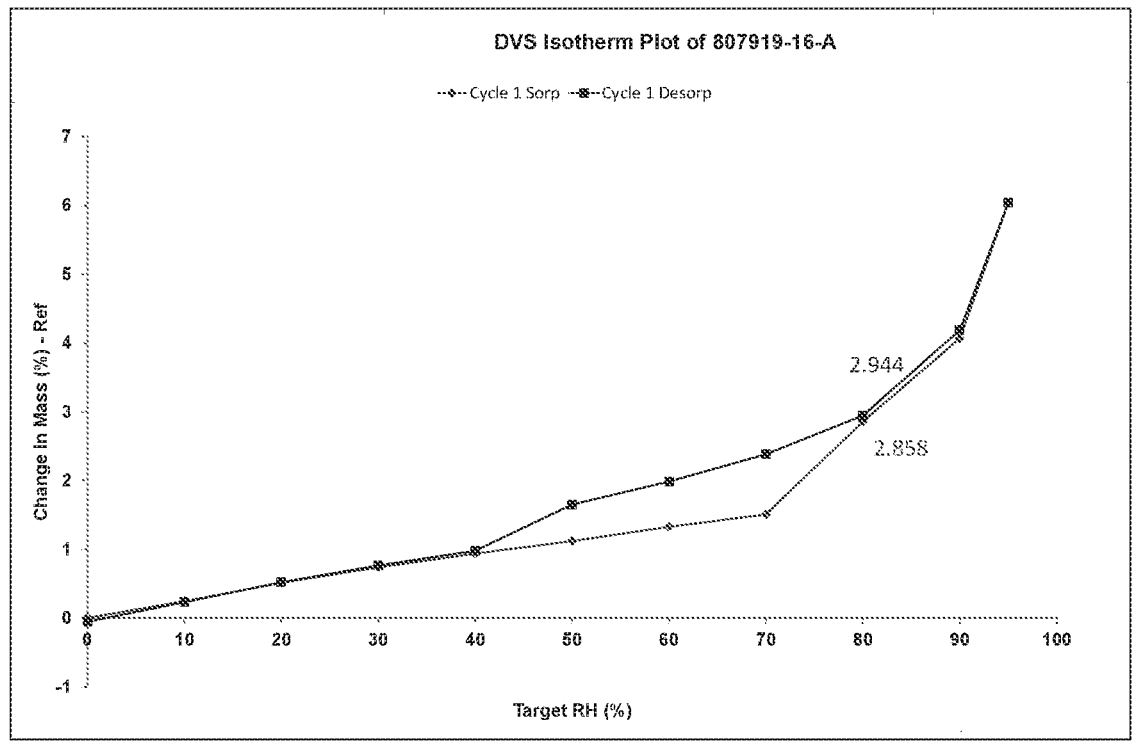
FIG. 32 illustrates a DVS plot of mono-HCl salt crystal form Type A (807919-16-A).
Figure 33:
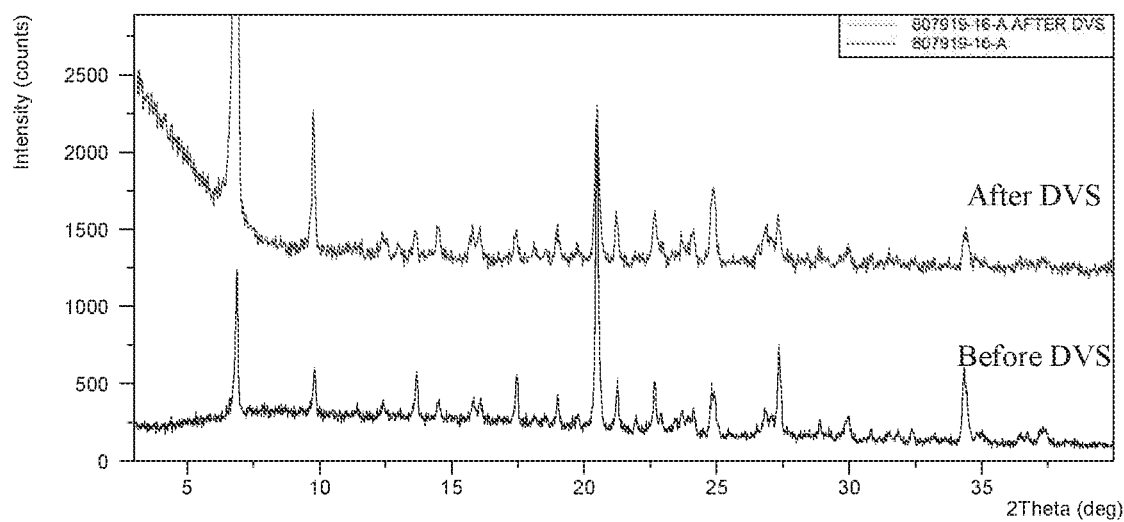
FIG. 33 illustrates a XRPD overlay of mono-HCl salt crystal form Type A (807919-16-A) pre and post DVS test.
Figure 34:
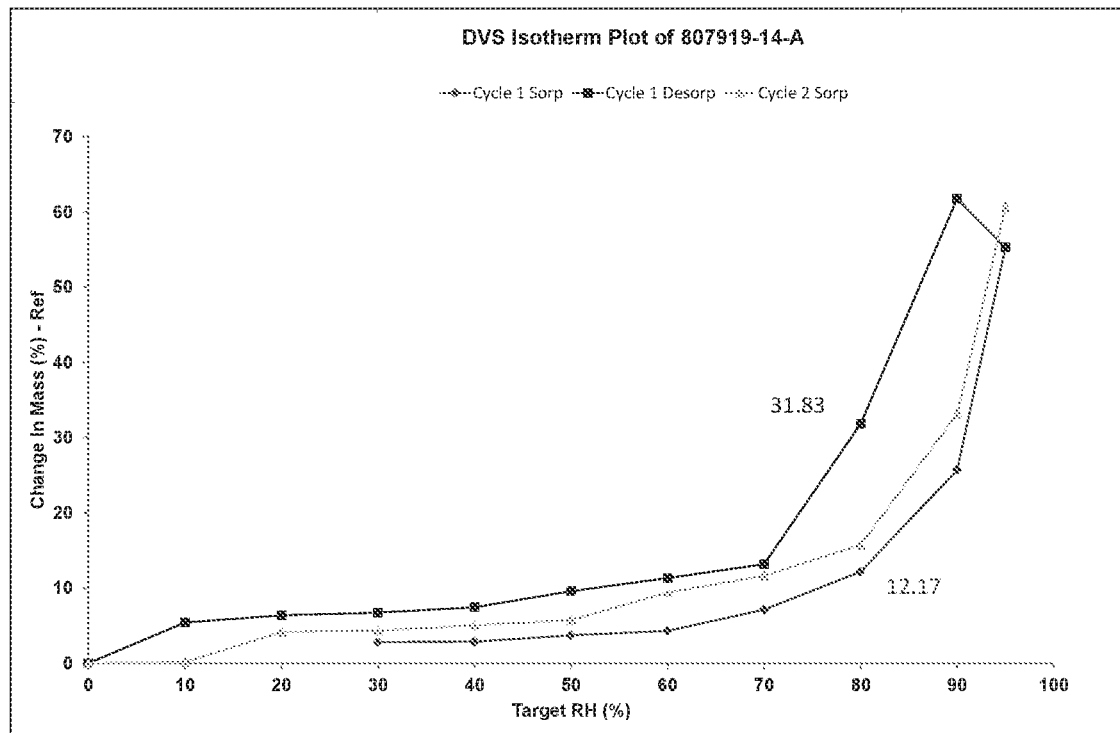
FIG. 34 illustrates a DVS plot of di-HCl salt crystal form Type A (807919-14-A).
Figure 35:
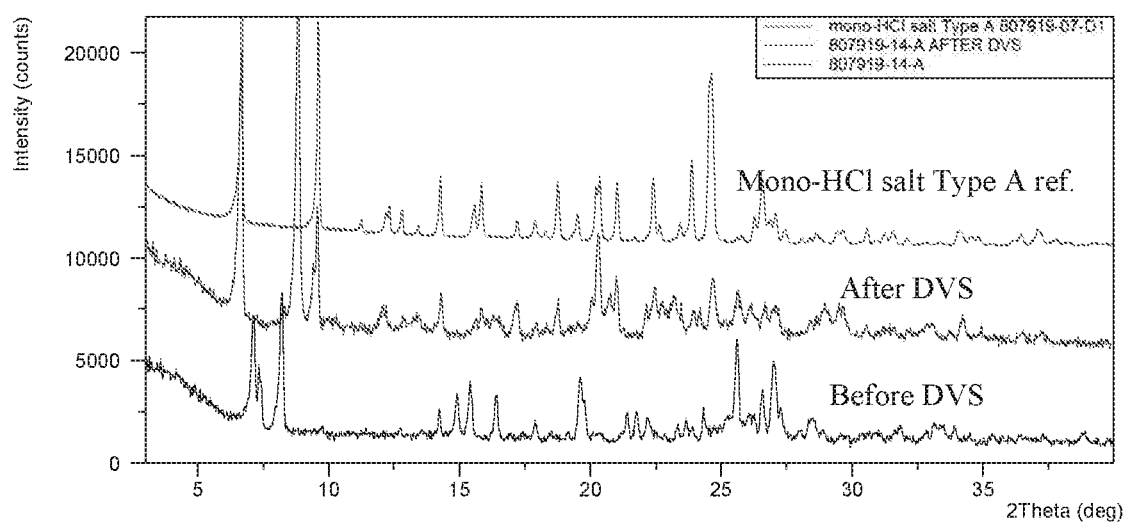
FIG. 35 illustrates a XRPD overlay of di-HCl salt crystal form Type A (807919-14-A) pre and post DVS test.
Figure 36:
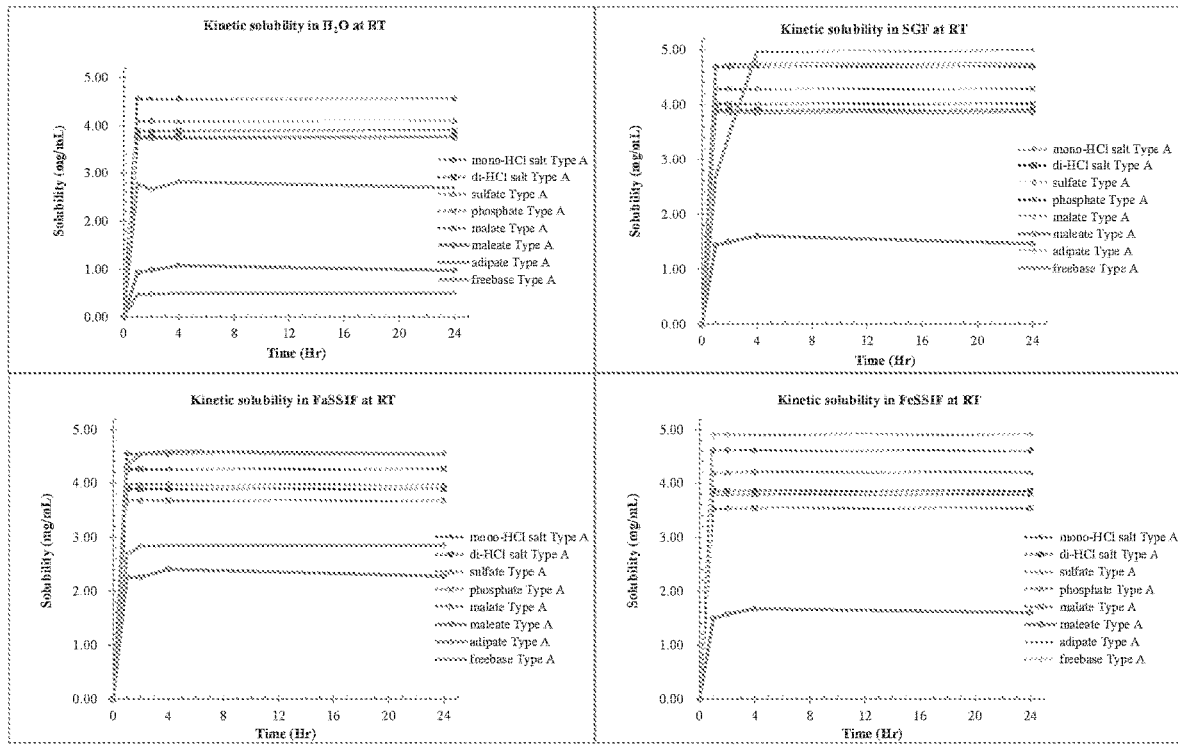
FIG. 36 illustrates kinetic solubility of seven crystal forms described herein and freebase crystal forms (short dashes: clear solutions were observed during the evaluation).

DVS plots displayed in FIG. 32 and FIG. 34 illustrate that both HCl salt forms were hygroscopic. For mono-HCl salt Type A (807919-16-A), a water uptake of 2.9% was observed up to 80% RH and no form change was detected after DVS test (FIG. 33). For di-HCl salt Type A (807919-14-A), a water uptake of 12.2% was detected up to 80% RH and one plateau was observed at ~20% RH, suggesting the possible existence of a hydrate. In addition, di-HCl salt Type A converted to a new form which contains diffraction peaks of mono-HCl salt Type A after DVS evaluation (FIG. 35), indicating the disproportionation risk of di-HCl salt Type A at high relative humidity.

2.3.2 Kinetic Solubility

Kinetic solubility of seven salt leads was measured in water and three bio-relevant media (SGF, FeSSIF, and FeSSIF) at RT, using freebase Type A (807919-05-A) as control. All solubility samples (initial solid loading of ~5 mg/mL) were kept rolling on a rolling incubator at a speed of 25 rpm, and sampled at 1, 2, 4 and 24 hours, respectively. After being centrifuged and separated using 0.45 μm Nylon filter, filtrates were collected for HPLC and pH test, and wet cakes for XRPD characterization. If clear solutions were obtained after 24 hours, accurate concentration and purity were measured for the solutions.

Figure 37:
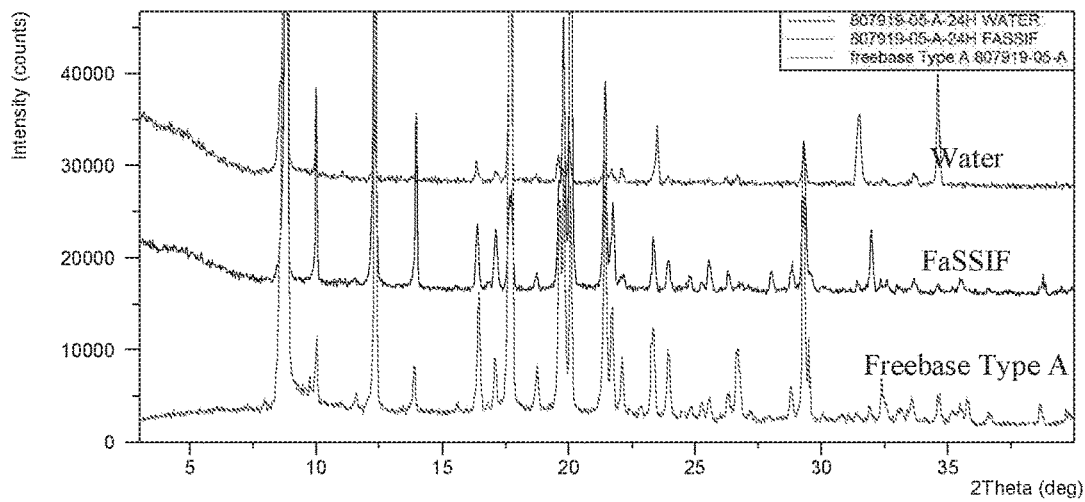
FIG. 37 illustrates a XRPD overlay of freebase crystal form Type A (807919-05-A) after suspended for 24 hrs.
Figure 38:
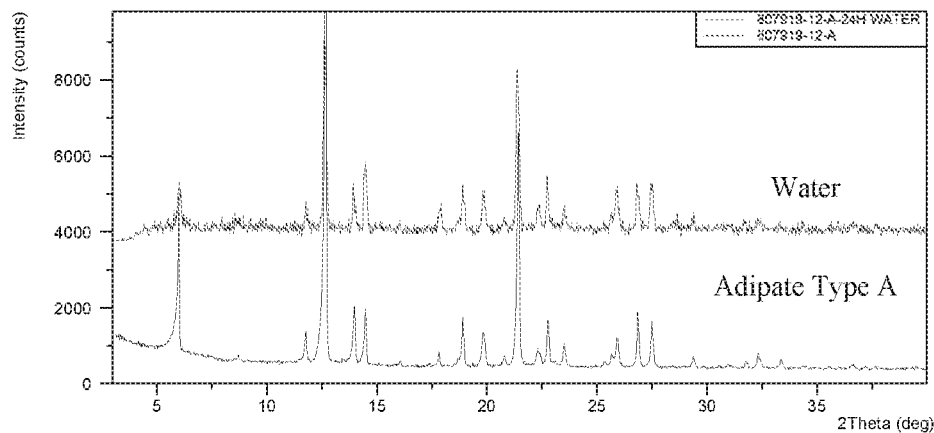
FIG. 38 illustrates a XRPD overlay of adipate crystal form Type A (807919-12-A) after suspended for 24 hrs.
Figure 39:
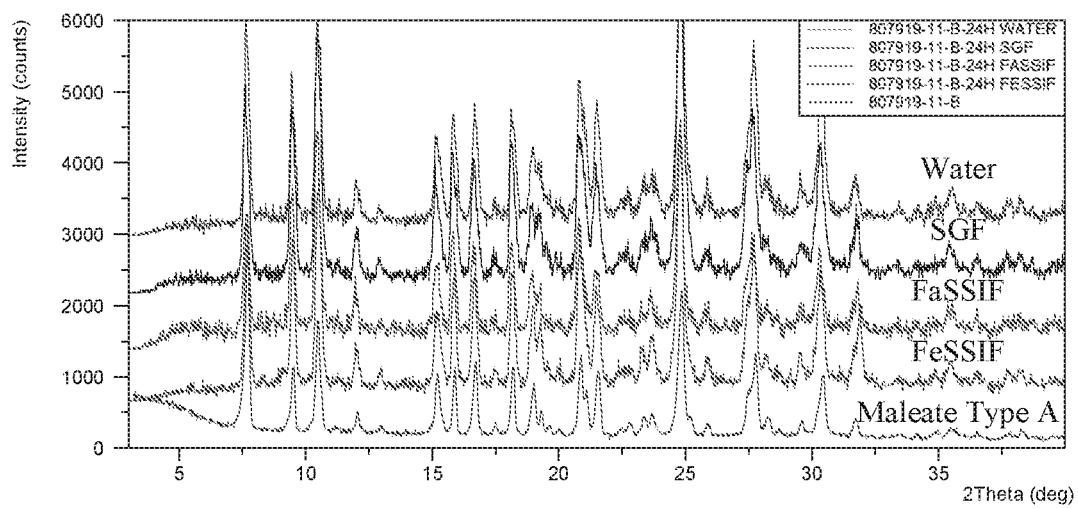
FIG. 39 illustrates a XRPD overlay of maleate crystal form Type A (807919-11-B) after suspended for 24 hrs.
Figure 40:
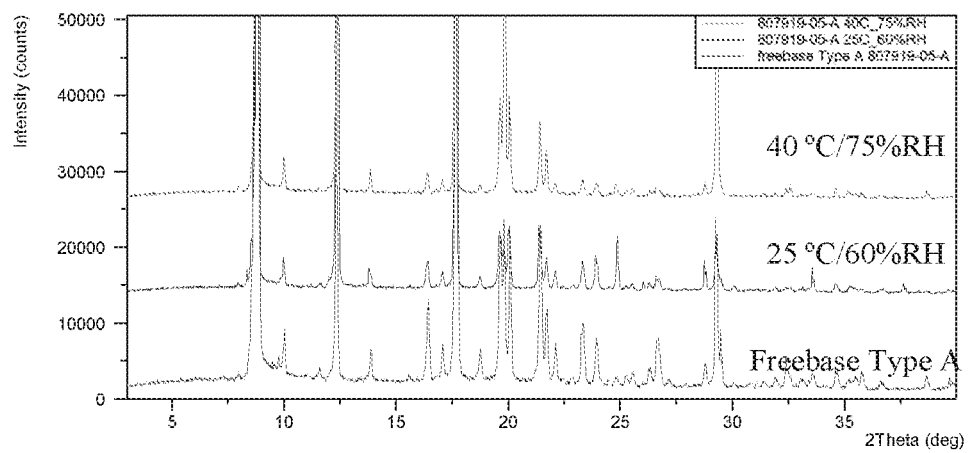
FIG. 40 illustrates a XRPD overlay of freebase crystal form Type A (807919-05-A) pre and post stability test.
Figure 41:
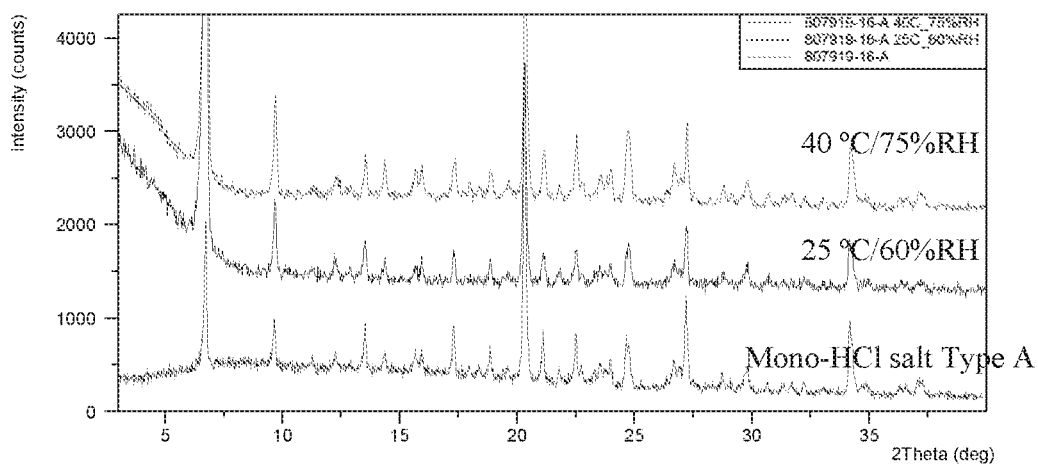
FIG. 41 illustrates a XRPD overlay of mono-HCl salt crystal form Type A (807919-16-A) pre and post stability test.
Figure 42:
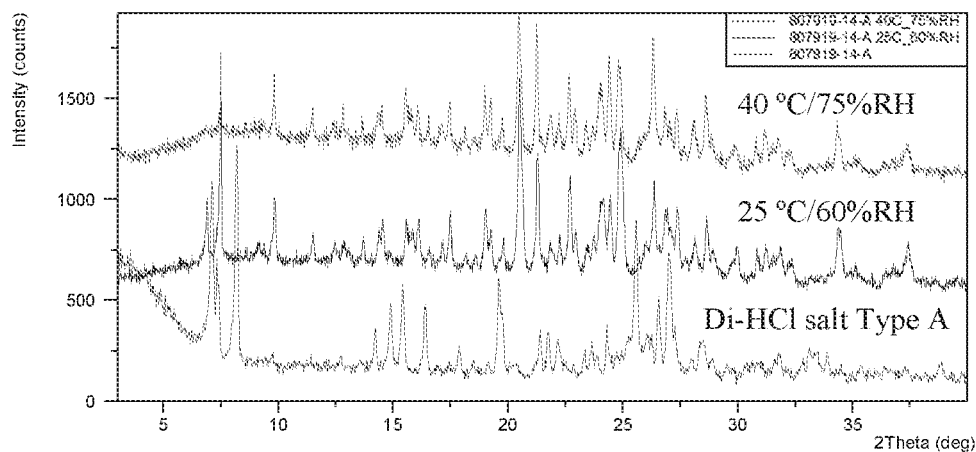
FIG. 42 illustrates a XRPD overlay of di-HCl salt crystal form Type A (807919-14-A) pre and post stability test.
Figure 43:
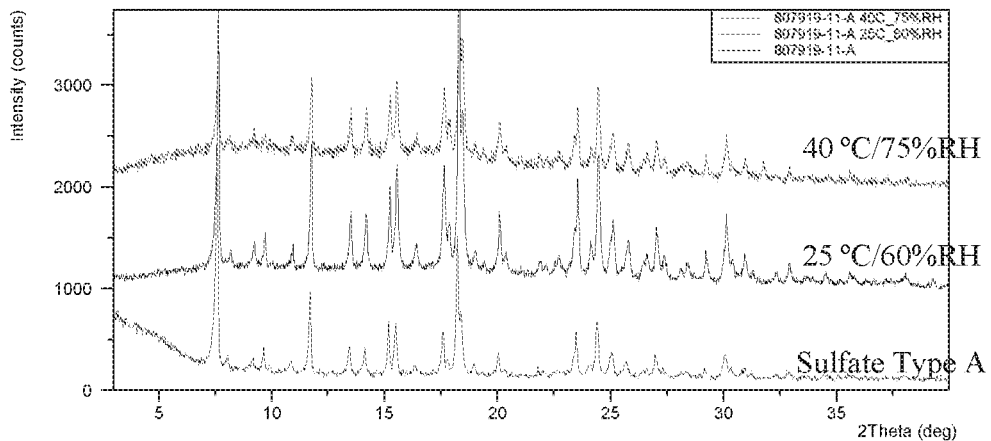
FIG. 43 illustrates a XRPD overlay of sulfate crystal form Type A (807919-11-A) pre and post stability test.
Figure 44:
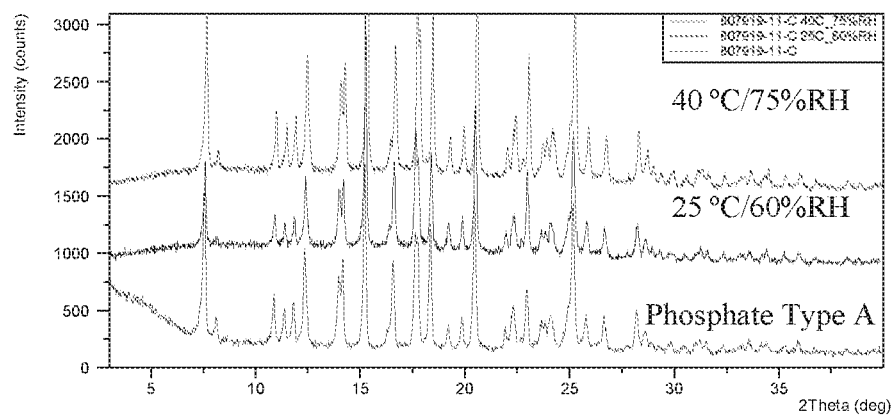
FIG. 44 illustrates a XRPD overlay of phosphate crystal form Type A (807919-11-C) pre and post stability test.
Figure 45:
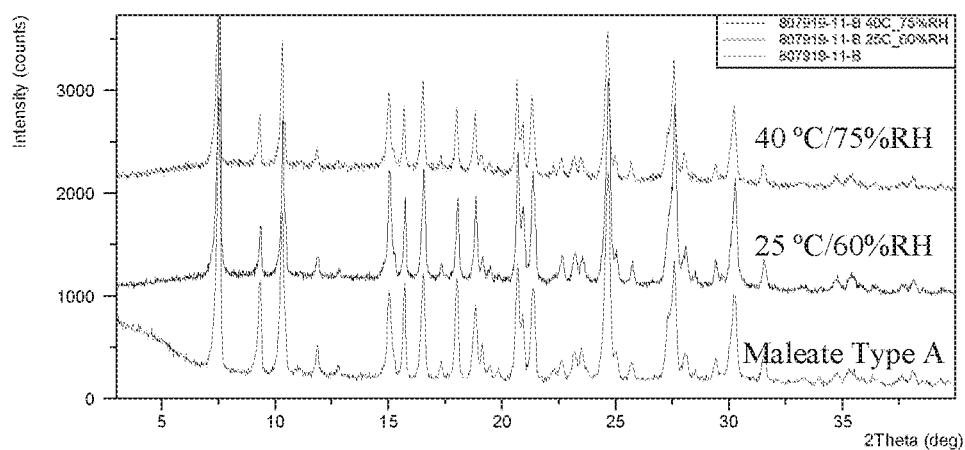
FIG. 45 illustrates a XRPD overlay of maleate crystal form Type A (807919-11-B) pre and post stability test.
Figure 46:
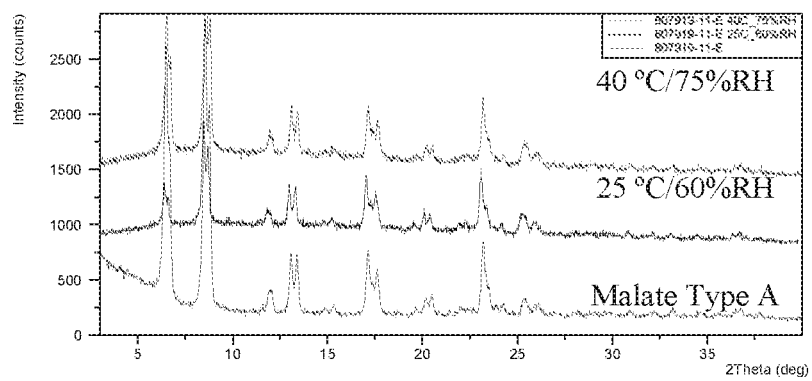
FIG. 46 illustrates a XRPD overlay of malate crystal form Type A (807919-11-E) pre and post stability test.
Figure 47:
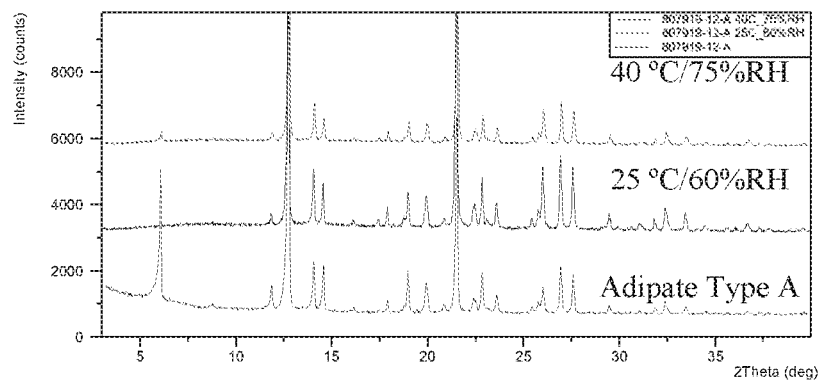
FIG. 47 illustrates a XRPD overlay of adipate crystal form Type A (807919-12-A) pre and post stability test.

The results were summarized in Table 2-11, and the kinetic solubility profiles are displayed in FIGS. 36A-D. Compared with freebase Type A, mono-HCl salt Type A, di-HCl salt Type A, sulfate Type A, phosphate Type A, malate Type A, and adipate Type A shows improved or comparable solubility in water and bio-relevant buffers. Also, remaining solids after suspended 24 hours shows no form change (FIG. 37-38). Meanwhile, decreased solubility was observed in SGF, FaSSIF, and FeSSIF after the formation of mono-maleate (maleate Type A) while no form change was detected after kinetic solubility evaluation (FIG. 39). In addition, no degradation was observed for clear solutions after 24 hours as evidenced by the HPLC results in Table 2-12.

TABLE 2-11

Summary of kinetic solubility results at RT

| | 1 hr | | | 2 hrs | | | 4 hrs | | | 24 hrs | | |
|---|---|---|---|---|---|---|---|---|---|---|---|---|
| Solid Form | S | pH | FC | S | pH | FC | S | pH | FC | S | pH | FC |
| Kinetic Solubility in Water | | | | | | | | | | | | |
| Mono-HCl salt Type A | C | N/A | N/A | C | N/A | N/A | C | N/A | N/A | 4.5* | 4.7 | N/A |
| Di-HCl salt Type A | C | N/A | N/A | C | N/A | N/A | C | N/A | N/A | 3.8* | 2.0 | N/A |
| Sulfate Type A | C | N/A | N/A | C | N/A | N/A | C | N/A | N/A | 4.1* | 2.2 | N/A |
| Phosphate Type A | C | N/A | N/A | C | N/A | N/A | C | N/A | N/A | 3.9* | 4.2 | N/A |
| Malate Type A | C | N/A | N/A | C | N/A | N/A | C | N/A | N/A | 3.7* | 4.3 | N/A |
| Maleate Type A | 0.93 | 4.2 | No | 0.98 | 4.3 | No | 1.1 | 4.2 | No | 0.97 | 5.2 | No |
| Adipate Type A | 2.8 | 5.9 | No | 2.7 | 5.8 | No | 2.8 | 5.9 | No | 2.7 | 6.0 | No |
| Freebase Type A | 0.5 | 8.4 | No | 0.5 | 8.6 | No | 0.5 | 8.1 | No | 0.5 | 8.1 | No |

TABLE 2-11-continued

Summary of kinetic solubility results at RT

| Solid Form | 1 hr | | | 2 hrs | | | 4 hrs | | | 24 hrs | | |
|---|---|---|---|---|---|---|---|---|---|---|---|---|
| | S | pH | FC | S | pH | FC | S | pH | FC | S | pH | FC |
| Kinetic Solubility in SGF | | | | | | | | | | | | |
| Mono-HCl salt Type A | C | N/A | N/A | C | N/A | N/A | C | N/A | N/A | 4.7* | 1.8 | N/A |
| Di-HCl salt Type A | C | N/A | N/A | C | N/A | N/A | C | N/A | N/A | 3.9* | 1.6 | N/A |
| Sulfate Type A | C | N/A | N/A | C | N/A | N/A | C | N/A | N/A | 3.9* | 1.8 | N/A |
| Phosphate Type A | C | N/A | N/A | C | N/A | N/A | C | N/A | N/A | 4.0* | 2.2 | N/A |
| Malate Type A | C | N/A | N/A | C | N/A | N/A | C | N/A | N/A | 4.3* | 2.4 | N/A |
| Maleate Type A | 1.4 | 2.0 | No | 1.5 | 2.0 | No | 1.6 | 2.1 | No | 1.5 | 1.9 | No |
| Adipate Type A | 4.7 | 3.4 | N/A* | C | N/A | N/A | C | N/A | N/A | 4.7* | 3.4 | N/A |
| Freebase Type A | 2.7 | 3.6 | N/A* | 3.5 | 5.0 | N/A* | 5.0 | 5.0 | N/A | 5.0 | 4.9 | N/A |
| Kinetic Solubility in FaSSIF | | | | | | | | | | | | |
| Mono-HCl salt Type A | C | N/A | N/A | C | N/A | N/A | C | N/A | N/A | 4.5* | 6.3 | N/A |
| Di-HCl salt Type A | C | N/A | N/A | C | N/A | N/A | C | N/A | N/A | 3.9* | 3.5 | N/A |
| Sulfate Type A | C | N/A | N/A | C | N/A | N/A | C | N/A | N/A | 4.0* | 3.2 | N/A |
| Phosphate Type A | C | N/A | N/A | C | N/A | N/A | C | N/A | N/A | 4.3* | 6.4 | N/A |
| Malate Type A | C | N/A | N/A | C | N/A | N/A | C | N/A | N/A | 3.7* | 5.5 | N/A |
| Maleate Type A | 2.2 | 6.1 | No | 2.3 | 6.3 | No | 2.4 | 6.1 | No | 2.3 | 6.1 | No |
| Adipate Type A | 4.3 | 6.4 | No | 4.5 | 6.2 | N/A* | 4.6 | 6.4 | N/A* | 4.5* | 6.4 | N/A |
| Freebase Type A | 2.7 | 7.0 | No | 2.8 | 7.0 | No | 2.8 | 7.1 | No | 2.9 | 7.0 | No |
| Kinetic Solubility in FeSSIF | | | | | | | | | | | | |
| Mono-HCl salt Type A | C | N/A | N/A | C | N/A | N/A | C | N/A | N/A | 4.6* | 5.0 | N/A |
| Di-HCl salt Type A | C | N/A | N/A | C | N/A | N/A | C | N/A | N/A | 3.9* | 4.9 | N/A |
| Sulfate Type A | C | N/A | N/A | C | N/A | N/A | C | N/A | N/A | 4.2* | 4.8 | N/A |
| Phosphate Type A | C | N/A | N/A | C | N/A | N/A | C | N/A | N/A | 3.8* | 5.0 | N/A |
| Malate Type A | C | N/A | N/A | C | N/A | N/A | C | N/A | N/A | 3.5* | 4.8 | N/A |
| Maleate Type A | 1.5 | 4.9 | No | 1.6 | 5.0 | No | 1.7 | 5.0 | No | 1.6 | 5.2 | No |
| Adipate Type A | C | N/A | N/A | C | N/A | N/A | C | N/A | N/A | 4.2* | 5.0 | N/A |
| Freebase Type A | 4.9 | N/A | N/A | 4.9 | N/A | N/A | 4.9 | N/A | N/A | 4.9* | 5.4 | N/A |

S: Solubility, pH: Final pH of supernatant, FC: Solid form change.
C: Clear, N/A: No data was available, N/A*: Limited solid for analysis.
*The concentration and pH data of clear solutions were collected.

TABLE 2-12

HPLC purity results of clear samples after kinetic solubility test

| Crystal Form (Batch No.) | Condition | HPLC Purity | |
|---|---|---|---|
| | | Area % | % of Initial |
| Mono-HCl salt Type A (807919-16-A) | Initial | 99.54 | — |
| | Water | 99.56 | 100.0 |
| | SGF | 99.55 | 100.0 |
| | FaSSIF | 99.61 | 100.1 |
| | FeSSIF | 99.56 | 100.0 |
| Di-HCl salt Type A (807919-14-A) | Initial | 99.56 | — |
| | Water | 99.51 | 99.9 |
| | SGF | 99.56 | 100.0 |
| | FaSSIF | 99.57 | 100.0 |
| | FeSSIF | 99.57 | 100.0 |

TABLE 2-12-continued

HPLC purity results of clear samples after kinetic solubility test

| Crystal Form (Batch No.) | Condition | HPLC Purity Area % | % of Initial |
|---|---|---|---|
| Sulfate Type A (807919-11-A) | Initial | 99.32 | — |
| | Water | 99.31 | 100.0 |
| | SGF | 99.30 | 100.0 |
| | FaSSIF | 99.36 | 100.0 |
| | FeSSIF | 99.31 | 100.0 |
| Phosphate Type A (807919-11-C) | Initial | 99.31 | — |
| | Water | 99.34 | 100.0 |
| | SGF | 99.33 | 100.0 |
| | FaSSIF | 99.34 | 100.0 |
| | FeSSIF | 99.30 | 100.0 |
| Malate Type A (807919-11-E) | Initial | 99.81 | — |
| | Water | 99.80 | 100.0 |
| | SGF | 99.73 | 99.9 |
| | FaSSIF | 99.78 | 100.0 |
| | FeSSIF | 99.86 | 100.1 |
| Adipate Type A (807919-12-A) | Initial | 99.90 | — |
| | SGF | 99.87 | 100.0 |
| | FeSSIF | 99.94 | 100.0 |
| Freebase Type A (807919-05-A) | Initial | 99.32 | — |
| | FeSSIF | 99.25 | 99.9 |

2.3.3 Physical and Chemical Stability

Physicochemical stability of seven salt leads was evaluated under 25° C./60% RH and 40° C./75% RH for one week, using freebase Type A (807919-05-A) as control. Stability samples were characterized by XRPD and HPLC, with the results summarized in Table 2-13. The XRPD patterns were shown from FIG. 40-47, indicating no form change for investigated forms except di-HCl salt Type A. Also, no substantial purity change was observed for seven leads and freebase Type A. All the data indicated good physical and chemical stability for mono-HCl salt Type A, sulfate Type A, phosphate Type A, maleate Type A, malate Type A, adipate Type A, and freebase Type A under tested conditions at least one week.

TABLE 2-13

Stability evaluation summary of salt leads and freebase Type A

| Crystal Form (Batch No.) | HPLC Purity (Initial, area %) | Condition | HPLC Purity Area % | % of Initial | Form change |
|---|---|---|---|---|---|
| Freebase Type A (807919-05-A) | 99.32 | 25° C./60% RH | 99.15 | 99.8 | No |
| | | 40° C./75% RH | 99.28 | 100.0 | No |
| Mono-HCl salt Type A (807919-16-A) | 99.54 | 25° C./60% RH | 99.46 | 99.9 | No |
| | | 40° C./75% RH | 99.47 | 99.9 | No |
| Di-HCl salt Type A (807919-14-A) | 99.56 | 25° C./60% RH | 99.62 | 100.1 | Yes |
| | | 40° C./75% RH | 99.70 | 100.1 | Yes |
| Sulfate Type A (807919-11-A) | 99.32 | 25° C./60% RH | 99.33 | 100.0 | No |
| | | 40° C./75% RH | 99.37 | 100.1 | No |
| Phosphate Type A (807919-11-C) | 99.31 | 25° C./60% RH | 99.31 | 100.0 | No |
| | | 40° C./75% RH | 99.37 | 100.1 | No |
| Maleate Type A (807919-11-B) | 99.32 | 25° C./60% RH | 99.32 | 100.0 | No |
| | | 40° C./75% RH | 99.36 | 100.0 | No |
| Malate Type A (807919-11-E) | 99.81 | 25° C./60% RH | 99.83 | 100.0 | No |
| | | 40° C./75% RH | 99.77 | 100.0 | No |
| Adipate Type A (807919-12-A) | 99.90 | 25° C./60% RH | 99.88 | 100.0 | No |
| | | 40° C./75% RH | 99.89 | 100.0 | No |

2.4 Conclusions

A total of 32 crystalline hits were generated via salt screening. Based on the characterization results, seven salt leads, namely mono-HCl salt Type A, di-HCl salt Type A, sulfate Type A, phosphate Type A, maleate Type A, malate Type A, and adipate Type A, were selected to re-prepared for further evaluation including hygroscopicity, kinetic solubility, and solid-state stability. Considering the results summarized in Table 2-14 and Table 2-15, sulfate was recommended as a salt candidate for further polymorphism investigation.

TABLE 2-14

Characterization summary of salt leads and freebase Type A (I/II)

| Crystal Form | Mono-HCl salt Type A | Di-HCl salt Type A | Sulfate Type A | Phosphate Type A |
|---|---|---|---|---|
| Batch No. | 807919-16-A | 807919-14-A | 807919-11-A | 807919-11-C |
| Speculated Form | Anhydrate | Hydrate/Solvate | Anhydrate | Anhydrate |
| Safety Class* | I | I | I | I |
| Stoichiometry (acid/base) | 1.01 | 2.15 | 1.03 | 1.07 |

TABLE 2-14-continued

Characterization summary of salt leads and freebase Type A (I/II)

| Crystal Form | Mono-HCl salt Type A | Di-HCl salt Type A | Sulfate Type A | Phosphate Type A |
|---|---|---|---|---|
| Crystallinity | High | High | High | High |
| Weight Loss (%) | 1.1 | 1.2 | 0.9 | 1.2 |
| Endotherm (onset, ° C.) | 246.7, 264.8 | (99.5, 191.7, 250.7, 261.9)** | 214.4 | (250.9, 254.2)** |
| HPLC Purity (area %) | 99.54 | 99.53 | 99.19 | 99.36 |
| Morphology | | Small particles (<10 μm) and aggregation | | |
| Water Uptake at 25° C./80% RH | 2.9 | 12.2 | 0.4 | 1.1 |
| Form Change Post DVS Test | No | Yes | No | No |
| Kinetic Solubility at RT (mg/mL) | | >3.8 (water/bio-relevant media) | | |
| One-week Solid-state Stability | | Good physiochemical stability under 25° C./60% RH and 40° C./75% RH at least one week for all salt forms except di-HCl salt Type A exhibited form change | | |

*Safety class of acid used, according to *Handbook of Pharmaceutical Salts: Properties, Selection and Uses*, Wiley-VCH: Zurich, 2002.
**peak temperature

TABLE 2-15

Characterization summary of salt leads and freebase Type A (II/II)

| Crystal Form | Maleate Type A | Malate Type A | Adipate Type A | Freebase Type A |
|---|---|---|---|---|
| Batch No. | 807919-11-B | 807919-11-E | 807919-12-A | 807919-05-A |
| Speculated Form | Anhydrate | Anhydrate | Anhydrate | Anhydrate |
| Safety Class* | I | I | I | — |
| Stoichiometry (acid/base) | 0.96 | 1.02 | 0.52 | — |
| Crystallinity | High | High | High | High |
| Weight Loss (%) | 1.3 | 1.0 | 0.9 | 0.3 |
| Endotherm (onset, ° C.) | 224.1 | 192.9 | 218.0 | 193.3 |
| HPLC Purity (area %) | 99.19 | 99.88 | 99.94 | 99.09 |
| Morphology | Small particles (<10 μm) and aggregation | Irregular particles and aggregation | Small particles (<10 μm) and aggregation | |
| Water Uptake at 25° C./80% RH | 0.4 | 0.2 | 0.7 | 0.1 |
| Form Change Post DVS Test | No | No | No | No |
| Kinetic Solubility at RT (mg/mL) | ~1.0 (water) ~1.5 (bio-relevant media) | >3.5 (water/bio-relevant media) | ~2.7 (water) >4.2 (bio-relevant media) | ~0.5 (water) ~2.9 (FaSSIF) >4.9 (SGF/FeSSIF) |
| One-week Solid-state Stability | | Good physiochemical stability under 25° C./60% RH and 40° C./75% RH | | |

*Safety class of acid used, according to *Handbook of Pharmaceutical Salts: Properties, Selection and Uses*, Wiley-VCH: Zurich, 2002.

3 Polymorphism Investigation on Sulfate
3.1 Polymorph Screening Summary

Using re-prepared sulfate Type A (807919-21-A) as starting material, polymorph screening experiments were conducted under 100 conditions with different crystallization or solid transition methods. The detailed procedures can be found in Section 5.5.

As results summarized in Table 3-1 and Table 3-2, three crystal forms were obtained, with starting sulfate Type A as an anhydrate, sulfate Type B as a DMSO solvate, and hemi-sulfate Type A as a hydrate.

TABLE 3-1

Summary of polymorph screening experiments

| Method | No. of Experiments | Crystal Form |
|---|---|---|
| Anti-solvent Addition | 18 | Sulfate Type A |
| Solid Vapor Diffusion | 13 | Sulfate Type A, B |
| Solution Vapor Diffusion | 10 | Sulfate Type A |
| Slow Evaporation | 8 | Sulfate Type A, hemi-sulfate Type A |

TABLE 3-1-continued

Summary of polymorph screening experiments

| Method | No. of Experiments | Crystal Form |
|---|---|---|
| Polymer-induced Crystallization | 6 | Sulfate Type A |
| Slurry at RT/50° C. | 38 | Sulfate Type A, hemi-sulfate Type A |
| Slow Cooling | 7 | Sulfate Type A, B |
| Total | 100 | Sulfate Type A/B, hemi-sulfate Type A |

TABLE 3-2

Characterization summary of sulfate forms

| Crystal Form (Sample ID) | Crystallization Condition | Wt Loss (%) | Endotherm (onset, ° C.) | Stoichiometry (acid/base) | HPLC purity (area %) | Comment |
|---|---|---|---|---|---|---|
| Sulfate Type A (807919-21-A) | Reactive crystallization in THF | 2.0 | 209.6 | 1.1 | 99.4 | Anhydrate |
| Sulfate Type B (807919-25-A13) | Solid vapor diffusion in DMSO | 11.7 | 111.2, 202.2 | N/A | N/A | DMSO solvate |
| Hemi-sulfate Type A (807919-34-A) | Reactive crystallization acetone/$H_2O$ ($a_w$ = 0.8) | 5.9 | 105.3*, 217.0 | 0.5 | 99.6 | Hydrate |

*peak temperature

3.1.1 Sulfate Type B

Figure 48:
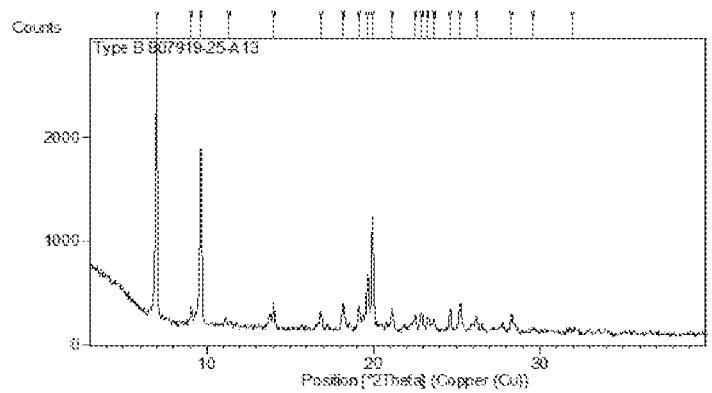
FIG. 48 illustrates a XRPD pattern of sulfate crystal form Type B (807919-25-A13).

Sulfate Type B sample (807919-25-A13) was obtained via solid vapor diffusion in DMSO at RT, with the XRPD pattern displayed in FIG. 48. XRPD data for sulfate Type B provide (peak shift within ±0.2°) primary peaks at 7.0, 9.6, and 20.0; secondary peaks at 18.2, 19.6, and 25.2; and tertiary peaks at 14.0, 24.6, and 28.3.

Figure 49:
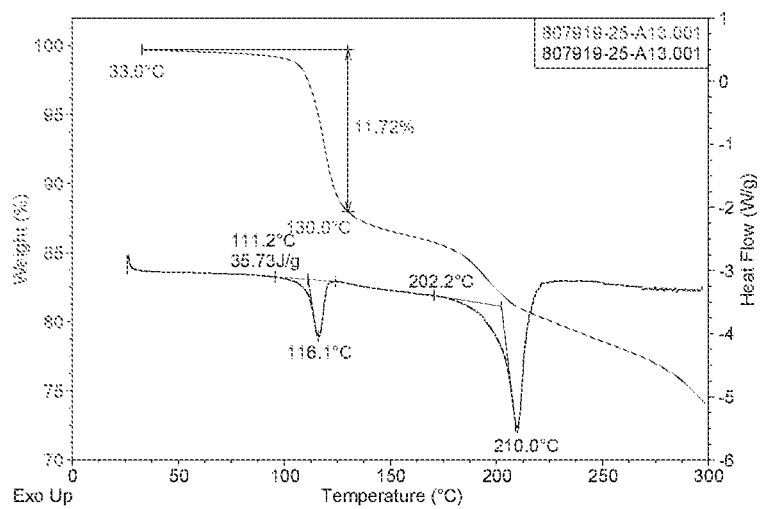
FIG. 49 illustrates TGA/DSC curves of sulfate crystal form Type B (807919-25-A13).
Figure 50:
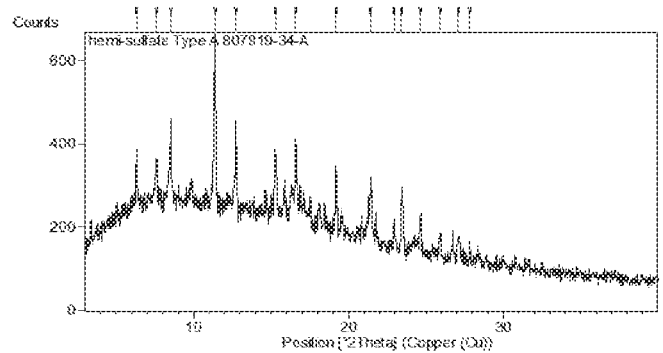
FIG. 50 illustrates a XRPD pattern of hemi-sulfate crystal form Type A (807919-34-A).

TGA and DSC results were shown in FIG. 49. A weight loss of 11.7% was observed up to 130° C. and DSC shows two endothermic peaks at 111.2° C. and 202.2° C. (onset temperature) before decomposition, with the first due to desolvation and second attributed to melting. Sulfate Type B converts to anhydrate sulfate Type A after being heated to 120° C. Also, DMSO content of 11.3% was detected by $^1H$ NMR, which was consistent with weight loss in TGA. Considering all the characterization data, sulfate Type B was calculated as a DMSO solvate.

3.1.2 Hemi-Sulfate Type A

Figure 51:
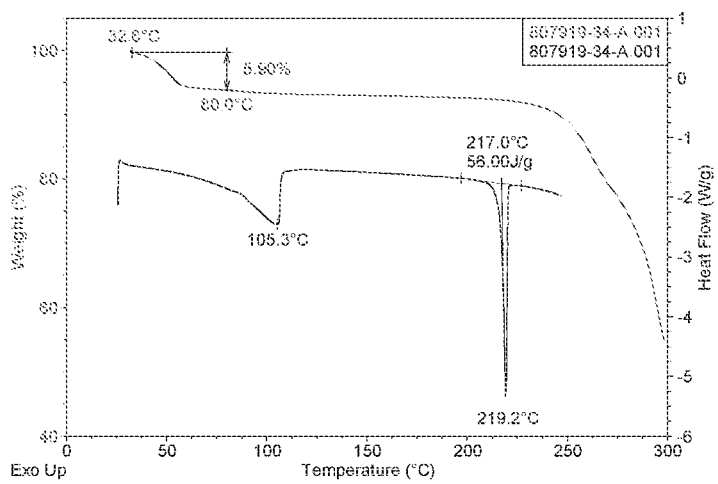
FIG. 51 illustrates TGA/DSC curves of hemi-sulfate crystal form Type A (807919-34-A).

Hemi-sulfate Type A was obtained in acetone/$H_2O$ ($a_w$=0.8) system. Hemi-sulfate Type A sample (807919-34-A) was generated via reactive crystallization in acetone/$H_2O$ ($a_w$=0.8) at RT, with a molar charge ratio of 0.5:1 (acid/base). The XRPD pattern was shown in FIG. 50 and TGA/DSC data were displayed in FIG. 51. XRPD data for hemi-sulfate Type A provide (peak shift within ±0.2°) primary peaks at 8.5, 11.4, and 12.7; secondary peaks at 6.3, 16.6, and 19.2; and tertiary peaks at 7.6, 15.3, and 23.4.

A weight loss of 5.9% was observed up to 80° C. in TGA and DSC result shows two endothermic peaks at 105.3° C. and 219.2° C. (peak temperature) before decomposition, with the first due to dehydration and the second attributed to melting. A purity of 99.6 area % was detected via HPLC (Table 3-3). $^1H$ NMR results shows limited acetone detected. Combined with the stoichiometry of 0.50 (acid/base) detected by HPLC/IC, sample (807919-34-A) was speculated as a hydrate of hemi-sulfate.

TABLE 3-3

HPLC purity profile of hemi-sulfate Type A (807919-34-A)

| # | RRT | Area % |
|---|---|---|
| 1 | 0.75 | 0.05 |
| 2 | 0.83 | 0.33 |
| 3 | 1.00 | 99.62 |
| — | — | — |

3.2 Stability Research for Sulfate Type A

3.2.1 Disproportionation Risk Study

Figure 52:
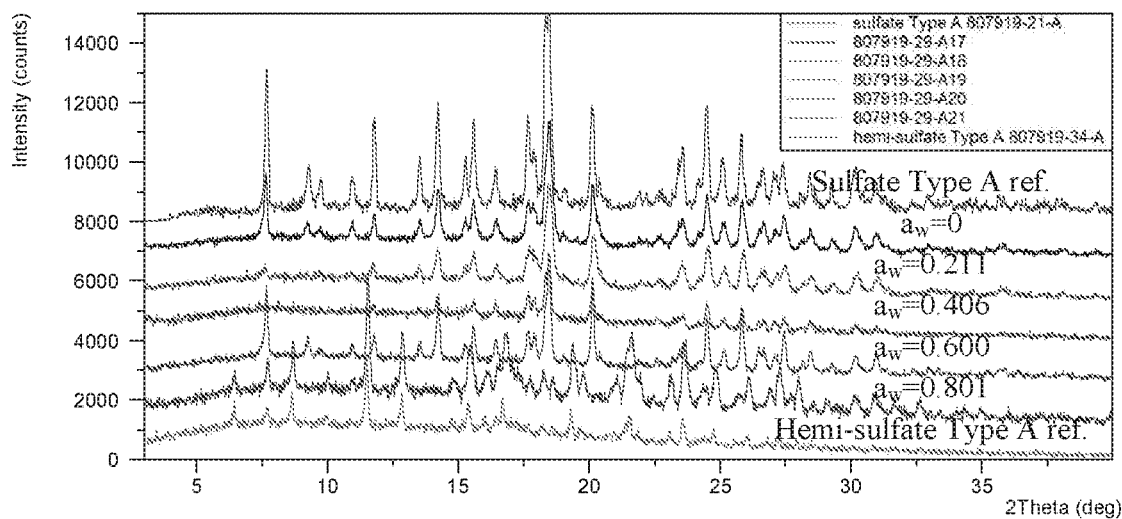
FIG. 52 illustrates a XRPD overlay of slurry experiments at RT.

A series of slurry experiments were performed at various water activities (0-0.8) to evaluate the disproportionation risk. For details, about 15 mg sulfate Type A sample were weighed to 0.5 mL acetone/$H_2O$ systems with $a_w$ range from 0 to 0.8. After the suspensions stirred at RT for 5 days, the remaining solids were characterized by XRPD. As results shown in Table 3-4 and FIG. 52, no form change was observed when $a_w$ lower than 0.6 while hemi-sulfate Type A was generated at $a_w$=0.8, suggesting the disproportionation risk of sulfate Type A at high relative humidity.

TABLE 3-4

Summary of slurry experiments results at RT

| Experiment ID | Starting Form | Acetone/$H_2O$ (v:v) | $a_w$* | Final Form |
|---|---|---|---|---|
| 807919-29-A17 | | 1000:0 | 0 | Sulfate Type A |
| 807919-29-A18 | | 984:16 | 0.211 | Sulfate Type A |
| 807919-29-A19 | Sulfate Type A | 948:52 | 0.406 | Sulfate Type A |
| 807919-29-A20 | | 857:143 | 0.600 | Sulfate Type A |
| 807919-29-A21 | | 604:396 | 0.801 | Hemi-sulfate Type A |

*calculated value

3.2.2 Thermo-Stability Study

Figure 53:
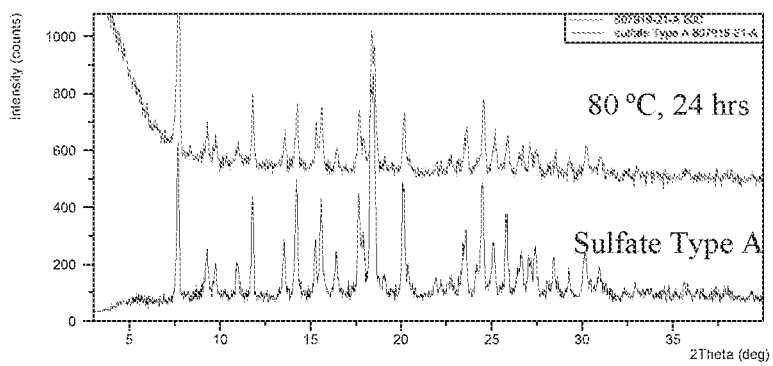
FIG. 53 illustrates a XRPD overlay of sulfate crystal form Type A (807919-21-A) before and after storage.

To understand the thermo-stability under elevated temperature, sulfate Type A sample (807919-21-A) was stored at 80° C. for 24 hours and then tested by XRPD and HPLC. As displayed in Table 3-5 and FIG. 53, no solid form change or HPLC impurity increase was observed, suggesting good physical and chemical stability under the tested condition.

TABLE 3-5

HPLC purity profile of sulfate Type A
(807919-21-A) before and after storage

| | Area (%) | |
|---|---|---|
| RRT | Initial | 80° C./24 hrs |
| 0.75 | 0.11 | 0.07 |
| 0.83 | 0.64 | 0.63 |
| 1.00 | 99.14 | 99.21 |
| 1.42 | 0.11 | 0.09 |

3.3 Conclusions

A total of three crystal forms were obtained via polymorph screening, including two mono-sulfate (anhydrate Type A/DMSO solvate Type B) and hemi-sulfate Type A.

In addition, the disproportionation risk and thermo-stability were evaluated for sulfate Type A. As results show: 1) sulfate Type A converted to hemi-sulfate Type A at $a_w$=0.8, suggesting the disproportionation risk at high relative humidity, 2) sulfate Type A shows no substantial change in crystal form or HPLC purity, indicating the good thermo-stability after storage at 80° C. for 24 hours. Based on the polymorph screening and evaluation results, sulfate Type A was speculated as the thermodynamically stable form at RT of mono-sulfate.

4. Conclusions

Salt screening for resiquimod freebase was performed under 100 conditions and a total of 32 crystalline hits were isolated. Based on the characterization results, seven salt leads of mono-HCl salt, di-HCl salt, sulfate, phosphate, maleate, malate, and adipate were selected as leading salts for further evaluation including hygroscopicity, kinetic solubility, and solid-state stability. As evidenced by the results, sulfate with good physicochemical properties was recommended as salt candidate. Using sulfate Type A as starting material, a polymorph screening was performed under 100 conditions and three crystalline forms were observed, including one anhydrate (Type A), one DMSO solvate (Type B), and one hemi-sulfate, suggesting sulfate Type A as a leading form of mono-sulfate. In addition, sulfate Type A shows good physicochemical properties under 80° C. for 24 hours but could convert to hemi-sulfate at high relative humidity.

5.1 Characterization of Starting Materials 5.1.1 Starting Freebase of Salt Screening The starting freebase (sample resiquimod, with a CP ID of 807919-05-A) was characterized by XRPD, PLM, TGA, DSC, HPLC, and DVS.

Figure 54:
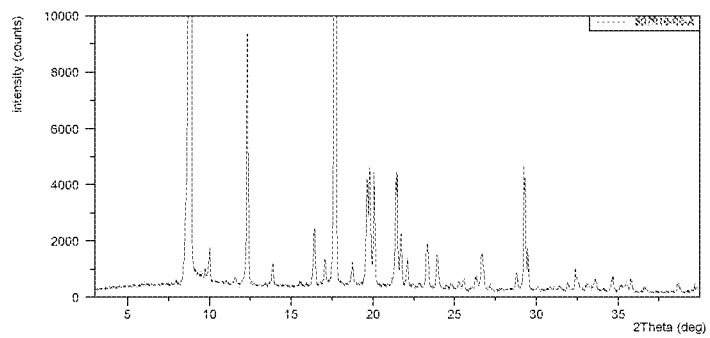
FIG. 54 illustrates a XRPD pattern of freebase crystal form Type A (807919-05-A).
Figure 55:
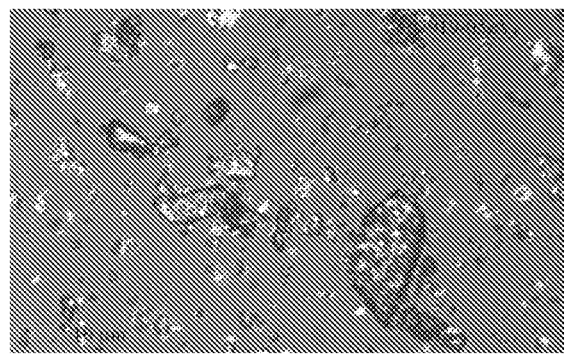
FIG. 55 illustrates a PLM image of freebase crystal form Type A (807919-05-A).
Figure 56:
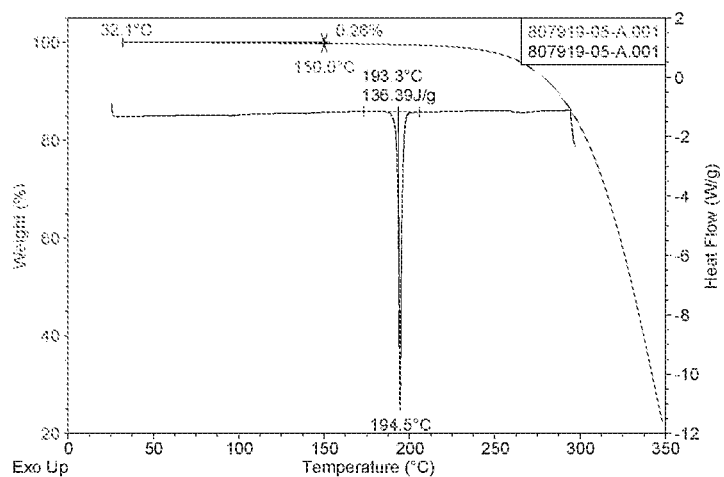
FIG. 56 illustrates TGA/DSC curves of freebase crystal form Type A (807919-05-A).
Figure 57:
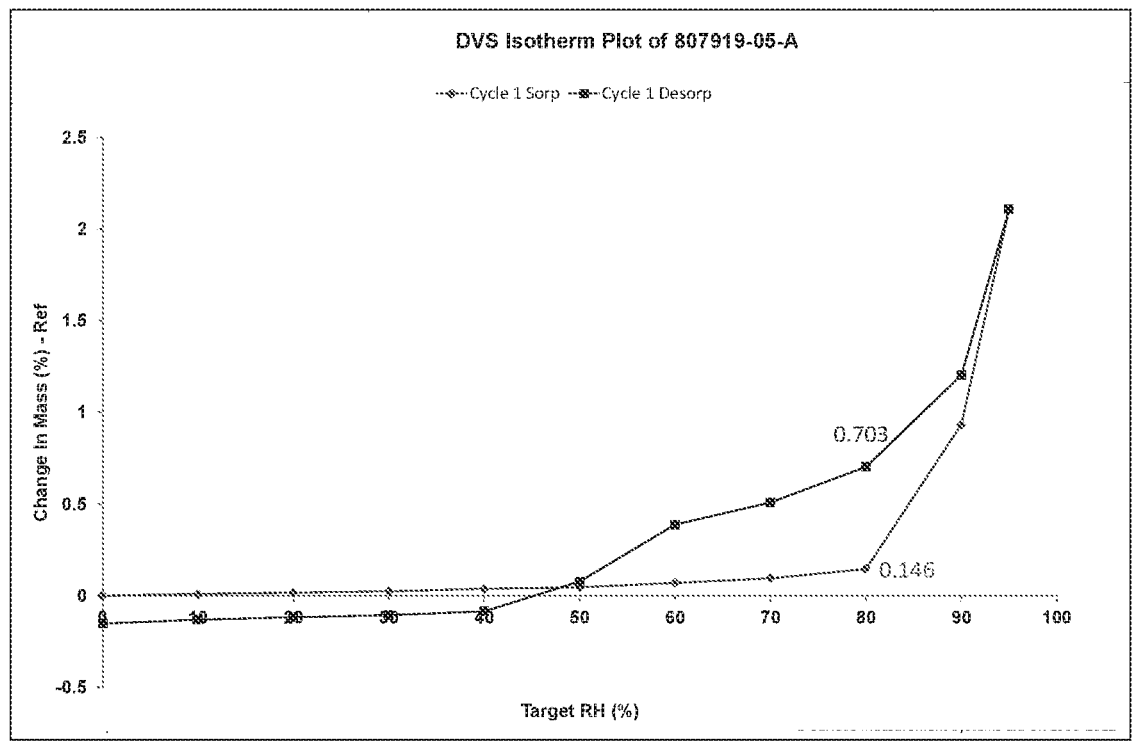
FIG. 57 illustrates a DVS plot of freebase crystal form Type A (807919-05-A).
Figure 58:
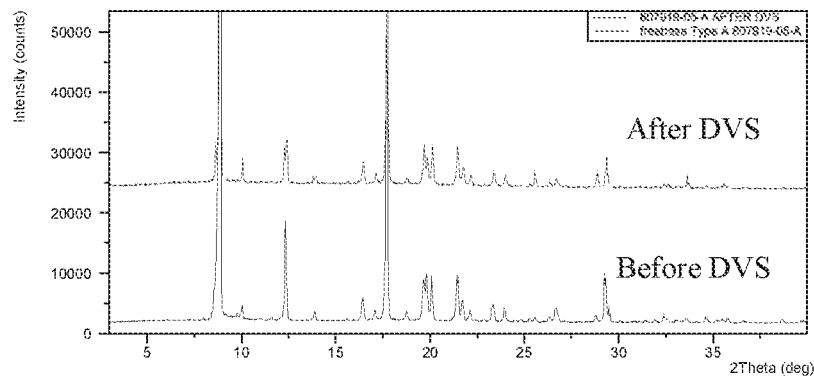
FIG. 58 illustrates a XRPD overlay of freebase crystal form Type A (807919-05-A) before and after DVS test.

XRPD result in FIG. 54 shows the sample (807919-05-A) was crystalline and defined as freebase Type A. PLM image displayed in FIG. 55 illustrated aggregation of small particles (<10 μm). As per TGA and DSC results shown in FIG. 56, a weight loss of 0.3% was observed up to 150° C. in TGA and the DSC curve show a single endothermic peak at 193.3° C. (onset temperature). A purity of 99.1 area % was detected via HPLC (Table 5-1). DVS plot in FIG. 57 shows a water uptake of 0.1% up to 80% RH, suggesting freebase Type A was non-hygroscopic. Also, no form change was observed after DVS evaluation in FIG. 58.

The received freebase Type A (807919-05-A) was used as the starting material for salt screening. Solubility of Type A was estimated in nine solvents at RT. Approximately 2 mg of solids were weighed into each 3-mL glass vial, to which each of the solvents in Table 5-2 was added in increments of 100 μL until the solids dissolved completely or the total volume reached 1 mL. Solubility ranges of the starting material summarized in Table 5-2 were used to guide the solvent selection for salt screening.

TABLE 5-1

HPLC purity profile of freebase Type A (807919-05-A)

| # | RRT | Area % |
|---|---|---|
| 1 | 0.75 | 0.05 |
| 2 | 0.83 | 0.72 |
| 3 | 0.87 | 0.05 |
| 4 | 1.00 | 99.09 |
| 5 | 1.44 | 0.10 |

TABLE 5-2

Solubility estimation of freebase Type A (807919-05-A) at RT

| Solvent | Solubility (mg/mL) | Solvent | Solubility (mg/mL) |
|---|---|---|---|
| MeOH | S > 42.0 | DCM | 2.1 < S < 7.0 |
| EtOH | 22.0 < S < 44.0 | EtOAc | 2.0 < S < 6.7 |
| THF | 20.0 < S < 40.0 | n-heptane | S < 2.1 |
| Acetone | 7.3 < S < 22.0 | H$_2$O | S < 2.0 |
| ACN | 2.2 < S < 7.3 | — | — |

5.1.2 Starting Sulfate of Polymorph Screening

Figure 59:
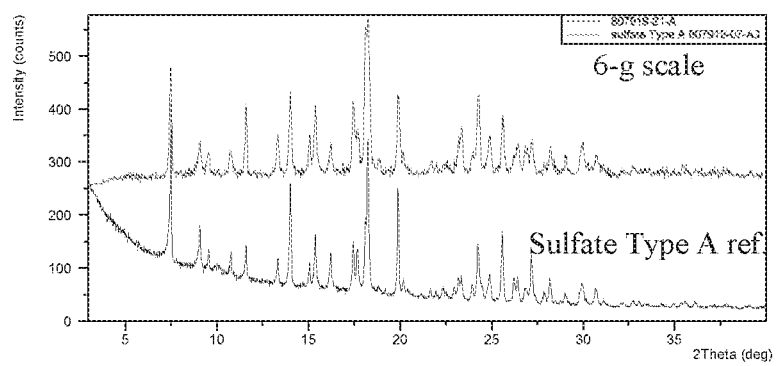
FIG. 59 illustrates XRPD patterns of sulfate crystal form Type A batches.
Figure 60:
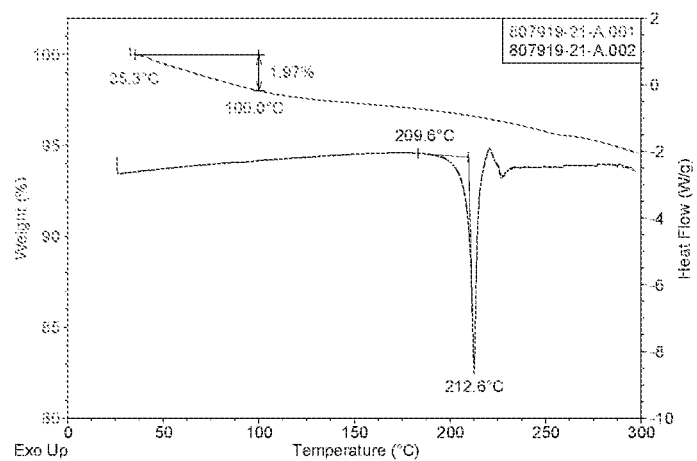
FIG. 60 illustrates TGA/DSC curves of sulfate crystal form Type A (807919-21-A).
Figure 61:
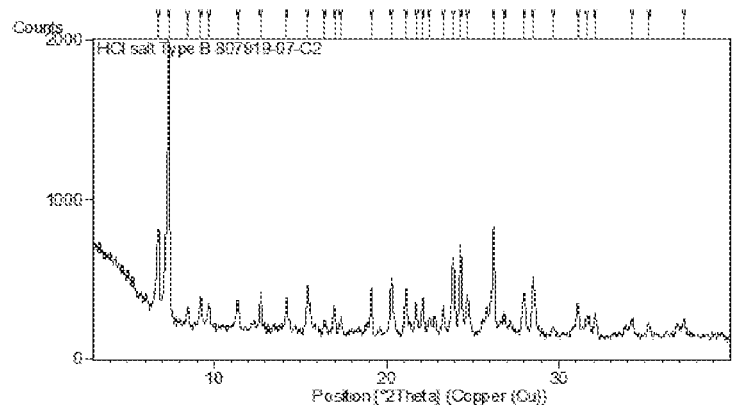
FIG. 61 illustrates XRPD patterns of HCl salt crystal forms.

XRPD comparison in FIG. 59 indicated sulfate Type A (807919-21-A) was successfully re-prepared on 6-g scale. Detailed procedures were provided in Table 5-3. As per TGA and DSC results shown in FIG. 60, a weight loss of 2.0% was observed up to 100° C. and DSC data show a sharp melting peak at 209.6° C. (onset temperature). Also, a purity of 99.4 area % was detected via HPLC in Table 5-4 and the stoichiometry was determined as 1.11 (acid/base) by HPLC/IC.

The re-prepared sulfate Type A (807919-21-A) was used as the starting material of polymorph screening. The solubility data in Table 5-5 were collected adopting the same procedures as Section 5.1.1 and used to guide the solvent selection in polymorph screening design.

TABLE 5-3

Preparation procedures of sulfate Type A (807919-21-A)
Preparation Procedures

1. Weigh 4 g freebase (807919-05-A) into a 200-mL glass vial and dissolve the solids with 80 mL THF at 50° C.
2. Measure 1.3 g of sulfuric acid (charge ratio of 1:1, acid/base) and dilute with 20 mL THF.
3. Add the acid solution to the freebase solution drop by drop with stirring magnetically at a speed of 1500 rpm.
4. Add ~50 mg seed (807919-11-A) into the system and continue to stir at RT overnight.
5. Sampling for XRPD and DSC analysis, and both results conform to the reference.
6. Mix the 4-g batch with the 1-g batch (807919-20-A) prepared previously and stir for 1 hr.

TABLE 5-3-continued

Preparation procedures of sulfate Type A (807919-21-A)
Preparation Procedures

7. Vacuum filter and dry the wet cake at 50° C. for 2 hrs followed by vacuum drying at RT overnight.
8. Collect 6.4 g solids for analysis (approximate yield of 96.8%).

TABLE 5-4

HPLC purity profile of sulfate Type A (807919-21-A)

| # | RRT | Area % |
|---|-----|--------|
| 1 | 0.84 | 0.58 |
| 2 | 1.00 | 99.36 |
| 3 | 1.40 | 0.06 |
| — | — | — |

TABLE 5-5

Solubility estimation of sulfate Type A (807919-21-A) at RT

| Solvent | Solubility (mg/mL) | Solvent | Solubility (mg/mL) |
|---|---|---|---|
| MeOH | 20.0 < S < 40.0 | 2-MeTHF | S < 2.2 |
| EtOH | 7.0 < S < 21.0 | 1,4-dioxane | S < 2.1 |
| IPA | S < 2.2 | Anisole | S < 2.2 |
| IBA | S < 2.1 | ACN | S < 2.2 |
| Acetone | S < 2.0 | CHCl$_3$ | S < 2.0 |
| MEK | S < 2.0 | n-heptane | S < 2.1 |
| MIBK | S < 2.1 | toluene | S < 2.0 |
| EtOAc | S < 2.2 | DMAc | S > 40.0 |
| IPAc | S < 2.0 | DMSO | S > 44.0 |
| Ethyl lactate | S < 2.2 | NMP | S > 44.0 |
| MTBE | S < 2.3 | H$_2$O | S > 44.0 |
| THF | S < 2.3 | DCM | S < 2.3 |

5.2 Abbreviations for Solvents Used

The abbreviations for solvents used are listed in Table 5-6.

TABLE 5-6

Abbreviations of solvents

| Abbreviation | Solvent | Abbreviation | Solvent |
|---|---|---|---|
| MeOH | Methanol | THF | Tetrahydrofuran |
| EtOH | Ethanol | 2-MeTHF | 2-Methyltetrahydrofuran |
| IPA | Isopropyl alcohol | DCM | Dichloromethane |
| IBA | Isobutyl alcohol | CHCl$_3$ | Trichloromethane |
| MEK | 2-Butanone | ACN | Acetonitrile |
| MIBK | 4-Methyl-2-pentanone | DMSO | Dimethylsulfoxide |
| EtOAc | Ethyl acetate | DMAc | N,N-Dimethylacetamide |
| IPAc | Isopropyl acetate | NMP | 1-Methyl-2-pyrrolidone |
| MTBE | Methyl tert-butyl ether | — | — |

5.3 Instruments and Methods 5.3.1 XRPD

For XRPD analysis, a PANalytical Empyrean X-ray powder diffractometer was used. The parameters used are listed in Table 5-7.

TABLE 5-7

Parameters for XRPD test

| Parameter | Value |
|---|---|
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (° 2TH) | 3°-40° |
| Step size (° 2TH) | 0.013 |
| Scan speed (°/min) | About 10 |

5.3.2 TGA/DSC

TGA data were collected using a TA Q500/Q5000 TGA from TA Instruments. DSC was performed using a TA Q200/Q2000 DSC from TA Instruments. Detailed parameters used are listed in Table 5-8.

TABLE 5-8

Parameters for TGA and DSC test

| Parameters | TGA | DSC |
|---|---|---|
| Method | Ramp | Ramp |
| Sample pan | Platinum, open | Aluminum, crimped |
| Temperature | RT - desired temperature | |
| Heating rate | 10° C./min | |
| Purge gas | N$_2$ | |

5.3.3 HPLC

Agilent 1100 HPLC was utilized to analyze purity and solubility, with detailed method listed in Table 5-9 and Table 5-10.

TABLE 5-9

HPLC method for purity test

| HPLC | Agilent 1100 with DAD Detector |
|---|---|
| Column | Alltima C18, 150 × 4.6 mm, 5 μm |
| Mobile phase | A: 0.1% TFA in H$_2$O<br>B: 0.1% TFA in Acetonitrile |

| | Time (min) | % B |
|---|---|---|
| Gradient table | 0.0 | 10 |
| | 10.0 | 40 |
| | 18.0 | 90 |
| | 20.0 | 90 |
| | 20.1 | 10 |
| | 23.0 | 10 |
| Run time | 23.0 min | |
| Post time | 0.0 min | |
| Flow rate | 1.0 mL/min | |
| Injection volume | 5 μL | |
| Detector wavelength | UV at 228 nm, reference 500 nm | |
| Column temperature | 40° C. | |
| Sampler temperature | RT | |
| Diluent | Acetonitrile:H$_2$O = 1:1 | |

TABLE 5-10

| HPLC method for solubility test | |
| --- | --- |
| HPLC | Agilent 1100 with DAD Detector |
| Column | Waters Xbridge C18, 150 × 4.6 mm, 5 μm |
| Mobile phase | A: 0.1% TFA in $H_2O$ |
| | B: 0.1% TFA in Acetonitrile |

| | Time (min) | % B |
| --- | --- | --- |
| Gradient table | 0.0 | 10 |
| | 5.0 | 90 |
| | 7.0 | 90 |
| | 7.1 | 10 |
| | 10.0 | 10 |
| Run time | 10.0 min | |
| Post time | 0.0 min | |
| Flow rate | 1.0 mL/min | |
| Injection volume | 10 μL | |
| Detector wavelength | UV at 228 nm, reference 500 nm | |
| Column temperature | 40° C. | |
| Sampler temperature | RT | |
| Diluent | Acetonitrile:$H_2O$ = 1:1 | |

5.3.4 IC

IC method for counter-ion content measurement was listed in Table 5-11 below.

TABLE 5-11

| IC method for counter-ion content measurement | |
| --- | --- |
| Parameters | Settings |
| Column | IonPac AS18 Analytical Column (4 × 250 mm) |
| Mobile Phase | 25 mM NaOH |
| Injection volume | 25 μL |
| Flow rate | 1.0 mL/min |
| Cell temperature | 35° C. |
| Column temperature | 35° C. |
| Current | 80 mA |

TABLE 5-11-continued

| IC method for counter-ion content measurement | |
| --- | --- |
| Parameters | Settings |
| Run Time | 8 mins ($Cl^-$), 28 mins ($PO_4^{3-}$), |
| | 12 mins ($SO_4^{2-}/NO_3^-$) |
| | 14 mins ($C_2O_4^{2-}$) |

5.3.5 PLM

Polarized light microscopic picture was captured on Axio Lab. A1 upright microscope at room temperature.

5.3.6 DVS

DVS was measured via a SMS (Surface Measurement Systems) DVS Intrinsic. The relative humidity at 25° C. were calibrated against deliquescence point of LiCl, $Mg(NO_3)_2$ and KCl. Actual parameters for DVS test were listed in Table 5-12.

TABLE 5-12

| Parameters for DVS test | |
| --- | --- |
| Parameters | DVS |
| Temperature | 25° C. |
| Sample size | 10~20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 0% RH to 95% RH |
| RH step size | 10% RH from 0% RH to 90% RH |
| | 5% RH from 90% RH to 95% RH |

5.3.7 $^1$H NMR $^1$H NMR spectrum was collected on Bruker 400M NMR Spectrometer using DMSO-d6 as solvent.

5.3.8 pKa pKa was determined on Sirius T3™ according to the manufacturer's instructions and the parameters for pKa test was listed in Table 5-13.

TABLE 5-13

| Parameters for pKa test | |
| --- | --- |
| pH electrode | Ag/AgCl, double junction reference |
| Stirrer | Overhead, variable speed, computer controlled |
| Temperature probe | Thermocouple, Temperature measured with every datapoint |
| Temperature control | Peltier, Range: 12° C. to 70° C. |
| Turbidity detection | Turbidity sensor |
| Precision dispensers | Water, Acid, Base |
| MultiTip dispenser | Multi-tip capillary bundle |
| Electrode storage/calibration | Home position for electrode storage and pH7 buffer positions for calibration |
| Washes | Two static washes and flowing water wash station |
| Purge gas | Two internal flow meters, nitrogen supply required |
| CoSolvents | Methanol, DMSO and MDM |
| System standardisation | Sirius Four-Plus ™ procedure |
| pH-range | 2.0-12.0 |
| Assay volume | 0.5 to 3.5 mls |

5.4 Characterization of Crystalline Hits from Salt Screening

5.4.1 HCl Salt Type B

A total of two HCl salt crystal forms were obtained from screening. HCl salt Type A (807919-07-D1) was obtained via solution crystallization (molar charge of 1:1) in THF and Type B (807919-07-C2) was generated via reactive crystallization (molar ratio of 2:1, acid/base) in EtOAc at RT. The XRPD patterns were displayed in FIG. 69. XRPD data for HCl salt Type B show (peak shift within ±0.2°) primary peaks at 7.4, 24.3, and 26.2; secondary peaks at 6.7, 15.4, and 20.3; and tertiary peaks at 12.7, 19.1, and 28.5.

Figure 62:
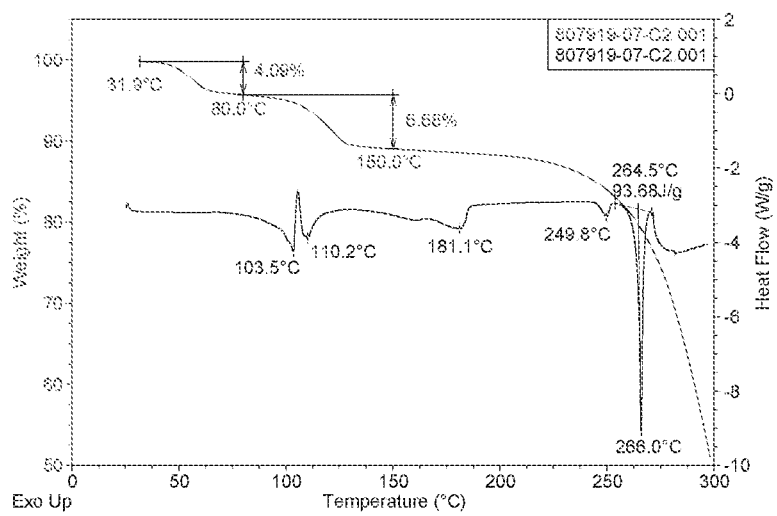
FIG. 62 illustrates TGA/DSC curves of HCl salt crystal form Type B (807919-07-C2).
Figure 63:
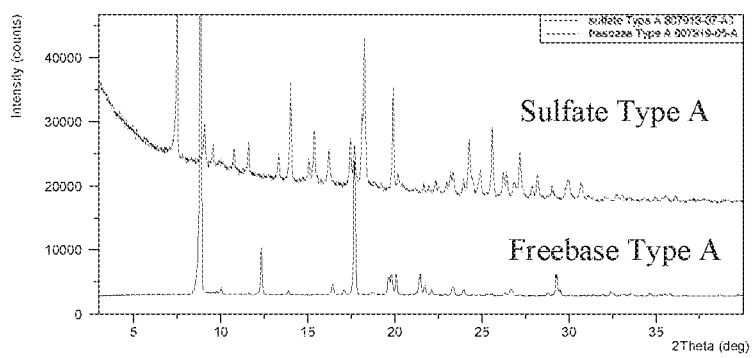
FIG. 63 illustrates a XRPD pattern of sulfate crystal form Type A (807919-07-A3).

For HCl salt Type B, TGA and DSC data (FIG. 62) show a two-step weight loss of 10.8% up to 150° C. and multiple endotherms before decomposition and five endotherms at 103.5° C., 110.2° C., 181.1° C., 249.8° C. and 266.0° C. (peak temperature) before decomposition. The stoichiometry of 1.73 (acid/base) was determined by HPLC/IC and a purity of 99.2 area % was detected by HPLC in Table 5-15.

TABLE 5-14

HPLC purity profile of HCl salt Type A (807919-07-D1)

| # | RRT | Area % |
|---|---|---|
| 1 | 0.79 | 0.09 |
| 2 | 1.00 | 99.91 |

TABLE 5-15

HPLC purity profile of HCl salt Type B (807919-07-C2)

| # | RRT | Area % |
|---|---|---|
| 1 | 0.79 | 0.71 |
| 2 | 1.00 | 99.21 |
| 3 | 1.48 | 0.09 |
| — | — | — |

5.4.2 Sulfate

Figure 64:
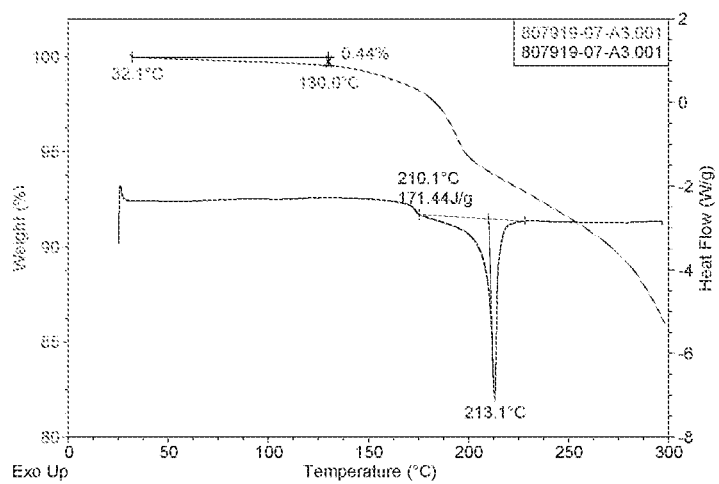
FIG. 64 illustrates TGA/DSC curves of sulfate crystal form Type A (807919-07-A3).
Figure 65:
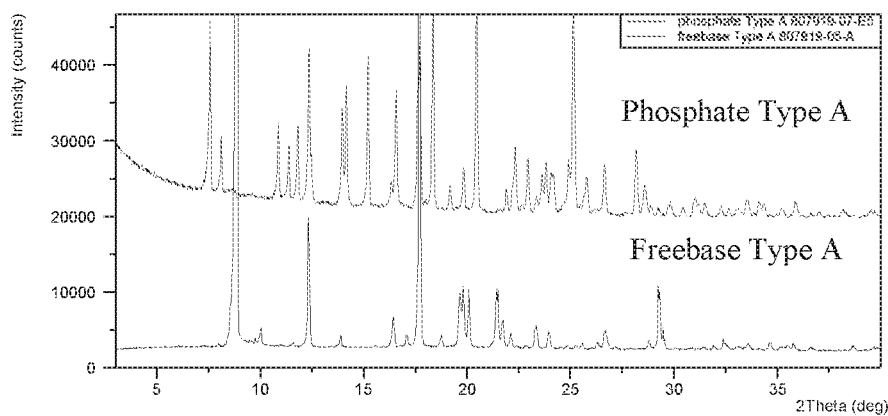
FIG. 65 illustrates a XRPD pattern of phosphate crystal form Type A (807919-07-E5).

One sulfate crystal form was generated via screening. Sulfate Type A (807919-07-A3) was produced via solution crystallization in acetone (molar ratio of 1:1) at RT and its XRPD pattern was shown in FIG. 63. As per TGA and DSC data shown in FIG. 64, a weight loss of 0.4% was viewed up to 130° C. and the DSC curve shows an endothermic peak at 210.1° C. (onset temperature). A purity of 99.3 area % was detected by HPLC in Table 5-16 and the stoichiometry of sulfate Type A (807919-07-A3) was determined as 0.98 (acid/base) by HPLC/IC.

TABLE 5-16

HPLC purity profile of sulfate Type A (807919-07-A3)

| # | RRT | Area % |
|---|---|---|
| 1 | 0.79 | 0.64 |
| 2 | 1.00 | 99.28 |
| 3 | 1.48 | 0.08 |
| — | — | — |

5.4.3 Phosphate

Figure 66:
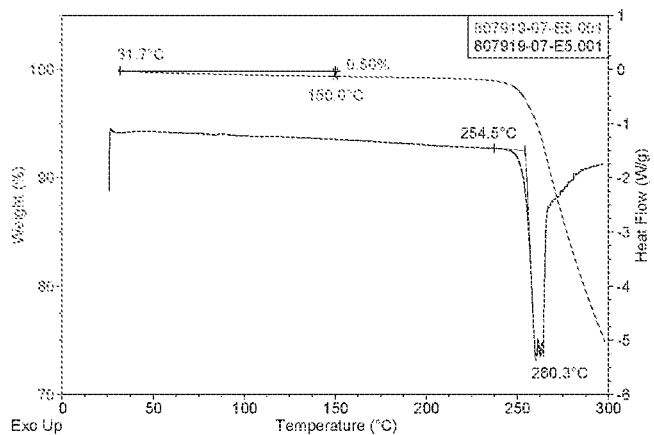
FIG. 66 illustrates TGA/DSC curves of phosphate crystal form Type A (807919-07-E5).
Figure 67:
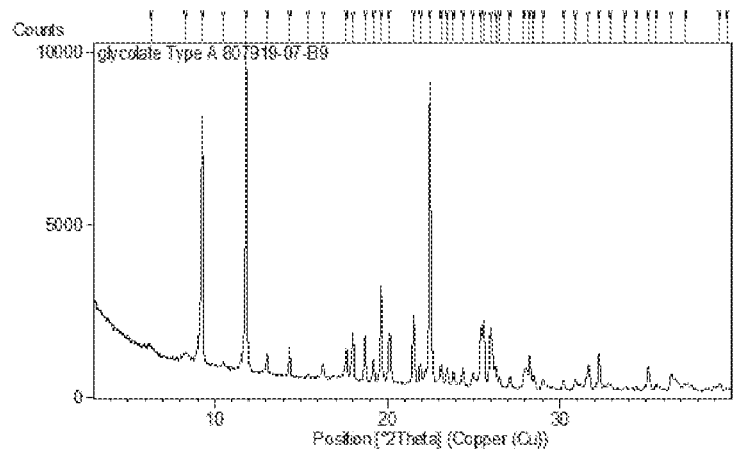
FIG. 67 illustrates a XRPD pattern of glycolate crystal form Type A (807919-07-B9).

One phosphate crystal form was obtained from screening. Phosphate Type A (807919-07-E5) was obtained via solution crystallization (molar ratio of 1:1) in MeOH/H$_2$O (9:1, v/v) at RT, and its XRPD pattern was shown in FIG. 65. TGA and DSC curves (FIG. 66) show a weight loss of 0.5% up to 150° C. and an endotherm at 254.5° C. (onset temperature) possibly due to melting along with decomposition. Also, a purity of 99.9 area % was detected by HPLC in Table 5-17 and the stoichiometry was determined as 0.92 (acid/base) for phosphate Type A (807919-07-E5) via HPLC/IC.

TABLE 5-17

HPLC purity profile of phosphate Type A (807919-07-E5)

| # | RRT | Area % |
|---|---|---|
| 1 | 0.79 | 0.08 |
| 2 | 1.00 | 99.92 |

5.4.4 Glycolate

One glycolate crystal form was obtained via screening. Glycolate Type A (807919-07-B9) was generated via reactive crystallization (molar ratio of 1:1) in EtOH at RT. The XRPD pattern was displayed in FIG. 67. XRPD data for glycolate Type A provide (peak shift within ±0.2°) primary peaks at 9.3, 11.8, and 22.5; secondary peaks at 14.4, 19.7, and 25.6; and tertiary peaks at 13.1, 18.0, and 21.5.

Figure 68:
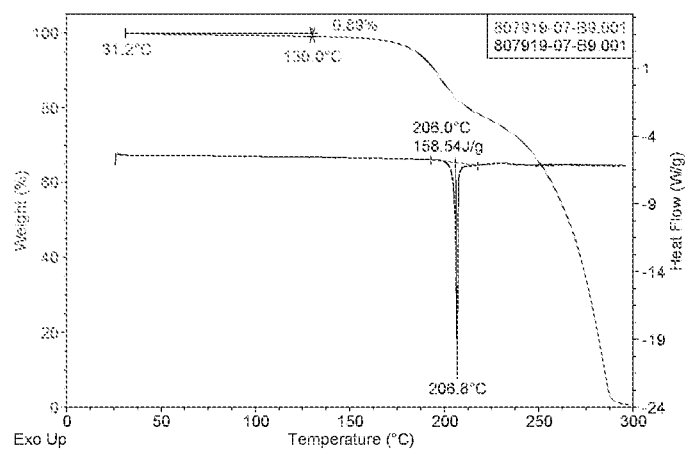
FIG. 68 illustrates TGA/DSC curves of glycolate crystal form Type A (807919-07-B9).
Figure 69:
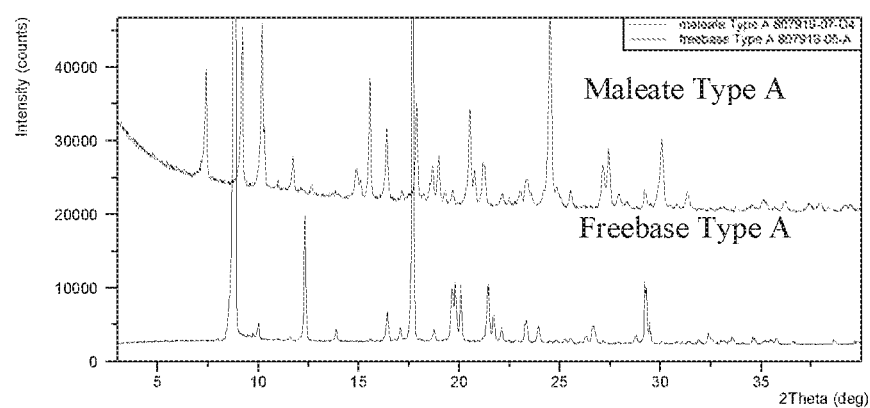
FIG. 69 illustrates a XRPD pattern of maleate crystal form Type A (807919-07-D4).

As per TGA and DSC data in FIG. 68, a weight loss of 0.9% was observed up to 130° C. and the DSC result shows a sharp endothermic peak at 206.0° C. (onset temperature) before decomposition. Also, a purity of 99.7 area % was detected by HPLC in Table 5-18 and the stoichiometry of glycolate Type A (807919-07-B9) was determined as 1.04 (acid/base) by $^1$H NMR.

TABLE 5-18

HPLC purity profile of glycolate Type A (807919-07-B9)

| # | RRT | Area % |
|---|---|---|
| 1 | 0.79 | 0.18 |
| 2 | 1.00 | 99.74 |
| 3 | 1.48 | 0.08 |
| — | — | — |

5.4.5 Maleate

One maleate crystal form was obtained via screening. Maleate Type A (807919-07-D4) was generated via reactive crystallization (molar ratio of 1:1) in THF at RT. The XRPD pattern was displayed in FIG. 69.

Figure 70:
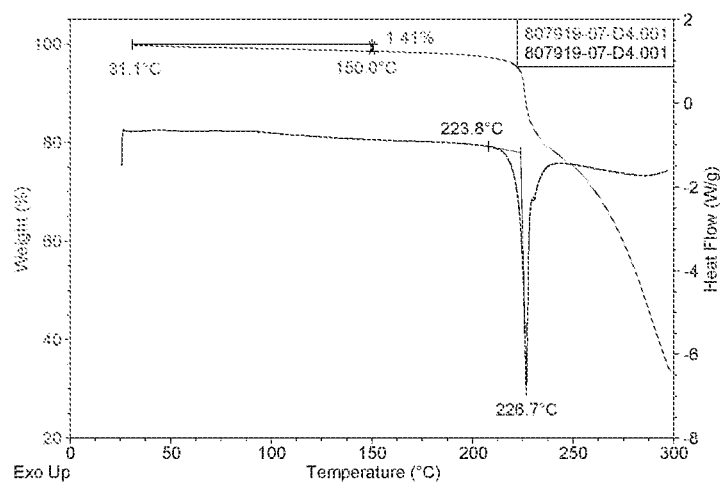
FIG. 70 illustrates TGA/DSC curves of maleate crystal form Type A (807919-07-D4).
Figure 71:
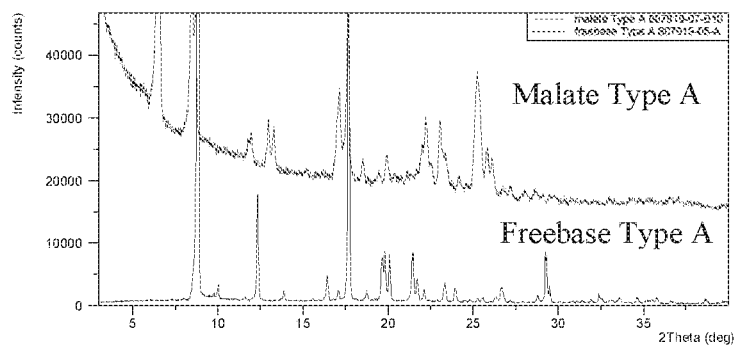
FIG. 71 illustrates a XRPD pattern of malate crystal form Type A (807919-07-B10).

TGA and DSC results in FIG. 70 show a weight loss of 1.4% up to 150° C. and an endothermic peak at 223.8° C. (onset temperature) possibly due to melting. Also, a purity of 99.3 area % was detected by HPLC in Table 5-19 and the stoichiometric ratio was speculated as 0.98 (acid/base) by $^1$H NMR.

TABLE 5-19

HPLC purity profile of maleate Type A (807919-07-D4)

| # | RRT | Area % |
|---|---|---|
| 1 | 0.79 | 0.67 |
| 2 | 1.00 | 99.25 |
| 3 | 1.48 | 0.09 |
| — | — | — |

5.4.6 Malate

One malate crystal form was obtained via screening. Malate Type A (807919-07-B10) was generated via reactive crystallization (charge molar ratio of 1:1) in EtOH at RT. The XRPD pattern was displayed in FIG. 71.

Figure 72:
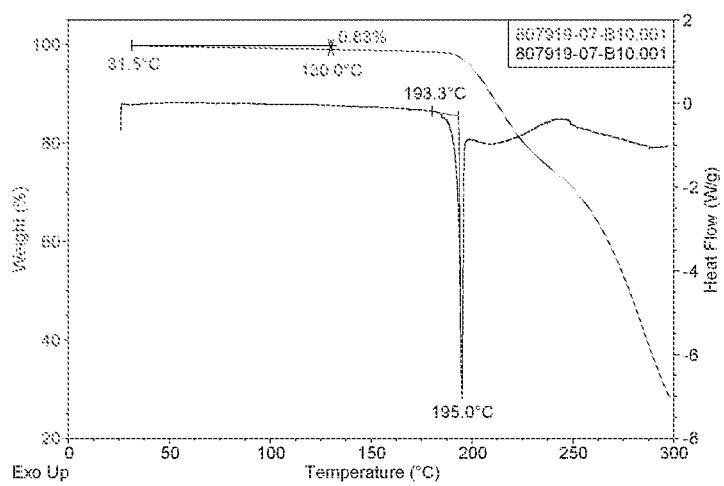
FIG. 72 illustrates TGA/DSC curves of malate crystal form Type A (807919-07-B10).
Figure 73:
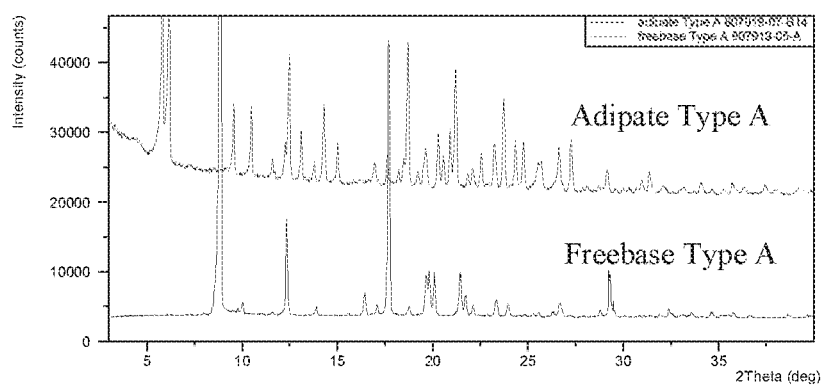
FIG. 73 illustrates a XRPD pattern of adipate crystal form Type A (807919-07-B14).

As per TGA and DSC data in FIG. 72, a weight loss of 0.8% was viewed up to 130° C. and DSC result shows a sharp endotherm at 193.3° C. (onset temperature), possibly due to melting. Also, a purity of 99.9 area % was detected by HPLC in Table 5-20 and the stoichiometric ratio was determined as 1.04 (acid/freebase) by $^1$H NMR.

TABLE 5-20

HPLC purity profile of malate Type A (807919-07-B10)

| # | RRT | Area % |
|---|-----|--------|
| 1 | 0.79 | 0.07 |
| 2 | 1.00 | 99.87 |
| 3 | 1.48 | 0.07 |

5.4.7 Adipate

Figure 74:
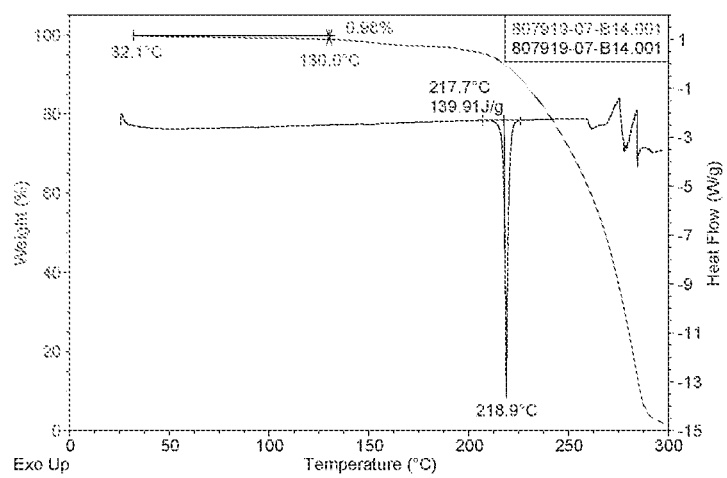
FIG. 74 illustrates TGA/DSC curves of adipate crystal form Type A (807919-07-B14).
Figure 75:
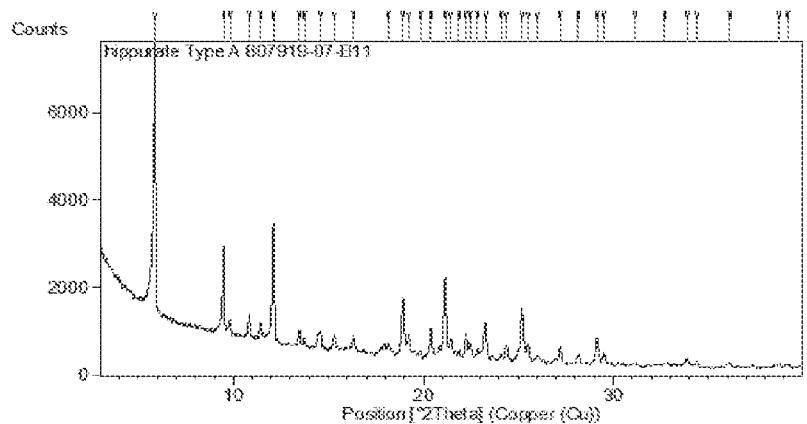
FIG. 75 illustrates a XRPD pattern of hippurate crystal form Type A (807919-07-B11).

One adipate crystal form was obtained from screening. Adipate Type A (807919-07-B14) was produced via reactive crystallization (molar ratio of 1:1) in EtOH at RT. XRPD pattern and TGA/DSC curves were shown in FIG. 73 and FIG. 74 respectively.

A weight loss of 1.0% was observed up to 130° C. in TGA and DSC result shows an endothermic peak at 217.7° C. (onset temperature) possibly due to melting. Also, a purity of 100.0 area % was detected by HPLC in Table 5-21 and the stoichiometry of adipate Type A (807919-07-B14) was speculated as 0.52 (acid/base) by $^1$H NMR.

TABLE 5-21

HPLC purity profile of adipate Type A (807919-07-B14)

| # | RRT | Area % |
|---|-----|--------|
| 1 | 0.79 | 0.05 |
| 2 | 1.00 | 99.95 |

5.4.8 Hippurate

One hippurate crystal form was obtained via screening. Hippurate Type A (807919-07-B11) was generated via reactive crystallization (molar ratio of 1:1) in EtOH at RT. XRPD pattern was displayed in FIG. 75. XRPD data for hippurate Type A provide (peak shift within ±0.2°) primary peaks at 5.9, 9.5, and 12.1; secondary peaks at 18.9, 21.2, and 25.2; and tertiary peaks at 10.8, 23.3, and 29.2.

Figure 76:
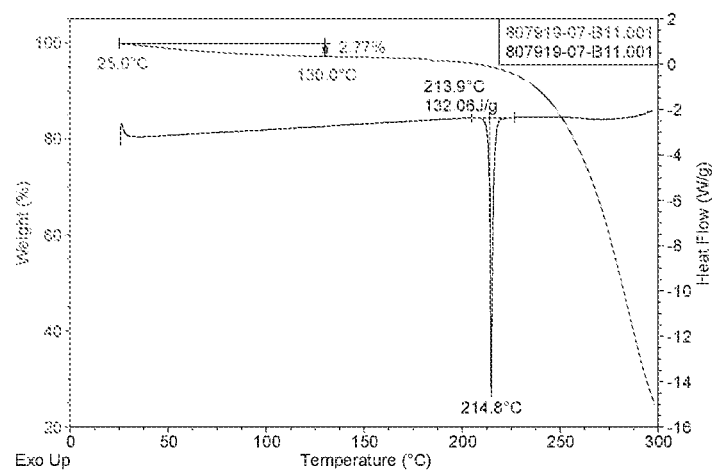
FIG. 76 illustrates TGA/DSC curves of hippurate crystal form Type A (807919-07-B11).
Figure 77:
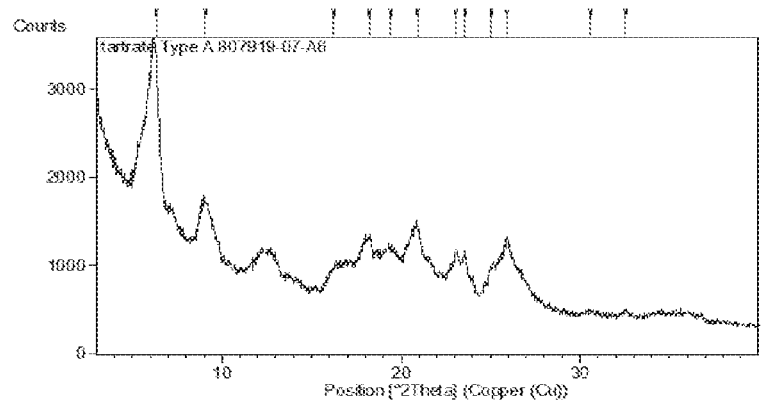
FIG. 77 illustrates XRPD patterns of tartrate crystal form Type A (807919-07-A6).

TGA and DSC results in FIG. 76 show a weight loss of 2.8% before 130° C. and an endothermic peak at 213.9° C. (onset temperature) before decomposition. Also, a purity of 99.6 area % was detected by HPLC in Table 5-22. The stoichiometric ratio was determined as 1.00 (acid/base) by $^1$H NMR.

TABLE 5-22

HPLC purity profile of hippurate Type A (807919-07-B11)

| # | RRT | Area % |
|---|-----|--------|
| 1 | 0.79 | 0.05 |
| 2 | 1.00 | 99.61 |
| 3 | 1.48 | 0.08 |

5.4.9 Tartrate

A total of three tartrate crystal forms were obtained via screening. Tartrate Type A (807919-07-A6), Type B (807919-07-E6), and Type C (807919-07-B6) were generated via reactive crystallization in acetone, MeOH/H$_2$O (9:1, v/v), and EtOH at RT respectively, with a molar charge ratio of 1:1. The XRPD pattern for tartrate Type A is displayed in FIG. 77. XRPD data for tartrate Type A provide (peak shift within ±0.2°) primary peaks at 6.3, 18.2, and 20.9; secondary peaks at 9.1, 19.4, and 25.9; and tertiary peaks at 16.3, 23.1, and 23.6.

Figure 78:
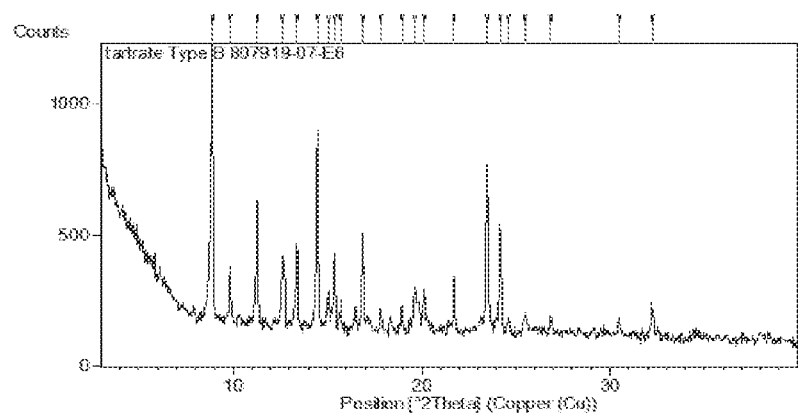
FIG. 78 illustrates XRPD patterns of tartrate crystal form Type B (807919-07-E6).

The XRPD pattern for Tartrate Type B is displayed in FIG. 78. XRPD data for tartrate Type B provide (peak shift within ±0.2°) primary peaks at 8.9, 14.5, and 23.5; secondary peaks at 11.3, 16.9, and 24.2; and tertiary peaks at 9.9, 13.4, and 15.4.

Figure 79:
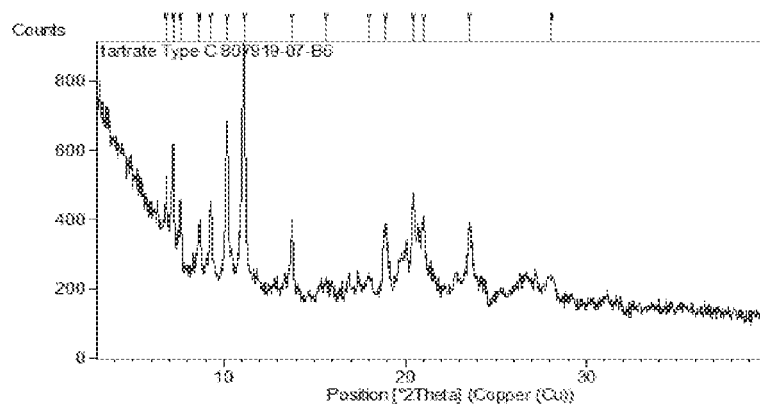
FIG. 79 illustrates XRPD patterns of tartrate crystal Type C (807919-07-B6).

The XRPD pattern for Tartrate Type C is displayed in FIG. 79. XRPD data for tartrate Type C provide (peak shift within ±0.2°) primary peaks at 7.2, 10.2, and 11.1; secondary peaks at 9.3, 13.8, and 18.9; and tertiary peaks at 8.7, 20.4, and 23.5.

Figure 80:
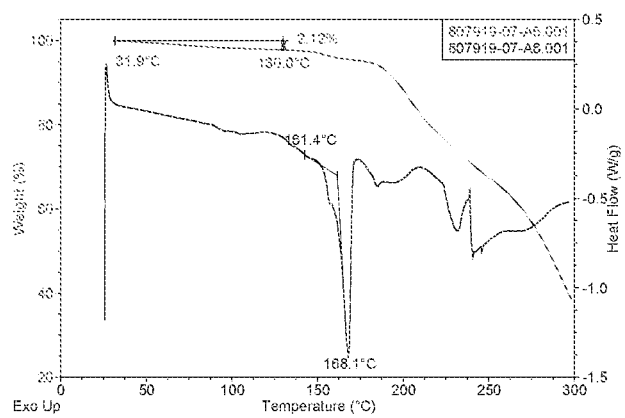
FIG. 80 illustrates TGA/DSC curves of tartrate crystal form Type A (807919-07-A6).
Figure 81:
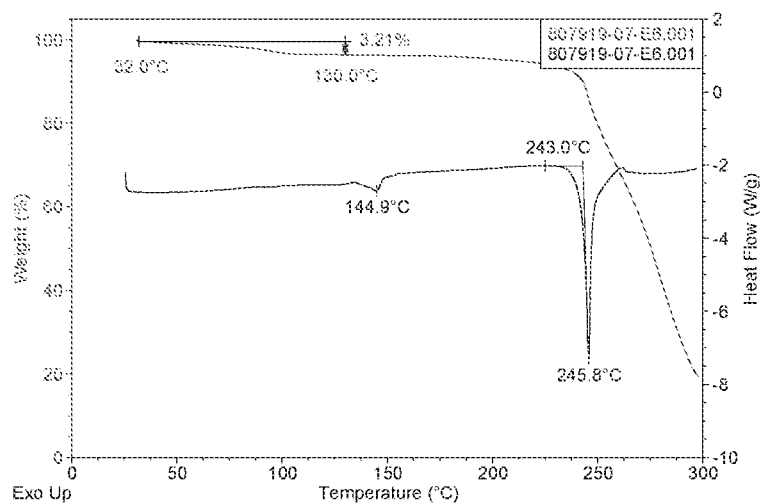
FIG. 81 illustrates TGA/DSC curves of tartrate crystal form Type B (807919-07-E6).
Figure 82:
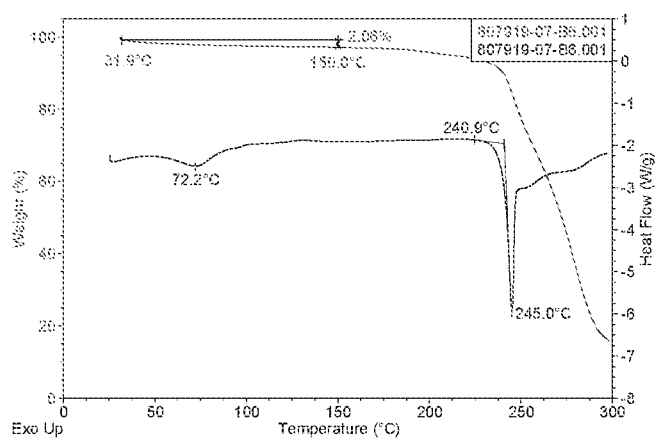
FIG. 82 illustrates TGA/DSC curves of tartrate crystal form Type C (807919-07-B6).

For Type A, a weight loss of 2.1% was observed up to 130° C. and DSC data (FIG. 80) shows an endothermic peak at 161.4° C. (onset temperature) before decomposition. For Type B, TGA and DSC results in FIG. 81 show a weight loss of 3.2% up to 130° C. and two endothermic peaks at 144.9° C. and 245.8° C. (peak temperature) before decomposition. For Type C, a weight loss of 2.1% was viewed up to 150° C. in TGA and DSC result (FIG. 82) shows an endotherm at 72.2° C. (peak temperature) before melting at 240.9° C. (onset temperature) before decomposition.

Also, the stoichiometric ratio was determined as 1.02 (acid/base) for Type A, 0.52 (acid/base) for Type B and C by $^1$H NMR.

5.4.10 Fumarate

Figure 83:
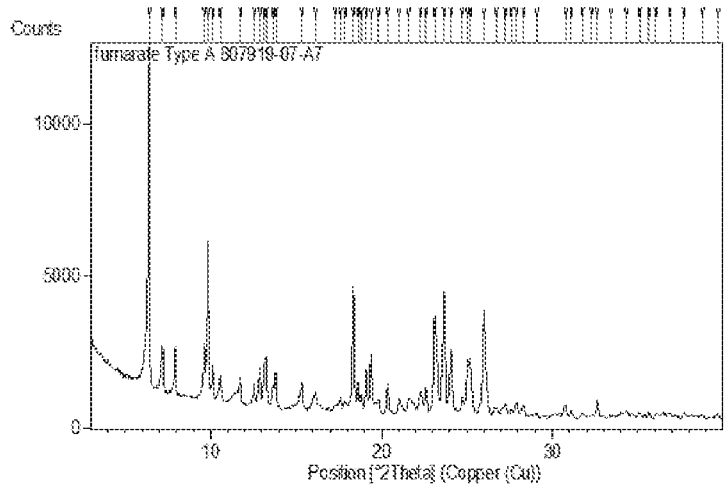
FIG. 83 illustrates XRPD patterns of fumarate crystal form Type A (807919-07-A7).

A total of three fumarate crystal forms were obtained via screening. Fumarate Type A (807919-07-A7), Type B (807919-07-E7), and Type C (807919-07-C7) were generated via reactive crystallization (molar ratio of 1:1) in acetone, MeOH/H$_2$O (9:1, v/v), and EtOAc at RT respectively. The XRPD pattern for fumarate Type A is shown in FIG. 83. XRPD data for fumarate Type A provide (peak shift within ±0.2°) primary peaks at 6.4, 9.9, and 18.4; secondary peaks at 7.9, 23.7, and 26.0; and tertiary peaks at 7.2, 13.3, and 25.2.

Figure 84:
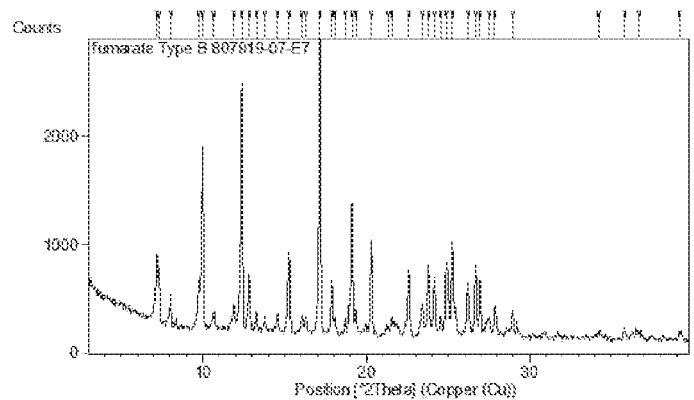
FIG. 84 illustrates XRPD patterns of fumarate crystal form Type B (807919-07-E7).

The XRPD patterns for fumarate Type B are shown in FIG. 84. XRPD data for fumarate Type B provide (peak shift within ±0.2°) primary peaks at 10.0, 12.4, and 17.2; secondary peaks at 15.3, 19.1, and 20.3; and tertiary peaks at 17.2, 22.6, and 24.9.

Figure 85:
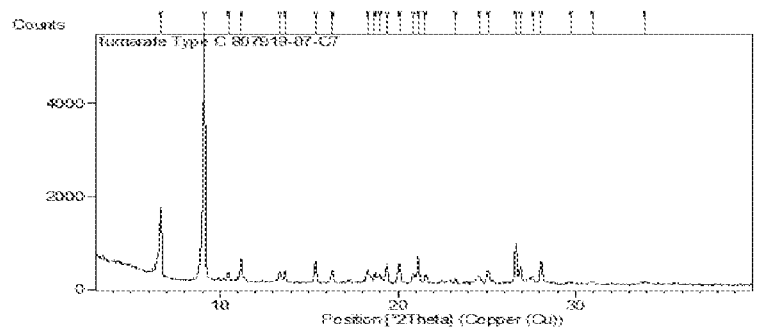
FIG. 85 illustrates XRPD patterns of fumarate crystal form Type C (807919-07-C7).

The XRPD patterns for fumarate Type C are shown in FIG. 85. XRPD data for fumarate Type C provide (peak shift within ±0.2°) primary peaks at 6.7, 9.1, and 26.6; secondary peaks at 11.2, 15.4, and 20.1; and tertiary peaks at 13.7, 19.4, and 21.1.

Figure 86:
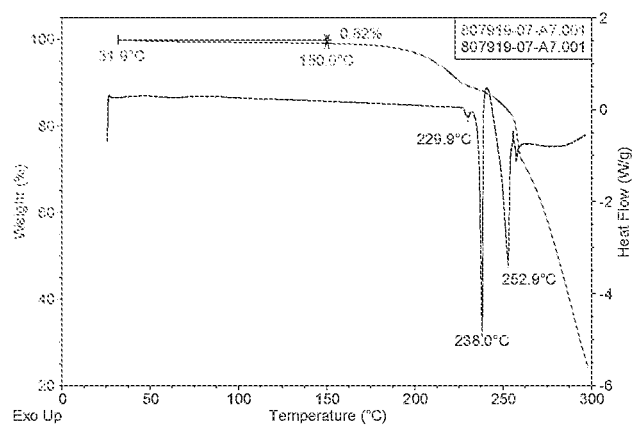
FIG. 86 illustrates TGA/DSC curves of fumarate crystal form Type A (807919-07-A7).
Figure 87:
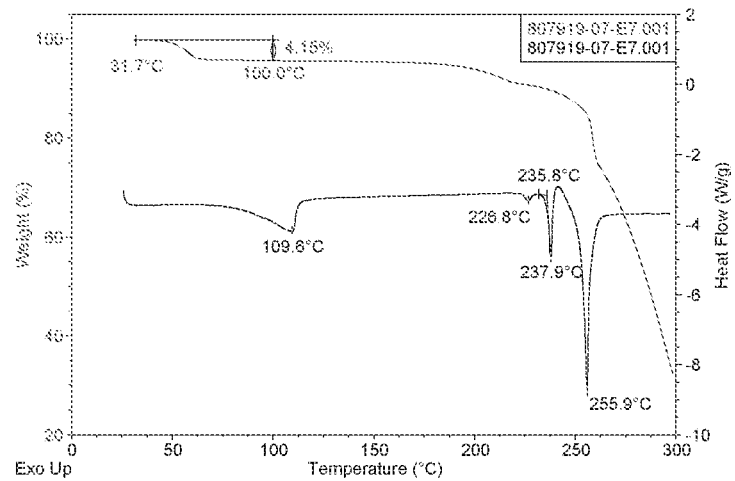
FIG. 87 illustrates TGA/DSC curves of fumarate crystal form Type B (807919-07-E7).
Figure 88:
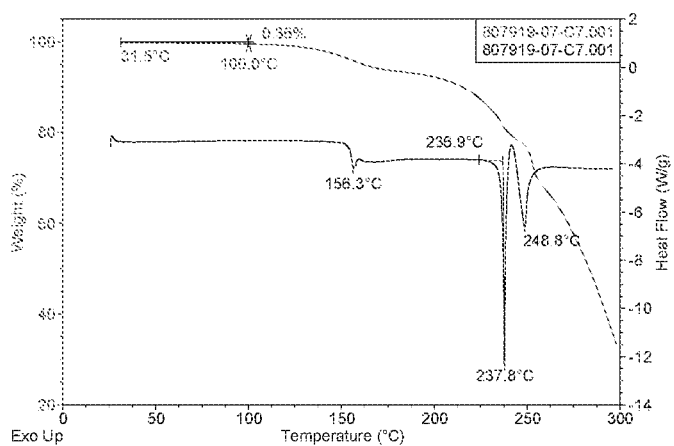
FIG. 88 illustrates TGA/DSC curves of fumarate crystal form Type C (807919-07-C7).

For Type A, TGA and DSC data shows a weight loss of 0.8% up to 150° C. and three endothermic peaks at 229.9° C., 238.0° C. and 252.9° C. (peak temperature) before decomposition (FIG. 86). For Type B, TGA and DSC data shows a weight loss of 4.2% up to 100° C. and four endothermic peaks at 109.6° C., 226.8° C., 237.9° C. and 255.9° C. (peak temperature) before decomposition (FIG. 87). For Type C, TGA and DSC data show a weight loss of 0.4% up to 100° C. and four endothermic peaks at 156.3° C., 237.8° C. and 248.8° C. (peak temperature) before decomposition (FIG. 88).

Figure 89:
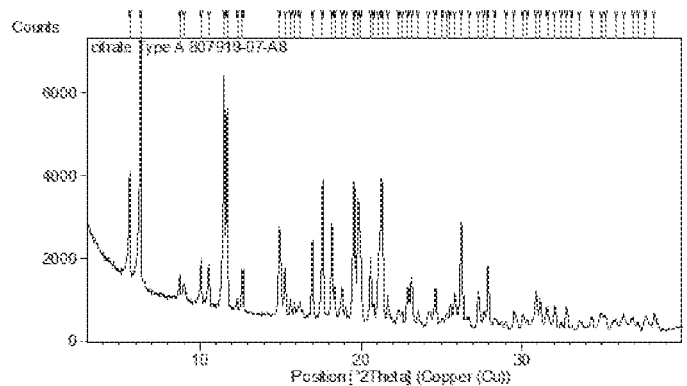
FIG. 89 illustrates XRPD patterns of citrate crystal form Type A (807919-07-A8).

Also, the stoichiometry was determined as 0.81, 0.61, and 1.03 (acid/base) for Type A~C by $^1$H NMR 5.4.11 Citrate Two citrate crystal forms were obtained via screening. Citrate Type A (807919-07-A8) and Type B (807919-07-B8) were produced via reactive crystallization (molar ratio of 1:1) in acetone and EtOH at RT. The XRPD pattern for citrate Type A is shown in FIG. 89. XRPD data for citrate Type A provide (peak shift within ±0.2°) primary peaks at 6.3, 11.5, and 21.3; secondary peaks at 14.9, 17.6, and 19.6; and tertiary peaks at 5.7, 10.0, and 26.3.

Figure 90:
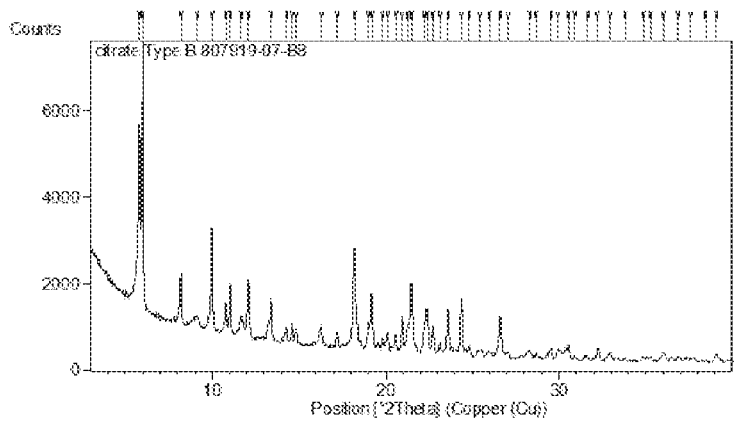
FIG. 90 illustrates XRPD patterns of citrate crystal form Type B (807919-07-B8).

The XRPD patterns for citrate Type B are shown in FIG. 90. XRPD data for citrate Type B provide (peak shift within ±0.2°) primary peaks at 6.0, 10.0, and 18.2; secondary peaks at 8.2, 12.1, and 21.5; and tertiary peaks at 11.0, 13.4, and 19.2.

Figure 91:
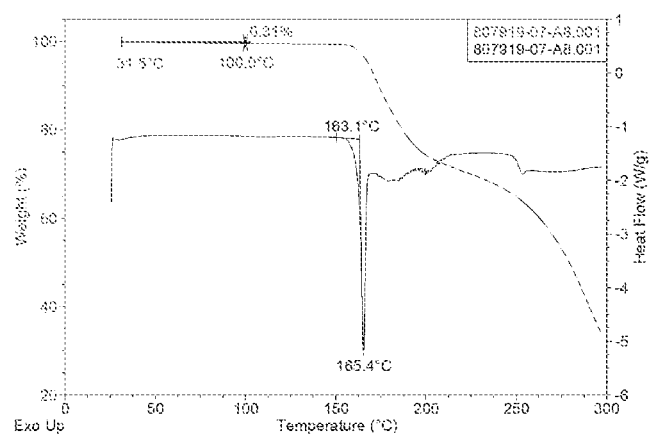
FIG. 91 illustrates TGA/DSC curves of citrate crystal form Type A (807919-07-A8).
Figure 92:
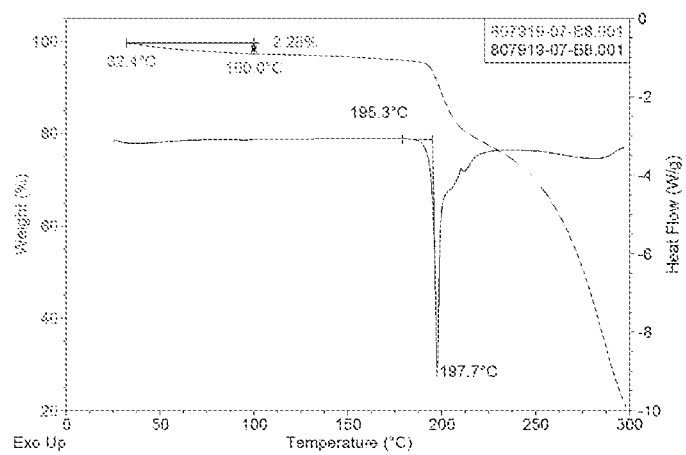
FIG. 92 illustrates TGA/DSC curves of citrate crystal form Type B (807919-07-B8).
Figure 93:
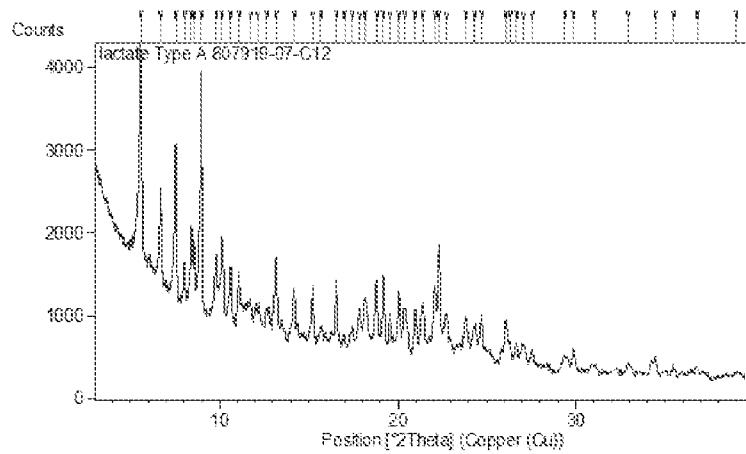
FIG. 93 illustrates XRPD patterns of lactate crystal form Type A (807919-07-C12).

For Type A, a weight loss of 0.3% was viewed up to 100° C. and DSC result (FIG. 91) shows a sharp endothermic peak at 163.1° C. (onset temperature) before decomposition. For Type B, TGA and DSC data in FIG. 92 shows a weight loss of 2.3% before 100° C. and a sharp endothermic peak at 195.3° C. (onset temperature) before decomposition.

Figure 108:
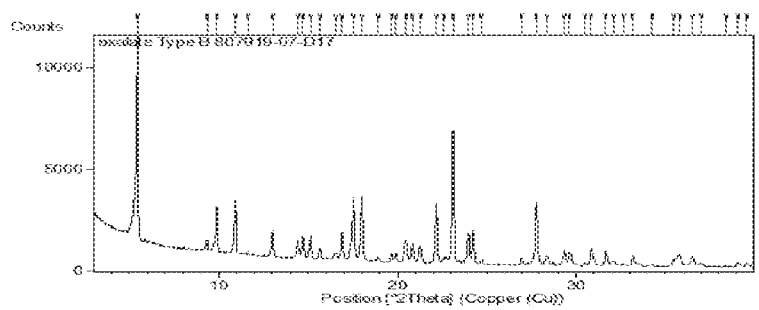
FIG. 108 illustrates XRPD patterns of oxalate crystal form Type B (807919-07-D17).
Figure 109:
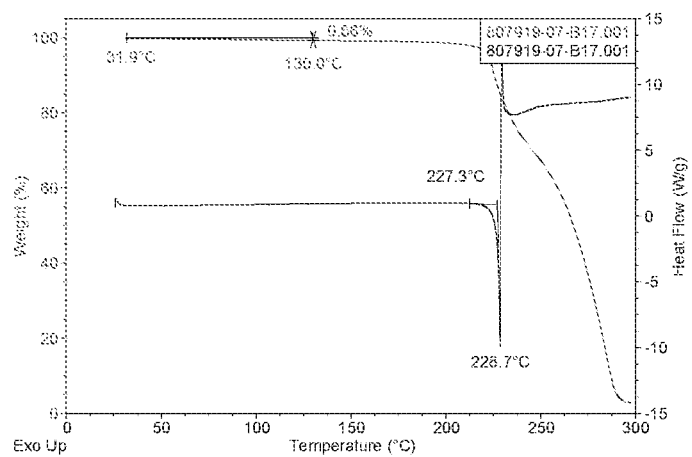
FIG. 109 illustrates TGA/DSC curves of oxalate crystal form Type A (807919-07-B17).

Also, the stoichiometric ratio was determined as 1.02 and 0.53 (acid/base) for Type A and B by $^1$H NMR in FIG. 108 and FIG. 109, respectively.

5.4.12 Lactate

Two lactate crystal forms were obtained via screening. Lactate Type A (807919-07-C12) and Type B (807919-07-A12) were generated via reactive crystallization (molar ratio of 1:1) in EtOAc and acetone at RT. The XRPD pattern for lactate Type A is displayed in FIG. 93. XRPD data for lactate Type A provide (peak shift within ±0.2°) primary peaks at 5.6, 7.5, and 9.0; secondary peaks at 6.7, 10.1, and 22.3; and tertiary peaks at 8.4, 13.2, and 19.2.

Figure 94:
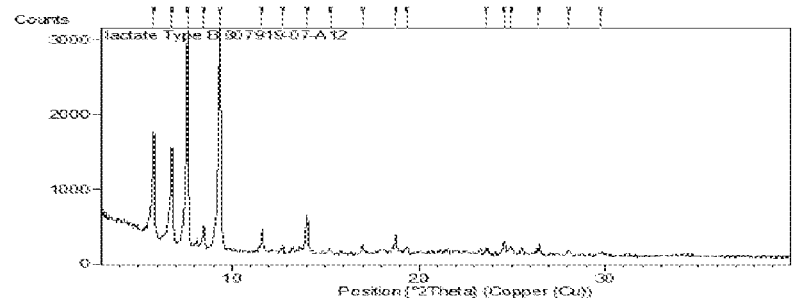
FIG. 94 illustrates XRPD patterns of lactate crystal Type B (807919-07-A12).

The XRPD patterns for lactate Type B are shown in FIG. 94. XRPD data for lactate Type B provide (peak shift within ±0.2°) primary peaks at 5.8, 7.6, and 9.4; secondary peaks at 6.8, 11.6, and 14.0; and tertiary peaks at 8.5, 18.8, and 25.6.

Figure 95:
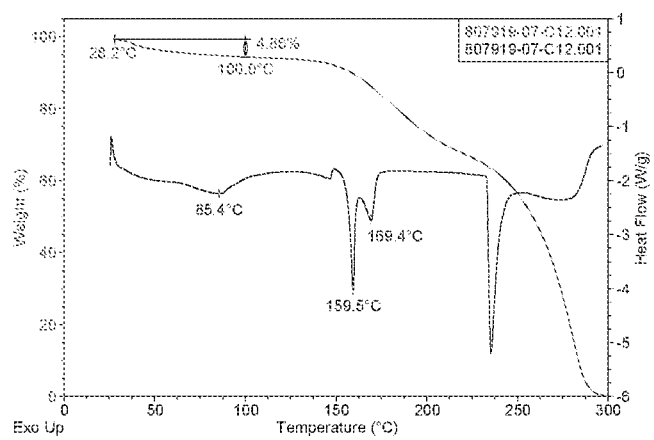
FIG. 95 illustrates TGA/DSC curves of lactate crystal form Type A (807919-07-C12).
Figure 96:
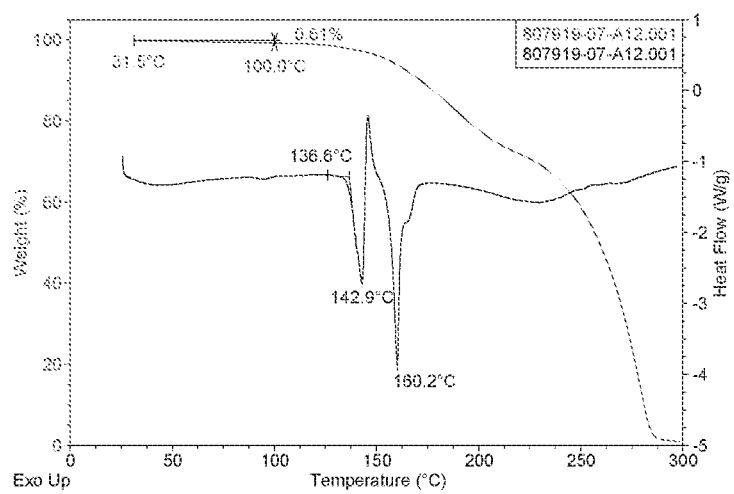
FIG. 96 illustrates TGA/DSC curves of lactate crystal form Type B (807919-07-A12).
Figure 97:
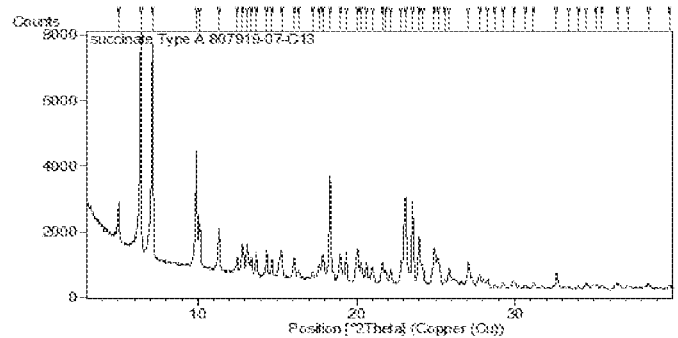
FIG. 97 illustrates XRPD patterns of succinate crystal Type A (807919-07-C13).

For Type A, a weight loss of 4.9% was observed up to 100° C. in TGA and DSC result in FIG. 95 show endothermic peaks at 85.4° C., 159.5° C. and 169.4° C. (peak temperature) before decomposition. For Type B, TGA and DSC result in FIG. 96 shows a weight loss of 0.6% up to 100° C. and two endothermic peaks at 142.9° C. and 160.2° C. (peak temperature) before decomposition.

Also, the stoichiometric ratio was determined as 1.07 and 0.96 (acid/base) for lactate Type A and B by $^1$H NMR 5.4.13 Succinate Two succinate crystal forms were obtained via screening. Succinate Type A (807919-07-C13) and Type B (807919-07-E13) were generated via reactive crystallization (molar ratio of 1:1) in EtOAc and MeOH/H$_2$O (9:1, v/v) at RT. The XRPD pattern for succinate Type A is displayed in FIG. 97. XRPD data for succinate Type A provide (peak shift within ±0.2°) primary peaks at 6.4, 7.1, and 9.9; secondary peaks at 11.3, 18.4, and 23.1; and tertiary peaks at 5.0, 20.1, and 24.9.

Figure 98:
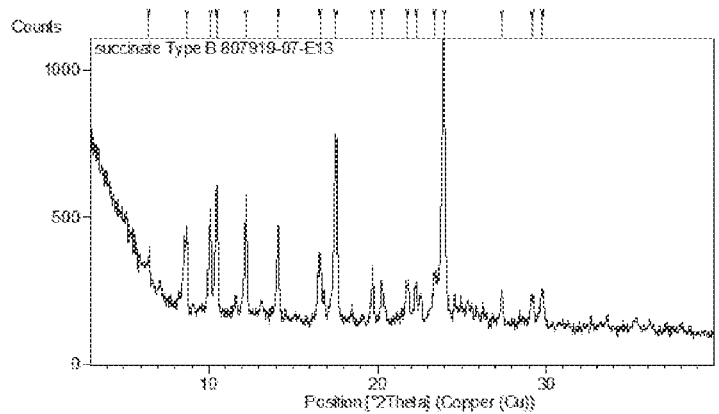
FIG. 98 illustrates XRPD patterns of succinate crystal Type B (807919-07-E13).

The XRPD pattern for succinate Type B is shown in FIG. 98. XRPD data for succinate Type B provide (peak shift within ±0.2°) primary peaks at 10.5, 17.5, and 23.9; secondary peaks at 8.7, 12.2, and 14.1; and tertiary peaks at 16.6, 19.7, and 22.3.

Figure 99:
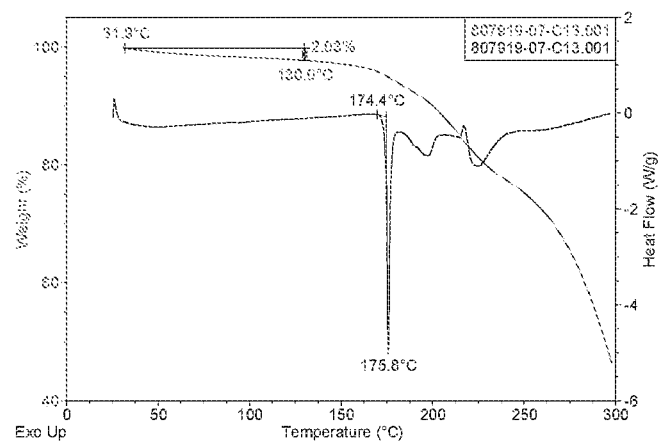
FIG. 99 illustrates TGA/DSC curves of succinate crystal form Type A (807919-07-C13).
Figure 100:
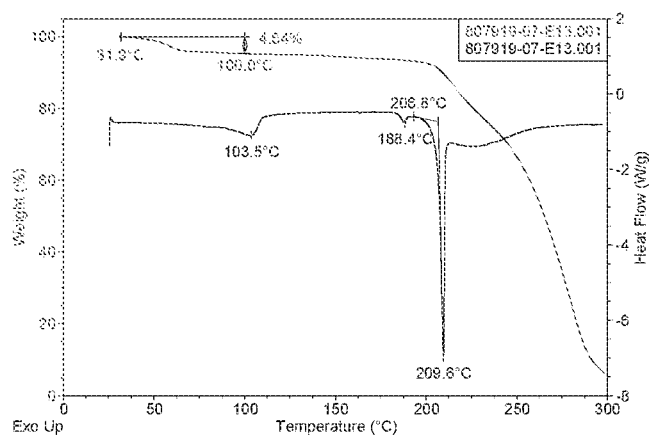
FIG. 100 illustrates TGA/DSC curves of succinate crystal form Type B (807919-07-E13).
Figure 101:
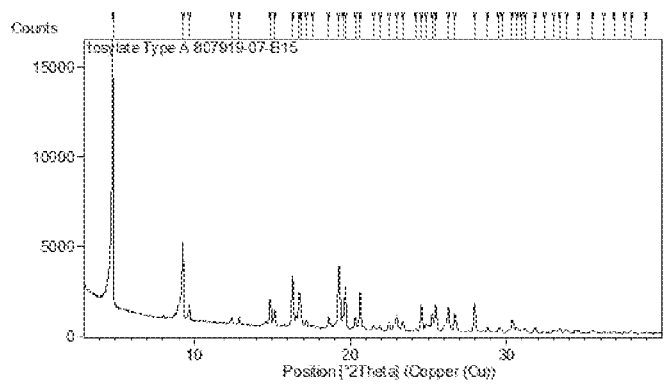
FIG. 101 illustrates XRPD patterns of tosylate crystal Type A (807919-07-B15).

For Type A, TGA and DSC results in FIG. 99 show a weight loss of 2.0% up to 130° C. and a sharp endothermic peak at 174.4° C. (onset temperature) before decomposition. For Type B, data (FIG. 100) show a weight loss of 4.6% up to 100° C. and three endothermic peaks at 103.5° C., 188.4° C. and 209.6° C. (peak temperature) before decomposition. Also, the stoichiometric ratio was determined as 1.00 and 0.52 (acid/base) by $^1$H NMR.

5.4.14 Tosylate

Two tosylate crystal forms were obtained via screening. Tosylate Type A (807919-07-B15) and Type B (807919-07-D15) were generated via reactive crystallization (molar ratio of 1:1) in EtOH and THF at RT. The XRPD pattern for tosylate Type A is displayed in FIG. 101. XRPD data for tosylate Type A provide (peak shift within ±0.2°) primary peaks at 4.8, 9.3, and 19.2; secondary peaks at 14.9, 16.3, and 19.7; and tertiary peaks at 20.7, 24.6, and 27.9.

Figure 102:
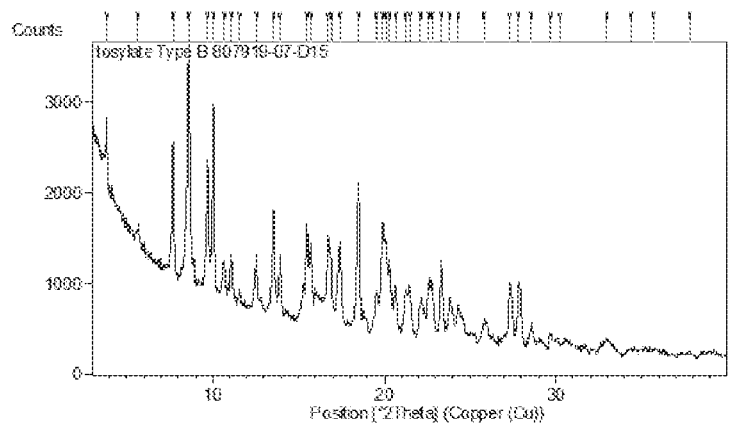
FIG. 102 illustrates XRPD patterns of tosylate crystal Type B (807919-07-D15).

The XRPD pattern for tosylate Type B is shown in FIG. 102. XRPD data for tosylate Type B provide (peak shift within ±0.2°) primary peaks at 7.7, 8.6, and 10.0; secondary peaks at 13.5, 15.5, and 19.9; and tertiary peaks at 17.4, 23.3, and 27.8.

Figure 103:
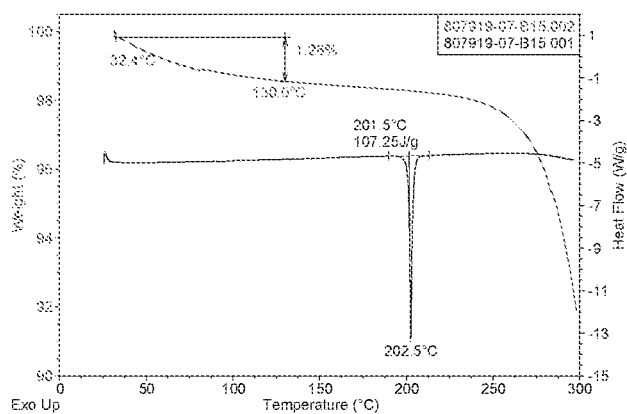
FIG. 103 illustrates TGA/DSC curves of tosylate crystal form Type A (807919-07-B15).
Figure 104:
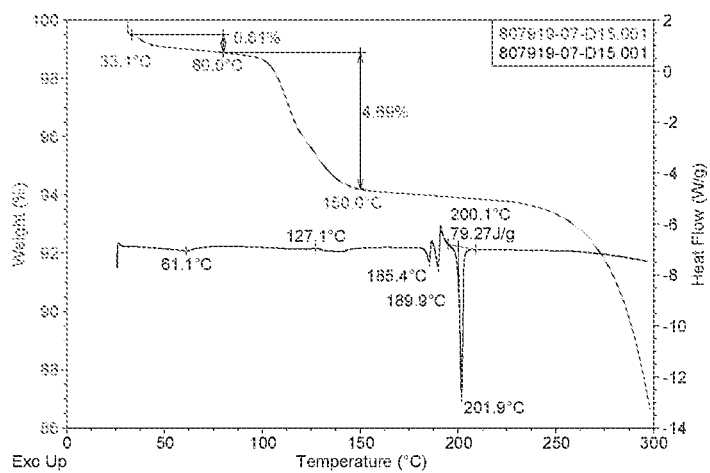
FIG. 104 illustrates TGA/DSC curves of tosylate crystal form Type B (807919-07-D15).
Figure 105:
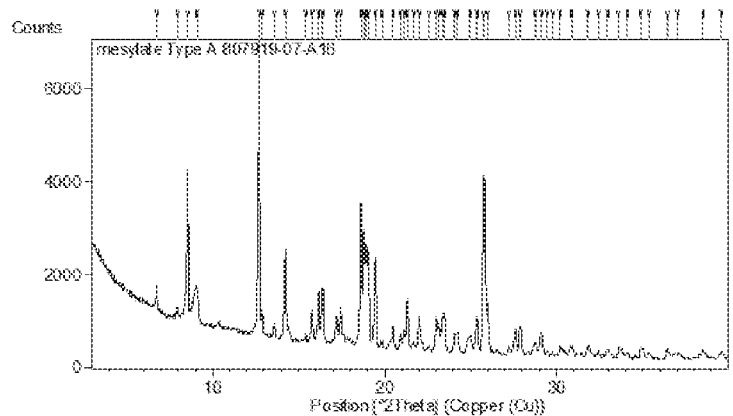
FIG. 105 illustrates a XRPD pattern of mesylate crystal form Type A (807919-07-A16).

For Type A, TGA and DSC results in FIG. 103 show a weight loss of 1.3% up to 130° C. and a sharp endothermic peak at 201.5° C. (onset temperature) before decomposition. For Type B, data (FIG. 104) show a weight loss of 5.3% up to 150° C. and four endothermic peaks at 61.1° C., 185.4° C., 189.9° C. and 201.9° C. (peak temperature) before decomposition. Also, the stoichiometric ratio was determined as 0.89 and 0.92 (acid/base) for Type A and B by $^1$H NMR.

5.4.15 Mesylate

One mesylate crystal form was obtained via screening. Mesylate Type A (807919-07-A16) was generated via reactive crystallization (molar ratio of 1:1) in acetone at RT. The XRPD pattern was displayed in FIG. 105. XRPD data for mesylate Type A provide (peak shift within ±0.2°) primary peaks at 8.6, 12.7, and 25.8; secondary peaks at 14.2, 18.6, and 19.5; and tertiary peaks at 16.4, 17.4, and 21.3.

Figure 106:
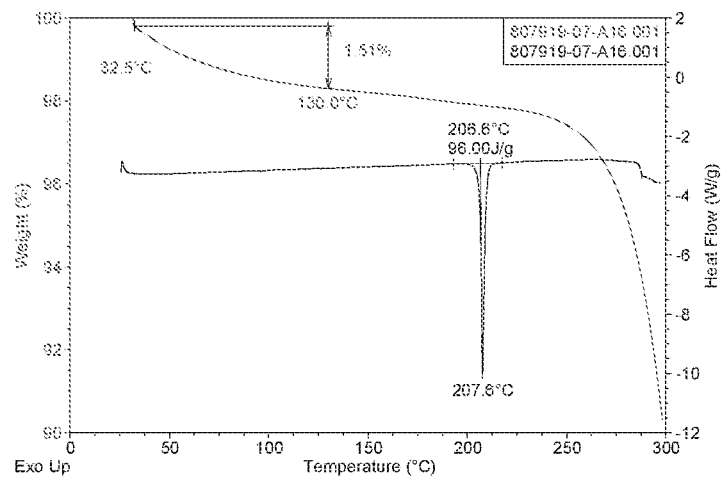
FIG. 106 illustrates TGA/DSC curves of mesylate crystal form Type A (807919-07-A16).
Figure 107:
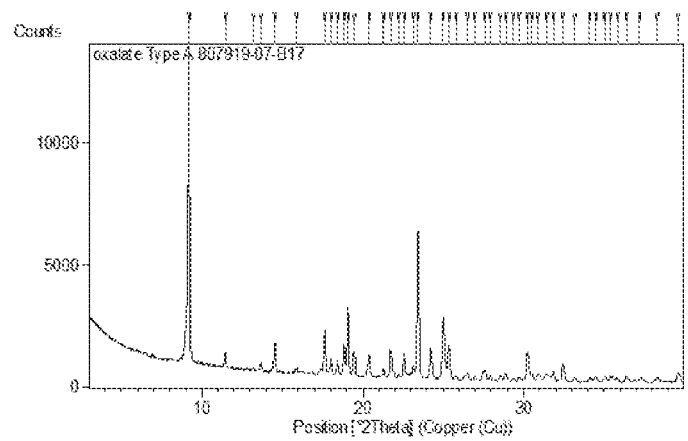
FIG. 107 illustrates XRPD patterns of oxalate crystal form Type A (807919-07-B17).

As per TGA and DSC data in FIG. 106, it shows a weight loss of 1.5% up to 130° C. and a sharp endothermic peak at 206.6° C. (onset temperature) before decomposition. Also, the stoichiometric ratio was determined as 0.93 (acid/base) by $^1$H NMR.

5.4.16 Oxalate

Two oxalate crystal forms were obtained via screening. Oxalate Type A (807919-07-B17) and Type B (807919-07-D17) were produced via reactive crystallization (molar ratio of 1:1) in EtOH and THF at RT respectively. The XRPD pattern for oxalate Type A is displayed in FIG. 107. XRPD data for oxalate Type A provide (peak shift within ±0.2°) primary peaks at 9.2, 19.1, and 23.4; secondary peaks at 14.5, 17.7, and 25.0; and tertiary peaks at 11.5, 22.6, and 30.2.

The XRPD pattern for oxalate Type B is shown in FIG. 108. XRPD data for oxalate Type B provide (peak shift within ±0.2°) primary peaks at 5.4, 18.0, and 23.1; secondary peaks at 9.9, 10.9, and 27.8; and tertiary peaks at 13.0, 16.9, and 24.2.

Figure 110:
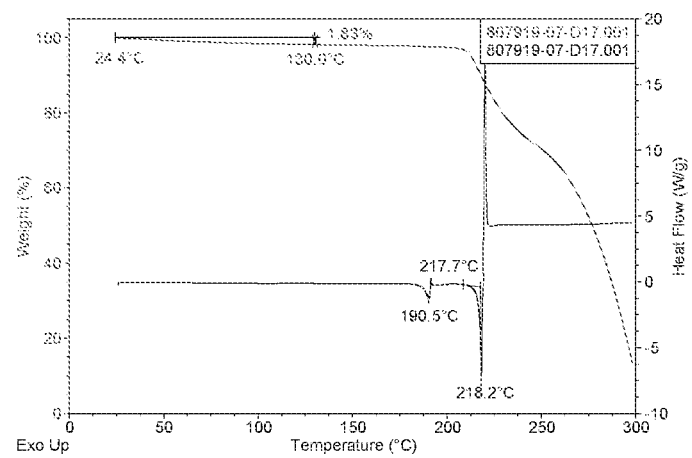
FIG. 110 illustrates TGA/DSC curves of oxalate crystal form Type B (807919-07-D17).
Figure 111:
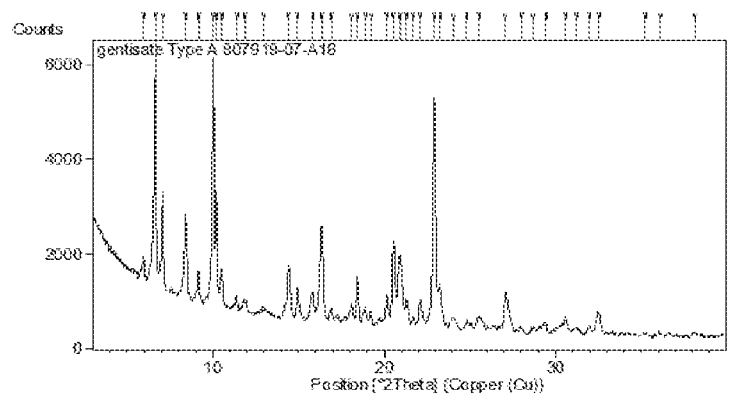
FIG. 111 illustrates XRPD patterns of gentisate crystal form Type A (807919-07-A18).

For Type A, TGA and DSC data (FIG. 109) show a weight loss of 0.7% up to 130° C. and a sharp endothermic peak at 227.3° C. (onset temperature) before decomposition. For Type B, TGA and DSC results (FIG. 110) show a weight loss of 1.8% up to 130° C. and two endothermic peaks at 190.5° C. and 218.2° C. (peak temperature) before decomposition. Also, the stoichiometric ratio was speculated as 0.92 and 1.02 (acid/base) for Type A and B by HPLC/IC.

5.4.17 Gentisate

A total of two gentisate crystal forms were obtained via screening. Gentisate Type A (807919-07-A18) and Type B (807919-07-E18) were generated via reactive crystallization (molar ratio of 1:1) in acetone and MeOH/H$_2$O (9:1, v/v) at RT respectively. The XRPD pattern for gentisate Type A is displayed in FIG. 111. XRPD data for gentisate Type A provide (peak shift within ±0.2°) primary peaks at 6.7, 10.0, and 22.9; secondary peaks at 7.1, 8.4, and 16.4; and tertiary peaks at 14.4, 18.4, and 20.5.

Figure 112:
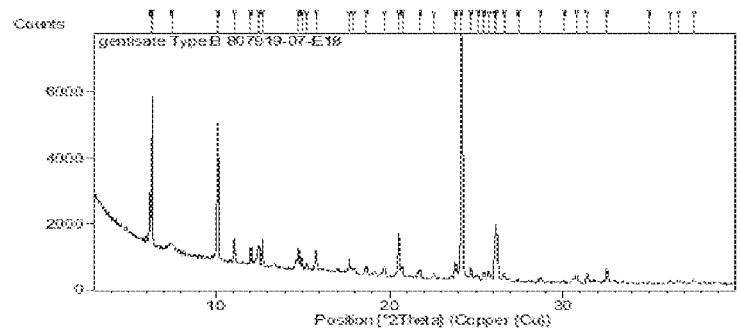
FIG. 112 illustrates XRPD patterns of gentisate crystal form Type B (807919-07-E18).

The XRPD pattern for gentisate Type B is shown in FIG. 112. XRPD data for gentisate Type B provide (peak shift within ±0.2°) primary peaks at 6.3, 10.1, and 24.2; secondary peaks at 12.7, 20.6, and 26.2; and tertiary peaks at 11.1, 14.8, and 15.8.

Figure 113:
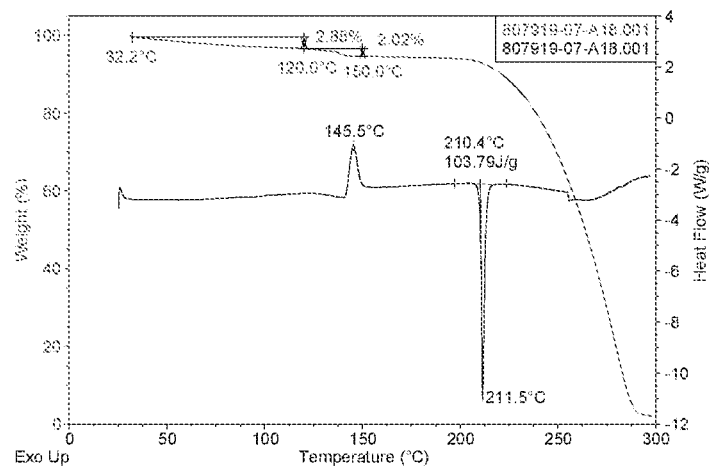
FIG. 113 illustrates TGA/DSC curves of gentisate crystal form Type A (807919-07-A18).
Figure 114:
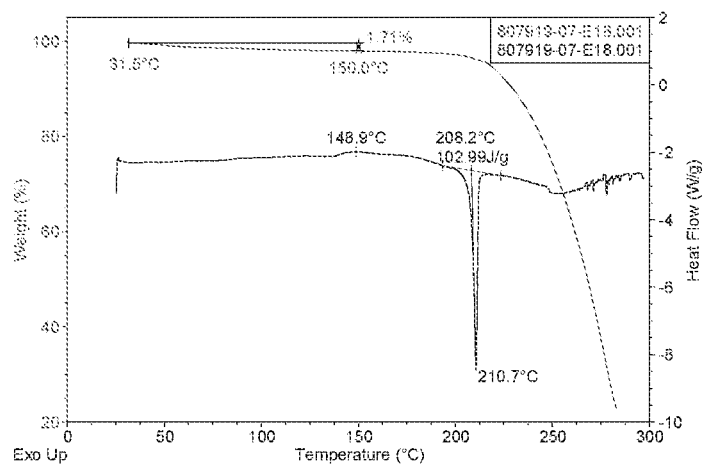
FIG. 114 illustrates TGA/DSC curves of gentisate crystal form Type B (807919-07-E18).

For Type A, TGA and DSC data (FIG. 113) show a weight loss of 4.9% up to 150° C. and an endothermic peak at 210.4° C. (onset temperature) and an exothermic peak at 145.5° C. (peak temperature) before decomposition. For Type B, TGA and DSC results in FIG. 114 show a weight loss of 1.7% up to 150° C. and an endothermic peak at 208.2° C. (onset temperature) and an exothermic peak at 148.5° C. (peak temperature) before decomposition. Also, the stoichiometric ratio was determined as 0.99 and 1.00 (acid/base) for Type A and B by $^1$H NMR.

5.4.18 Benzoate

Figure 115:
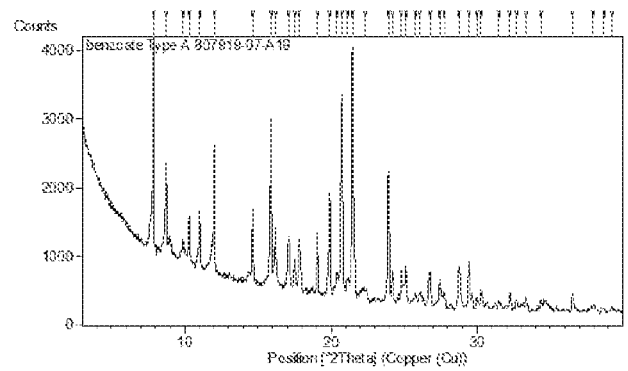
FIG. 115 illustrates XRPD patterns of benzoate crystal form Type A (807919-07-A19).

A total of two benzoate crystal forms were obtained from screening. Benzoate Type A (807919-07-A19) and Type B (807919-07-E19) were produced via reactive crystallization (molar ratio of 1:1) in acetone and MeOH/H$_2$O (9:1, v/v) at RT. The XRPD pattern for benzoate Type A is shown in FIG. 115. XRPD data for benzoate Type A provide (peak shift within ±0.2°) primary peaks at 7.9, 20.8, and 21.5; secondary peaks at 12.0, 15.6, and 23.9; and tertiary peaks at 8.7, 19.9, and 29.4.

Figure 116:
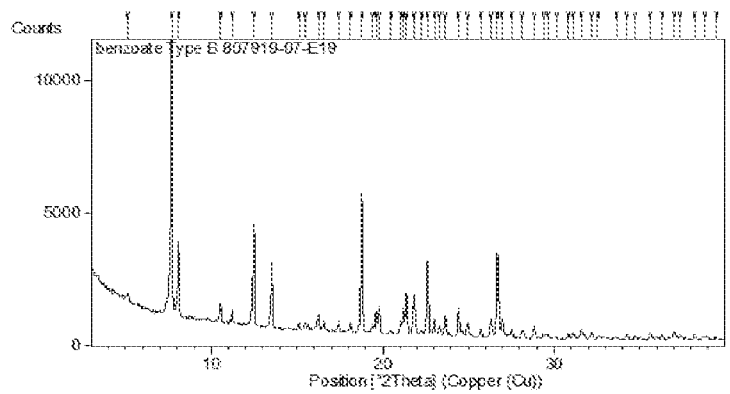
FIG. 116 illustrates XRPD patterns of benzoate crystal Type B (807919-07-E19).

The XRPD pattern for benzoate Type B is shown in FIG. 116. XRPD data for benzoate Type B provide (peak shift within ±0.2°) primary peaks at 7.7, 12.5, and 18.8; secondary peaks at 13.5, 22.6, and 26.7; and tertiary peaks at 19.8, 21.4, and 24.4.

Figure 117:
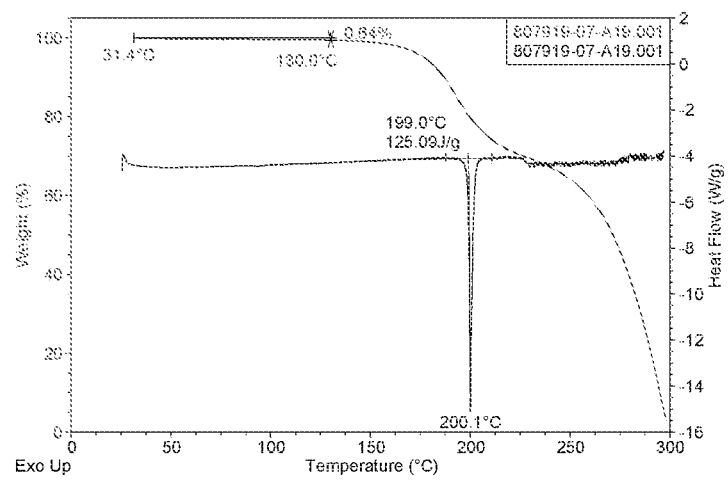
FIG. 117 illustrates TGA/DSC curves of benzoate crystal form Type A (807919-07-A19).
Figure 118:
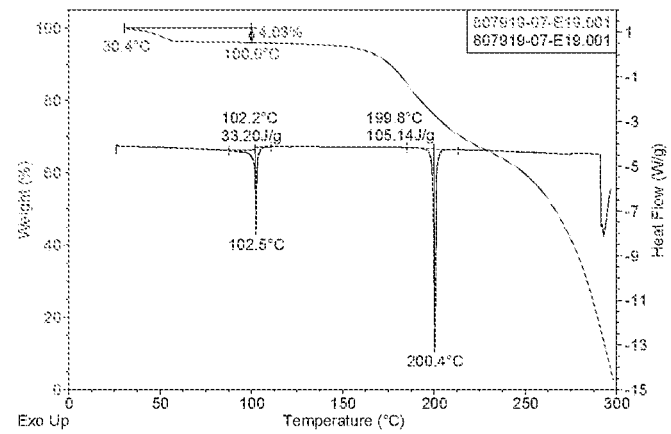
FIG. 118 illustrates TGA/DSC curves of benzoate crystal form Type B (807919-07-E19).
Figure 119:
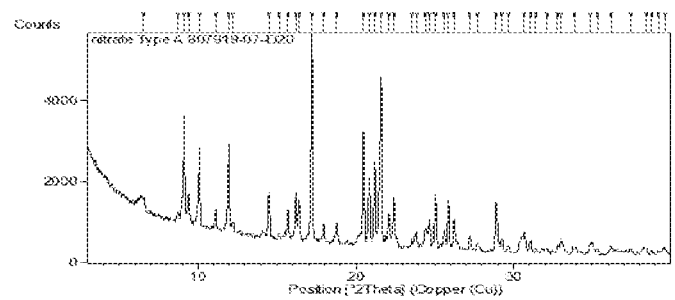
FIG. 119 illustrates XRPD patterns of nitrate crystal form Type A (807919-07-D20).

For Type A, TGA and DSC results (FIG. 117) show a weight loss of 0.6% up to 130° C. and an endothermic peak at 199.0° C. (onset temperature) before decomposition. For Type B, TGA and DSC data in FIG. 118 show a weight loss of 4.0% up to 100° C. and two endothermic peaks at 102.2° C. and 199.8° C. (onset temperature) before decomposition. Also, the stoichiometry was speculated as 0.98 and 0.99 (acid/base) for Type A and B by $^1$H NMR.

5.4.19 Nitrate

Two nitrate crystal forms were obtained via screening. Nitrate Type A (807919-07-D20) and Type B (807919-07-B20) were generated via solution crystallization (molar ratio of 1:1) in THF and EtOH at RT. The XRPD pattern for nitrate Type A is displayed in FIG. 119. XRPD data for nitrate Type A provide (peak shift within ±0.2°) primary peaks at 17.2, 20.5, and 21.6; secondary peaks at 9.1, 10.1, and 12.0; and tertiary peaks at 14.5, 16.2, and 25.0.

Figure 120:
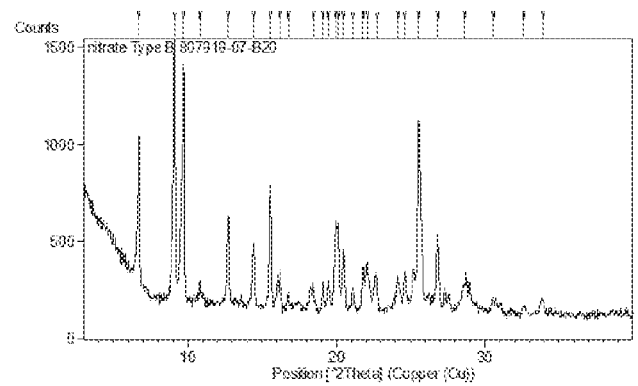

The XRPD pattern for nitrate Type B is shown in FIG. 120. XRPD data for nitrate Type B provide (peak shift within ±0.2°) primary peaks at 6.7, 9.1, and 25.5; secondary peaks at 9.7, 12.7, and 15.6; and tertiary peaks at 14.4, 20.1, and 26.8.

Figure 121:
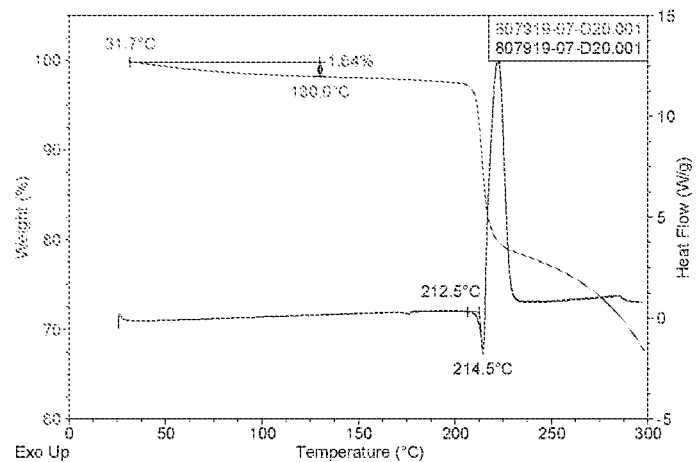
Figure 122:
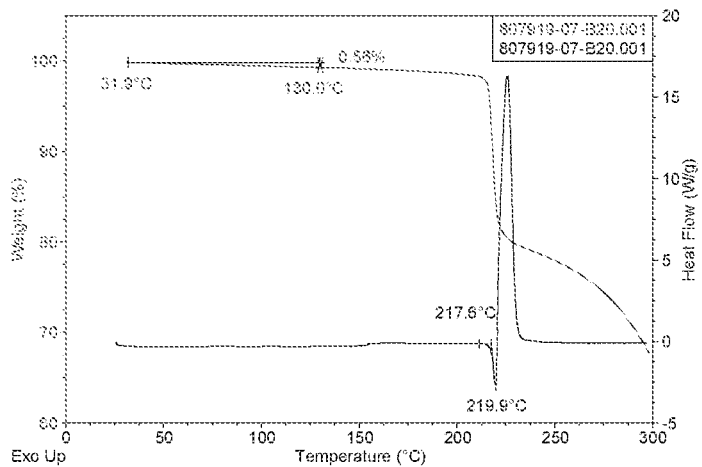
Figure 123:
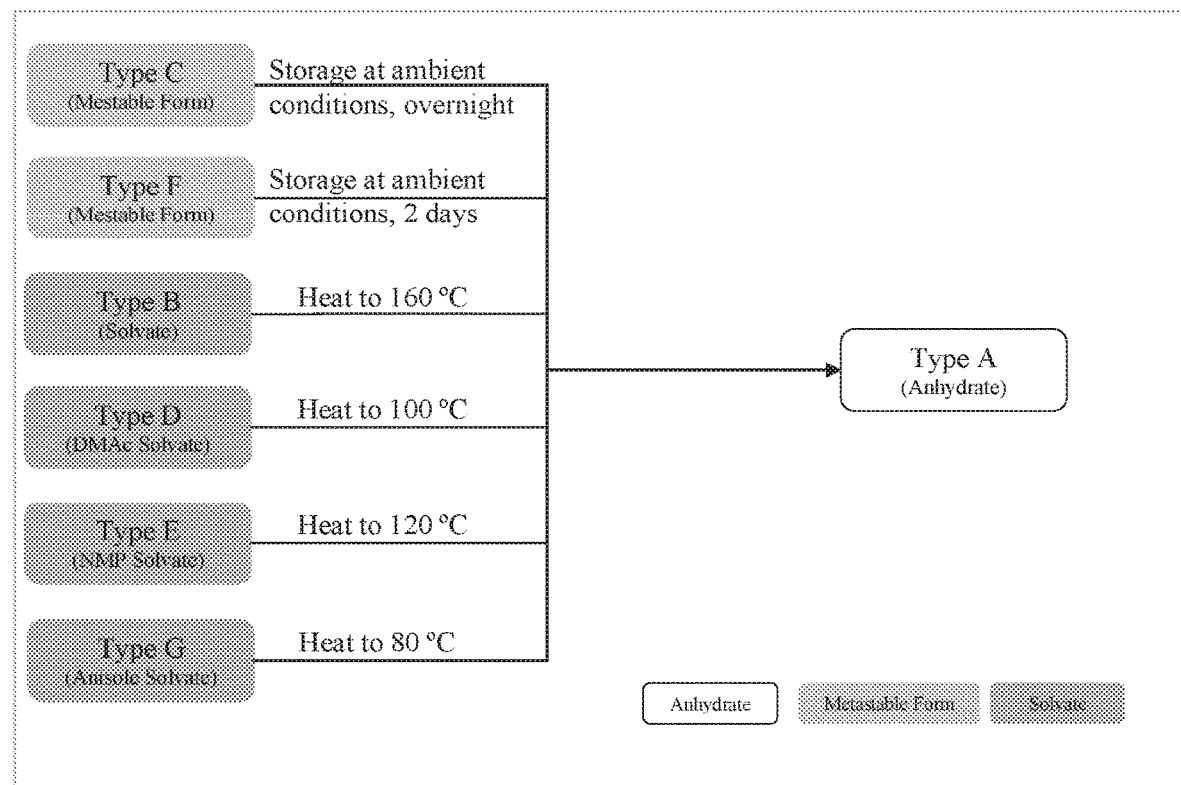
Figure 124:
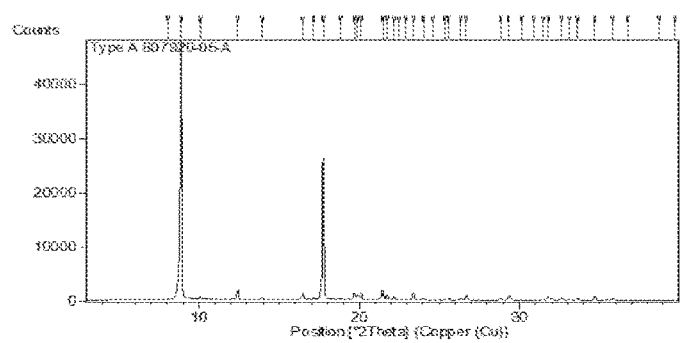

For Type A, TGA and DSC results in FIG. 121 show a weight loss of 1.6% up to 130° C. and a sharp endothermic peak at 212.5° C. (onset temperature) before decomposition. For Type B, TGA and DSC results (FIG. 122) show a weight loss of 0.6% up to 130° C. and a sharp endothermic peak at 217.6° C. (onset temperature) before decomposition. Also, the stoichiometric ratio was determined as 1.04 (acid/base) for both Type A and B by H PLC/IC.

5.5 Experiments of Polymorph Screening for Sulfate 5.5.1 Anti-Solvent Addition

A total of 18 anti-solvent addition experiments were carried out. About 15 mg of starting sulfate (807919-21-A) was dissolved in 0.1-2.5 mL solvent to obtain a clear solution, and the solution was magnetically stirred followed by addition of 0.2 mL anti-solvent per step until precipitate appeared or the total amount of anti-solvent reached 15.0 mL. The obtained precipitate was isolated for XRPD analysis. Results in Table 5-23 show that no new form was obtained.

TABLE 5-23

Summary of anti-solvent addition experiments

| Experiment ID | Solvent (v:v) | Anti-solvent | Solid Form |
|---|---|---|---|
| 807919-24-A1 | MeOH | MIBK | Sulfate Type A |
| 807919-24-A2 | | EtOAc | Sulfate Type A |
| 807919-24-A3 | | 1,4-dioxane | Sulfate Type A |
| 807919-24-A4** | | CHCl$_3$ | Sulfate Type A |
| 807919-24-A5 | | Toluene | Sulfate Type A |
| 807919-24-A6 | EtOH | n-heptane | Sulfate Type A |
| 807919-24-A7 | | MEK | Sulfate Type A |
| 807919-24-A8 | | IPAc | Sulfate Type A |
| 807919-24-A9 | IPA/ACN (1:1) | MTBE | Sulfate Type A |
| 807919-24-A10* | | Toluene | Sulfate Type A |
| 807919-24-A11 | IPA/DCM (3:2) | n-heptane | Sulfate Type A |
| 807919-24-A12* | | Toluene | Sulfate Type A |
| 807919-24-A13** | DMSO | Ethyl lactate | Clear |
| 807919-24-A14 | | THF | Sulfate Type A |
| 807919-24-A15 | NMP | MIBK | Sulfate Type A |
| 807919-24-A16 | | 2-MeTHF | Sulfate Type A |
| 807919-24-A17 | DMAc | Acetone | Sulfate Type A |
| 807919-24-A18 | | MTBE | Sulfate Type A |

*solid was observed after stirring the clear solution from anti-solvent addition at 5° C. for 2 days.
**no solid was obtained via stirring the clear solution at 5° C. and then evaporation was employed.

5.5.2 Solid Vapor Diffusion

Solid vapor diffusion experiments were conducted using 13 different solvents. Approximate 10 mg of starting sulfate (807919-21-A) was weighed into a 3-mL vial, which was placed into a 20-mL vial with 2 mL of volatile solvent. The 20-mL vial was sealed with a cap and kept at RT for 7 days allowing solvent vapor to interact with sample. The solids were tested by XRPD and the results summarized in Table 5-24 show that sulfate Type A and B were generated.

TABLE 5-24

Summary of solid vapor diffusion experiments

| Experiment ID | Solvent | Solid Form |
|---|---|---|
| 807919-25-A1 | H$_2$O | Sulfate Type A |
| 807919-25-A2 | DCM | Sulfate Type A |
| 807919-25-A3 | EtOH | Sulfate Type A |
| 807919-25-A4 | MeOH | Sulfate Type A |
| 807919-25-A5 | ACN | Sulfate Type A |
| 807919-25-A6 | THF | Sulfate Type A |
| 807919-25-A7 | CHCl$_3$ | Sulfate Type A |
| 807919-25-A8 | Acetone | Sulfate Type A |
| 807919-25-A9 | DMF | Sulfate Type A |
| 807919-25-A10 | EtOAc | Sulfate Type A |
| 807919-25-A11 | 1,4-dioxane | Sulfate Type A |
| 807919-25-A12 | IPA | Sulfate Type A |
| 807919-25-A13 | DMSO | Sulfate Type B |

5.5.3 Liquid Vapor Diffusion

Ten liquid vapor diffusion experiments were conducted. Approximate 15 mg of starting sulfate (807919-21-A) was dissolved in appropriate solvent to obtain a clear solution in a 3-mL vial. This solution was then placed into a 20-mL vial with 3 mL of volatile solvents. The 20-mL vial was sealed with a cap and kept at RT allowing sufficient time for organic vapor to interact with the solution. The precipitates were isolated for XRPD analysis. After 7 days, solids were isolated for XRPD analysis. The results summarized in Table 5-25 show that only sulfate Type A was obtained.

TABLE 5-25

Summary of liquid vapor diffusion experiments

| Experiment ID | Solvent (v:v) | Anti-solvent | Solid Form |
|---|---|---|---|
| 807919-26-A1 | MeOH | MEK | Sulfate Type A |
| 807919-26-A2 | | IPAc | Sulfate Type A |
| 807919-26-A3 | | 2-MeTHF | Sulfate Type A |
| 807919-26-A4 | EtOH | Ethyl lactate | Sulfate Type A |
| 807919-26-A5 | | 1,4-dioxane | Sulfate Type A |
| 807919-26-A6 | IPA/ACN (1:1) | Acetone | Sulfate Type A |
| 807919-26-A7 | IPA/DCM (3:2) | MTBE | Sulfate Type A |
| 807919-26-A8 | NMP | THF | Sulfate Type A |
| 807919-26-A9 | DMSO | EtOAc | Sulfate Type A |
| 807919-26-A10 | DMAc | CHCl$_3$ | Sulfate Type A |

5.5.4 Slow Evaporation

Slow evaporation experiments were performed under eight conditions. Briefly, ~15 mg of starting sulfate (807919-21-A) was dissolved in 0.1-2.5 mL of solvent in a 3-mL glass vial. If not dissolved completely, suspensions were filtered using a nylon membrane (pore size of 0.45 μm) and the filtrates would be used instead for the follow-up steps. The visually clear solutions were subjected to evaporation at desired temperature with vials sealed by PARAFILM®. The solids were isolated for XRPD analysis, and the results summarized in Table 5-26 indicated that a mixture of sulfate Type A and hemi-sulfate Type A were generated.

TABLE 5-26

Summary of slow evaporation experiments

| Experiment ID | Solvent (v:v) | Temperature | Solid Form |
|---|---|---|---|
| 807919-27-A1 | MeOH | RT | Sulfate Type A |
| 807919-27-A2 | EtOH | | Sulfate Type A |
| 807919-27-A3 | IPA/ACN (1:1) | | Sulfate Type A |
| 807919-27-A4 | IPA/DCM (3:2) | | Sulfate Type A |
| 807919-27-A5 | H$_2$O | | Sulfate Type A + Hemi-sulfate Type A |
| 807919-27-A6 | DMSO | 50° C. | Sulfate Type A |
| 807919-27-A7 | NMP | | Sulfate Type A |
| 807919-27-A8 | DMAc | | Sulfate Type A |

5.5.5 Polymer Induced Crystallization

Polymer induced crystallization experiments were performed with two sets of polymer mixtures in three solvents. Approximate 15 mg of starting sulfate (807919-21-A) was dissolved in appropriate solvent to obtain a clear solution in a 3-mL vial. About 2 mg of polymer mixture was added into 3-mL glass vial. All the samples were subjected to evaporation at RT to induce precipitation. The solids were isolated for XRPD analysis. Results summarized in Table 5-27 show that only sulfate Type A was produced.

TABLE 5-27

Summary of polymer induced crystallization experiments

| Experiment ID | Solvent (v:v) | Polymer | Solid Form |
|---|---|---|---|
| 807919-28-A1 | MeOH | Polymer mixture A | Sulfate Type A |
| 807919-28-A2 | EtOH | | Sulfate Type A |
| 807919-28-A3 | IPA/ACN (1:1) | | Sulfate Type A |
| 807919-28-A4 | MeOH | Polymer mixture B | Sulfate Type A |
| 807919-28-A5 | EtOH | | Sulfate Type A |
| 807919-28-A6 | IPA/ACN (1:1) | | Sulfate Type A |

Polymer mixture A: polyvinyl pyrrolidone (PVP), polyvinyl alcohol (PVA), polyvinylchloride (PVC), polyvinyl acetate (PVAC), hypromellose (HPMC), methyl cellulose (MC) (mass ratio of 1:1:1:1:1:1)
Polymer mixture B: polycaprolactone (PCL), polyethylene glycol (PEG), poly(methyl methacrylate) (PMMA) sodium alginate (SA), and hydroxyethyl cellulose (HEC) (mass ratio of 1:1:1:1:1).

5.5.6 Slurry at RT

Slurry conversion experiments were conducted at RT in different solvent systems. About 15 mg of starting sulfate (807919-21-A) was suspended in 0.5 mL of solvent in a 1.5-mL glass vial. After the suspension was stirred magnetically for 5 days at RT, the remaining solids were isolated for XRPD analysis. Results summarized in Table 5-28 indicated that hemi-sulfate Type A was generated besides sulfate Type A.

TABLE 5-28

Summary of slurry conversion experiments at RT

| Experiment ID | Solvent (v:v) | Solid Form |
|---|---|---|
| 807919-29-A1 | IPA | Sulfate Type A |
| 807919-29-A2 | IBA | Sulfate Type A |
| 807919-29-A3 | MEK | Sulfate Type A |
| 807919-29-A4 | MIBK | Sulfate Type A |
| 807919-29-A5 | EtOAc | Sulfate Type A |
| 807919-29-A6 | IPAc | Sulfate Type A |
| 807919-29-A7 | Ethyl lactate | Sulfate Type A |
| 807919-29-A8 | MTBE | Sulfate Type A |
| 807919-29-A9 | THF | Sulfate Type A |
| 807919-29-A10 | 2-MeTHF | Sulfate Type A |
| 807919-29-A11 | 1,4-dioxane | Sulfate Type A |
| 807919-29-A12 | Anisole | Sulfate Type A |
| 807919-29-A13 | ACN | Sulfate Type A |
| 807919-29-A14 | DCM | Sulfate Type A |
| 807919-29-A15 | MeOH/toluene (1:3) | Sulfate Type A |
| 807919-29-A16 | EtOH/n-heptane (1:3) | Sulfate Type A |
| 807919-29-A17 | Acetone | Sulfate Type A |
| 807919-29-A18 | Acetone/H$_2$O (a$_w$ = 0.2) | Sulfate Type A |
| 807919-29-A19 | Acetone/H$_2$O (a$_w$ = 0.4) | Sulfate Type A |
| 807919-29-A20 | Acetone/H$_2$O (a$_w$ = 0.6) | Sulfate Type A |
| 807919-29-A21 | Acetone/H$_2$O (a$_w$ = 0.8) | Hemi-sulfate Type A |

5.5.7 Slurry at 50° C.

Slurry conversion experiments were also conducted at 50° C. in different solvent systems. About 15 mg of starting sulfate (807919-21-A) was suspended in 0.3 mL of solvent in a 1.5-mL glass vial. After the suspension was stirred for about 6 days at 50° C., the remaining solids were isolated for XRPD analysis. Results summarized in Table 5-29 indicated that only sulfate Type A was obtained.

TABLE 5-29

Summary of slurry conversion experiments at 50° C.

| Experiment ID | Solvent (v:v) | Solid Form |
|---|---|---|
| 807919-30-A1 | IPA | Sulfate Type A |
| 807919-30-A2 | IBA | Sulfate Type A |
| 807919-30-A3 | MEK | Sulfate Type A |
| 807919-30-A4 | MIBK | Sulfate Type A |
| 807919-30-A5 | EtOAc | Sulfate Type A |
| 807919-30-A6 | IPAc | Sulfate Type A |
| 807919-30-A7 | Ethyl lactate | Sulfate Type A |
| 807919-30-A8 | MTBE | Sulfate Type A |
| 807919-30-A9 | THF | Sulfate Type A |
| 807919-30-A10 | 2-MeTHF | Sulfate Type A |
| 807919-30-A11 | 1,4-dioxane | Sulfate Type A |
| 807919-30-A12 | Anisole | Sulfate Type A |
| 807919-30-A13 | ACN | Sulfate Type A |
| 807919-30-A14 | CHCl$_3$ | Sulfate Type A |
| 807919-30-A15 | MeOH/toluene (1:3) | Sulfate Type A |
| 807919-30-A16 | EtOH/n-heptane (1:3) | Sulfate Type A |
| 807919-30-A17 | Acetone | Sulfate Type A |

5.5.8 Slow Cooling

Slow cooling experiments were conducted in seven solvent systems. About 20 mg of starting sulfate (807919-21-A) was suspended in 1.0 mL solvent in a 3-mL glass vial at RT. The suspension was then heated to 50° C., equilibrated for about two hours and filtered to a new vial using a nylon membrane (pore size of 0.45 μm). Filtrates were slowly cooled down to 5° C. at a rate of 0.1° C./min. Clear solutions were transferred to cooling at −20° C. for 2 days and the final clear solutions were subjected to evaporation at RT. Results summarized in Table 5-30 indicated sulfate Type A and B were generated.

TABLE 5-30

Summary of slow cooling experiments

| Experiment ID | Solvent (v:v) | Solid Form |
| --- | --- | --- |
| 807919-31-A1* | MeOH/toluene (1:1) | Sulfate Type A |
| 807919-31-A2 | EtOH/n-heptane (1:1) | N/A |
| 807919-31-A3 | IPA/ACN (1:1) | Sulfate Type A |
| 807919-31-A4 | IPA/DCM (3:2) | Sulfate Type A |
| 807919-31-A5 | DMSO/EtOAc (1:3) | Sulfate Type A + B |
| 807919-31-A6 | NMP/MIBK (1:3) | Clear |
| 807919-31-A7 | DMAc/MTBE (1:3) | Sulfate Type A |

N/A: limited solid for XRPD analysis.
*solid was obtained at −20° C.

Example 2

1. Summary

Polymorph screening for resiquimod freebase was preformed and its polymorphism towards identifying a suitable crystal form for further pharmaceutical development was evaluated.

The starting material (Batch No.: 144875-48-9) as received was characterized by X-ray powder diffraction (XRPD), thermo-gravimetric analysis (TGA), and differential scanning calorimetry (DSC). The characterization results indicated the starting material conformed to freebase Type A—an anhydrate.

Using Type A as starting material, a polymorph screening was performed under 100 conditions through methods of anti-solvent addition, evaporation, slow cooling, slurry conversion, vapor diffusion and polymer-induced crystallization. Based on the XRPD comparison, a total of eight crystal forms were isolated, including one anhydrate (Type A), two metastable forms (Type C and F), four solvates (Type B, D, E, and G), and one acetate/acetic acid co-crystal (sample H). The characterization results were summarized in Table 2-1. As the inter-conversion illustration displayed in FIG. 144, all metastable forms and solvates converted to Type A after storage at ambient conditions or heating experiments, suggesting Type A was the thermodynamically stable form at room temperature (RT, 20±3° C.).

Type A was selected as a leading form and further evaluated on hygroscopicity and solid-state stability. Hygroscopicity was assessed using dynamic vapor sorption (DVS) at 25° C., and result indicated Type A was non-hygroscopic. Physicochemical stability was investigated under 25° C./60% RH and 40° C./75% RH for one week, and 80° C. for 24 hours. No crystal form change or decrease of HPLC purity was observed, indicating good physical and chemical stability for Type A under tested conditions.

2. Characterization of Crystal Forms

Polymorph screening was performed under 100 experimental conditions, with eight crystal forms obtained, including one anhydrate (Type A), two metastable forms (Type C/F), four solvates (Type B/D/E/G), and one acetate/acetic acid co-crystal (sample H). The inter-conversion relationships among these forms were studied via storage and heating experiments, with the results illustrated in FIG. 144.

TABLE 2-1

Characterization summary of crystal forms from screening

| Crystal Form (Sample ID) | Crystallization Conditions | Endotherm (peak, ° C.) | Wt Loss (%) | Solvent Residual | Speculated Form |
| --- | --- | --- | --- | --- | --- |
| Type A (807920-05-A) | Not disclosed | 194.1 | 2.5 | N/A* | Anhydrate |
| Type C (807920-11-A11) | Solid vapor diffusion 1,4-dioxane | N/A | N/A | N/A | Metastable form |
| Type F (807920-09-A4) | Slow cooling MEK | N/A | N/A | N/A | Metastable form |
| Type B (807920-07-A13) | Evaporation IBA/Toluene | 158.4, 192.9 | 10.8 | Toluene 4.3% | |
| Type B (807920-08-A7) | Evaporation EtOAc | 146.7, 191.9 | 9.3 | EtOAc 5.2% | Isomorphic forms |
| Type B (807920-12-A2) | Solution vapor diffusion THF/H₂O | 143.7, 194.4 | 6.5 | THF 6.1% | |
| Type D (807920-12-A9) | Solution vapor diffusion DMAc/MTBE | 94.1, 193.2 | 18.4 | DMAc 18.3% | DMAc solvate |
| Type E (807920-16-A3) | Slurry NMP/MTBE | 134.0, 187.4 | 25.5 | NMP 22.9% | NMP solvate |
| Type G (807920-19-F) | Fast cooling Anisole | 84.7, 193.9 | 14.6 | Anisole 12.4% | Anisole solvate |
| Sample H (807920-22-A1) | Anti-solvent addition Ethyl lactate/ n-heptane/Acetic acid | 151.6, 156.9 | 12.1 | Acetic acid 8.2% | Acetate/ acetic acid co-crystal |

N/A: no data was collected due to the form transformation to Type A.
N/A*: no data was available.

Preparation procedures for crystal forms described below are described in Table 2-1a.

TABLE 2-3

Preparation procedures of salts

| Crystal Form | Preparation Procedures |
|---|---|
| Isomorphism Type B (807920-12-A2) Method 1 | 1. Weigh 15.3 mg freebase Type A into 2.0 mL IBA to get a clear solution.<br>2. Add 15.0 mL toluene as anti-solvent to the system and clear solution was obtained.<br>3. Transfer the solution to stirring at 5° C. 2 days and clear solution was observed.<br>4. Transfer the solution to evaporation to dryness at RT.<br>5. Isolate the solids for analysis. |
| Isomorphism Type B (807920-12-A2) Method 2 | 1. Weigh 8.5 mg freebase Type A into 2.0 mL EtOAc to get a clear solution.<br>2. Transfer the solution to evaporation at RT<br>3. Isolate the solids for analysis. |
| Isomorphism Type B (807920-12-A2) Method 3 | 1. Weigh 60.1 mg freebase Type A into 4.0 mL THF to get a clear solution.<br>2. Pippte 1.0 mL freebase solution to a 3-mL glass vial.<br>3. Seal the vial into the 20-mL glass vial with 3-mL $H_2O$ and keep the system at RT for 6 days.<br>4. Isolate the solids for analysis. |
| DMAc Solvate Type D (807920-12-A9) | 1. Weigh 15.3 mg freebase Type A to 0.1 mL DMAc to get a clear solution in a 3-mL glass vial.<br>2. Seal the vial into the 20-mL glass vial with 3-mL MTBE and keep the system at RT for 6 days.<br>3. Isolate the solids for analysis. |
| NMP Solvate Type E (807920-16-A3) | 1. Weigh 30.6 mg freebase Type A to 0.3 mL NMP to get a clear solution at RT.<br>2. Add 0.6 mL MTBE to induce precipitate.<br>3. Transfer the sample to stirring at 4° C. overnight.<br>4. Isolate the solids for analysis. |
| Anisole Solvate Type G (807920-19-F) | 1. Weigh 59.0 mg freebase Type A to 4.5 mL anisole and stir at 50° C. for 1 hr to get a clear solution.<br>2. Keep the sample at 50° C. for another 30 min and then transfer to −20° C.<br>3. Isolate the solids for analysis after 4 days. |
| Metastable Form Type C (807920-11-A11) | 1. Weigh 10.1 mg freebase Type A into a 3-mL glass vial.<br>2. Seal the vial into the 20-mL glass vial with 2-mL 1,4-dioxane and keep the system at RT.<br>3. Isolate the solids for analysis after 7 days. |
| Metastable Form Type F (807920-09-A4) | 1. Weigh 14.4 mg freebase Type A to 1.0 mL MEK and stir at 50° C. for 2 hrs to get a suspension.<br>2. Filter the suspension and transfer the solution to slow cooling (50° C. to 5° C., 0.1° C./min).<br>3. Isolate the solids for analysis after 14 days. |

2.1 Anhydrate (Type A)

Starting material (Batch No.: 144875-48-9, with a CP ID 807920-05-A) was characterized by XRPD, TGA, DSC, and HPLC. The XRPD result in FIG. 124 conformed to the Type A reference (807919-05-A). XRPD patterns are displayed in FIG. 141 and provide (peak shift within ±0.2°) primary peaks at 8.9, 12.4, and 17.7; secondary peaks at 19.7, 21.5, and 23.4; and tertiary peaks at 16.5, 20.1, and 26.7.

Figure 125:
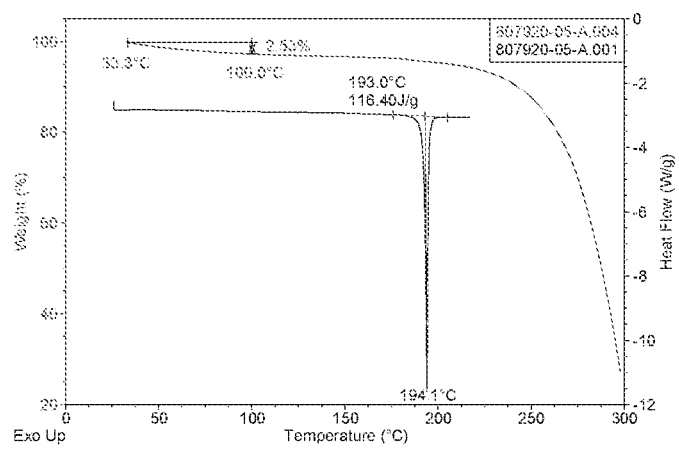
Figure 126:
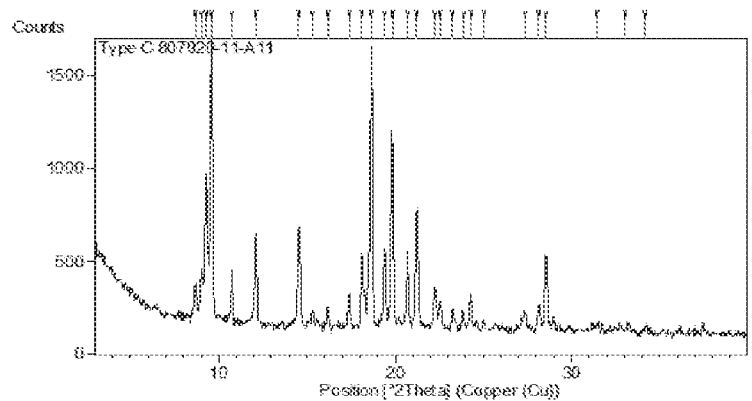

TGA and DSC data for the anhydrate Type A crystal form show (FIG. 125) a weight loss of 2.5% up to 100° C. and a sharp endothermic peak at 193.0° C. (onset temperature) before decomposition. Also, a purity of 99.4 area % was detected by HPLC in Table 2-2. Considering all the results, Type A was deemed as an anhydrate.

TABLE 2-2

HPLC purity profile of Type A (807920-05-A)

| # | RRT | Area % |
|---|---|---|
| 1 | 0.75 | 0.08 |
| 2 | 0.83 | 0.24 |
| 3 | 0.87 | 0.05 |
| 4 | 1.00 | 99.41 |

TABLE 2-2-continued

HPLC purity profile of Type A (807920-05-A)

| # | RRT | Area % |
|---|---|---|
| 5 | 1.07 | 0.10 |
| 6 | 1.61 | 0.13 |

2.2 Metastable Form
2.2.1 Type C

Type C was generated in 1,4-dioxane system. Type C sample (807920-11-A11) was obtained via solid vapor diffusion in 1,4-dioxane. As XRPD pattern displayed in FIG. 126, Type C converted to Type A after dried at ambient conditions overnight, suggesting metastable form for Type C at ambient conditions. XRPD patterns provide (peak shift within ±0.2°) primary peaks at 9.6, 18.7, and 19.8; secondary peaks at 12.1, 14.5, and 21.2; and tertiary peaks at 17.4, 20.7, and 28.5.

2.2.2 Type F

Figure 127:
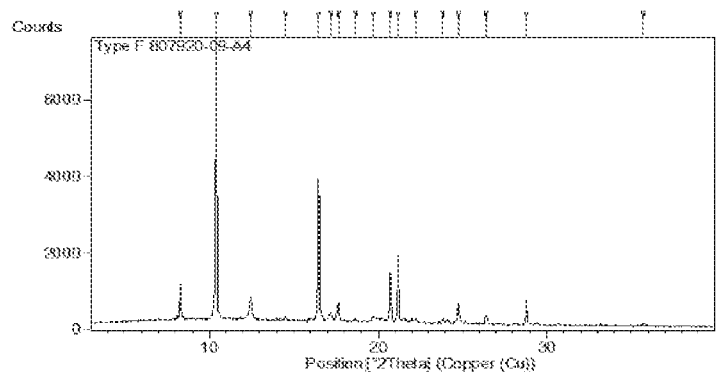
Figure 128:
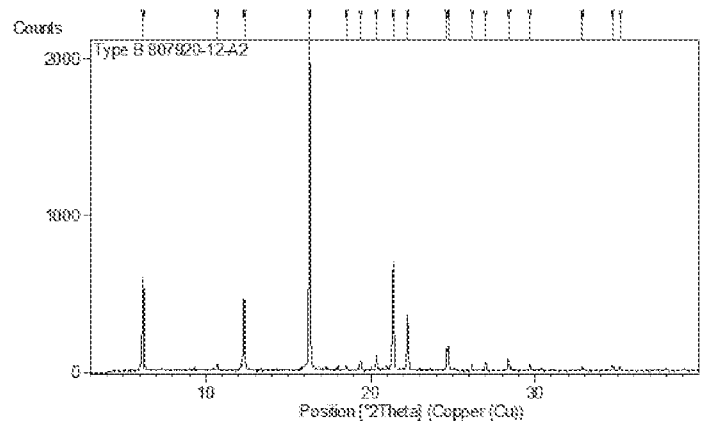

Type F sample (807920-09-A4) was obtained via slow cooling in MEK and the XRPD pattern was displayed in FIG. 127. XRPD patterns provide (peak shift within ±0.2°) primary peaks at 10.4, 16.5, and 21.2; secondary peaks at 8.3, 20.7, and 28.8; and tertiary peaks at 12.5, 17.7, and 24.8.

After storage at ambient conditions for 2 days, Type F converted to Type A, indicating Type F was metastable at ambient conditions.

2.3 Solvate 2.3.1 Type B

Isomorphism occurred to Type B. It can be prepared in several solvent systems, including IBA/toluene, EtOAc, THF/H$_2$O, and etc. XRPD patterns of Type B were displayed in FIG. 128. XRPD patterns provide (peak shift within ±0.2°) primary peaks at 6.2, 16.3, and 21.4; secondary peaks at 12.3, 22.3, and 24.7; and tertiary peaks at 20.4, 27.0, and 28.4.

Figure 129:
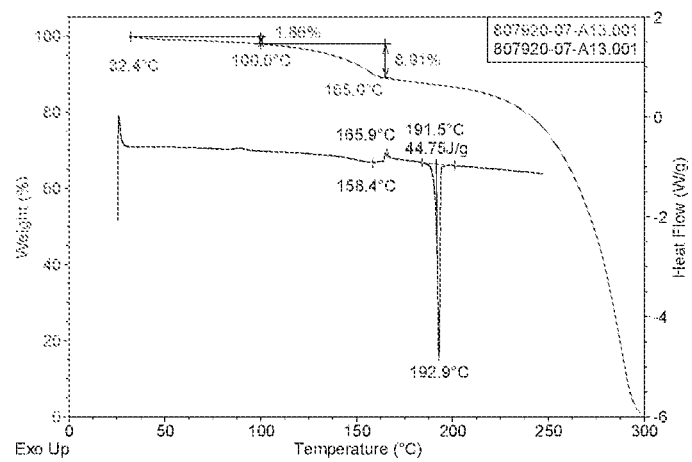
Figure 130:
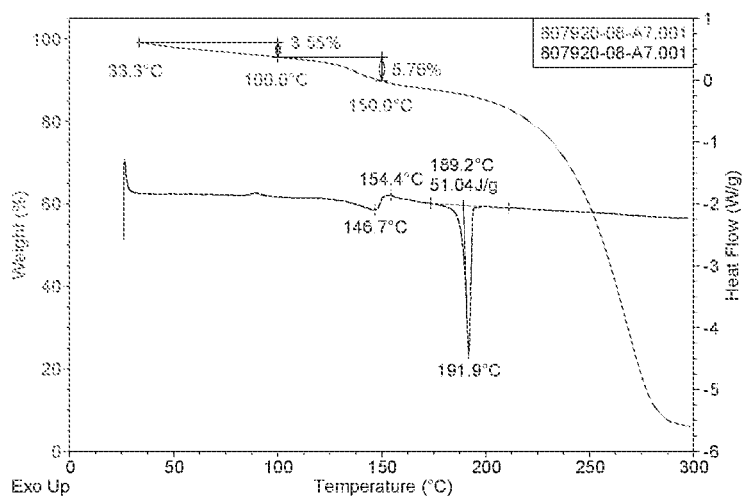
Figure 131:
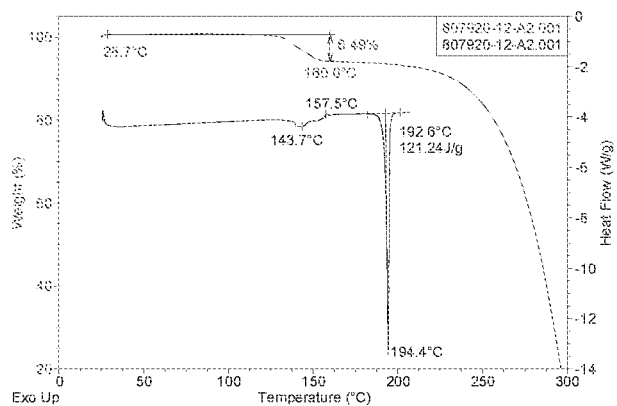

Three batches of the isomorphism Type B crystal form were produced. Batch 1: TGA and DSC data (FIG. 129) show a weight loss of 10.8% up to 165° C. and two endothermic peaks at 158.4° C. and 192.9° C. (peak temperature) before decomposition. Batch 2: TGA and DSC data (FIG. 130) show a weight loss of 9.3% up to 150° C. and two endothermic peaks at 146.7° C. and 191.9° C. (peak temperature) before decomposition. Batch 3: TGA and DSC data (FIG. 131) show a weight loss of 6.5% up to 160° C. and two endothermic peaks at 143.7° C. and 194.4° C. (peak temperature) before decomposition.

Also, $^1$H NMR confirm a EtOAc content of 5.2% in Type B sample (807920-08-A7), which suggested EtOAc solvate for Type B (807920-08-A7). Also, $^1$H NMR confirm a THF content of 6.1% in Type B sample (807920-12-A2), which suggested THF solvate for Type B (807920-12-A2).

TABLE 2-3

HPLC purity profiles of Type B (807920-07-A13) before and after heating

| | Area (%) | |
| --- | --- | --- |
| RRT | Initial Type B | Type B heated to 160° C. |
| 0.69 | 0.09 | — |
| 0.75 | 0.13 | 0.09 |
| 0.83 | 0.38 | 0.29 |
| 0.87 | 0.09 | 0.06 |
| 1.00 | 99.09 | 99.51 |
| 1.04 | 0.10 | — |
| 1.07 | 0.12 | 0.05 |

2.3.2 Type D

Type D sample (807920-12-A9) was prepared via solution vapor diffusion in DMAc/MTBE. XRPD pattern was shown in FIG. 157. XRPD patterns are displayed in FIG. 132 and provide (peak shift within ±0.2°) primary peaks at 8.7, 17.6, and 23.9; secondary peaks at 11.2, 21.2, and 22.8; and tertiary peaks at 9.1, 15.5, and 16.9. TGA and DSC data (FIG. 133) show a weight loss of 18.4% up to 90° C. and two endothermic peaks at 87.2° C. and 190.2° C. (onset temperature) before decomposition. Also, $^1$H NMR confirm a DMAc content of 18.3% in Type D Sample, indicating DMAc solvate for Type D.

2.3.3 Type E

Type E was generated in NMP/MTBE system. Type E sample was obtained via slurry in NMP/MTBE (1:2, v/v) at RT. The XRPD pattern is displayed in FIG. 134. XRPD patterns provide (peak shift within ±0.2°) primary peaks at 8.7, 17.9, and 23.9; secondary peaks at 16.9, 21.3, and 22.9; and tertiary peaks at 9.2, 11.2, and 12.5. TGA and DSC data (FIG. 135) show a weight loss of 25.5% up to 120° C. and two endothermic peaks at 134.0° C. and 187.4° C. (peak temperature) before decomposition. Also, 1H NMR shows NMP content of 22.9% was detected, which was consistent with the TGA weight loss, indicating Type E was a NMP solvate.

2.3.4 Type G

Type G was generated in anisole system. Type G sample (807920-19-F) was obtained via fast cooling from 50° C. to −20° C. and the XRPD pattern displayed in FIG. 136. XRPD patterns provide (peak shift within ±0.2°) primary peaks at 9.7, 13.3, and 19.2; secondary peaks at 8.9, 13.8, 28.0; and tertiary peaks at 12.4, 20.6, and 23.4. TGA and DSC data (FIG. 137) show a weight loss of 14.6% up to 100° C. and two endothermic peaks at 64.5° C. and 193.0° C. (onset temperature) before decomposition. $^1$H NMR results indicate anisole of 12.4% was detected, which was consistent with the second weight loss in TGA, suggesting anisole solvate for Type G.

2.4 Salt/Co-Crystal (Sample H)

Sample H (807920-22-A1) was obtained via anti-solvent addition in ethyl lactate/n-heptane with additional acetic acid (molar ratio 0.4:1, acid/base) and a mixture of Type A and sample H was generated via anti-solvent addition in ethyl lactate/n-heptane (with acetic acid content detected in ethyl lactate). The XRPD patterns shown in FIG. 138 provide (peak shift within ±0.2°) primary peaks at 9.7, 13.3, and 19.2; secondary peaks at 8.9, 13.8, 28.0; and tertiary peaks at 12.4, 20.6, and 23.4. TGA and DSC data (FIG. 139) show a weight loss of 14.6% up to 100° C. and two endothermic peaks at 64.5° C. and 193.0° C. (onset temperature) before decomposition. Also, the acetic acid content of 0.47:1 (molar ratio, acid/base) was determined by $^1$H NMR. Combined with the characterization data, sample H was speculated as an acetate/acetic acid co-crystal.

3. Evaluation of Leading Type A

Since all solvates and metastable forms converted to Type A after storage or heating experiments, anhydrate Type A was the thermodynamically stable form at RT and selected to be further evaluated on hygroscopicity and solid-state stability. Results show: 1) Type A was non-hygroscopic as evidenced by the limited water uptake in DVS; 2) Type A had good physicochemical properties under 25° C./60% RH and 40° C./75% RH for one week, and 80° C. for 24 hours.

3.1 Hygroscopicity

DVS isotherm plot was collected at 25° C. to investigate the solid form stability as a function of humidity for anhydrate Type A (807919-05-A). Solids were pre-dried at 0% RH to remove the unbounded solvent or water before started. As DVS plot shown in FIG. 140, a water uptake of 0.1% was observed up to 80% RH, suggesting Type A (807919-05-A) was non-hygroscopic. Also, no form change was observed after DVS test (FIG. 140).

3.2 Solid-State Stability

Physicochemical stability of Type A (807919-05-A) was evaluated under 25° C./60% RH and 40° C./75% RH for one week, and 80° C. (closed) for 24 hours. Stability samples were characterized by XRPD and HPLC, with the results summarized in Table 3-1 and FIG. 142. No change was observed in HPLC purity or crystal form, suggesting good physical and chemical stability for Type A (807919-05-A) under tested conditions.

TABLE 3-1

| Stability evaluation summary of Type A (807919-05-A) | | | | | |
|---|---|---|---|---|---|
| Crystal Form | HPLC Purity | | HPLC Purity | | Form |
| (Sample ID) | (Initial, area %) | Condition | Area % | % of Initial | Change |
| Freebase Type A (807919-05-A)* | 99.32 | 25° C./60% RH, 1 week | 99.15 | 99.8 | No |
| | | 40° C./75% RH, 1 week | 99.28 | 100.0 | No |
| Freebase Type A (807919-05-A) | 99.15 | 80° C., 24 hrs | 99.23 | 100.1 | No |

*Data was collected in salt screening section.

4. Conclusion

Using compound 001 freebase Type A as the starting material, a total of 100 polymorph screening experiments were set up, and XRPD analysis of the solids revealed that eight crystal forms were obtained. Form identification results show that there were one anhydrate (Type A), two metastable forms (Type C/F), four solvates (Type B/D/E/G), and one acetate/acetic acid co-crystal (sample H). The inter-conversion results show Type B~G all converted to Type A after heating or storage, indicating good physical stability for Type A. Type A was further evaluated by hygroscopicity and solid-state stability. The results show Type A was non-hygroscopic and possessed good physico-chemical properties under 25° C./60% RH and 40° C./75% RH for one week, and 80° C. for 24 hours. Combined with the characterization results, Type A was recommended for further pharmaceutical development.

5. Other 5.1 Sample Information

Starting materials as received were used directly in polymorph screening and evaluation experiments, with the detailed information provided in Table 5-1.

TABLE 5-1

| Detailed information of starting materials | | | |
|---|---|---|---|
| Compound | Batch No. | CP ID | Crystal Form |
| 001 | 144875-48-9 | 807920-05-A | Type A |
| | NA | 807919-05-A | Type A |

NA: no information was available.

5.2 Abbreviation for Solvents Used

The solvent abbreviations are listed in Table 5-2.

TABLE 5-2

| Abbreviations of solvents | | | |
|---|---|---|---|
| Abbreviation | Solvent | Abbreviation | Solvent |
| MeOH | Methanol | THF | Tetrahydrofuran |
| EtOH | Ethanol | 2-MeTHF | 2-Methyltetrahydrofuran |
| IPA | Isopropyl alcohol | DCM | Dichloromethane |
| IBA | Isobutyl alcohol | $CHCl_3$ | Trichloromethane |
| MEK | 2-Butanone | ACN | Acetonitrile |
| MIBK | 4-Methyl-2-pentanone | DMSO | Dimethylsulfoxide |
| EtOAc | Ethyl acetate | DMAc | N,N-Dimethylacetamide |
| IPAc | Isopropyl acetate | NMP | 1-Methyl-2-pyrrolidone |
| MTBE | Methyl tert-butyl ether | — | — |

5.3 Instruments and Methods 5.3.1 XRPD

For XRPD analysis, a PANalytical Empyrean X-ray powder diffract meter was used. The XRPD parameters used are listed in Table 5-3.

TABLE 5-3

| Parameters for XRPD test | |
|---|---|
| Parameters | XRPD (Reflection Mode) |
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (° 2TH) | 3°-40° |
| Step size (° 2TH) | 0.0130 |
| Scan speed (°/min) | About 7 |

5.3.2 TGA and DSC

TGA data were collected using a TA Q500/Q5000 TGA from TA Instruments. DSC was performed using a TA Q200/Q2000 DSC from TA Instruments. Detailed parameters used are listed in Table 5-4.

TABLE 5-4

| Parameters for TGA and DSC test | | |
|---|---|---|
| Parameters | TGA | DSC |
| Method | Ramp | Ramp |
| Sample pan | Platinum, open | Aluminum, crimped |
| Temperature | RT - desired temperature | 25° C. - desired temperature |
| Heating rate | 10° C./min | 10° C./min |
| Purge gas | $N_2$ | $N_2$ |

5.3.3 HPLC

Agilent 1100 HPLC was utilized to analyze purity, with detailed method was listed in Table 5-5.

TABLE 0-1

| HPLC method for purity test | | |
|---|---|---|
| HPLC | Agilent 1100 with DAD Detector | |
| Column | Alltima C18, 150 × 4.6 mm, 5 μm | |
| Mobile phase | A: 0.1% TFA in $H_2O$ | |
| | B: 0.1% TFA in Acetonitrile | |
| | Time (min) | % B |
| Gradient table | 0.0 | 10 |
| | 10.0 | 40 |
| | 18.0 | 90 |
| | 20.0 | 90 |
| | 20.1 | 10 |
| | 23.0 | 10 |
| Run time | 23.0 min | |
| Post time | 0.0 min | |
| Flow rate | 1.0 mL/min | |
| Injection volume | 5 μL | |
| Detector wavelength | UV at 228 nm, reference 500 nm | |

TABLE 0-1-continued

HPLC method for purity test

| Column temperature | 40° C. |
|---|---|
| Sampler temperature | RT |
| Diluent | Acetonitrile:$H_2O$ = 1:1 |

5.3.4 DVS

DVS was measured via a SMS (Surface Measurement Systems) DVS Intrinsic. The relative humidity at 25° C. were calibrated against deliquescence point of LiCl, $Mg(NO_3)_2$ and KCl. Actual parameters for DVS test were listed in Table 5-6.

TABLE 5-6

Parameters for DVS test

| Parameters | DVS |
|---|---|
| Temperature | 25° C. |
| Sample size | 10~20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 0% RH to 95% RH |
| RH step size | 10% RH from 0% RH to 90% RH |
|  | 5% RH from 90% RH to 95% RH |

5.3.5 Solution NMR

Solution NMR was collected on Bruker 400M NMR Spectrometer using DMSO-d6.

5.4 Polymorph Screening

The solubility of starting material (807920-05-A) was estimated at RT. Approximately 2 mg solids were added into a 3-mL glass vial. Solvents were then added step wise (100 μL per step) into the vials until the solids were dissolved or a total volume of 1 mL was reached. Results summarized in Table 5-7 were used to guide the solvent selection in polymorph screening.

Polymorph screening experiments were performed using different crystallization or solid transition methods. The methods utilized and crystal forms identified are summarized in Table 5-8.

TABLE 5-7

Approximate solubility of starting material (807920-05-A) at RT

| Solvent | Solubility (mg/mL) | Solvent | Solubility (mg/mL) |
|---|---|---|---|
| n-heptane | S < 2.0 | 2-MeTHF | 7.0 < S < 21.0 |
| $H_2O$ | S < 2.1 | Acetone | 7.1 < S < 25.0 |
| MTBE | S < 2.2 | IPA | 8.3 < S < 25.0 |
| toluene | S < 2.2 | IBA | 8.3 < S < 25.0 |
| Anisole | S < 2.3 | THF | 21.0 < S < 42.0 |
| MEK | 2.0 < S < 6.7 | Ethyl lactate | 22.0 < S < 44.0 |
| IPAc | 2.1 < S < 7.0 | $CHCl_3$ | 22.0 < S < 44.0 |
| MIBK | 2.2 < S < 7.3 | EtOH | 23.0 < S < 46.0 |
| EtOAc | 2.3 < S < 7.7 | NMP | S > 40.0 |
| ACN | 2.5 < S < 8.3 | DMSO | S > 44.0 |
| 1,4-dioxane | 6.7 < S < 20.0 | MeOH | S > 46.0 |
| DCM | 6.7 < S < 20.0 | DMAc | S > 48.0 |

TABLE 5-8

Summary of polymorph screening experiments

| Method | No. of Experiments | Crystal Form |
|---|---|---|
| Anti-solvent Addition | 20 | Type A, B, G, sample H |
| Slow Evaporation | 10 | Type A, B |
| Slow Cooling | 10 | Type A, B, F, G |
| Polymer-induced Crystallization | 6 | Type A, B |
| Solid Vapor Diffusion | 13 | Type A, C |
| Solution Vapor Diffusion | 10 | Type A, B, D, E |
| Slurry at RT/50° C. | 31 | Type A, C |
| Total | 100 | Type A~G, sample H |

5.4.1 Anti-Solvent Addition

A total of 20 anti-solvent addition experiments were carried out. About 15 mg of starting material (807920-05-A) was dissolved in 0.1-2.3 mL solvent to obtain a clear solution, and the solution was magnetically stirred followed by addition of 0.2 mL anti-solvent per step till precipitate appeared or the total amount of anti-solvent reached 15.0 mL. The obtained precipitate was isolated for XRPD analysis. Results in Table 5-9 show that Type B, G, and sample H were generated besides Type A.

TABLE 5-9

Summary of anti-solvent addition experiments

| Experiment ID | Solvent | Anti-solvent | Solid Form |
|---|---|---|---|
| 807920-07-A1 | MeOH | $H_2O$ | Type A |
| 807920-07-A2** | IPA |  | Clear |
| 807920-07-A3** | Acetone |  | Type A |
| 807920-07-A4** | THF |  | Type A |
| 807920-07-A5 | DMSO |  | Type A |
| 807920-07-A6 | DMAc |  | Type A |
| 807920-07-A7 | NMP |  | Type A |
| 807920-07-A8 | EtOH | n-heptane | Type A |
| 807920-07-A9 | THF |  | Type A + B |
| 807920-07-A10 | 2-MeTHF |  | Type A + B |
| 807920-07-A11 | Ethyl lactate |  | Type A + Sample H |
| 807920-07-A12 | $CHCl_3$ |  | Type A + B |
| 807920-07-A13** | IBA | Toluene | Type B |
| 807920-07-A14 | DCM |  | Type A |
| 807920-07-A15* | 1,4-dioxane |  | Type A |
| 807920-07-A16* | MeOH | MTBE | Type A |
| 807920-07-A17** | Acetone |  | Type B |
| 807920-07-A18 | $CHCl_3$ |  | Type A |
| 807920-07-A19** | EtOH | Anisole | Type G |
| 807920-07-A20 | DCM |  | Clear |

*solids were observed after stirring the clear solution from anti-solvent addition at 5° C. for 2 days.
**no solid was obtained via stirring the clear solution at 5° C. and then evaporation was employed.

5.4.2 Slow Evaporation

Slow evaporation experiments were performed under ten conditions. Briefly, ~15 mg of starting material (807920-05-A) was dissolved in 1.0-2.0 mL of solvent in a 3-mL glass vial. If not dissolved completely, suspensions were filtered using a nylon membrane (pore size of 0.45 μm) and the filtrates would be used instead for the follow-up steps. The visually clear solutions were subjected to evaporation at RT with vials sealed by Parafilm®. The solids were isolated for XRPD analysis, and the results summarized in Table 5-10 indicated that Type A and B were obtained.

TABLE 5-10

Summary of slow evaporation experiments

| Experiment ID | Solvent (v:v) | Solid Form |
|---|---|---|
| 807920-08-A1 | MeOH | Type A |
| 807920-08-A2 | IPA | Type A |
| 807920-08-A3 | Acetone | Type A |
| 807920-08-A4 | DCM | Type A |
| 807920-08-A5 | THF | Type A |
| 807920-08-A6 | ACN | Type A + B |
| 807920-08-A7 | EtOAc | Type B |
| 807920-08-A8 | EtOH/H$_2$O (1:1) | Type A |
| 807920-08-A9 | 2-MeTHF/n-heptane (1:1) | Type B |
| 807920-08-A10 | CHCl$_3$/n-heptane (1:1) | Type A + B |

5.4.3 Slow Cooling

Slow cooling experiments were conducted in ten solvent systems. About 15 mg of starting material (807920-05-A) was suspended in 1.0 mL of solvent in a 3-mL glass vial at RT. The suspension was then heated to 50° C., equilibrated for about two hours and filtered using a nylon membrane (pore size of 0.45 μm). Filtrates were slowly cooled down to 5° C. at a rate of 0.1° C./min. The obtained solids were kept isothermal at 5° C. before isolated for XRPD analysis. Clear solutions were transferred to −20° C. and if it was still clear, they were subjected to evaporation at RT. Results summarized in Table 5-11 indicated Type B, F, and G were generated besides Type A.

TABLE 5-11

Summary of slow cooling experiments

| Experiment ID | Solvent (v:v) | Solid Form |
|---|---|---|
| 807920-09-A1 | ACN | Type A |
| 807920-09-A2 | EtOAc | Type A |
| 807920-09-A3 | IPAc | Type A |
| 807920-09-A4 | MEK | Type F |
| 807920-09-A5 | MIBK | Type A + B |
| 807920-09-A6* | Anisole | Type G |
| 807920-09-A7 | Acetone/H$_2$O (1:3) | Type A |
| 807920-09-A8 | EtOH/n-heptane (1:3) | Type A |
| 807920-09-A9 | THF/toluene (1:3) | Type A + B |
| 807920-09-A10 | CHCl$_3$/MTBE (1:3) | Type B |

No solids were obtained via slow cooling and all samples were transferred to −20° C.
*limited solid was obtained and system was subjected to evaporation at RT.

5.4.4 Polymer Induced Crystallization

Polymer induced crystallization experiments were performed with two sets of polymer mixtures in seven solvents. Approximate 15 mg of starting material (807920-05-A) was dissolved in appropriate solvent to obtain a clear solution in a 3-mL vial. About 2 mg of polymer mixture was added into 3-mL glass vial. All the samples were subjected to evaporation at RT to induce precipitation. The solids were isolated for XRPD analysis. Results summarized in Table 5-12 show that Type A and B were produced.

TABLE 5-12

Summary of polymer induced crystallization experiments

| Experiment ID | Solvent | Polymer | Solid Form |
|---|---|---|---|
| 807920-10-A1 | MeOH | | Type A |
| 807920-10-A2 | Acetone | Polymer mixture A | Type A |
| 807920-10-A3 | THF | | Type A |
| 807920-10-A4 | MeOH | | Type B |

TABLE 5-12-continued

Summary of polymer induced crystallization experiments

| Experiment ID | Solvent | Polymer | Solid Form |
|---|---|---|---|
| 807920-10-A5 | Acetone | Polymer mixture B | Type A |
| 807920-10-A6 | THF | | Type A |

Polymer mixture A: polyvinyl pyrrolidone (PVP), polyvinyl alcohol (PVA), polyvinylchloride (PVC), polyvinyl acetate (PVAC), hypromellose (HPMC), methyl cellulose (MC) (mass ratio of 1:1:1:1:1:1) Polymer mixture B: polycaprolactone (PCL), polyethylene glycol (PEG), poly(methyl methacrylate) (PMMA) sodium alginate (SA), and hydroxyethyl cellulose (HEC) (mass ratio of 1:1:1:1:1).

5.4.5 Solid Vapor Diffusion

Solid vapor diffusion experiments were conducted using 13 different solvents. Approximate 10 mg of starting material (807920-05-A) was weighed into a 3-mL vial, which was placed into a 20-mL vial with 2 mL of volatile solvent. The 20-mL vial was sealed with a cap and kept at RT for 7 days allowing solvent vapor to interact with sample. The solids were tested by XRPD and the results summarized in Table 5-13 show that Type A and C were generated.

TABLE 5-13

Summary of solid vapor diffusion experiments

| Experiment ID | Solvent | Solid Form |
|---|---|---|
| 807920-11-A1 | H$_2$O | Type A |
| 807920-11-A2 | DCM | Type A |
| 807920-11-A3 | EtOH | Type A |
| 807920-11-A4 | MeOH | Type A |
| 807920-11-A5 | ACN | Type A |
| 807920-11-A6 | THF | Type A |
| 807920-11-A7 | CHCl$_3$ | Type A |
| 807920-11-A8 | Acetone | Type A |
| 807920-11-A9 | DMF | Type A |
| 807920-11-A10 | EtOAc | Type A |
| 807920-11-A11 | 1,4-dioxane | Type C |
| 807920-11-A12 | IPA | Type A |
| 807920-11-A13 | DMSO | Type A |

5.4.6 Liquid Vapor Diffusion

Ten liquid vapor diffusion experiments were conducted. Approximate 15 mg of starting material (807920-05-A) was dissolved in appropriate solvent to obtain a clear solution in a 3-mL vial. This solution was then placed into a 20-mL vial with 3 mL of volatile solvents. The 20-mL vial was sealed with a cap and kept at RT allowing sufficient time for organic vapor to interact with the solution. The precipitates were isolated for XRPD analysis. After 6 days, solids were isolated for XRPD analysis. The results summarized in Table 5-14 show that Type B, D, and E were generated besides Type A.

TABLE 5-14

Summary of liquid vapor diffusion experiments

| Experiment ID | Solvent | Anti-solvent | Solid Form |
|---|---|---|---|
| 807920-12-A1 | EtOH | H$_2$O | Type A |
| 807920-12-A2 | THF | | Type B |
| 807920-12-A3 | CHCl$_3$ | Toluene | Type A + B |
| 807920-12-A4 | 2-MeTHF | | Type A |
| 807920-12-A5 | Acetone | n-heptane | Type A |
| 807920-12-A6 | IBA | | Clear |
| 807920-12-A7 | DCM | | Type A |
| 807920-12-A8 | Ethyl lactate | MTBE | Clear |
| 807920-12-A9 | DMAc | | Type D |
| 807920-12-A10 | NMP | | Type E |

5.4.7 Slurry at RT

Slurry conversion experiments were conducted at RT in different solvent systems. About 15 mg of starting material (807920-05-A) was suspended in 0.5 mL of solvent in a 1.5-mL glass vial. After the suspension was stirred magnetically for 3 days at RT, the remaining solids were isolated for XRPD analysis. Results summarized in Table 5-15 indicated that only Type A was obtained.

TABLE 5-15

Summary of slurry conversion experiments at RT

| Experiment ID | Solvent (v:v) | Solid Form |
|---|---|---|
| 807920-13-A1 | ACN | Type A |
| 807920-13-A2 | EtOAc | Type A |
| 807920-13-A3 | IPAc | Type A |
| 807920-13-A4 | MEK | Type A |
| 807920-13-A5 | MIBK | Type A |
| 807920-13-A6 | Anisole | Type A |
| 807920-13-A7 | 2-MeTHF | Type A |
| 807920-13-A8 | 1,4-dioxane | Type A |
| 807920-13-A9 | IPA | Type A |
| 807920-13-A10 | IBA | Type A |
| 807920-13-A11 | MeOH/H$_2$O (1:3) | Type A |
| 807920-13-A12 | THF/n-heptane (1:3) | Type A |
| 807920-13-A13 | DCM/toluene (1:3) | Type A |
| 807920-13-A14 | acetone/H$_2$O (a$_w$ = 0.2) | Type A |
| 807920-13-A15 | acetone/H$_2$O (a$_w$ = 0.4) | Type A |
| 807920-13-A16 | acetone/H$_2$O (a$_w$ = 0.6) | Type A |
| 807920-13-A17 | acetone/H$_2$O (a$_w$ = 0.8) | Type A |

5.4.8 Slurry at 50° C.

Slurry conversion experiments were also conducted at 50° C. in different solvent systems. About 15 mg of starting material (807920-05-A) was suspended in 0.3 mL of solvent in a 1.5-mL glass vial. After the suspension was stirred for about 3 days at 50° C., the remaining solids were isolated for XRPD analysis. Results summarized in Table 5-16 indicated that Type A and C were obtained.

TABLE 5-16

Summary of slurry conversion experiments at 50° C.

| Experiment ID | Solvent (v:v) | Solid Form |
|---|---|---|
| 807920-14-A1 | ACN | Type A |
| 807920-14-A2 | EtOAc | Type A |
| 807920-14-A3 | IPAc | Type A |
| 807920-14-A4 | MEK | Type A |
| 807920-14-A5 | MIBK | Type A |
| 807920-14-A6 | Anisole | Type A |
| 807920-14-A7 | 2-MeTHF | Type A |
| 807920-14-A8 | 1,4-dioxane | Type C |
| 807920-14-A9 | IPA | Type A |
| 807920-14-A10 | IBA | Type A |
| 807920-14-A11 | MeOH/H$_2$O (1:5) | Type A |
| 807920-14-A12 | THF/n-heptane (1:5) | Type A |
| 807920-14-A13 | CHCl$_3$/toluene (1:5) | Type A |
| 807920-14-A14 | H$_2$O | Type A |

The preceding disclosures are illustrative embodiments. It should be appreciated by those of skill in the art that the techniques disclosed herein elucidate representative techniques that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A compound, which is resiquimod in the form of a sulfate salt in crystal form A.

2. The compound of claim 1, wherein the sulfate salt is a monosulfate salt.

3. The compound of claim 1, wherein the sulfate salt is an anhydrate.

4. The compound of claim 1, wherein crystal form A is characterized by x-ray powder diffraction (XRPD) spectrum that comprises peaks at about 7 to about 8 degrees 2θ, about 13.5 to about 14.5 degrees 2θ, about 19 to about 20 degrees 2θ, and about 19.5 to about 20.5 degrees 2θ, as determined by XRPD using Cu Kα1 and Cu Kα2 radiation.

5. A dosage form, comprising the compound of claim 1.

6. The dosage form of claim 5, which is a solid dosage form.

7. The dosage form of claim 5, which is a semi-solid dosage form.

8. The dosage form of claim 5, which is a liquid dosage form.

9. A composition, comprising the compound of claim 1.

10. A composition, comprising the compound of claim 2.

11. A composition, comprising the compound of claim 3.

12. A composition, comprising the compound of claim 4.

13. A pharmaceutical composition, comprising the compound of claim 1 and a pharmaceutically acceptable carrier.

14. A pharmaceutical composition, comprising the compound of claim 2 and a pharmaceutically acceptable carrier.

15. A pharmaceutical composition, comprising the compound of claim 3 and a pharmaceutically acceptable carrier.

16. A pharmaceutical composition, comprising the compound of claim 4 and a pharmaceutically acceptable carrier.

17. A method of treating a cancer in a subject in need thereof, comprising administering the compound of claim 1 to the subject.

18. A method of treating a tumor in a subject in need thereof, comprising administering the compound of claim 1 to the subject.

19. A method of treating a carcinoma in a subject in need thereof, comprising administering the compound of claim 1 to the subject.

20. A method of treating a sarcoma in a subject in need thereof, comprising administering the compound of claim 1 to the subject.

21. A method of treating a blastoma in a subject in need thereof, comprising administering the compound of claim 1 to the subject.

* * * * *